(12) United States Patent
Kajihara et al.

(10) Patent No.: US 7,985,731 B2
(45) Date of Patent: Jul. 26, 2011

(54) SUGAR CHAIN ADDED GLP-1 PEPTIDE

(75) Inventors: Yasuhiro Kajihara, Yokohama (JP);
Takashi Tsuji, Nagareyama (JP); Izumi Sakamoto, Tokushima (JP); Yuri Nambu, Tokushima (JP); Kazuhiro Fukae, Tokushima (JP); Katsunari Tezuka, Tokushima (JP); Hiroaki Asai, Tokushima (JP)

(73) Assignee: Otsuka Chemical Holdings Co., Ltd. (JP)

( * ) Notice: Subject to any disclaimer, the term of this patent is extended or adjusted under 35 U.S.C. 154(b) by 177 days.

(21) Appl. No.: 12/140,866

(22) Filed: Jun. 17, 2008

(65) Prior Publication Data

US 2009/0111739 A1    Apr. 30, 2009

Related U.S. Application Data

(60) Provisional application No. 60/929,425, filed on Jun. 27, 2007.

(30) Foreign Application Priority Data

Jun. 19, 2007    (JP) .................................. 2007-160951

(51) Int. Cl.
*A61K 38/26*    (2006.01)
*A61K 38/14*    (2006.01)

(52) U.S. Cl. ........................................ 514/7.2; 514/20.9

(58) Field of Classification Search .......................... None
See application file for complete search history.

(56) References Cited

U.S. PATENT DOCUMENTS

| 2005/0222382 A1 | 10/2005 | Kajihara |
| 2007/0060543 A1 | 3/2007 | Kajihara et al. |

FOREIGN PATENT DOCUMENTS

| EP | 1 961 764 A1 | 8/2008 |
| JP | 2005-095331 A1 | 10/2005 |
| JP | 2006-520818 A | 9/2006 |
| WO | WO 2004/005330 A1 | 1/2004 |
| WO | WO 2005/010053 A1 | 2/2005 |
| WO | WO 2006/010143 A2 | 1/2006 |
| WO | WO 2007/063907 A1 | 6/2007 |

OTHER PUBLICATIONS

"Short Communication: Renal Tubular Vacuolation in Animals Treated with Polyethylene-Glycol-Conjugated Proteins"—A. Bendele et al.—Toxicological Sciences 42, (1998)—pp. 152-157.
"Isolation and Characterization of Exendin-4, an Exendin-3 Analogue, from *Heloderma suspectum* Venom"—J. Eng et al.—The Journal of Biological Chemistry—vol. 267, No. 11, Issue of Apr. 15, 1992—pp. 7402-7405.
"Metabolic effects of the incretin mimetic exenatide in the treatment of type 2 diabetes"—C.A. Schnabel et al.—Vascular Health and Risk Management 2006:2(I) pp. 69-77.
"Efficacy and Safety of Incretin Therapy in Type 2 Diabetes: Systematic Review and Meta-analysis"—R.E. Amori et al.—JAMA—Aug. 27, 2008—pp. 194-206.
"β-Cell Failure in Diabetes and Preservation by Clinical Treatment"—B.L. Wajchenberg—Endocrine Reviews 28(2): 187-218—Copyright 2007 by The Endocrine Society.
Journal of the Japan Diabetes Society, vol. 51, Supplemental 1, Abstracts of 51$^{st}$ Annual Meeting of the Japan Diabetes Society—May 22-24, 2008; Published on Apr. 25, 2008—pp. 1-2.
Translation of Journal of the Japan Diabetes Society, vol. 51, Supplemental 1, Abstracts of 51$^{st}$ Annual Meeting of the Japan Diabetes Society—May 22-24, 2008; Published on Apr. 25, 2008—pp. 1-2.
Meurer, Janet A. et al., Properties of Native and in Vitro Glycosylated Forms of the Glucagon-Like Peptide-1 Receptor Antagonist Exending (9-39_; Metabolism, vol. 48, No. 5 (Jun. 1999); pp. 716-724.

*Primary Examiner* — Robert Landsman
*Assistant Examiner* — Gyan Chandra
(74) *Attorney, Agent, or Firm* — Brinks Hofer Gilson & Lione

(57) ABSTRACT

The present invention relates to an oligosaccharide chain added GLP-1 peptide that has higher stability in blood than that of GLP-1 and, preferably, exhibits higher activity of controlling blood-sugar levels than that of GLP-1. The present invention relates to an oligosaccharide chain added GLP-1 peptide having GLP-1 activity, wherein at least one amino acid is substituted with an oligosaccharide chain added amino acid, in: (a) GLP-1; (b) a peptide having the amino acid sequence of GLP-1 with deletion, substitution or addition of one or several amino acids; or (c) a GLP-1 analog.

14 Claims, 11 Drawing Sheets

```
                        SEQUENCE LISTING

<160> NUMBER OF SEQ ID NOS: 153

<210> SEQ ID NO 1
<211> LENGTH: 31
<212> TYPE: PRT
<213> ORGANISM: artificial sequence
<220> FEATURE:
<223> OTHER INFORMATION: glycosylated GLP-1 peptide
<220> FEATURE:
<221> NAME/KEY: MISC_FEATURE
<222> LOCATION: (12)..(12)
<223> OTHER INFORMATION: Xaa18: Ser, glycosylated Cys or glycosylated
      Asn.
<220> FEATURE:
<221> NAME/KEY: MISC_FEATURE
<222> LOCATION: (13)..(13)
<223> OTHER INFORMATION: Xaa19: Tyr, glycosylated Cys or glycosylated
      Asn.
<220> FEATURE:
<221> NAME/KEY: MISC_FEATURE
<222> LOCATION: (16)..(16)
<223> OTHER INFORMATION: Xaa22: Gly, glycosylated Cys or glycosylated
      Asn.
<220> FEATURE:
<221> NAME/KEY: MISC_FEATURE
<222> LOCATION: (20)..(20)
<223> OTHER INFORMATION: Xaa26: Lys, glycosylated Cys or glycosylated
      Asn.
<220> FEATURE:
<221> NAME/KEY: MISC_FEATURE
<222> LOCATION: (30)..(30)
<223> OTHER INFORMATION: Xaa36: Arg, glycosylated Cys or glycosylated
      Asn.
<220> FEATURE:
<221> NAME/KEY: MISC_FEATURE
<222> LOCATION: (31)..(31)
<223> OTHER INFORMATION: Xaa37: Gly, -NH2, Gly-glycosylated Cys or
      Gly-glycosylated Asn.
<220> FEATURE:
<221> NAME/KEY: MISC_FEATURE
<222> LOCATION: (31)..(31)
<223> OTHER INFORMATION: When Xaa18 is Ser, Xaa19 is Tyr, Xaa22 is Gly,
      Xaa26 is Lys and Xaa36 is Arg, Xaa37 is Gly-glycosylated Cys or
      Gly-glycosylated Asn.
```

-continued

```
<400> SEQUENCE: 1

His Ala Glu Gly Thr Phe Thr Ser Asp Val Ser Xaa Xaa Leu Glu Xaa
1               5                   10                  15

Gln Ala Ala Xaa Glu Phe Ile Ala Trp Leu Val Lys Gly Xaa Xaa
            20                  25                  30

<210> SEQ ID NO 2
<211> LENGTH: 31
<212> TYPE: PRT
<213> ORGANISM: human

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 30
<212> TYPE: PRT
<213> ORGANISM: artificial sequence
<220> FEATURE:
<223> OTHER INFORMATION: GLP-1(7-36)NH2
<220> FEATURE:
<221> NAME/KEY: MOD_RES
<222> LOCATION: (30)..(30)
<223> OTHER INFORMATION: AMIDATION

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 31
<212> TYPE: PRT
<213> ORGANISM: artificial sequence
<220> FEATURE:
<223> OTHER INFORMATION: amino acid sequence of (a1)
<220> FEATURE:
<221> NAME/KEY: CARBOHYD
<222> LOCATION: (12)..(12)

<400> SEQUENCE: 4

His Ala Glu Gly Thr Phe Thr Ser Asp Val Ser Cys Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 5
<211> LENGTH: 31
<212> TYPE: PRT
<213> ORGANISM: artificial sequence
<220> FEATURE:
<223> OTHER INFORMATION: amino acid sequence of (a2)
<220> FEATURE:
<221> NAME/KEY: CARBOHYD
<222> LOCATION: (16)..(16)

<400> SEQUENCE: 5

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Arg Gly
            20                  25                  30
```

```
<210> SEQ ID NO 6
<211> LENGTH: 31
<212> TYPE: PRT
<213> ORGANISM: artificial sequence
<220> FEATURE:
<223> OTHER INFORMATION: amino acid sequence of (a3)
<220> FEATURE:
<221> NAME/KEY: CARBOHYD
<222> LOCATION: (20)..(20)

<400> SEQUENCE: 6

His Ala Glu Gly Thr Phe Thr Ser Asp Val Ser Ser Tyr Leu Glu Gly
 1               5                  10                  15

Gln Ala Ala Cys Glu Phe Ile Ala Trp Leu Val Lys Gly Arg Gly
            20                  25                  30

<210> SEQ ID NO 7
<211> LENGTH: 31
<212> TYPE: PRT
<213> ORGANISM: artificial sequence
<220> FEATURE:
<223> OTHER INFORMATION: amino acid sequence of (a4)
<220> FEATURE:
<221> NAME/KEY: CARBOHYD
<222> LOCATION: (30)..(30)

<400> SEQUENCE: 7

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Cys Gly
            20                  25                  30

<210> SEQ ID NO 8
<211> LENGTH: 32
<212> TYPE: PRT
<213> ORGANISM: artificial sequence
<220> FEATURE:
<223> OTHER INFORMATION: amino acid sequence of (a5)
<220> FEATURE:
<221> NAME/KEY: CARBOHYD
<222> LOCATION: (32)..(32)

<400> SEQUENCE: 8

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly Cys
            20                  25                  30

<210> SEQ ID NO 9
<211> LENGTH: 31
<212> TYPE: PRT
<213> ORGANISM: artificial sequence
<220> FEATURE:
<223> OTHER INFORMATION: amino acid sequence of (a6)
<220> FEATURE:
<221> NAME/KEY: CARBOHYD
<222> LOCATION: (13)..(13)

<400> SEQUENCE: 9

His Ala Glu Gly Thr Phe Thr Ser Asp Val Ser Ser Cys Leu Glu Gly
 1               5                  10                  15

Gln Ala Ala Lys Glu Phe Ile Ala Trp Leu Val Lys Gly Arg Gly
            20                  25                  30

<210> SEQ ID NO 10
<211> LENGTH: 31
<212> TYPE: PRT
<213> ORGANISM: artificial sequence
```

```
<220> FEATURE:
<223> OTHER INFORMATION: amino acid sequence of (a7)
<220> FEATURE:
<221> NAME/KEY: CARBOHYD
<222> LOCATION: (12)..(12)

<400> SEQUENCE: 10

His Ala Glu Gly Thr Phe Thr Ser Asp Val Ser Asn Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 11
<211> LENGTH: 31
<212> TYPE: PRT
<213> ORGANISM: artificial sequence
<220> FEATURE:
<223> OTHER INFORMATION: amino acid sequence of (a8)
<220> FEATURE:
<221> NAME/KEY: CARBOHYD
<222> LOCATION: (16)..(16)

<400> SEQUENCE: 11

His Ala Glu Gly Thr Phe Thr Ser Asp Val Ser Ser Tyr Leu Glu Asn
 1               5                  10                  15

Gln Ala Ala Lys Glu Phe Ile Ala Trp Leu Val Lys Gly Arg Gly
            20                  25                  30

<210> SEQ ID NO 12
<211> LENGTH: 31
<212> TYPE: PRT
<213> ORGANISM: artificial sequence
<220> FEATURE:
<223> OTHER INFORMATION: amino acid sequence of (a9)
<220> FEATURE:
<221> NAME/KEY: CARBOHYD
<222> LOCATION: (20)..(20)

<400> SEQUENCE: 12

His Ala Glu Gly Thr Phe Thr Ser Asp Val Ser Ser Tyr Leu Glu Gly
 1               5                  10                  15

Gln Ala Ala Asn Glu Phe Ile Ala Trp Leu Val Lys Gly Arg Gly
            20                  25                  30

<210> SEQ ID NO 13
<211> LENGTH: 31
<212> TYPE: PRT
<213> ORGANISM: artificial sequence
<220> FEATURE:
<223> OTHER INFORMATION: amino acid sequence of (a10)
<220> FEATURE:
<221> NAME/KEY: CARBOHYD
<222> LOCATION: (30)..(30)

<400> SEQUENCE: 13

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Asn Gly
            20                  25                  30

<210> SEQ ID NO 14
<211> LENGTH: 32
<212> TYPE: PRT
<213> ORGANISM: artificial sequence
<220> FEATURE:
<223> OTHER INFORMATION: amino acid sequence of (a11)
```

```
<220> FEATURE:
<221> NAME/KEY: CARBOHYD
<222> LOCATION: (32)..(32)

<400> SEQUENCE: 14

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Asn
            20                  25                  30

<210> SEQ ID NO 15
<211> LENGTH: 31
<212> TYPE: PRT
<213> ORGANISM: artificial sequence
<220> FEATURE:
<223> OTHER INFORMATION: amino acid sequence of (a12)
<220> FEATURE:
<221> NAME/KEY: CARBOHYD
<222> LOCATION: (13)..(13)

<400> SEQUENCE: 15

His Ala Glu Gly Thr Phe Thr Ser Asp Val Ser Ser Asn Leu Glu Gly
1               5                   10                  15

Gln Ala Ala Lys Glu Phe Ile Ala Trp Leu Val Lys Gly Arg Gly
            20                  25                  30

<210> SEQ ID NO 16
<211> LENGTH: 30
<212> TYPE: PRT
<213> ORGANISM: artificial sequence
<220> FEATURE:
<223> OTHER INFORMATION: amino acid sequence of (a13)
<220> FEATURE:
<221> NAME/KEY: CARBOHYD
<222> LOCATION: (12)..(12)
<220> FEATURE:
<221> NAME/KEY: MOD_RES
<222> LOCATION: (30)..(30)
<223> OTHER INFORMATION: AMIDATION

<400> SEQUENCE: 16

His Ala Glu Gly Thr Phe Thr Ser Asp Val Ser Cys Tyr Leu Glu Gly
1               5                   10                  15

Gln Ala Ala Lys Glu Phe Ile Ala Trp Leu Val Lys Gly Arg
            20                  25                  30

<210> SEQ ID NO 17
<211> LENGTH: 30
<212> TYPE: PRT
<213> ORGANISM: artificial sequence
<220> FEATURE:
<223> OTHER INFORMATION: amino acid sequence of (a14)
<220> FEATURE:
<221> NAME/KEY: CARBOHYD
<222> LOCATION: (16)..(16)
<220> FEATURE:
<221> NAME/KEY: MOD_RES
<222> LOCATION: (30)..(30)
<223> OTHER INFORMATION: AMIDATION

<400> SEQUENCE: 17

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Arg
            20                  25                  30
```

```
<210> SEQ ID NO 18
<211> LENGTH: 30
<212> TYPE: PRT
<213> ORGANISM: artificial sequence
<220> FEATURE:
<223> OTHER INFORMATION: amino acid sequence of (a15)
<220> FEATURE:
<221> NAME/KEY: CARBOHYD
<222> LOCATION: (20)..(20)
<220> FEATURE:
<221> NAME/KEY: MOD_RES
<222> LOCATION: (30)..(30)
<223> OTHER INFORMATION: AMIDATION
<220> FEATURE:
<221> NAME/KEY: MOD_RES
<222> LOCATION: (30)..(30)

<400> SEQUENCE: 18

His Ala Glu Gly Thr Phe Thr Ser Asp Val Ser Ser Tyr Leu Glu Gly
1               5                   10                  15

Gln Ala Ala Cys Glu Phe Ile Ala Trp Leu Val Lys Gly Arg
            20                  25                  30

<210> SEQ ID NO 19
<211> LENGTH: 30
<212> TYPE: PRT
<213> ORGANISM: artificial sequence
<220> FEATURE:
<223> OTHER INFORMATION: amino acid sequence of (a16)
<220> FEATURE:
<221> NAME/KEY: CARBOHYD
<222> LOCATION: (30)..(30)
<220> FEATURE:
<221> NAME/KEY: MOD_RES
<222> LOCATION: (30)..(30)
<223> OTHER INFORMATION: AMIDATION

<400> SEQUENCE: 19

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys
            20                  25                  30

<210> SEQ ID NO 20
<211> LENGTH: 30
<212> TYPE: PRT
<213> ORGANISM: artificial sequence
<220> FEATURE:
<223> OTHER INFORMATION: amino acid sequence of (a17)
<220> FEATURE:
<221> NAME/KEY: CARBOHYD
<222> LOCATION: (13)..(13)
<220> FEATURE:
<221> NAME/KEY: MOD_RES
<222> LOCATION: (30)..(30)
<223> OTHER INFORMATION: AMIDATION

<400> SEQUENCE: 20

His Ala Glu Gly Thr Phe Thr Ser Asp Val Ser Ser Cys Leu Glu Gly
1               5                   10                  15

Gln Ala Ala Lys Glu Phe Ile Ala Trp Leu Val Lys Gly Arg
            20                  25                  30

<210> SEQ ID NO 21
<211> LENGTH: 30
<212> TYPE: PRT
<213> ORGANISM: artificial sequence
<220> FEATURE:
<223> OTHER INFORMATION: amino acid sequence of (a18)
```

```
<220> FEATURE:
<221> NAME/KEY: CARBOHYD
<222> LOCATION: (12)..(12)
<220> FEATURE:
<221> NAME/KEY: MOD_RES
<222> LOCATION: (30)..(30)
<223> OTHER INFORMATION: AMIDATION

<400> SEQUENCE: 21

His Ala Glu Gly Thr Phe Thr Ser Asp Val Ser Asn Tyr Leu Glu Gly
1               5                   10                  15

Gln Ala Ala Lys Glu Phe Ile Ala Trp Leu Val Lys Gly Arg
            20                  25                  30

<210> SEQ ID NO 22
<211> LENGTH: 30
<212> TYPE: PRT
<213> ORGANISM: artificial sequence
<220> FEATURE:
<223> OTHER INFORMATION: amino acid sequence of (a19)
<220> FEATURE:
<221> NAME/KEY: CARBOHYD
<222> LOCATION: (16)..(16)
<220> FEATURE:
<221> NAME/KEY: MOD_RES
<222> LOCATION: (30)..(30)
<223> OTHER INFORMATION: AMIDATION

<400> SEQUENCE: 22

His Ala Glu Gly Thr Phe Thr Ser Asp Val Ser Ser Tyr Leu Glu Asn
1               5                   10                  15

Gln Ala Ala Lys Glu Phe Ile Ala Trp Leu Val Lys Gly Arg
            20                  25                  30

<210> SEQ ID NO 23
<211> LENGTH: 30
<212> TYPE: PRT
<213> ORGANISM: artificial sequence
<220> FEATURE:
<223> OTHER INFORMATION: amino acid sequence of (a20)
<220> FEATURE:
<221> NAME/KEY: CARBOHYD
<222> LOCATION: (20)..(20)
<220> FEATURE:
<221> NAME/KEY: MOD_RES
<222> LOCATION: (30)..(30)
<223> OTHER INFORMATION: AMIDATION

<400> SEQUENCE: 23

His Ala Glu Gly Thr Phe Thr Ser Asp Val Ser Ser Tyr Leu Glu Gly
1               5                   10                  15

Gln Ala Ala Asn Glu Phe Ile Ala Trp Leu Val Lys Gly Arg
            20                  25                  30

<210> SEQ ID NO 24
<211> LENGTH: 30
<212> TYPE: PRT
<213> ORGANISM: artificial sequence
<220> FEATURE:
<223> OTHER INFORMATION: amino acid sequence of (a21)
<220> FEATURE:
<221> NAME/KEY: CARBOHYD
<222> LOCATION: (30)..(30)
<220> FEATURE:
<221> NAME/KEY: MOD_RES
<222> LOCATION: (30)..(30)
<223> OTHER INFORMATION: AMIDATION
```

```
<400> SEQUENCE: 24

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Asn
            20                  25                  30

<210> SEQ ID NO 25
<211> LENGTH: 30
<212> TYPE: PRT
<213> ORGANISM: artificial sequence
<220> FEATURE:
<223> OTHER INFORMATION: amino acid sequence of (a22)
<220> FEATURE:
<221> NAME/KEY: CARBOHYD
<222> LOCATION: (13)..(13)
<220> FEATURE:
<221> NAME/KEY: MOD_RES
<222> LOCATION: (30)..(30)
<223> OTHER INFORMATION: AMIDATION

<400> SEQUENCE: 25

His Ala Glu Gly Thr Phe Thr Ser Asp Val Ser Ser Asn Leu Glu Gly
1               5                   10                  15

Gln Ala Ala Lys Glu Phe Ile Ala Trp Leu Val Lys Gly Arg
            20                  25                  30

<210> SEQ ID NO 26
<211> LENGTH: 32
<212> TYPE: PRT
<213> ORGANISM: artificial sequence
<220> FEATURE:
<223> OTHER INFORMATION: amino acid sequence of (a23)
<220> FEATURE:
<221> NAME/KEY: CARBOHYD
<222> LOCATION: (12)..(12)
<220> FEATURE:
<221> NAME/KEY: CARBOHYD
<222> LOCATION: (16)..(16)
<220> FEATURE:
<221> NAME/KEY: CARBOHYD
<222> LOCATION: (32)..(32)

<400> SEQUENCE: 26

His Ala Glu Gly Thr Phe Thr Ser Asp Val Ser Cys Tyr Leu Glu Cys
1               5                   10                  15

Gln Ala Ala Lys Glu Phe Ile Ala Trp Leu Val Lys Gly Arg Gly Cys
            20                  25                  30

<210> SEQ ID NO 27
<211> LENGTH: 31
<212> TYPE: PRT
<213> ORGANISM: artificial sequence
<220> FEATURE:
<223> OTHER INFORMATION: amino acid sequence of (a24)
<220> FEATURE:
<221> NAME/KEY: CARBOHYD
<222> LOCATION: (12)..(12)
<220> FEATURE:
<221> NAME/KEY: CARBOHYD
<222> LOCATION: (16)..(16)
<220> FEATURE:
<221> NAME/KEY: CARBOHYD
<222> LOCATION: (20)..(20)

<400> SEQUENCE: 27

His Ala Glu Gly Thr Phe Thr Ser Asp Val Ser Cys Tyr Leu Glu Cys
1               5                   10                  15

Gln Ala Ala Cys Glu Phe Ile Ala Trp Leu Val Lys Gly Arg Gly
            20                  25                  30
```

```
<210> SEQ ID NO 28
<211> LENGTH: 32
<212> TYPE: PRT
<213> ORGANISM: artificial sequence
<220> FEATURE:
<223> OTHER INFORMATION: amino acid sequence of (a25)
<220> FEATURE:
<221> NAME/KEY: CARBOHYD
<222> LOCATION: (20)..(20)
<220> FEATURE:
<221> NAME/KEY: CARBOHYD
<222> LOCATION: (30)..(30)
<220> FEATURE:
<221> NAME/KEY: CARBOHYD
<222> LOCATION: (32)..(32)

<400> SEQUENCE: 28

His Ala Glu Gly Thr Phe Thr Ser Asp Val Ser Ser Tyr Leu Glu Gly
1               5                   10                  15

Gln Ala Ala Asn Glu Phe Ile Ala Trp Leu Val Lys Gly Asn Gly Asn
            20                  25                  30

<210> SEQ ID NO 29
<211> LENGTH: 30
<212> TYPE: PRT
<213> ORGANISM: artificial sequence
<220> FEATURE:
<223> OTHER INFORMATION: amino acid sequence of (a26)
<220> FEATURE:
<221> NAME/KEY: CARBOHYD
<222> LOCATION: (12)..(12)
<220> FEATURE:
<221> NAME/KEY: CARBOHYD
<222> LOCATION: (16)..(16)
<220> FEATURE:
<221> NAME/KEY: CARBOHYD
<222> LOCATION: (20)..(20)
<220> FEATURE:
<221> NAME/KEY: MOD_RES
<222> LOCATION: (30)..(30)
<223> OTHER INFORMATION: AMIDATION

<400> SEQUENCE: 29

His Ala Glu Gly Thr Phe Thr Ser Asp Val Ser Asn Tyr Leu Glu Asn
1               5                   10                  15

Gln Ala Ala Asn Glu Phe Ile Ala Trp Leu Val Lys Gly Arg
            20                  25                  30

<210> SEQ ID NO 30
<211> LENGTH: 31
<212> TYPE: PRT
<213> ORGANISM: artificial sequence
<220> FEATURE:
<223> OTHER INFORMATION: amino acid sequence having blocking groups
      (Example 1)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
```

```
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Cys having blocking group Trt
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 30

His Ala Glu Gly Thr Phe Thr Ser Asp Val Ser Cys Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 31
<211> LENGTH: 31
<212> TYPE: PRT
<213> ORGANISM: artificial sequence
<220> FEATURE:
<223> OTHER INFORMATION: amino acid sequence having blocking groups
      (Comparative Example 1)
<220> FEATURE:
<221> NAME/KEY: MISC_FEATURE
<222> LOCATION: (1)..(1)
<223> OTHER INFORMATION: His having a blocking group Trt
<220> FEATURE:
<221> NAME/KEY: MISC_FEATURE
<222> LOCATION: (3)..(3)
<223> OTHER INFORMATION: Glu having a blocking group OtBu
<220> FEATURE:
<221> NAME/KEY: MISC_FEATURE
<222> LOCATION: (5)..(5)
<223> OTHER INFORMATION: Thr having a blocking group tBu
```

```
<220> FEATURE:
<221> NAME/KEY: MISC_FEATURE
<222> LOCATION: (7)..(7)
<223> OTHER INFORMATION: Thr having a blocking group tBu
<220> FEATURE:
<221> NAME/KEY: MISC_FEATURE
<222> LOCATION: (8)..(8)
<223> OTHER INFORMATION: Ser having a blocking group tBu
<220> FEATURE:
<221> NAME/KEY: MISC_FEATURE
<222> LOCATION: (9)..(9)
<223> OTHER INFORMATION: Asp having a blocking group OtBu
<220> FEATURE:
<221> NAME/KEY: MISC_FEATURE
<222> LOCATION: (11)..(11)
<223> OTHER INFORMATION: Ser having a blocking group tBu
<220> FEATURE:
<221> NAME/KEY: MISC_FEATURE
<222> LOCATION: (12)..(12)
<223> OTHER INFORMATION: Ser having a blocking group tBu
<220> FEATURE:
<221> NAME/KEY: MISC_FEATURE
<222> LOCATION: (13)..(13)
<223> OTHER INFORMATION: Tyr having a blocking group tBu
<220> FEATURE:
<221> NAME/KEY: MISC_FEATURE
<222> LOCATION: (15)..(15)
<223> OTHER INFORMATION: Glu having a blocking group OtBu
<220> FEATURE:
<221> NAME/KEY: MISC_FEATURE
<222> LOCATION: (17)..(17)
<223> OTHER INFORMATION: Gln having a blocking group Trt
<220> FEATURE:
<221> NAME/KEY: MISC_FEATURE
<222> LOCATION: (20)..(20)
<223> OTHER INFORMATION: Lys having a blocking group Boc
<220> FEATURE:
<221> NAME/KEY: MISC_FEATURE
<222> LOCATION: (21)..(21)
<223> OTHER INFORMATION: Glu having a blocking group OtBu
<220> FEATURE:
<221> NAME/KEY: MISC_FEATURE
<222> LOCATION: (25)..(25)
<223> OTHER INFORMATION: Trp having a blocking group Boc
<220> FEATURE:
<221> NAME/KEY: MISC_FEATURE
<222> LOCATION: (28)..(28)
<223> OTHER INFORMATION: Lys having a blocking group Boc
<220> FEATURE:
<221> NAME/KEY: MISC_FEATURE
<222> LOCATION: (30)..(30)
<223> OTHER INFORMATION: Arg having a blocking group Pbf

<400> SEQUENCE: 31

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 32
<211> LENGTH: 31
<212> TYPE: PRT
<213> ORGANISM: artificial sequence
<220> FEATURE:
<223> OTHER INFORMATION: amino acid sequence having blocking groups
      (Example 6)
<220> FEATURE:
<221> NAME/KEY: MISC_FEATURE
<222> LOCATION: (1)..(1)
<223> OTHER INFORMATION: His having a blocking group Trt
<220> FEATURE:
<221> NAME/KEY: MISC_FEATURE
<222> LOCATION: (3)..(3)
<223> OTHER INFORMATION: Glu having a blocking group OtBu
```

```
<220> FEATURE:
<221> NAME/KEY: MISC_FEATURE
<222> LOCATION: (5)..(5)
<223> OTHER INFORMATION: Thr having a blocking group tBu
<220> FEATURE:
<221> NAME/KEY: MISC_FEATURE
<222> LOCATION: (7)..(7)
<223> OTHER INFORMATION: Thr having a blocking group tBu
<220> FEATURE:
<221> NAME/KEY: MISC_FEATURE
<222> LOCATION: (8)..(8)
<223> OTHER INFORMATION: Ser having a blocking group tBu
<220> FEATURE:
<221> NAME/KEY: MISC_FEATURE
<222> LOCATION: (9)..(9)
<223> OTHER INFORMATION: Asp having a blocking group OtBu
<220> FEATURE:
<221> NAME/KEY: MISC_FEATURE
<222> LOCATION: (11)..(11)
<223> OTHER INFORMATION: Ser having a blocking group tBu
<220> FEATURE:
<221> NAME/KEY: MISC_FEATURE
<222> LOCATION: (12)..(12)
<223> OTHER INFORMATION: Ser having a blocking group tBu
<220> FEATURE:
<221> NAME/KEY: MISC_FEATURE
<222> LOCATION: (13)..(13)
<223> OTHER INFORMATION: Tyr having a blocking group tBu
<220> FEATURE:
<221> NAME/KEY: MISC_FEATURE
<222> LOCATION: (15)..(15)
<223> OTHER INFORMATION: Glu having a blocking group OtBu
<220> FEATURE:
<221> NAME/KEY: MISC_FEATURE
<222> LOCATION: (17)..(17)
<223> OTHER INFORMATION: Gln having a blocking group Trt
<220> FEATURE:
<221> NAME/KEY: MISC_FEATURE
<222> LOCATION: (20)..(20)
<223> OTHER INFORMATION: Lys having a blocking group Boc
<220> FEATURE:
<221> NAME/KEY: MISC_FEATURE
<222> LOCATION: (21)..(21)
<223> OTHER INFORMATION: Glu having a blocking group OtBu
<220> FEATURE:
<221> NAME/KEY: MISC_FEATURE
<222> LOCATION: (25)..(25)
<223> OTHER INFORMATION: Trp having a blocking group Boc
<220> FEATURE:
<221> NAME/KEY: MISC_FEATURE
<222> LOCATION: (28)..(28)
<223> OTHER INFORMATION: Lys having a blocking group Boc
<220> FEATURE:
<221> NAME/KEY: MISC_FEATURE
<222> LOCATION: (30)..(30)
<223> OTHER INFORMATION: Arg having a blocking group Pbf

<400> SEQUENCE: 32

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 33
<211> LENGTH: 31
<212> TYPE: PRT
<213> ORGANISM: artificial sequence
<220> FEATURE:
<223> OTHER INFORMATION: amino acid sequence having blocking groups
      (Exapmle 6)
<220> FEATURE:
<221> NAME/KEY: MISC_FEATURE
<222> LOCATION: (1)..(1)
<223> OTHER INFORMATION: His having blocking groups Trt and Boc
```

```
<220> FEATURE:
<221> NAME/KEY: MISC_FEATURE
<222> LOCATION: (3)..(3)
<223> OTHER INFORMATION: Glu having a blocking group OtBu
<220> FEATURE:
<221> NAME/KEY: MISC_FEATURE
<222> LOCATION: (5)..(5)
<223> OTHER INFORMATION: Thr having a blocking group tBu
<220> FEATURE:
<221> NAME/KEY: MISC_FEATURE
<222> LOCATION: (7)..(7)
<223> OTHER INFORMATION: Thr having a blocking group tBu
<220> FEATURE:
<221> NAME/KEY: MISC_FEATURE
<222> LOCATION: (8)..(8)
<223> OTHER INFORMATION: Ser having a blocking group tBu
<220> FEATURE:
<221> NAME/KEY: MISC_FEATURE
<222> LOCATION: (9)..(9)
<223> OTHER INFORMATION: Asp having a blocking group OtBu
<220> FEATURE:
<221> NAME/KEY: MISC_FEATURE
<222> LOCATION: (11)..(11)
<223> OTHER INFORMATION: Ser having a blocking group tBu
<220> FEATURE:
<221> NAME/KEY: MISC_FEATURE
<222> LOCATION: (12)..(12)
<223> OTHER INFORMATION: Ser having a blocking group tBu
<220> FEATURE:
<221> NAME/KEY: MISC_FEATURE
<222> LOCATION: (13)..(13)
<223> OTHER INFORMATION: Tyr having a blocking group tBu
<220> FEATURE:
<221> NAME/KEY: MISC_FEATURE
<222> LOCATION: (15)..(15)
<223> OTHER INFORMATION: Glu having a blocking group OtBu
<220> FEATURE:
<221> NAME/KEY: MISC_FEATURE
<222> LOCATION: (17)..(17)
<223> OTHER INFORMATION: Gln having a blocking group Trt
<220> FEATURE:
<221> NAME/KEY: MISC_FEATURE
<222> LOCATION: (20)..(20)
<223> OTHER INFORMATION: Lys having a blocking group Boc
<220> FEATURE:
<221> NAME/KEY: MISC_FEATURE
<222> LOCATION: (21)..(21)
<223> OTHER INFORMATION: Glu having a blocking group OtBu
<220> FEATURE:
<221> NAME/KEY: MISC_FEATURE
<222> LOCATION: (25)..(25)
<223> OTHER INFORMATION: Trp having a blocking group Boc
<220> FEATURE:
<221> NAME/KEY: MISC_FEATURE
<222> LOCATION: (28)..(28)
<223> OTHER INFORMATION: Lys having a blocking group Boc
<220> FEATURE:
<221> NAME/KEY: MISC_FEATURE
<222> LOCATION: (30)..(30)
<223> OTHER INFORMATION: Arg having a blocking group Pbf

<400> SEQUENCE: 33

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 34
<211> LENGTH: 18
<212> TYPE: PRT
<213> ORGANISM: artificial sequence
<220> FEATURE:
<223> OTHER INFORMATION: amino acid sequence having blocking groups
      (Example 7)
```

```
-continued

<220> FEATURE:
<221> NAME/KEY: MISC_FEATURE
<222> LOCATION: (2)..(2)
<223> OTHER INFORMATION: Glu having a blocking group OtBu
<220> FEATURE:
<221> NAME/KEY: MISC_FEATURE
<222> LOCATION: (4)..(4)
<223> OTHER INFORMATION: Gln having a blocking group Trt
<220> FEATURE:
<221> NAME/KEY: MISC_FEATURE
<222> LOCATION: (7)..(7)
<223> OTHER INFORMATION: Lys having a blocking group Boc
<220> FEATURE:
<221> NAME/KEY: MISC_FEATURE
<222> LOCATION: (8)..(8)
<223> OTHER INFORMATION: Glu having a blocking group OtBu
<220> FEATURE:
<221> NAME/KEY: MISC_FEATURE
<222> LOCATION: (12)..(12)
<223> OTHER INFORMATION: Trp having a blocking group Boc
<220> FEATURE:
<221> NAME/KEY: MISC_FEATURE
<222> LOCATION: (15)..(15)
<223> OTHER INFORMATION: Lys having a blocking group Boc
<220> FEATURE:
<221> NAME/KEY: MISC_FEATURE
<222> LOCATION: (17)..(17)
<223> OTHER INFORMATION: Arg having a blocking group Pbf

<400> SEQUENCE: 34

Leu Glu Gly Gln Ala Ala Lys Glu Phe Ile Ala Trp Leu Val Lys Gly
1               5                   10                  15

Arg Gly

<210> SEQ ID NO 35
<211> LENGTH: 19
<212> TYPE: PRT
<213> ORGANISM: artificial sequence
<220> FEATURE:
<223> OTHER INFORMATION: amino acid sequence having blocking groups
      (Example 7)
<220> FEATURE:
<221> NAME/KEY: CARBOHYD
<222> LOCATION: (1)..(1)
<223> OTHER INFORMATION: Asn glycosylated by asialo oligosaccharide
      chain
<220> FEATURE:
<221> NAME/KEY: MISC_FEATURE
<222> LOCATION: (3)..(3)
<223> OTHER INFORMATION: Glu having a blocking group OtBu
<220> FEATURE:
<221> NAME/KEY: MISC_FEATURE
<222> LOCATION: (5)..(5)
<223> OTHER INFORMATION: Gln having a blocking group Trt
<220> FEATURE:
<221> NAME/KEY: MISC_FEATURE
<222> LOCATION: (8)..(8)
<223> OTHER INFORMATION: Lys having a blocking group Boc
<220> FEATURE:
<221> NAME/KEY: MISC_FEATURE
<222> LOCATION: (9)..(9)
<223> OTHER INFORMATION: Glu having a blocking group OtBu
<220> FEATURE:
<221> NAME/KEY: MISC_FEATURE
<222> LOCATION: (13)..(13)
<223> OTHER INFORMATION: Trp having a blocking group Boc
<220> FEATURE:
<221> NAME/KEY: MISC_FEATURE
<222> LOCATION: (16)..(16)
<223> OTHER INFORMATION: Lys having a blocking group Boc
<220> FEATURE:
<221> NAME/KEY: MISC_FEATURE
<222> LOCATION: (18)..(18)
<223> OTHER INFORMATION: Arg having a blocking group Pbf
```

-continued

```
<400> SEQUENCE: 35

Asn Leu Glu Gly Gln Ala Ala Lys Glu Phe Ile Ala Trp Leu Val Lys
1               5                   10                  15

Gly Arg Gly

<210> SEQ ID NO 36
<211> LENGTH: 31
<212> TYPE: PRT
<213> ORGANISM: artificial sequence
<220> FEATURE:
<223> OTHER INFORMATION: amino acid sequence having blocking groups
<220> FEATURE:
<221> NAME/KEY: MISC_FEATURE
<222> LOCATION: (1)..(1)
<223> OTHER INFORMATION: His having a blocking group Trt
<220> FEATURE:
<221> NAME/KEY: MISC_FEATURE
<222> LOCATION: (3)..(3)
<223> OTHER INFORMATION: Glu having a blocking group OtBu
<220> FEATURE:
<221> NAME/KEY: MISC_FEATURE
<222> LOCATION: (5)..(5)
<223> OTHER INFORMATION: Thr having a blocking group tBu
<220> FEATURE:
<221> NAME/KEY: MISC_FEATURE
<222> LOCATION: (7)..(7)
<223> OTHER INFORMATION: Thr having a blocking group tBu
<220> FEATURE:
<221> NAME/KEY: MISC_FEATURE
<222> LOCATION: (8)..(8)
<223> OTHER INFORMATION: Ser having a blocking group tBu
<220> FEATURE:
<221> NAME/KEY: MISC_FEATURE
<222> LOCATION: (9)..(9)
<223> OTHER INFORMATION: Asp having a blocking group OtBu
<220> FEATURE:
<221> NAME/KEY: MISC_FEATURE
<222> LOCATION: (11)..(11)
<223> OTHER INFORMATION: Ser having a blocking group tBu
<220> FEATURE:
<221> NAME/KEY: MISC_FEATURE
<222> LOCATION: (12)..(12)
<223> OTHER INFORMATION: Ser having a blocking group tBu
<220> FEATURE:
<221> NAME/KEY: CARBOHYD
<222> LOCATION: (13)..(13)
<223> OTHER INFORMATION: Asn glycosylated by asialo oligosaccharide
      chain
<220> FEATURE:
<221> NAME/KEY: MISC_FEATURE
<222> LOCATION: (15)..(15)
<223> OTHER INFORMATION: Glu having a blocking group OtBu
<220> FEATURE:
<221> NAME/KEY: MISC_FEATURE
<222> LOCATION: (17)..(17)
<223> OTHER INFORMATION: Gln having a blocking group Trt
<220> FEATURE:
<221> NAME/KEY: MISC_FEATURE
<222> LOCATION: (20)..(20)
<223> OTHER INFORMATION: Lys having a blocking group Boc
<220> FEATURE:
<221> NAME/KEY: MISC_FEATURE
<222> LOCATION: (21)..(21)
<223> OTHER INFORMATION: Glu having a blocking group OtBu
<220> FEATURE:
<221> NAME/KEY: MISC_FEATURE
<222> LOCATION: (25)..(25)
<223> OTHER INFORMATION: Trp having a blocking group Boc
<220> FEATURE:
<221> NAME/KEY: MISC_FEATURE
<222> LOCATION: (28)..(28)
<223> OTHER INFORMATION: Lys having a blocking group Boc
<220> FEATURE:
<221> NAME/KEY: MISC_FEATURE
<222> LOCATION: (30)..(30)
<223> OTHER INFORMATION: Arg having a blocking group Pbf
```

```
<400> SEQUENCE: 36

His Ala Glu Gly Thr Phe Thr Ser Asp Val Ser Ser Asn Leu Glu Gly
1               5                   10                  15

Gln Ala Ala Lys Glu Phe Ile Ala Trp Leu Val Lys Gly Arg Gly
            20                  25                  30

<210> SEQ ID NO 37
<211> LENGTH: 32
<212> TYPE: PRT
<213> ORGANISM: artificial sequence
<220> FEATURE:
<223> OTHER INFORMATION: amino acid sequence having blocking groups
      (Example 8)
<220> FEATURE:
<221> NAME/KEY: MISC_FEATURE
<222> LOCATION: (1)..(1)
<223> OTHER INFORMATION: Cys having blocking group Trt
<220> FEATURE:
<221> NAME/KEY: MISC_FEATURE
<222> LOCATION: (2)..(2)
<223> OTHER INFORMATION: His having blocking group Trt
<220> FEATURE:
<221> NAME/KEY: MISC_FEATURE
<222> LOCATION: (4)..(4)
<223> OTHER INFORMATION: Glu having blocking group OtBu
<220> FEATURE:
<221> NAME/KEY: MISC_FEATURE
<222> LOCATION: (6)..(6)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Thr having blocking group tBu
<220> FEATURE:
<221> NAME/KEY: MISC_FEATURE
<222> LOCATION: (9)..(9)
<223> OTHER INFORMATION: Ser having blocking group tBu
<220> FEATURE:
<221> NAME/KEY: MISC_FEATURE
<222> LOCATION: (10)..(10)
<223> OTHER INFORMATION: Asp having blocking group OtBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Ser having blocking group tBu
<220> FEATURE:
<221> NAME/KEY: MISC_FEATURE
<222> LOCATION: (14)..(14)
<223> OTHER INFORMATION: Tyr having blocking group tBu
<220> FEATURE:
<221> NAME/KEY: MISC_FEATURE
<222> LOCATION: (16)..(16)
<223> OTHER INFORMATION: Glu having blocking group OtBu
<220> FEATURE:
<221> NAME/KEY: MISC_FEATURE
<222> LOCATION: (18)..(18)
<223> OTHER INFORMATION: Gln having blocking group Trt
<220> FEATURE:
<221> NAME/KEY: MISC_FEATURE
<222> LOCATION: (21)..(21)
<223> OTHER INFORMATION: Lys having blocking group Boc
<220> FEATURE:
<221> NAME/KEY: MISC_FEATURE
<222> LOCATION: (22)..(22)
<223> OTHER INFORMATION: Glu having blocking group OtBu
<220> FEATURE:
<221> NAME/KEY: MISC_FEATURE
<222> LOCATION: (26)..(26)
<223> OTHER INFORMATION: Trp having blocking group Boc
<220> FEATURE:
<221> NAME/KEY: MISC_FEATURE
<222> LOCATION: (29)..(29)
<223> OTHER INFORMATION: Lys having blocking group Boc
```

```
<220> FEATURE:
<221> NAME/KEY: MISC_FEATURE
<222> LOCATION: (31)..(31)
<223> OTHER INFORMATION: Arg having blocking group Pbf

<400> SEQUENCE: 37

Cys His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Gly
            20                  25                  30

<210> SEQ ID NO 38
<211> LENGTH: 31
<212> TYPE: PRT
<213> ORGANISM: artificial sequence
<220> FEATURE:
<223> OTHER INFORMATION: amino acid sequence having blocking groups
      (Example 9)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (2)..(2)
<223> OTHER INFORMATION: Cys having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
```

```
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 38

His Cys Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 39
<211> LENGTH: 31
<212> TYPE: PRT
<213> ORGANISM: artificial sequence
<220> FEATURE:
<223> OTHER INFORMATION: amino acid sequence having blocking groups
      (Example 10)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Cys having blocking group Trt
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
```

```
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 39

His Ala Cys Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 40
<211> LENGTH: 31
<212> TYPE: PRT
<213> ORGANISM: artificial sequence
<220> FEATURE:
<223> OTHER INFORMATION: amino acid sequence having blocking groups
      (Example 11)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (4)..(4)
<223> OTHER INFORMATION: Cys having blocking group Trt
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
```

```
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 40

His Ala Glu Cys Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 41
<211> LENGTH: 31
<212> TYPE: PRT
<213> ORGANISM: artificial sequence
<220> FEATURE:
<223> OTHER INFORMATION: amino acid sequence having blocking groups
      (Example 12)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Cys having blocking group Trt
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
```

```
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 41

His Ala Glu Gly Cys Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 42
<211> LENGTH: 31
<212> TYPE: PRT
<213> ORGANISM: artificial sequence
<220> FEATURE:
<223> OTHER INFORMATION: amino acid sequence having blocking groups
      (Example 13)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (6)..(6)
<223> OTHER INFORMATION: Cys having blocking group Trt
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
```

```
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 42

His Ala Glu Gly Thr Cys Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 43
<211> LENGTH: 31
<212> TYPE: PRT
<213> ORGANISM: artificial sequence
<220> FEATURE:
<223> OTHER INFORMATION: amino acid sequence having blocking groups
      (Example 14)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Cys having blocking group Trt
<220> FEATURE:
<221> NAME/KEY: MISC_FEATURE
<222> LOCATION: (9)..(9)
<223> OTHER INFORMATION: Asp having blocking group OtBu
```

```
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 43

His Ala Glu Gly Thr Phe Thr Cys Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 44
<211> LENGTH: 31
<212> TYPE: PRT
<213> ORGANISM: artificial sequence
<220> FEATURE:
<223> OTHER INFORMATION: amino acid sequence having blocking groups
      (Example 15)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
```

```
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (10)..(10)
<223> OTHER INFORMATION: Cys having blocking group Trt
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 44

His Ala Glu Gly Thr Phe Thr Ser Asp Cys Ser Ser Tyr Leu Glu Gly
1               5                   10                  15
Gln Ala Ala Lys Glu Phe Ile Ala Trp Leu Val Lys Gly Arg Gly
            20                  25                  30

<210> SEQ ID NO 45
<211> LENGTH: 31
<212> TYPE: PRT
<213> ORGANISM: artificial sequence
<220> FEATURE:
<223> OTHER INFORMATION: amino acid sequence having blocking groups
      (Example 16)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
```

```
-continued

<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (14)..(14)
<223> OTHER INFORMATION: Cys having blocking group Trt
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 45

His Ala Glu Gly Thr Phe Thr Ser Asp Val Ser Ser Tyr Cys Glu Gly
1               5                   10                  15

Gln Ala Ala Lys Glu Phe Ile Ala Trp Leu Val Lys Gly Arg Gly
            20                  25                  30

<210> SEQ ID NO 46
<211> LENGTH: 31
<212> TYPE: PRT
<213> ORGANISM: artificial sequence
<220> FEATURE:
<223> OTHER INFORMATION: amino acid sequence having blocking groups
      (Example 17)
<220> FEATURE:
<221> NAME/KEY: MISC_FEATURE
<222> LOCATION: (1)..(1)
<223> OTHER INFORMATION: His having blocking group Trt
```

```
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (18)..(18)
<223> OTHER INFORMATION: Cys having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 46

His Ala Glu Gly Thr Phe Thr Ser Asp Val Ser Ser Tyr Leu Glu Gly
1               5                   10                  15

Gln Cys Ala Lys Glu Phe Ile Ala Trp Leu Val Lys Gly Arg Gly
            20                  25                  30

<210> SEQ ID NO 47
<211> LENGTH: 31
<212> TYPE: PRT
<213> ORGANISM: artificial sequence
```

-continued

```
<220> FEATURE:
<223> OTHER INFORMATION: amino acid sequence having blocking groups
      (Example 18)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (19)..(19)
<223> OTHER INFORMATION: Cys having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 47

His Ala Glu Gly Thr Phe Thr Ser Asp Val Ser Ser Tyr Leu Glu Gly
1               5                   10                  15

Gln Ala Cys Lys Glu Phe Ile Ala Trp Leu Val Lys Gly Arg Gly
            20                  25                  30
```

```
<210> SEQ ID NO 48
<211> LENGTH: 31
<212> TYPE: PRT
<213> ORGANISM: artificial sequence
<220> FEATURE:
<223> OTHER INFORMATION: amino acid sequence having blocking groups
      (Example 19)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Cys having blocking group Trt
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 48

His Ala Glu Gly Thr Phe Thr Ser Asp Val Ser Ser Tyr Leu Glu Gly
1               5                   10                  15

Gln Ala Ala Lys Cys Phe Ile Ala Trp Leu Val Lys Gly Arg Gly
                20                  25                  30
```

-continued

```
<210> SEQ ID NO 49
<211> LENGTH: 31
<212> TYPE: PRT
<213> ORGANISM: artificial sequence
<220> FEATURE:
<223> OTHER INFORMATION: amino acid sequence having blocking groups
      (Example 20)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (22)..(22)
<223> OTHER INFORMATION: Cys having blocking group Trt
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf
```

-continued

```
<400> SEQUENCE: 49

His Ala Glu Gly Thr Phe Thr Ser Asp Val Ser Ser Tyr Leu Glu Gly
1               5                   10                  15

Gln Ala Ala Lys Glu Cys Ile Ala Trp Leu Val Lys Gly Arg Gly
            20                  25                  30

<210> SEQ ID NO 50
<211> LENGTH: 31
<212> TYPE: PRT
<213> ORGANISM: artificial sequence
<220> FEATURE:
<223> OTHER INFORMATION: amino acid sequence having blocking groups
      (Example 21)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (24)..(24)
<223> OTHER INFORMATION: Cys having blocking group Trt
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
```

```
<220> FEATURE:
<221> NAME/KEY: MISC_FEATURE
<222> LOCATION: (30)..(30)
<223> OTHER INFORMATION: Arg having blocking group Pbf

<400> SEQUENCE: 50

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 51
<211> LENGTH: 31
<212> TYPE: PRT
<213> ORGANISM: artificial sequence
<220> FEATURE:
<223> OTHER INFORMATION: amino acid sequence having blocking groups
      (Example 22)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
```

```
<220> FEATURE:
<221> NAME/KEY: MISC_FEATURE
<222> LOCATION: (26)..(26)
<223> OTHER INFORMATION: Cys having blocking group Trt
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 51

His Ala Glu Gly Thr Phe Thr Ser Asp Val Ser Ser Tyr Leu Glu Gly
1               5                   10                  15

Gln Ala Ala Lys Glu Phe Ile Ala Trp Cys Val Lys Gly Arg Gly
            20                  25                  30

<210> SEQ ID NO 52
<211> LENGTH: 31
<212> TYPE: PRT
<213> ORGANISM: artificial sequence
<220> FEATURE:
<223> OTHER INFORMATION: amino acid sequence having blocking groups
      (Example 23)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
```

```
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Cys having blocking group Trt
<220> FEATURE:
<221> NAME/KEY: MISC_FEATURE
<222> LOCATION: (30)..(30)
<223> OTHER INFORMATION: Arg having blocking group Pbf

<400> SEQUENCE: 52

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Arg Gly
            20                  25                  30

<210> SEQ ID NO 53
<211> LENGTH: 31
<212> TYPE: PRT
<213> ORGANISM: artificial sequence
<220> FEATURE:
<223> OTHER INFORMATION: amino acid sequence having blocking groups
      (Example 24)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (16)..(16)
<223> OTHER INFORMATION: Cys having blocking group Trt
```

```
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 53

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Arg Gly
            20                  25                  30

<210> SEQ ID NO 54
<211> LENGTH: 31
<212> TYPE: PRT
<213> ORGANISM: artificial sequence
<220> FEATURE:
<223> OTHER INFORMATION: amino acid sequence having blocking groups
      (Example 25)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
```

```
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Cys having blocking group Trt
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 54

His Ala Glu Gly Thr Phe Thr Ser Asp Val Ser Ser Tyr Leu Glu Gly
1               5                   10                  15

Gln Ala Ala Cys Glu Phe Ile Ala Trp Leu Val Lys Gly Arg Gly
            20                  25                  30

<210> SEQ ID NO 55
<211> LENGTH: 31
<212> TYPE: PRT
<213> ORGANISM: artificial sequence
<220> FEATURE:
<223> OTHER INFORMATION: amino acid sequence having blocking groups
      (Example 26)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
```

```
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (24)..(24)
<223> OTHER INFORMATION: Cys having blocking group Trt
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 55

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 56
<211> LENGTH: 31
<212> TYPE: PRT
<213> ORGANISM: artificial sequence
<220> FEATURE:
<223> OTHER INFORMATION: amino acid sequence having blocking groups
      (Example 27)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
```

-continued

```
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Cys having blocking group Trt
<220> FEATURE:
<221> NAME/KEY: MISC_FEATURE
<222> LOCATION: (30)..(30)
<223> OTHER INFORMATION: Arg having blocking group Pbf

<400> SEQUENCE: 56

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Arg Gly
            20                  25                  30

<210> SEQ ID NO 57
<211> LENGTH: 31
<212> TYPE: PRT
<213> ORGANISM: artificial sequence
<220> FEATURE:
<223> OTHER INFORMATION: amino acid sequence having blocking groups
      (Example 28)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
```

```
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Cys having blocking group Trt

<400> SEQUENCE: 57

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 58
<211> LENGTH: 31
<212> TYPE: PRT
<213> ORGANISM: artificial sequence
<220> FEATURE:
<223> OTHER INFORMATION: amino acid sequence having blocking groups
      (Example 29)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
```

```
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (16)..(16)
<223> OTHER INFORMATION: Cys having blocking group Trt
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 58

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Arg Gly
            20                  25                  30

<210> SEQ ID NO 59
<211> LENGTH: 31
<212> TYPE: PRT
<213> ORGANISM: artificial sequence
<220> FEATURE:
<223> OTHER INFORMATION: amino acid sequence having blocking groups
      (Example 30)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
```

```
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (24)..(24)
<223> OTHER INFORMATION: Cys having blocking group Trt
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 59

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 60
<211> LENGTH: 31
<212> TYPE: PRT
<213> ORGANISM: artificial sequence
<220> FEATURE:
<223> OTHER INFORMATION: amino acid sequence having blocking groups
      (Example 31)
```

```
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Cys having blocking group Trt
<220> FEATURE:
<221> NAME/KEY: MISC_FEATURE
<222> LOCATION: (30)..(30)
<223> OTHER INFORMATION: Arg having blocking group Pbf

<400> SEQUENCE: 60

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Arg Gly
            20                  25                  30

<210> SEQ ID NO 61
<211> LENGTH: 31
<212> TYPE: PRT
<213> ORGANISM: artificial sequence
```

```
<220> FEATURE:
<223> OTHER INFORMATION: amino acid sequence having blocking groups
      (Example 32)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (16)..(16)
<223> OTHER INFORMATION: Cys having blocking group Trt
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 61

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Arg Gly
            20                  25                  30
```

```
<210> SEQ ID NO 62
<211> LENGTH: 31
<212> TYPE: PRT
<213> ORGANISM: artificial sequence
<220> FEATURE:
<223> OTHER INFORMATION: amino acid sequence having blocking groups
      (Example 33)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (24)..(24)
<223> OTHER INFORMATION: Cys having blocking group Trt
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf
```

<400> SEQUENCE: 62

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 63
<211> LENGTH: 31
<212> TYPE: PRT
<213> ORGANISM: artificial sequence
<220> FEATURE:
<223> OTHER INFORMATION: amino acid sequence having blocking groups
      (Example 34)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Cys having blocking group Trt
<220> FEATURE:
<221> NAME/KEY: MISC_FEATURE
<222> LOCATION: (30)..(30)
<223> OTHER INFORMATION: Arg having blocking group Pbf

```
<400> SEQUENCE: 63

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Arg Gly
            20                  25                  30

<210> SEQ ID NO 64
<211> LENGTH: 12
<212> TYPE: PRT
<213> ORGANISM: artificial sequence
<220> FEATURE:
<223> OTHER INFORMATION: amino acid sequence having blocking groups
      (Example 35)
<220> FEATURE:
<221> NAME/KEY: MISC_FEATURE
<222> LOCATION: (1)..(1)
<223> OTHER INFORMATION: Thr having blocking group tBu
<220> FEATURE:
<221> NAME/KEY: MISC_FEATURE
<222> LOCATION: (2)..(2)
<223> OTHER INFORMATION: Ser having blocking group tBu
<220> FEATURE:
<221> NAME/KEY: MISC_FEATURE
<222> LOCATION: (3)..(3)
<223> OTHER INFORMATION: Asp having blocking group OtBu
<220> FEATURE:
<221> NAME/KEY: MISC_FEATURE
<222> LOCATION: (5)..(5)
<223> OTHER INFORMATION: Ser having blocking group tBu
<220> FEATURE:
<221> NAME/KEY: MISC_FEATURE
<222> LOCATION: (6)..(6)
<223> OTHER INFORMATION: Ser having blocking group tBu
<220> FEATURE:
<221> NAME/KEY: MISC_FEATURE
<222> LOCATION: (7)..(7)
<223> OTHER INFORMATION: Tyr having blocking group tBu
<220> FEATURE:
<221> NAME/KEY: MISC_FEATURE
<222> LOCATION: (9)..(9)
<223> OTHER INFORMATION: Glu having blocking group OtBu
<220> FEATURE:
<221> NAME/KEY: MISC_FEATURE
<222> LOCATION: (11)..(11)
<223> OTHER INFORMATION: Gln having blocking group Trt

<400> SEQUENCE: 64

Thr Ser Asp Val Ser Ser Tyr Leu Glu Gly Gln Ala
1               5                   10

<210> SEQ ID NO 65
<211> LENGTH: 13
<212> TYPE: PRT
<213> ORGANISM: artificial sequence
<220> FEATURE:
<223> OTHER INFORMATION: amino acid sequence having blocking groups
      (Example 35)
<220> FEATURE:
<221> NAME/KEY: CARBOHYD
<222> LOCATION: (1)..(1)
<223> OTHER INFORMATION: Asn glycosylated by asialo oligosaccharide
      chain
<220> FEATURE:
<221> NAME/KEY: MISC_FEATURE
<222> LOCATION: (2)..(2)
<223> OTHER INFORMATION: Thr having blocking group tBu
<220> FEATURE:
<221> NAME/KEY: MISC_FEATURE
<222> LOCATION: (3)..(3)
<223> OTHER INFORMATION: Ser having blocking group tBu
<220> FEATURE:
<221> NAME/KEY: MISC_FEATURE
<222> LOCATION: (4)..(4)
<223> OTHER INFORMATION: Asp having blocking group OtBu
```

```
<220> FEATURE:
<221> NAME/KEY: MISC_FEATURE
<222> LOCATION: (6)..(6)
<223> OTHER INFORMATION: Ser having blocking group tBu
<220> FEATURE:
<221> NAME/KEY: MISC_FEATURE
<222> LOCATION: (7)..(7)
<223> OTHER INFORMATION: Ser having blocking group tBu
<220> FEATURE:
<221> NAME/KEY: MISC_FEATURE
<222> LOCATION: (8)..(8)
<223> OTHER INFORMATION: Tyr having blocking group tBu
<220> FEATURE:
<221> NAME/KEY: MISC_FEATURE
<222> LOCATION: (10)..(10)
<223> OTHER INFORMATION: Glu having blocking group OtBu
<220> FEATURE:
<221> NAME/KEY: MISC_FEATURE
<222> LOCATION: (12)..(12)
<223> OTHER INFORMATION: Gln having blocking group Trt

<400> SEQUENCE: 65

Asn Thr Ser Asp Val Ser Ser Tyr Leu Glu Gly Gln Ala
1               5                   10

<210> SEQ ID NO 66
<211> LENGTH: 18
<212> TYPE: PRT
<213> ORGANISM: artificial sequence
<220> FEATURE:
<223> OTHER INFORMATION: amino acid sequence having blocking groups
      (Example 35)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: CARBOHYD
<222> LOCATION: (6)..(6)
<223> OTHER INFORMATION: Asn glycosylated by asialo oligosaccharide
      chain
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
```

```
<220> FEATURE:
<221> NAME/KEY: MISC_FEATURE
<222> LOCATION: (17)..(17)
<223> OTHER INFORMATION: Gln having blocking group Trt

<400> SEQUENCE: 66

His Ala Glu Gly Thr Asn Thr Ser Asp Val Ser Ser Tyr Leu Glu Gly
1               5                   10                  15

Gln Ala

<210> SEQ ID NO 67
<211> LENGTH: 18
<212> TYPE: PRT
<213> ORGANISM: artificial sequence
<220> FEATURE:
<223> OTHER INFORMATION: amino acid sequence having blocking groups
      (Example 35)
<220> FEATURE:
<221> NAME/KEY: MISC_FEATURE
<222> LOCATION: (1)..(1)
<223> OTHER INFORMATION: His having blocking group Trt and Boc
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: CARBOHYD
<222> LOCATION: (6)..(6)
<223> OTHER INFORMATION: Asn glycosylated by asialo oligosaccharide
      chain
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt

<400> SEQUENCE: 67

His Ala Glu Gly Thr Asn Thr Ser Asp Val Ser Ser Tyr Leu Glu Gly
1               5                   10                  15

Gln Ala
```

```
<210> SEQ ID NO 68
<211> LENGTH: 18
<212> TYPE: PRT
<213> ORGANISM: artificial sequence
<220> FEATURE:
<223> OTHER INFORMATION: amino acid sequence having leaving groups
      (Example 35)
<220> FEATURE:
<221> NAME/KEY: CARBOHYD
<222> LOCATION: (6)..(6)
<223> OTHER INFORMATION: Asn glycosylated by asialo oligosaccharide
      chain
<220> FEATURE:
<221> NAME/KEY: MISC_FEATURE
<222> LOCATION: (18)..(18)
<223> OTHER INFORMATION: Ala having leaving group PhS

<400> SEQUENCE: 68

His Ala Glu Gly Thr Asn Thr Ser Asp Val Ser Ser Tyr Leu Glu Gly
1               5                   10                  15

Gln Ala

<210> SEQ ID NO 69
<211> LENGTH: 13
<212> TYPE: PRT
<213> ORGANISM: artificial sequence
<220> FEATURE:
<223> OTHER INFORMATION: amino acid sequence having blocking groups
      (Example 35)
<220> FEATURE:
<221> NAME/KEY: MISC_FEATURE
<222> LOCATION: (1)..(1)
<223> OTHER INFORMATION: Cys having blocking group Trt
<220> FEATURE:
<221> NAME/KEY: MISC_FEATURE
<222> LOCATION: (2)..(2)
<223> OTHER INFORMATION: Lys having blocking group Boc
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (7)..(7)
<223> OTHER INFORMATION: Trp having blocking group Boc
<220> FEATURE:
<221> NAME/KEY: MISC_FEATURE
<222> LOCATION: (10)..(10)
<223> OTHER INFORMATION: Lys having blocking group Boc
<220> FEATURE:
<221> NAME/KEY: MISC_FEATURE
<222> LOCATION: (12)..(12)
<223> OTHER INFORMATION: Arg having blocking group Pbf

<400> SEQUENCE: 69

Cys Lys Glu Phe Ile Ala Trp Leu Val Lys Gly Arg Gly
1               5                   10

<210> SEQ ID NO 70
<211> LENGTH: 13
<212> TYPE: PRT
<213> ORGANISM: artificial sequence
<220> FEATURE:
<223> OTHER INFORMATION: amino acid sequence (Example 35)

<400> SEQUENCE: 70

Cys Lys Glu Phe Ile Ala Trp Leu Val Lys Gly Arg Gly
1               5                   10

<210> SEQ ID NO 71
<211> LENGTH: 19
<212> TYPE: PRT
<213> ORGANISM: artificial sequence
```

```
<220> FEATURE:
<223> OTHER INFORMATION: amino acid sequence having blocking groups
      (Example 36)
<220> FEATURE:
<221> NAME/KEY: MISC_FEATURE
<222> LOCATION: (1)..(1)
<223> OTHER INFORMATION: Tyr having blocking group tBu
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Gln having blocking group Trt
<220> FEATURE:
<221> NAME/KEY: MISC_FEATURE
<222> LOCATION: (8)..(8)
<223> OTHER INFORMATION: Lys having blocking group Boc
<220> FEATURE:
<221> NAME/KEY: MISC_FEATURE
<222> LOCATION: (9)..(9)
<223> OTHER INFORMATION: Glu having blocking group OtBu
<220> FEATURE:
<221> NAME/KEY: MISC_FEATURE
<222> LOCATION: (13)..(13)
<223> OTHER INFORMATION: Trp having blocking group Boc
<220> FEATURE:
<221> NAME/KEY: MISC_FEATURE
<222> LOCATION: (16)..(16)
<223> OTHER INFORMATION: Lys having blocking group Boc
<220> FEATURE:
<221> NAME/KEY: MISC_FEATURE
<222> LOCATION: (18)..(18)
<223> OTHER INFORMATION: Arg having blocking group Pbf

<400> SEQUENCE: 71

Tyr Leu Glu Gly Gln Ala Ala Lys Glu Phe Ile Ala Trp Leu Val Lys
1               5                   10                  15

Gly Arg Gly

<210> SEQ ID NO 72
<211> LENGTH: 20
<212> TYPE: PRT
<213> ORGANISM: artificial sequence
<220> FEATURE:
<223> OTHER INFORMATION: amino acid sequence having blocking groups
      (Example 36)
<220> FEATURE:
<221> NAME/KEY: CARBOHYD
<222> LOCATION: (1)..(1)
<223> OTHER INFORMATION: Asn glycosylated by asialo oligosaccharide
      chain
<220> FEATURE:
<221> NAME/KEY: MISC_FEATURE
<222> LOCATION: (2)..(2)
<223> OTHER INFORMATION: Tyr having blocking group tBu
<220> FEATURE:
<221> NAME/KEY: MISC_FEATURE
<222> LOCATION: (4)..(4)
<223> OTHER INFORMATION: Glu having blocking group OtBu
<220> FEATURE:
<221> NAME/KEY: MISC_FEATURE
<222> LOCATION: (6)..(6)
<223> OTHER INFORMATION: Gln having blocking group Trt
<220> FEATURE:
<221> NAME/KEY: MISC_FEATURE
<222> LOCATION: (9)..(9)
<223> OTHER INFORMATION: Lys having blocking group Boc
<220> FEATURE:
<221> NAME/KEY: MISC_FEATURE
<222> LOCATION: (10)..(10)
<223> OTHER INFORMATION: Glu having blocking group OtBu
<220> FEATURE:
<221> NAME/KEY: MISC_FEATURE
<222> LOCATION: (14)..(14)
<223> OTHER INFORMATION: Trp having blocking group Boc
```

```
<220> FEATURE:
<221> NAME/KEY: MISC_FEATURE
<222> LOCATION: (17)..(17)
<223> OTHER INFORMATION: Lys having blocking group Boc
<220> FEATURE:
<221> NAME/KEY: MISC_FEATURE
<222> LOCATION: (19)..(19)
<223> OTHER INFORMATION: Arg having blocking group Pbf

<400> SEQUENCE: 72

Asn Tyr Leu Glu Gly Gln Ala Ala Lys Glu Phe Ile Ala Trp Leu Val
1               5                   10                  15

Lys Gly Arg Gly
            20

<210> SEQ ID NO 73
<211> LENGTH: 31
<212> TYPE: PRT
<213> ORGANISM: artificial sequence
<220> FEATURE:
<223> OTHER INFORMATION: amino acid sequence having blocking groups
      (Example 36)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Asn glycosylated by asialo oligosaccharide
      chain
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
```

```
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 73

His Ala Glu Gly Thr Phe Thr Ser Asp Val Ser Asn Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 74
<211> LENGTH: 15
<212> TYPE: PRT
<213> ORGANISM: artificial sequence
<220> FEATURE:
<223> OTHER INFORMATION: amino acid sequence having blocking groups
      (Example 37)
<220> FEATURE:
<221> NAME/KEY: MISC_FEATURE
<222> LOCATION: (1)..(1)
<223> OTHER INFORMATION: Gln having blocking group Trt
<220> FEATURE:
<221> NAME/KEY: MISC_FEATURE
<222> LOCATION: (4)..(4)
<223> OTHER INFORMATION: Lys having blocking group Boc
<220> FEATURE:
<221> NAME/KEY: MISC_FEATURE
<222> LOCATION: (5)..(5)
<223> OTHER INFORMATION: Glu having blocking group OtBu
<220> FEATURE:
<221> NAME/KEY: MISC_FEATURE
<222> LOCATION: (9)..(9)
<223> OTHER INFORMATION: Trp having blocking group Boc
<220> FEATURE:
<221> NAME/KEY: MISC_FEATURE
<222> LOCATION: (12)..(12)
<223> OTHER INFORMATION: Lys having blocking group Boc
<220> FEATURE:
<221> NAME/KEY: MISC_FEATURE
<222> LOCATION: (14)..(14)
<223> OTHER INFORMATION: Arg having blocking group Pbf

<400> SEQUENCE: 74

Gln Ala Ala Lys Glu Phe Ile Ala Trp Leu Val Lys Gly Arg Gly
1               5                   10                  15

<210> SEQ ID NO 75
<211> LENGTH: 16
<212> TYPE: PRT
<213> ORGANISM: artificial sequence
<220> FEATURE:
<223> OTHER INFORMATION: amino acid sequence having blocking groups
      (Example 37)
<220> FEATURE:
<221> NAME/KEY: CARBOHYD
<222> LOCATION: (1)..(1)
<223> OTHER INFORMATION: Asn glycosylated by asialo oligosaccharide
      chain
<220> FEATURE:
<221> NAME/KEY: MISC_FEATURE
<222> LOCATION: (2)..(2)
<223> OTHER INFORMATION: Gln having blocking group Trt
<220> FEATURE:
<221> NAME/KEY: MISC_FEATURE
<222> LOCATION: (5)..(5)
<223> OTHER INFORMATION: Lys having blocking group Boc
```

```
<220> FEATURE:
<221> NAME/KEY: MISC_FEATURE
<222> LOCATION: (6)..(6)
<223> OTHER INFORMATION: Glu having blocking group OtBu
<220> FEATURE:
<221> NAME/KEY: MISC_FEATURE
<222> LOCATION: (10)..(10)
<223> OTHER INFORMATION: Trp having blocking group Boc
<220> FEATURE:
<221> NAME/KEY: MISC_FEATURE
<222> LOCATION: (13)..(13)
<223> OTHER INFORMATION: Lys having blocking group Boc
<220> FEATURE:
<221> NAME/KEY: MISC_FEATURE
<222> LOCATION: (15)..(15)
<223> OTHER INFORMATION: Arg having blocking group Pbf

<400> SEQUENCE: 75

Asn Gln Ala Ala Lys Glu Phe Ile Ala Trp Leu Val Lys Gly Arg Gly
1               5                   10                  15

<210> SEQ ID NO 76
<211> LENGTH: 31
<212> TYPE: PRT
<213> ORGANISM: artificial sequence
<220> FEATURE:
<223> OTHER INFORMATION: amino acid sequence having blocking groups
      (Example 37)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (16)..(16)
<223> OTHER INFORMATION: Asn glycosylated by asialo oligosaccharide
      chain
<220> FEATURE:
<221> NAME/KEY: MISC_FEATURE
<222> LOCATION: (17)..(17)
<223> OTHER INFORMATION: Gln having blocking group Trt
```

```
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 76

His Ala Glu Gly Thr Phe Thr Ser Asp Val Ser Ser Tyr Leu Glu Asn
 1               5                  10                  15

Gln Ala Ala Lys Glu Phe Ile Ala Trp Leu Val Lys Gly Arg Gly
            20                  25                  30

<210> SEQ ID NO 77
<211> LENGTH: 18
<212> TYPE: PRT
<213> ORGANISM: artificial sequence
<220> FEATURE:
<223> OTHER INFORMATION: amino acid sequence having blocking groups
      (Example 38)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
```

```
<220> FEATURE:
<221> NAME/KEY: MISC_FEATURE
<222> LOCATION: (17)..(17)
<223> OTHER INFORMATION: Gln having blocking group Trt

<400> SEQUENCE: 77

His Ala Glu Gly Thr Phe Thr Ser Asp Val Ser Ser Tyr Leu Glu Gly
1               5                   10                  15

Gln Ala

<210> SEQ ID NO 78
<211> LENGTH: 18
<212> TYPE: PRT
<213> ORGANISM: artificial sequence
<220> FEATURE:
<223> OTHER INFORMATION: amino acid sequence having blocking groups
      (Example 38)
<220> FEATURE:
<221> NAME/KEY: MISC_FEATURE
<222> LOCATION: (1)..(1)
<223> OTHER INFORMATION: His having blocking group Trt and Boc
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt

<400> SEQUENCE: 78

His Ala Glu Gly Thr Phe Thr Ser Asp Val Ser Ser Tyr Leu Glu Gly
1               5                   10                  15

Gln Ala

<210> SEQ ID NO 79
<211> LENGTH: 18
<212> TYPE: PRT
<213> ORGANISM: artificial sequence
<220> FEATURE:
<223> OTHER INFORMATION: amino acid sequence having leaving groups
      (Example 38)
```

```
<220> FEATURE:
<221> NAME/KEY: MISC_FEATURE
<222> LOCATION: (18)..(18)
<223> OTHER INFORMATION: Ala having leaving group PhS

<400> SEQUENCE: 79

His Ala Glu Gly Thr Phe Thr Ser Asp Val Ser Ser Tyr Leu Glu Gly
1               5                   10                  15

Gln Ala

<210> SEQ ID NO 80
<211> LENGTH: 11
<212> TYPE: PRT
<213> ORGANISM: artificial sequence
<220> FEATURE:
<223> OTHER INFORMATION: amino acid sequence having blocking groups
      (Example 38)
<220> FEATURE:
<221> NAME/KEY: MISC_FEATURE
<222> LOCATION: (1)..(1)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Trp having blocking group Boc
<220> FEATURE:
<221> NAME/KEY: MISC_FEATURE
<222> LOCATION: (8)..(8)
<223> OTHER INFORMATION: Lys having blocking group Boc
<220> FEATURE:
<221> NAME/KEY: MISC_FEATURE
<222> LOCATION: (10)..(10)
<223> OTHER INFORMATION: Arg having blocking group Pbf

<400> SEQUENCE: 80

Glu Phe Ile Ala Trp Leu Val Lys Gly Arg Gly
1               5                   10

<210> SEQ ID NO 81
<211> LENGTH: 13
<212> TYPE: PRT
<213> ORGANISM: artificial sequence
<220> FEATURE:
<223> OTHER INFORMATION: amino acid sequence having blocking groups
      (Example 38)
<220> FEATURE:
<221> NAME/KEY: MISC_FEATURE
<222> LOCATION: (1)..(1)
<223> OTHER INFORMATION: Cys having blocking group Trt
<220> FEATURE:
<221> NAME/KEY: CARBOHYD
<222> LOCATION: (2)..(2)
<223> OTHER INFORMATION: Asn glycosylated by asialo oligosaccharide
      chain
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (7)..(7)
<223> OTHER INFORMATION: Trp having blocking group Boc
<220> FEATURE:
<221> NAME/KEY: MISC_FEATURE
<222> LOCATION: (10)..(10)
<223> OTHER INFORMATION: Lys having blocking group Boc
<220> FEATURE:
<221> NAME/KEY: MISC_FEATURE
<222> LOCATION: (12)..(12)
<223> OTHER INFORMATION: Arg having blocking group Pbf

<400> SEQUENCE: 81

Cys Asn Glu Phe Ile Ala Trp Leu Val Lys Gly Arg Gly
1               5                   10
```

```
<210> SEQ ID NO 82
<211> LENGTH: 18
<212> TYPE: PRT
<213> ORGANISM: artificial sequence
<220> FEATURE:
<223> OTHER INFORMATION: amino acid sequence having blocking groups
      (Example 39)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt

<400> SEQUENCE: 82

His Ala Glu Gly Thr Phe Thr Ser Asp Val Ser Ser Tyr Leu Glu Gly
1               5                   10                  15

Gln Ala

<210> SEQ ID NO 83
<211> LENGTH: 18
<212> TYPE: PRT
<213> ORGANISM: artificial sequence
<220> FEATURE:
<223> OTHER INFORMATION: amino acid sequence having blocking groups
      (Example 39)
<220> FEATURE:
<221> NAME/KEY: MISC_FEATURE
<222> LOCATION: (1)..(1)
<223> OTHER INFORMATION: His having blocking group Trt and Boc
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
```

```
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt

<400> SEQUENCE: 83

His Ala Glu Gly Thr Phe Thr Ser Asp Val Ser Ser Tyr Leu Glu Gly
1               5                   10                  15

Gln Ala

<210> SEQ ID NO 84
<211> LENGTH: 18
<212> TYPE: PRT
<213> ORGANISM: artificial sequence
<220> FEATURE:
<223> OTHER INFORMATION: amino acid sequence having leaving groups
      (Example 39)
<220> FEATURE:
<221> NAME/KEY: MISC_FEATURE
<222> LOCATION: (18)..(18)
<223> OTHER INFORMATION: Ala having leaving group PhS

<400> SEQUENCE: 84

His Ala Glu Gly Thr Phe Thr Ser Asp Val Ser Ser Tyr Leu Glu Gly
1               5                   10                  15

Gln Ala

<210> SEQ ID NO 85
<211> LENGTH: 10
<212> TYPE: PRT
<213> ORGANISM: artificial sequence
<220> FEATURE:
<223> OTHER INFORMATION: amino acid sequence having blocking groups
      (Example 39)
<220> FEATURE:
<221> NAME/KEY: MISC_FEATURE
<222> LOCATION: (4)..(4)
<223> OTHER INFORMATION: Trp having blocking group Boc
<220> FEATURE:
<221> NAME/KEY: MISC_FEATURE
<222> LOCATION: (7)..(7)
<223> OTHER INFORMATION: Lys having blocking group Boc
<220> FEATURE:
<221> NAME/KEY: MISC_FEATURE
<222> LOCATION: (9)..(9)
<223> OTHER INFORMATION: Arg having blocking group Pbf
```

-continued

```
<400> SEQUENCE: 85

Phe Ile Ala Trp Leu Val Lys Gly Arg Gly
1               5                   10

<210> SEQ ID NO 86
<211> LENGTH: 13
<212> TYPE: PRT
<213> ORGANISM: artificial sequence
<220> FEATURE:
<223> OTHER INFORMATION: amino acid sequence having blocking groups
      (Example 39)
<220> FEATURE:
<221> NAME/KEY: MISC_FEATURE
<222> LOCATION: (1)..(1)
<223> OTHER INFORMATION: Cys having blocking group Trt
<220> FEATURE:
<221> NAME/KEY: MISC_FEATURE
<222> LOCATION: (2)..(2)
<223> OTHER INFORMATION: Lys having blocking group Boc
<220> FEATURE:
<221> NAME/KEY: CARBOHYD
<222> LOCATION: (3)..(3)
<223> OTHER INFORMATION: Asn glycosylated by asialo oligosaccharide
      chain
<220> FEATURE:
<221> NAME/KEY: MISC_FEATURE
<222> LOCATION: (7)..(7)
<223> OTHER INFORMATION: Trp having blocking group Boc
<220> FEATURE:
<221> NAME/KEY: MISC_FEATURE
<222> LOCATION: (10)..(10)
<223> OTHER INFORMATION: Lys having blocking group Boc
<220> FEATURE:
<221> NAME/KEY: MISC_FEATURE
<222> LOCATION: (12)..(12)
<223> OTHER INFORMATION: Arg having blocking group Pbf

<400> SEQUENCE: 86

Cys Lys Asn Phe Ile Ala Trp Leu Val Lys Gly Arg Gly
1               5                   10

<210> SEQ ID NO 87
<211> LENGTH: 18
<212> TYPE: PRT
<213> ORGANISM: artificial sequence
<220> FEATURE:
<223> OTHER INFORMATION: amino acid sequence having blocking groups
      (Example 40)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
```

```
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt

<400> SEQUENCE: 87

His Ala Glu Gly Thr Phe Thr Ser Asp Val Ser Ser Tyr Leu Glu Gly
1               5                   10                  15

Gln Ala

<210> SEQ ID NO 88
<211> LENGTH: 18
<212> TYPE: PRT
<213> ORGANISM: artificial sequence
<220> FEATURE:
<223> OTHER INFORMATION: amino acid sequence having blocking groups
      (Example 40)
<220> FEATURE:
<221> NAME/KEY: MISC_FEATURE
<222> LOCATION: (1)..(1)
<223> OTHER INFORMATION: His having blocking group Trt and Boc
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
```

```
<400> SEQUENCE: 88

His Ala Glu Gly Thr Phe Thr Ser Asp Val Ser Ser Tyr Leu Glu Gly
1               5                   10                  15

Gln Ala

<210> SEQ ID NO 89
<211> LENGTH: 18
<212> TYPE: PRT
<213> ORGANISM: artificial sequence
<220> FEATURE:
<223> OTHER INFORMATION: amino acid sequence having leaving groups
      (Example 40)
<220> FEATURE:
<221> NAME/KEY: MISC_FEATURE
<222> LOCATION: (18)..(18)
<223> OTHER INFORMATION: Ala having leaving group PhS

<400> SEQUENCE: 89

His Ala Glu Gly Thr Phe Thr Ser Asp Val Ser Ser Tyr Leu Glu Gly
1               5                   10                  15

Gln Ala

<210> SEQ ID NO 90
<211> LENGTH: 9
<212> TYPE: PRT
<213> ORGANISM: artificial sequence
<220> FEATURE:
<223> OTHER INFORMATION: amino acid sequence having blocking groups
      (Example 40)
<220> FEATURE:
<221> NAME/KEY: MISC_FEATURE
<222> LOCATION: (3)..(3)
<223> OTHER INFORMATION: Trp having blocking group Boc
<220> FEATURE:
<221> NAME/KEY: MISC_FEATURE
<222> LOCATION: (6)..(6)
<223> OTHER INFORMATION: Lys having blocking group Boc
<220> FEATURE:
<221> NAME/KEY: MISC_FEATURE
<222> LOCATION: (8)..(8)
<223> OTHER INFORMATION: Arg having blocking group Pbf

<400> SEQUENCE: 90

Ile Ala Trp Leu Val Lys Gly Arg Gly
1               5

<210> SEQ ID NO 91
<211> LENGTH: 13
<212> TYPE: PRT
<213> ORGANISM: artificial sequence
<220> FEATURE:
<223> OTHER INFORMATION: amino acid sequence having blocking groups
      (Example 40)
<220> FEATURE:
<221> NAME/KEY: MISC_FEATURE
<222> LOCATION: (1)..(1)
<223> OTHER INFORMATION: Cys having blocking group Trt
<220> FEATURE:
<221> NAME/KEY: MISC_FEATURE
<222> LOCATION: (2)..(2)
<223> OTHER INFORMATION: Lys having blocking group Boc
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: CARBOHYD
<222> LOCATION: (4)..(4)
<223> OTHER INFORMATION: Asn glycosylated by asialo oligosaccharide
      chain
```

```
<220> FEATURE:
<221> NAME/KEY: MISC_FEATURE
<222> LOCATION: (7)..(7)
<223> OTHER INFORMATION: Trp having blocking group Boc
<220> FEATURE:
<221> NAME/KEY: MISC_FEATURE
<222> LOCATION: (10)..(10)
<223> OTHER INFORMATION: Lys having blocking group Boc
<220> FEATURE:
<221> NAME/KEY: MISC_FEATURE
<222> LOCATION: (12)..(12)
<223> OTHER INFORMATION: Arg having blocking group Pbf

<400> SEQUENCE: 91

Cys Lys Glu Asn Ile Ala Trp Leu Val Lys Gly Arg Gly
1               5                   10

<210> SEQ ID NO 92
<211> LENGTH: 7
<212> TYPE: PRT
<213> ORGANISM: artificial sequence
<220> FEATURE:
<223> OTHER INFORMATION: amino acid sequence having blocking groups
      (Example 41)
<220> FEATURE:
<221> NAME/KEY: MISC_FEATURE
<222> LOCATION: (1)..(1)
<223> OTHER INFORMATION: Trp having blocking group Boc
<220> FEATURE:
<221> NAME/KEY: MISC_FEATURE
<222> LOCATION: (4)..(4)
<223> OTHER INFORMATION: Lys having blocking group Boc
<220> FEATURE:
<221> NAME/KEY: MISC_FEATURE
<222> LOCATION: (6)..(6)
<223> OTHER INFORMATION: Arg having blocking group Pbf

<400> SEQUENCE: 92

Trp Leu Val Lys Gly Arg Gly
1               5

<210> SEQ ID NO 93
<211> LENGTH: 8
<212> TYPE: PRT
<213> ORGANISM: artificial sequence
<220> FEATURE:
<223> OTHER INFORMATION: amino acid sequence having blocking groups
      (Example 41)
<220> FEATURE:
<221> NAME/KEY: CARBOHYD
<222> LOCATION: (1)..(1)
<223> OTHER INFORMATION: Asn glycosylated by asialo oligosaccharide
      chain
<220> FEATURE:
<221> NAME/KEY: MISC_FEATURE
<222> LOCATION: (2)..(2)
<223> OTHER INFORMATION: Trp having blocking group Boc
<220> FEATURE:
<221> NAME/KEY: MISC_FEATURE
<222> LOCATION: (5)..(5)
<223> OTHER INFORMATION: Lys having blocking group Boc
<220> FEATURE:
<221> NAME/KEY: MISC_FEATURE
<222> LOCATION: (7)..(7)
<223> OTHER INFORMATION: Arg having blocking group Pbf

<400> SEQUENCE: 93

Asn Trp Leu Val Lys Gly Arg Gly
1               5

<210> SEQ ID NO 94
<211> LENGTH: 31
<212> TYPE: PRT
<213> ORGANISM: artificial sequence
```

```
<220> FEATURE:
<223> OTHER INFORMATION: amino acid sequence having blocking groups
      (Example 41)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (24)..(24)
<223> OTHER INFORMATION: Asn glycosylated by asialo oligosaccharide
      chain
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Arg having blocking group Pbf

<400> SEQUENCE: 94

His Ala Glu Gly Thr Phe Thr Ser Asp Val Ser Ser Tyr Leu Glu Gly
1               5                   10                  15

Gln Ala Ala Lys Glu Phe Ile Asn Trp Leu Val Lys Gly Arg Gly
            20                  25                  30
```

```
<210> SEQ ID NO 95
<211> LENGTH: 31
<212> TYPE: PRT
<213> ORGANISM: artificial sequence
<220> FEATURE:
<223> OTHER INFORMATION: amino acid sequence having blocking groups
      (Example 42)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Boc
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Asn glycosylated by asialo oligosaccharide
      chain

<400> SEQUENCE: 95

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Asn Gly
            20                  25                  30
```

```
<210> SEQ ID NO 96
<211> LENGTH: 18
<212> TYPE: PRT
<213> ORGANISM: artificial sequence
<220> FEATURE:
<223> OTHER INFORMATION: amino acid sequence having blocking groups
      (Example 46)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt

<400> SEQUENCE: 96

His Ala Glu Gly Thr Phe Thr Ser Asp Val Ser Ser Tyr Leu Glu Gly
1               5                   10                  15

Gln Ala

<210> SEQ ID NO 97
<211> LENGTH: 18
<212> TYPE: PRT
<213> ORGANISM: artificial sequence
<220> FEATURE:
<223> OTHER INFORMATION: amino acid sequence having blocking groups
      (Example 46)
<220> FEATURE:
<221> NAME/KEY: MISC_FEATURE
<222> LOCATION: (1)..(1)
<223> OTHER INFORMATION: His having blocking group Trt and Boc
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
```

```
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt

<400> SEQUENCE: 97

His Ala Glu Gly Thr Phe Thr Ser Asp Val Ser Ser Tyr Leu Glu Gly
1               5                   10                  15

Gln Ala

<210> SEQ ID NO 98
<211> LENGTH: 18
<212> TYPE: PRT
<213> ORGANISM: artificial sequence
<220> FEATURE:
<223> OTHER INFORMATION: amino acid sequence having leaving groups
      (Example 46)
<220> FEATURE:
<221> NAME/KEY: MISC_FEATURE
<222> LOCATION: (18)..(18)
<223> OTHER INFORMATION: Ala having leaving group PhS

<400> SEQUENCE: 98

His Ala Glu Gly Thr Phe Thr Ser Asp Val Ser Ser Tyr Leu Glu Gly
1               5                   10                  15

Gln Ala

<210> SEQ ID NO 99
<211> LENGTH: 7
<212> TYPE: PRT
<213> ORGANISM: artificial sequence
<220> FEATURE:
<223> OTHER INFORMATION: amino acid sequence having blocking groups
      (Example 46)
<220> FEATURE:
<221> NAME/KEY: MISC_FEATURE
<222> LOCATION: (1)..(1)
<223> OTHER INFORMATION: Trp having blocking group Boc
<220> FEATURE:
<221> NAME/KEY: MISC_FEATURE
<222> LOCATION: (4)..(4)
<223> OTHER INFORMATION: Lys having blocking group Boc
<220> FEATURE:
<221> NAME/KEY: MISC_FEATURE
<222> LOCATION: (6)..(6)
<223> OTHER INFORMATION: Arg having blocking group Pbf
```

```
<400> SEQUENCE: 99

Trp Leu Val Lys Gly Arg Gly
1               5

<210> SEQ ID NO 100
<211> LENGTH: 13
<212> TYPE: PRT
<213> ORGANISM: artificial sequence
<220> FEATURE:
<223> OTHER INFORMATION: amino acid sequence having blocking groups
      (Example 46)
<220> FEATURE:
<221> NAME/KEY: MISC_FEATURE
<222> LOCATION: (1)..(1)
<223> OTHER INFORMATION: Cys having blocking group Trt
<220> FEATURE:
<221> NAME/KEY: MISC_FEATURE
<222> LOCATION: (2)..(2)
<223> OTHER INFORMATION: Lys having blocking group Boc
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: CARBOHYD
<222> LOCATION: (6)..(6)
<223> OTHER INFORMATION: Asn glycosylated by dibenzyl disialo
      oligosaccharide chain
<220> FEATURE:
<221> NAME/KEY: MISC_FEATURE
<222> LOCATION: (7)..(7)
<223> OTHER INFORMATION: Trp having blocking group Boc
<220> FEATURE:
<221> NAME/KEY: MISC_FEATURE
<222> LOCATION: (10)..(10)
<223> OTHER INFORMATION: Lys having blocking group Boc
<220> FEATURE:
<221> NAME/KEY: MISC_FEATURE
<222> LOCATION: (12)..(12)
<223> OTHER INFORMATION: Arg having blocking group Pbf

<400> SEQUENCE: 100

Cys Lys Glu Phe Ile Asn Trp Leu Val Lys Gly Arg Gly
1               5                   10

<210> SEQ ID NO 101
<211> LENGTH: 31
<212> TYPE: PRT
<213> ORGANISM: artificial sequence
<220> FEATURE:
<223> OTHER INFORMATION: amino acid sequence having blocking groups
      (Example 48)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
<220> FEATURE:
<221> NAME/KEY: MISC_FEATURE
<222> LOCATION: (9)..(9)
<223> OTHER INFORMATION: Asp having blocking group OtBu
```

```
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Ser having blocking group tBu
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Cys having blocking group Trt
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Cys having blocking group Trt
<220> FEATURE:
<221> NAME/KEY: MISC_FEATURE
<222> LOCATION: (30)..(30)
<223> OTHER INFORMATION: Arg having blocking group Pbf

<400> SEQUENCE: 101

His Ala Glu Gly Thr Phe Thr Ser Asp Val Ser Ser Tyr Leu Glu Gly
1               5                   10                  15
Gln Ala Ala Cys Glu Phe Ile Ala Trp Leu Val Cys Gly Arg Gly
                20                  25                  30

<210> SEQ ID NO 102
<211> LENGTH: 31
<212> TYPE: PRT
<213> ORGANISM: artificial sequence
<220> FEATURE:
<223> OTHER INFORMATION: amino acid sequence having blocking groups
      (Example 49)
<220> FEATURE:
<221> NAME/KEY: MISC_FEATURE
<222> LOCATION: (1)..(1)
<223> OTHER INFORMATION: His having blocking group Trt
<220> FEATURE:
<221> NAME/KEY: MISC_FEATURE
<222> LOCATION: (3)..(3)
<223> OTHER INFORMATION: Glu having blocking group OtBu
<220> FEATURE:
<221> NAME/KEY: MISC_FEATURE
<222> LOCATION: (5)..(5)
<223> OTHER INFORMATION: Thr having blocking group tBu
<220> FEATURE:
<221> NAME/KEY: MISC_FEATURE
<222> LOCATION: (7)..(7)
<223> OTHER INFORMATION: Thr having blocking group tBu
<220> FEATURE:
<221> NAME/KEY: MISC_FEATURE
<222> LOCATION: (8)..(8)
<223> OTHER INFORMATION: Ser having blocking group tBu
```

```
<220> FEATURE:
<221> NAME/KEY: MISC_FEATURE
<222> LOCATION: (9)..(9)
<223> OTHER INFORMATION: Asp having blocking group OtBu
<220> FEATURE:
<221> NAME/KEY: MISC_FEATURE
<222> LOCATION: (11)..(11)
<223> OTHER INFORMATION: Ser having blocking group tBu
<220> FEATURE:
<221> NAME/KEY: MISC_FEATURE
<222> LOCATION: (12)..(12)
<223> OTHER INFORMATION: Cys having blocking group Trt
<220> FEATURE:
<221> NAME/KEY: MISC_FEATURE
<222> LOCATION: (13)..(13)
<223> OTHER INFORMATION: Tyr having blocking group tBu
<220> FEATURE:
<221> NAME/KEY: MISC_FEATURE
<222> LOCATION: (15)..(15)
<223> OTHER INFORMATION: Glu having blocking group OtBu
<220> FEATURE:
<221> NAME/KEY: MISC_FEATURE
<222> LOCATION: (17)..(17)
<223> OTHER INFORMATION: Gln having blocking group Trt
<220> FEATURE:
<221> NAME/KEY: MISC_FEATURE
<222> LOCATION: (20)..(20)
<223> OTHER INFORMATION: Lys having blocking group Trt
<220> FEATURE:
<221> NAME/KEY: MISC_FEATURE
<222> LOCATION: (21)..(21)
<223> OTHER INFORMATION: Glu having blocking group OtBu
<220> FEATURE:
<221> NAME/KEY: MISC_FEATURE
<222> LOCATION: (25)..(25)
<223> OTHER INFORMATION: Trp having blocking group Boc
<220> FEATURE:
<221> NAME/KEY: MISC_FEATURE
<222> LOCATION: (28)..(28)
<223> OTHER INFORMATION: Lys having blocking group Boc
<220> FEATURE:
<221> NAME/KEY: MISC_FEATURE
<222> LOCATION: (30)..(30)
<223> OTHER INFORMATION: Cys having blocking group Trt

<400> SEQUENCE: 102

His Ala Glu Gly Thr Phe Thr Ser Asp Val Ser Cys Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 103
<211> LENGTH: 31
<212> TYPE: PRT
<213> ORGANISM: artificial sequence
<220> FEATURE:
<223> OTHER INFORMATION: amino acid sequence of (b1) (Example 1)
<220> FEATURE:
<221> NAME/KEY: CARBOHYD
<222> LOCATION: (12)..(12)
<223> OTHER INFORMATION: Cys glycosylated by disialo oligosaccharide
      chain

<400> SEQUENCE: 103

His Ala Glu Gly Thr Phe Thr Ser Asp Val Ser Cys Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 104
<211> LENGTH: 31
<212> TYPE: PRT
<213> ORGANISM: artificial sequence
```

```
<220> FEATURE:
<223> OTHER INFORMATION: amino acid sequence of (b2) (Example 2)
<220> FEATURE:
<221> NAME/KEY: CARBOHYD
<222> LOCATION: (16)..(16)
<223> OTHER INFORMATION: Cys glycosylated by disialo oligosaccharide
      chain

<400> SEQUENCE: 104

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Arg Gly
            20                  25                  30

<210> SEQ ID NO 105
<211> LENGTH: 31
<212> TYPE: PRT
<213> ORGANISM: artificial sequence
<220> FEATURE:
<223> OTHER INFORMATION: amino acid sequence of (b3) (Example 3)
<220> FEATURE:
<221> NAME/KEY: CARBOHYD
<222> LOCATION: (20)..(20)
<223> OTHER INFORMATION: Cys glycosylated by disialo oligosaccharide
      chain

<400> SEQUENCE: 105

His Ala Glu Gly Thr Phe Thr Ser Asp Val Ser Ser Tyr Leu Glu Gly
1               5                   10                  15

Gln Ala Ala Cys Glu Phe Ile Ala Trp Leu Val Lys Gly Arg Gly
            20                  25                  30

<210> SEQ ID NO 106
<211> LENGTH: 31
<212> TYPE: PRT
<213> ORGANISM: artificial sequence
<220> FEATURE:
<223> OTHER INFORMATION: amino acid sequence of (b4) (Example 4)
<220> FEATURE:
<221> NAME/KEY: CARBOHYD
<222> LOCATION: (30)..(30)
<223> OTHER INFORMATION: Cys glycosylated by disialo oligosaccharide
      chain

<400> SEQUENCE: 106

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 107
<211> LENGTH: 32
<212> TYPE: PRT
<213> ORGANISM: artificial sequence
<220> FEATURE:
<223> OTHER INFORMATION: amino acid sequence of (b5) (Example 5)
<220> FEATURE:
<221> NAME/KEY: CARBOHYD
<222> LOCATION: (32)..(32)
<223> OTHER INFORMATION: Cys glycosylated by disialo oligosaccharide
      chain

<400> SEQUENCE: 107

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Cys
            20                  25                  30
```

```
<210> SEQ ID NO 108
<211> LENGTH: 32
<212> TYPE: PRT
<213> ORGANISM: artificial sequence
<220> FEATURE:
<223> OTHER INFORMATION: amino acid sequence of (b6) (Example 6)
<220> FEATURE:
<221> NAME/KEY: CARBOHYD
<222> LOCATION: (32)..(32)
<223> OTHER INFORMATION: Asn glycosylated by asialo oligosaccharide
      chain

<400> SEQUENCE: 108

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Asn
            20                  25                  30

<210> SEQ ID NO 109
<211> LENGTH: 31
<212> TYPE: PRT
<213> ORGANISM: artificial sequence
<220> FEATURE:
<223> OTHER INFORMATION: amino acid sequence of (b7) (Example 7)
<220> FEATURE:
<221> NAME/KEY: CARBOHYD
<222> LOCATION: (13)..(13)
<223> OTHER INFORMATION: Asn glycosylated by asialo oligosaccharide
      chain

<400> SEQUENCE: 109

His Ala Glu Gly Thr Phe Thr Ser Asp Val Ser Ser Asn Leu Glu Gly
1               5                   10                  15

Gln Ala Ala Lys Glu Phe Ile Ala Trp Leu Val Lys Gly Arg Gly
            20                  25                  30

<210> SEQ ID NO 110
<211> LENGTH: 32
<212> TYPE: PRT
<213> ORGANISM: artificial sequence
<220> FEATURE:
<223> OTHER INFORMATION: amino acid sequence of (b8) (Example 8)
<220> FEATURE:
<221> NAME/KEY: CARBOHYD
<222> LOCATION: (1)..(1)
<223> OTHER INFORMATION: Cys glycosylated by disialo oligosaccharide
      chain

<400> SEQUENCE: 110

Cys His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Gly
            20                  25                  30

<210> SEQ ID NO 111
<211> LENGTH: 31
<212> TYPE: PRT
<213> ORGANISM: artificial sequence
<220> FEATURE:
<223> OTHER INFORMATION: amino acid sequence of (b9) (Example 9)
<220> FEATURE:
<221> NAME/KEY: CARBOHYD
<222> LOCATION: (2)..(2)
<223> OTHER INFORMATION: Cys glycosylated by disialo oligosaccharide
      chain
```

-continued

```
<400> SEQUENCE: 111

His Cys Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 112
<211> LENGTH: 31
<212> TYPE: PRT
<213> ORGANISM: artificial sequence
<220> FEATURE:
<223> OTHER INFORMATION: amino acid sequence of (b10) (Example 10)
<220> FEATURE:
<221> NAME/KEY: CARBOHYD
<222> LOCATION: (3)..(3)
<223> OTHER INFORMATION: Cys glycosylated by disialo oligosaccharide
      chain

<400> SEQUENCE: 112

His Ala Cys Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 113
<211> LENGTH: 31
<212> TYPE: PRT
<213> ORGANISM: artificial sequence
<220> FEATURE:
<223> OTHER INFORMATION: amino acid sequence of (b11) (Example 11)
<220> FEATURE:
<221> NAME/KEY: CARBOHYD
<222> LOCATION: (4)..(4)
<223> OTHER INFORMATION: Cys glycosylated by disialo oligosaccharide
      chain

<400> SEQUENCE: 113

His Ala Glu Cys Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 114
<211> LENGTH: 31
<212> TYPE: PRT
<213> ORGANISM: artificial sequence
<220> FEATURE:
<223> OTHER INFORMATION: amino acid sequence of (b12) (Example 12)
<220> FEATURE:
<221> NAME/KEY: CARBOHYD
<222> LOCATION: (5)..(5)
<223> OTHER INFORMATION: Cys glycosylated by disialo oligosaccharide
      chain

<400> SEQUENCE: 114

His Ala Glu Gly Cys Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 115
<211> LENGTH: 31
<212> TYPE: PRT
<213> ORGANISM: artificial sequence
<220> FEATURE:
<223> OTHER INFORMATION: amino acid sequence of (b13) (Example 13)
```

```
<220> FEATURE:
<221> NAME/KEY: CARBOHYD
<222> LOCATION: (6)..(6)
<223> OTHER INFORMATION: Cys glycosylated by disialo oligosaccharide
      chain

<400> SEQUENCE: 115

His Ala Glu Gly Thr Cys Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 116
<211> LENGTH: 31
<212> TYPE: PRT
<213> ORGANISM: artificial sequence
<220> FEATURE:
<223> OTHER INFORMATION: amino acid sequence of (b14) (Example 14)
<220> FEATURE:
<221> NAME/KEY: CARBOHYD
<222> LOCATION: (8)..(8)
<223> OTHER INFORMATION: Cys glycosylated by disialo oligosaccharide
      chain

<400> SEQUENCE: 116

His Ala Glu Gly Thr Phe Thr Cys Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 117
<211> LENGTH: 31
<212> TYPE: PRT
<213> ORGANISM: artificial sequence
<220> FEATURE:
<223> OTHER INFORMATION: amino acid sequence of (b15) (Example 15)
<220> FEATURE:
<221> NAME/KEY: CARBOHYD
<222> LOCATION: (10)..(10)
<223> OTHER INFORMATION: Cys glycosylated by disialo oligosaccharide
      chain

<400> SEQUENCE: 117

His Ala Glu Gly Thr Phe Thr Ser Asp Cys Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 118
<211> LENGTH: 31
<212> TYPE: PRT
<213> ORGANISM: artificial sequence
<220> FEATURE:
<223> OTHER INFORMATION: amino acid sequence of (b16) (Example 16)
<220> FEATURE:
<221> NAME/KEY: CARBOHYD
<222> LOCATION: (14)..(14)
<223> OTHER INFORMATION: Cys glycosylated by disialo oligosaccharide
      chain

<400> SEQUENCE: 118

His Ala Glu Gly Thr Phe Thr Ser Asp Val Ser Ser Tyr Cys Glu Gly
1               5                   10                  15

Gln Ala Ala Lys Glu Phe Ile Ala Trp Leu Val Lys Gly Arg Gly
            20                  25                  30
```

```
<210> SEQ ID NO 119
<211> LENGTH: 31
<212> TYPE: PRT
<213> ORGANISM: artificial sequence
<220> FEATURE:
<223> OTHER INFORMATION: amino acid sequence of (b17) (Example 17)
<220> FEATURE:
<221> NAME/KEY: CARBOHYD
<222> LOCATION: (18)..(18)
<223> OTHER INFORMATION: Cys glycosylated by disialo oligosaccharide
      chain

<400> SEQUENCE: 119

His Ala Glu Gly Thr Phe Thr Ser Asp Val Ser Ser Tyr Leu Glu Gly
1               5                   10                  15

Gln Cys Ala Lys Glu Phe Ile Ala Trp Leu Val Lys Gly Arg Gly
            20                  25                  30

<210> SEQ ID NO 120
<211> LENGTH: 31
<212> TYPE: PRT
<213> ORGANISM: artificial sequence
<220> FEATURE:
<223> OTHER INFORMATION: amino acid sequence of (b18) (Example 18)
<220> FEATURE:
<221> NAME/KEY: CARBOHYD
<222> LOCATION: (19)..(19)
<223> OTHER INFORMATION: Cys glycosylated by disialo oligosaccharide
      chain

<400> SEQUENCE: 120

His Ala Glu Gly Thr Phe Thr Ser Asp Val Ser Ser Tyr Leu Glu Gly
1               5                   10                  15

Gln Ala Cys Lys Glu Phe Ile Ala Trp Leu Val Lys Gly Arg Gly
            20                  25                  30

<210> SEQ ID NO 121
<211> LENGTH: 31
<212> TYPE: PRT
<213> ORGANISM: artificial sequence
<220> FEATURE:
<223> OTHER INFORMATION: amino acid sequence of (b19) (Example 19)
<220> FEATURE:
<221> NAME/KEY: CARBOHYD
<222> LOCATION: (21)..(21)
<223> OTHER INFORMATION: Cys glycosylated by disialo oligosaccharide
      chain

<400> SEQUENCE: 121

His Ala Glu Gly Thr Phe Thr Ser Asp Val Ser Ser Tyr Leu Glu Gly
1               5                   10                  15

Gln Ala Ala Lys Cys Phe Ile Ala Trp Leu Val Lys Gly Arg Gly
            20                  25                  30

<210> SEQ ID NO 122
<211> LENGTH: 31
<212> TYPE: PRT
<213> ORGANISM: artificial sequence
<220> FEATURE:
<223> OTHER INFORMATION: amino acid sequence of (b20) (Example 20)
<220> FEATURE:
<221> NAME/KEY: CARBOHYD
<222> LOCATION: (22)..(22)
<223> OTHER INFORMATION: Cys glycosylated by disialo oligosaccharide
      chain
```

```
<400> SEQUENCE: 122

His Ala Glu Gly Thr Phe Thr Ser Asp Val Ser Ser Tyr Leu Glu Gly
1               5                   10                  15

Gln Ala Ala Lys Glu Cys Ile Ala Trp Leu Val Lys Gly Arg Gly
            20                  25                  30

<210> SEQ ID NO 123
<211> LENGTH: 31
<212> TYPE: PRT
<213> ORGANISM: artificial sequence
<220> FEATURE:
<223> OTHER INFORMATION: amino acid sequence of (b21) (Example 21)
<220> FEATURE:
<221> NAME/KEY: CARBOHYD
<222> LOCATION: (24)..(24)
<223> OTHER INFORMATION: Cys glycosylated by disialo oligosaccharide
      chain

<400> SEQUENCE: 123

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 124
<211> LENGTH: 31
<212> TYPE: PRT
<213> ORGANISM: artificial sequence
<220> FEATURE:
<223> OTHER INFORMATION: amino acid sequence of (b22) (Example 22)
<220> FEATURE:
<221> NAME/KEY: CARBOHYD
<222> LOCATION: (26)..(26)
<223> OTHER INFORMATION: Cys glycosylated by disialo oligosaccharide
      chain

<400> SEQUENCE: 124

His Ala Glu Gly Thr Phe Thr Ser Asp Val Ser Ser Tyr Leu Glu Gly
1               5                   10                  15

Gln Ala Ala Lys Glu Phe Ile Ala Trp Cys Val Lys Gly Arg Gly
            20                  25                  30

<210> SEQ ID NO 125
<211> LENGTH: 31
<212> TYPE: PRT
<213> ORGANISM: artificial sequence
<220> FEATURE:
<223> OTHER INFORMATION: amino acid sequence of (b23) (Example 23)
<220> FEATURE:
<221> NAME/KEY: CARBOHYD
<222> LOCATION: (28)..(28)
<223> OTHER INFORMATION: Cys glycosylated by disialo oligosaccharide
      chain

<400> SEQUENCE: 125

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Arg Gly
            20                  25                  30

<210> SEQ ID NO 126
<211> LENGTH: 31
<212> TYPE: PRT
<213> ORGANISM: artificial sequence
<220> FEATURE:
<223> OTHER INFORMATION: amino acid sequence of (b24) (Example 24)
```

```
<220> FEATURE:
<221> NAME/KEY: CARBOHYD
<222> LOCATION: (16)..(16)
<223> OTHER INFORMATION: Cys glycosylated by asialo oligosaccharide
      chain

<400> SEQUENCE: 126

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Arg Gly
            20                  25                  30

<210> SEQ ID NO 127
<211> LENGTH: 31
<212> TYPE: PRT
<213> ORGANISM: artificial sequence
<220> FEATURE:
<223> OTHER INFORMATION: amino acid sequence of (b25) (Example 25)
<220> FEATURE:
<221> NAME/KEY: CARBOHYD
<222> LOCATION: (20)..(20)
<223> OTHER INFORMATION: Cys glycosylated by asialo oligosaccharide
      chain

<400> SEQUENCE: 127

His Ala Glu Gly Thr Phe Thr Ser Asp Val Ser Ser Tyr Leu Glu Gly
1               5                   10                  15

Gln Ala Ala Cys Glu Phe Ile Ala Trp Leu Val Lys Gly Arg Gly
            20                  25                  30

<210> SEQ ID NO 128
<211> LENGTH: 31
<212> TYPE: PRT
<213> ORGANISM: artificial sequence
<220> FEATURE:
<223> OTHER INFORMATION: amino acid sequence of (b26) (Example 26)
<220> FEATURE:
<221> NAME/KEY: CARBOHYD
<222> LOCATION: (24)..(24)
<223> OTHER INFORMATION: Cys glycosylated by asialo oligosaccharide
      chain

<400> SEQUENCE: 128

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 129
<211> LENGTH: 31
<212> TYPE: PRT
<213> ORGANISM: artificial sequence
<220> FEATURE:
<223> OTHER INFORMATION: amino acid sequence of (b27) (Example 27)
<220> FEATURE:
<221> NAME/KEY: CARBOHYD
<222> LOCATION: (28)..(28)
<223> OTHER INFORMATION: Cys glycosylated by asialo oligosaccharide
      chain

<400> SEQUENCE: 129

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Arg Gly
            20                  25                  30
```

```
<210> SEQ ID NO 130
<211> LENGTH: 31
<212> TYPE: PRT
<213> ORGANISM: artificial sequence
<220> FEATURE:
<223> OTHER INFORMATION: amino acid sequence of (b28) (Example 28)
<220> FEATURE:
<221> NAME/KEY: CARBOHYD
<222> LOCATION: (30)..(30)
<223> OTHER INFORMATION: Cys glycosylated by asialo oligosaccharide
      chain

<400> SEQUENCE: 130

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 131
<211> LENGTH: 31
<212> TYPE: PRT
<213> ORGANISM: artificial sequence
<220> FEATURE:
<223> OTHER INFORMATION: amino acid sequence of (b29) (Example 29)
<220> FEATURE:
<221> NAME/KEY: CARBOHYD
<222> LOCATION: (16)..(16)
<223> OTHER INFORMATION: Cys glycosylated by diGlcNAc oligosaccharide
      chain

<400> SEQUENCE: 131

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Arg Gly
            20                  25                  30

<210> SEQ ID NO 132
<211> LENGTH: 31
<212> TYPE: PRT
<213> ORGANISM: artificial sequence
<220> FEATURE:
<223> OTHER INFORMATION: amino acid sequence of (b30) (Example 30)
<220> FEATURE:
<221> NAME/KEY: CARBOHYD
<222> LOCATION: (24)..(24)
<223> OTHER INFORMATION: Cys glycosylated by diGlcNAc oligosaccharide
      chain

<400> SEQUENCE: 132

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 133
<211> LENGTH: 31
<212> TYPE: PRT
<213> ORGANISM: artificial sequence
<220> FEATURE:
<223> OTHER INFORMATION: amino acid sequence of (b31) (Example 31)
<220> FEATURE:
<221> NAME/KEY: CARBOHYD
<222> LOCATION: (28)..(28)
<223> OTHER INFORMATION: Cys glycosyalated by diGlcNAc oligosaccharide
      chain
```

```
<400> SEQUENCE: 133

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Arg Gly
            20                  25                  30

<210> SEQ ID NO 134
<211> LENGTH: 31
<212> TYPE: PRT
<213> ORGANISM: artificial sequence
<220> FEATURE:
<223> OTHER INFORMATION: amino acid sequence of (b32) (Example 32)
<220> FEATURE:
<221> NAME/KEY: CARBOHYD
<222> LOCATION: (16)..(16)
<223> OTHER INFORMATION: Cys glycosylated by dimannose oligosaccharide
      chain

<400> SEQUENCE: 134

His Ala Glu Gly Thr Phe Thr Ser Asp Val Ser Ser Tyr Leu Glu Cys
1               5                   10                  15

Gln Ala Ala Lys Glu Phe Ile Ala Trp Leu Val Lys Gly Arg Gly
            20                  25                  30

<210> SEQ ID NO 135
<211> LENGTH: 31
<212> TYPE: PRT
<213> ORGANISM: artificial sequence
<220> FEATURE:
<223> OTHER INFORMATION: amino acid sequence of (b33) (Example 33)
<220> FEATURE:
<221> NAME/KEY: CARBOHYD
<222> LOCATION: (24)..(24)
<223> OTHER INFORMATION: Cys glycosylated by dimannose oligosaccharide
      chain

<400> SEQUENCE: 135

His Ala Glu Gly Thr Phe Thr Ser Asp Val Ser Ser Tyr Leu Glu Gly
1               5                   10                  15

Gln Ala Ala Lys Glu Phe Ile Cys Trp Leu Val Lys Gly Arg Gly
            20                  25                  30

<210> SEQ ID NO 136
<211> LENGTH: 31
<212> TYPE: PRT
<213> ORGANISM: artificial sequence
<220> FEATURE:
<223> OTHER INFORMATION: amino acid sequence of (b34) (Example 34)
<220> FEATURE:
<221> NAME/KEY: CARBOHYD
<222> LOCATION: (28)..(28)
<223> OTHER INFORMATION: Cys glycosylated by dimannose oligosaccharide
      chain

<400> SEQUENCE: 136

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Cys Gly Arg Gly
            20                  25                  30

<210> SEQ ID NO 137
<211> LENGTH: 31
<212> TYPE: PRT
<213> ORGANISM: artificial sequence
<220> FEATURE:
<223> OTHER INFORMATION: amino acid sequence of (b35) (Example 35)
```

```
<220> FEATURE:
<221> NAME/KEY: CARBOHYD
<222> LOCATION: (6)..(6)
<223> OTHER INFORMATION: Asn glycosylated by asialo oligosaccharide
      chain

<400> SEQUENCE: 137

His Ala Glu Gly Thr Asn Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 138
<211> LENGTH: 31
<212> TYPE: PRT
<213> ORGANISM: artificial sequence
<220> FEATURE:
<223> OTHER INFORMATION: amino acid sequence of (b36) (Example 36)
<220> FEATURE:
<221> NAME/KEY: CARBOHYD
<222> LOCATION: (12)..(12)
<223> OTHER INFORMATION: Asn glycosylated by asialo oligosaccharide
      chain

<400> SEQUENCE: 138

His Ala Glu Gly Thr Phe Thr Ser Asp Val Ser Asn Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 139
<211> LENGTH: 31
<212> TYPE: PRT
<213> ORGANISM: artificial sequence
<220> FEATURE:
<223> OTHER INFORMATION: amino acid sequence of (b37) (Example 37)
<220> FEATURE:
<221> NAME/KEY: CARBOHYD
<222> LOCATION: (16)..(16)
<223> OTHER INFORMATION: Asn glycosylated by asialo oligosaccharide
      chain

<400> SEQUENCE: 139

His Ala Glu Gly Thr Phe Thr Ser Asp Val Ser Ser Tyr Leu Glu Asn
1               5                   10                  15

Gln Ala Ala Lys Glu Phe Ile Ala Trp Leu Val Lys Gly Arg Gly
            20                  25                  30

<210> SEQ ID NO 140
<211> LENGTH: 31
<212> TYPE: PRT
<213> ORGANISM: artificial sequence
<220> FEATURE:
<223> OTHER INFORMATION: amino acid sequence of (b38) (Example 38)
<220> FEATURE:
<221> NAME/KEY: CARBOHYD
<222> LOCATION: (20)..(20)
<223> OTHER INFORMATION: Asn glycosylated by asialo oligosaccharide
      chain

<400> SEQUENCE: 140

His Ala Glu Gly Thr Phe Thr Ser Asp Val Ser Ser Tyr Leu Glu Gly
1               5                   10                  15

Gln Ala Ala Asn Glu Phe Ile Ala Trp Leu Val Lys Gly Arg Gly
            20                  25                  30
```

```
<210> SEQ ID NO 141
<211> LENGTH: 31
<212> TYPE: PRT
<213> ORGANISM: artificial sequence
<220> FEATURE:
<223> OTHER INFORMATION: amino acid sequence of (b39) (Example 39)
<220> FEATURE:
<221> NAME/KEY: CARBOHYD
<222> LOCATION: (21)..(21)
<223> OTHER INFORMATION: Asn glycosylatedby asialo oligosaccharide
      chain

<400> SEQUENCE: 141

His Ala Glu Gly Thr Phe Thr Ser Asp Val Ser Ser Tyr Leu Glu Gly
1               5                   10                  15

Gln Ala Ala Lys Asn Phe Ile Ala Trp Leu Val Lys Gly Arg Gly
            20                  25                  30

<210> SEQ ID NO 142
<211> LENGTH: 31
<212> TYPE: PRT
<213> ORGANISM: artificial sequence
<220> FEATURE:
<223> OTHER INFORMATION: amino acid sequence of (b40) (Example 40)
<220> FEATURE:
<221> NAME/KEY: CARBOHYD
<222> LOCATION: (22)..(22)
<223> OTHER INFORMATION: Asn glycosylated by asialo oligosaccharide
      chain

<400> SEQUENCE: 142

His Ala Glu Gly Thr Phe Thr Ser Asp Val Ser Ser Tyr Leu Glu Gly
1               5                   10                  15

Gln Ala Ala Lys Glu Asn Ile Ala Trp Leu Val Lys Gly Arg Gly
            20                  25                  30

<210> SEQ ID NO 143
<211> LENGTH: 31
<212> TYPE: PRT
<213> ORGANISM: artificial sequence
<220> FEATURE:
<223> OTHER INFORMATION: amino acid sequence of (b41) (Example 41)
<220> FEATURE:
<221> NAME/KEY: CARBOHYD
<222> LOCATION: (24)..(24)
<223> OTHER INFORMATION: Asn glycosylated by asialo oligosaccharide
      chain

<400> SEQUENCE: 143

His Ala Glu Gly Thr Phe Thr Ser Asp Val Ser Ser Tyr Leu Glu Gly
1               5                   10                  15

Gln Ala Ala Lys Glu Phe Ile Asn Trp Leu Val Lys Gly Arg Gly
            20                  25                  30

<210> SEQ ID NO 144
<211> LENGTH: 31
<212> TYPE: PRT
<213> ORGANISM: artificial sequence
<220> FEATURE:
<223> OTHER INFORMATION: amino acid sequence of (b42) (Example 42)
<220> FEATURE:
<221> NAME/KEY: CARBOHYD
<222> LOCATION: (30)..(30)
<223> OTHER INFORMATION: Asn glycosylated by asialo oligosaccharide
      chain
```

```
<400> SEQUENCE: 144

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Asn Gly
            20                  25                  30

<210> SEQ ID NO 145
<211> LENGTH: 31
<212> TYPE: PRT
<213> ORGANISM: artificial sequence
<220> FEATURE:
<223> OTHER INFORMATION: amino acid sequence of (b43) (Example 43)
<220> FEATURE:
<221> NAME/KEY: CARBOHYD
<222> LOCATION: (12)..(12)
<223> OTHER INFORMATION: Asn glycosylated by disialo oligosaccharide
      chain

<400> SEQUENCE: 145

His Ala Glu Gly Thr Phe Thr Ser Asp Val Ser Asn Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 146
<211> LENGTH: 31
<212> TYPE: PRT
<213> ORGANISM: artificial sequence
<220> FEATURE:
<223> OTHER INFORMATION: amino acid sequence of (b44) (Example 44)
<220> FEATURE:
<221> NAME/KEY: CARBOHYD
<222> LOCATION: (16)..(16)
<223> OTHER INFORMATION: Asn glycosylated by disialo oligosaccharide
      chain

<400> SEQUENCE: 146

His Ala Glu Gly Thr Phe Thr Ser Asp Val Ser Ser Tyr Leu Glu Asn
1               5                   10                  15

Gln Ala Ala Lys Glu Phe Ile Ala Trp Leu Val Lys Gly Arg Gly
            20                  25                  30

<210> SEQ ID NO 147
<211> LENGTH: 31
<212> TYPE: PRT
<213> ORGANISM: artificial sequence
<220> FEATURE:
<223> OTHER INFORMATION: amino acid sequence of (b45) (Example 45)
<220> FEATURE:
<221> NAME/KEY: CARBOHYD
<222> LOCATION: (24)..(24)
<223> OTHER INFORMATION: Asn glycosylated by disialo oligosaccharide
      chain

<400> SEQUENCE: 147

His Ala Glu Gly Thr Phe Thr Ser Asp Val Ser Ser Tyr Leu Glu Gly
1               5                   10                  15

Gln Ala Ala Lys Glu Phe Ile Asn Trp Leu Val Lys Gly Arg Gly
            20                  25                  30

<210> SEQ ID NO 148
<211> LENGTH: 31
<212> TYPE: PRT
<213> ORGANISM: artificial sequence
<220> FEATURE:
<223> OTHER INFORMATION: amino acid sequence of (b46) (Example 46)
```

```
<220> FEATURE:
<221> NAME/KEY: CARBOHYD
<222> LOCATION: (24)..(24)
<223> OTHER INFORMATION: Asn glycosylated by disialo oligosaccharide
      chain

<400> SEQUENCE: 148

His Ala Glu Gly Thr Phe Thr Ser Asp Val Ser Ser Tyr Leu Glu Gly
1               5                   10                  15

Gln Ala Ala Lys Glu Phe Ile Asn Trp Leu Val Lys Gly Arg Gly
            20                  25                  30

<210> SEQ ID NO 149
<211> LENGTH: 31
<212> TYPE: PRT
<213> ORGANISM: artificial sequence
<220> FEATURE:
<223> OTHER INFORMATION: amino acid sequence of (b47 (Example 47)
<220> FEATURE:
<221> NAME/KEY: CARBOHYD
<222> LOCATION: (30)..(30)
<223> OTHER INFORMATION: Asn glycosylated by disialo oligosaccharide
      chain

<400> SEQUENCE: 149

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Asn Gly
            20                  25                  30

<210> SEQ ID NO 150
<211> LENGTH: 31
<212> TYPE: PRT
<213> ORGANISM: artificial sequence
<220> FEATURE:
<223> OTHER INFORMATION: amino acid sequence of (b48) (Example 48)
<220> FEATURE:
<221> NAME/KEY: CARBOHYD
<222> LOCATION: (20)..(20)
<223> OTHER INFORMATION: Cys glycosylated by disialo oligosaccharide
      chain
<220> FEATURE:
<221> NAME/KEY: CARBOHYD
<222> LOCATION: (28)..(28)
<223> OTHER INFORMATION: Cys glycosylated by disialo oligosaccharide
      chain

<400> SEQUENCE: 150

His Ala Glu Gly Thr Phe Thr Ser Asp Val Ser Ser Tyr Leu Glu Gly
1               5                   10                  15

Gln Ala Ala Cys Glu Phe Ile Ala Trp Leu Val Cys Gly Arg Gly
            20                  25                  30

<210> SEQ ID NO 151
<211> LENGTH: 31
<212> TYPE: PRT
<213> ORGANISM: artificial sequence
<220> FEATURE:
<223> OTHER INFORMATION: amino acid sequence of (b49) (Example 49)
<220> FEATURE:
<221> NAME/KEY: CARBOHYD
<222> LOCATION: (12)..(12)
<223> OTHER INFORMATION: Cys glycosylated by disialo oligosaccharide
      chain
<220> FEATURE:
<221> NAME/KEY: CARBOHYD
<222> LOCATION: (30)..(30)
<223> OTHER INFORMATION: Cys glycosylated by disialo oligosaccharide
      chain
```

```
-continued

<400> SEQUENCE: 151

His Ala Glu Gly Thr Phe Thr Ser Asp Val Ser Cys Tyr Leu Glu Gly
1               5                   10                  15

Gln Ala Ala Lys Glu Phe Ile Ala Trp Leu Val Lys Gly Cys Gly
            20                  25                  30

<210> SEQ ID NO 152
<211> LENGTH: 35
<212> TYPE: DNA
<213> ORGANISM: artificial sequence
<220> FEATURE:
<223> OTHER INFORMATION: sense primer for mouse GLP-1 receptor

<400> SEQUENCE: 152
gttgctagcg ccaccatggc cagcacccca agcct                          35

<210> SEQ ID NO 153
<211> LENGTH: 31
<212> TYPE: DNA
<213> ORGANISM: artificial sequence
<220> FEATURE:
<223> OTHER INFORMATION: antisense primer for mouse GLP-1 receptor

<400> SEQUENCE: 153
cctgaattct cagctgtagg aactctggca g                              31
```

SUGAR CHAIN ADDED GLP-1 PEPTIDE

REFERENCE TO THE RELATED APPLICATIONS

This application claims priority under 35 U.S.C. §119(a)-(d) to Japanese Patent Application No. JP2007-160951 filed Jun. 19, 2007 and claims the benefits under 35 U.S.C. §119(e) of U.S. provisional Application Ser. No. 60/929,425 filed Jun. 27, 2007, the entire contents of which are hereby incorporated by reference.

TECHNICAL FIELD

The present invention relates to an oligosaccharide chain added GLP-1 peptide.

BACKGROUND ART

GLP-1 (glucagon-like peptide-1) is a peptide of intestinal origin that is deeply involved in regulation of glucose homeostasis. GLP-1 is synthesized in intestinal L-cells by the tissue-specific post-translational processing of preproglucagon which is a glucagon precursor and released into circulation in response to food intake. These peptides serve as main mediators of the entero-insular axis and act through the binding to particular receptors.

GLP-1 has been known to act mainly on the pancreas and promote the insulin release of β cells in a glucose concentration-dependent manner. It has also been suggested that GLP-1 is likely to suppress glucagon secretion, delay gastric emptying, and enhance peripheral glucose disposal.

The administration of GLP-1 to patients with non-insulin-dependent diabetes mellitus can normalize postprandial glucose levels, suggesting that GLP-1 may be used as a therapeutic drug. GLP-1 also has the effect of improving glycemic control in patients with insulin-dependent diabetes mellitus. Since the effect of promoting insulin release by GLP-1 depends on plasma glucose concentrations, GLP-1 mediates reduced insulin release at a low plasma glucose concentration and therefore advantageously causes no serious hypoglycemia. Thus, the highly safe treatment of diabetes can be achieved by controlling the amount of GLP-1 in blood as necessary. However, the half-life of GLP-1 in blood is as extremely short as 2 to 6 minutes, presenting the problem of its limited possibility as a therapeutic agent.

To solve such a problem, an attempt has been made to modify GLP-1. For example, Patent Document 1 discloses a PEGylated GLP-1 compound comprising a GLP-1 compound conjugated to at least 1 polyethylene glycol (PEG) molecule, wherein each PEG is bound with the GLP-1 compound at the Cys or Lys amino acid or at the carboxyl-terminal amino acid, and the PEGylated GLP-1 compound has an elimination half-life of at least 1 hour.

According to Patent Document 1, the obtained biologically active peptide has a longer half-life and highly delayed clearance compared to those of unPEGylated peptides. It has also been shown that the PEGylated GLP-1 compound and composition are useful in the treatment of the health condition such as diabetes, obesity and irritable bowel syndrome as well as reducing blood sugar level, suppressing gastric and/or intestinal motility, gastric and/or intestinal emptying, and controlling food intake (e.g., Non-patent document 1).

However, PEG is a compound that is not metabolized in vivo. Therefore, the continuous administration of the PEGylated GLP-1 compound accumulates PEG in vivo and might cause adverse reaction in the living bodies (Non-patent document 1).

Exendin-4 found from the saliva of a lizard (*Heloderma*) is a compound that is structurally similar to GLP-1 and has similar activity and high stability in blood (Non-patent Document 2) which has been placed on the market in U.S. However, exendin-4 has a nonhuman sequence and might induce neutralizing antibodies attributed to long-term administration, leading to attenuated efficacy ((Non-patent Documents 3-5).

On the other hand, it has become evident that oligosaccharide chains play various roles in vivo. They have been less well studied due to their complicated and diverse structures, though the importance of the studies is recognized. An attempt has been made on a method for obtaining a glycopeptide having constant composition (Patent Document 2). However, this production method is still less than sufficient from the viewpoint of convenience or large-scale production and is not practical method particularly for long oligosaccharide chains existing in vivo.

[Patent Document 1] National Publication of International Patent Application No. 2006-520818
[Patent Document 2] WO 2005-095331
[Non-patent document 1] Toxicological Science, 42, 152-157 (1998)
[Non-patent document 2] J Biol Chem. 267, 7402-5 (1992)
[Non-patent Document 3] Vascular Health and Risk Management 2, 69-77 (2006)
[Non-patent Document 4] JAMA. 298, 194-206 (2007)
[Non-patent Document 5] Endocrine Reviews 28, 187-218 (2007)

SUMMARY OF THE INVENTION

An object of the present invention is to provide an oligosaccharide chain added GLP-1 peptide that has higher stability in blood than that of GLP-1 and, more preferably, exhibits higher activity of controlling blood-sugar levels than that of GLP-1.

Means for Solving Problem

The present invention can have the following characteristics to solve the problem.

Specifically, the present invention provides an oligosaccharide chain added GLP-1 peptide having GLP-1 activity, wherein at least one amino acid is substituted with an oligosaccharide chain added amino acid, in
 (a) GLP-1;
 (b) a peptide having the amino acid sequence of GLP-1 with deletion, substitution or addition of one or several amino acids; or
 (c) a GLP-1 analog.

The present invention also provides an oligosaccharide chain added GLP-1 peptide having GLP-1 activity, wherein at least one amino acid is substituted with an oligosaccharide chain added amino acid, in
 (a) GLP-1; or
 (b) a peptide having the amino acid sequence of GLP-1 with deletion, substitution or addition of one or several amino acids and having GLP-1 activity.

The present invention also provides an oligosaccharide chain added GLP-1 peptide having GLP-1 activity, wherein the oligosaccharide chain added GLP-1 peptide is
 (a) an oligosaccharide chain added GLP-1 peptide having one or several amino acids further added to the C terminal (position 37) of GLP-1, wherein at least one of the added amino acids is substituted with an oligosaccharide chain added amino acid; or (b) an oligosaccharide chain added GLP-1 peptide having the amino acid sequence of the oligosaccharide chain added GLP-1 peptide defined in (a) with deletion, substitution or addition of one or several amino acids except the oligosaccharide chain added amino acid(s).

The present invention also provides an oligosaccharide chain added GLP-1 peptide having GLP-1 activity, wherein the oligosaccharide chain added GLP-1 peptide is (a) an oligosaccharide chain added GLP-1 peptide having one or several amino acids further added to the N terminal (position 7) of GLP-1, wherein at least one of the added amino acids is substituted with an oligosaccharide chain added amino acid; or (b) an oligosaccharide chain added GLP-1 peptide having the amino acid sequence of the oligosaccharide chain added GLP-1 peptide defined in (a) with deletion, substitution or addition of one or several amino acids except the oligosaccharide chain added amino acid(s).

The present invention also provides an oligosaccharide chain added GLP-1 peptide having GLP-1 activity, wherein the oligosaccharide chain added GLP-1 peptide is (a) an oligosaccharide chain added GLP-1 peptide wherein an amino acid at least one site selected from positions 18, 20, 22, 26, 30, 34 and 36 of GLP-1 is substituted with an oligosaccharide chain added amino acid; or (b) an oligosaccharide chain added GLP-1 peptide having the amino acid sequence of the oligosaccharide chain added GLP-1 peptide defined in (a) with deletion, substitution or addition of one or several amino acids except the oligosaccharide chain added amino acid(s).

Moreover, the present invention provides an oligosaccharide chain added GLP-1 peptide having GLP-1 activity, wherein at least two amino acids are substituted with oligosaccharide chain added amino acids, in (a) GLP-1;
(b) a peptide having the amino acid sequence of GLP-1 with deletion, substitution or addition of one or several amino acids; or
(c) a GLP-1 analog.

The present invention also provides an oligosaccharide chain added GLP-1 peptide having GLP-1 activity, wherein at least two amino acids are substituted with oligosaccharide chain added amino acids, in (a) GLP-1; or
(b) a peptide having the amino acid sequence of GLP-1 with deletion, substitution or addition of one or several amino acids.

The present invention also provides an oligosaccharide chain added GLP-1 peptide having GLP-1 activity, wherein at least two amino acids are substituted with oligosaccharide chain added amino acids, in (a) GLP-1; or
(b) a peptide having the amino acid sequence of GLP-1 with deletion, substitution or addition of one or several amino acids and having GLP-1 activity.

In the present invention, the oligosaccharide chain added amino acid can be preferably, but not limited to, oligosaccharide chain added Asn or oligosaccharide chain added Cys, depending on embodiments.

In the present invention, in the oligosaccharide chain added amino acid, the oligosaccharide chain may be linked to the amino acid via a linker or without a linker. Preferably, the oligosaccharide chain is linked to the amino acid without a linker (i.e., directly), depending on embodiments.

In the present invention, the oligosaccharide chain is generally preferably an oligosaccharide chain consisting of four or more sugars. However, an oligosaccharide chain consisting of five to eleven sugars may be preferable, depending on embodiments.

In the present invention, the oligosaccharide chain may be preferably, but not limited to, an oligosaccharide chain selected from the group consisting of disialo, monosialo, asialo, diGlcNAc and dimannose oligosaccharide chains, depending on embodiments.

In the present invention, the oligosaccharide chain may be preferably, but not limited to, an oligosaccharide chain represented by the following formula, depending on embodiments:

[Formula 1]

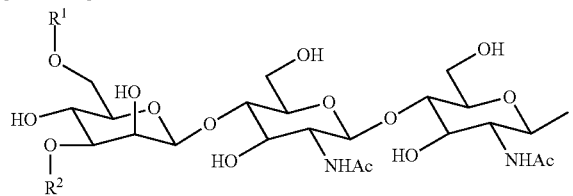

wherein
$R^1$ and $R^2$ are the same or different and each represents

[Formula 2]

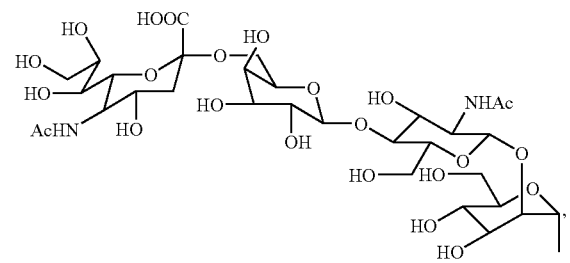

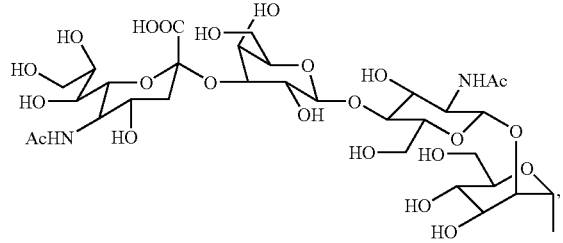

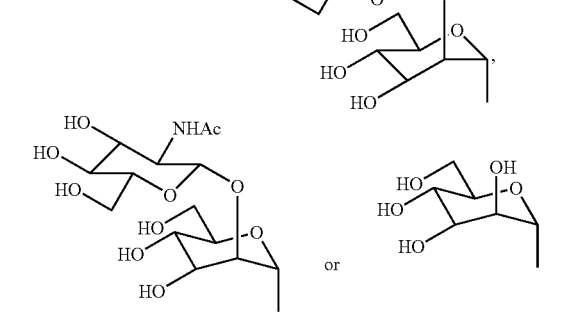

and
Ac represents an acetyl group.

In the present invention, the oligosaccharide chain is, preferably, substantially uniform. In the present invention, the oligosaccharide chains can be adjusted to have such a structure. According to the disclosure of the present invention, e.g., at least 90% or at least 99% uniformity can be achieved.

The oligosaccharide chain added GLP-1 peptide of the present invention, preferably, has higher stability in blood than that of GLP-1.

The oligosaccharide chain added GLP-1 peptide of the present invention can have the activity of controlling blood-sugar levels preferably at least 5 times, more preferably at least 10 times, even more preferably at least 20 times that of GLP-1 in OGTT (Oral Glucose Tolerance Test).

The oligosaccharide chain added GLP-1 peptide of the present invention can have DPP-IV resistance preferably at least 30 times, more preferably at least 50 times that of GLP-1.

The oligosaccharide chain added GLP-1 peptide of the present invention can be used as a novel active ingredient in medical application. Such medical application encompasses the treatment or prevention of diseases associated with GLP-1. Such diseases are typified by, e.g., diabetes.

Of course, one or any combination of the characteristics of the present invention described above is also incorporated in the oligosaccharide chain added GLP-1 peptide of the present invention.

Effect of the Invention

The oligosaccharide chain added GLP-1 peptide of the present invention has higher stability in blood than that of GLP-1. In one aspect of the present invention, the oligosaccharide chain added GLP-1 peptide of the present invention has higher activity of controlling blood-sugar levels than that of GLP-1. Accordingly, the oligosaccharide chain added GLP-1 peptide of the present invention can be administered at a lower dose and a smaller number of doses than those of GLP-1.

The oligosaccharide chain to be added to the oligosaccharide chain added GLP-1 peptide of the present invention is easily degraded in vivo and therefore, does not cause adverse reaction attributed to its accumulation in the living bodies.

Some or all of the oligosaccharide chains to be added to the oligosaccharide chain added GLP-1 peptide of the present invention exist in vivo in mammals including humans, birds, etc. They exhibit neither side effects nor antigenicity, when administered to living bodies. Therefore, they do not present the problem of allergic reactions or a loss of efficacy attributed to antibody production.

For previous oligosaccharide chains, particularly, long oligosaccharide chains, oligosaccharide chain added peptides (or proteins) having a uniform oligosaccharide chain structure were difficult to obtain in large amounts with constant quality. However, according to the production process of the present invention, the compound of the present invention, which is an oligosaccharide chain added peptide, can be supplied stably and conveniently in large amounts and is also very useful from the viewpoint of pharmaceutical production.

DETAILED DESCRIPTION OF THE PREFERRED EMBODIMENTS

Figure 1:
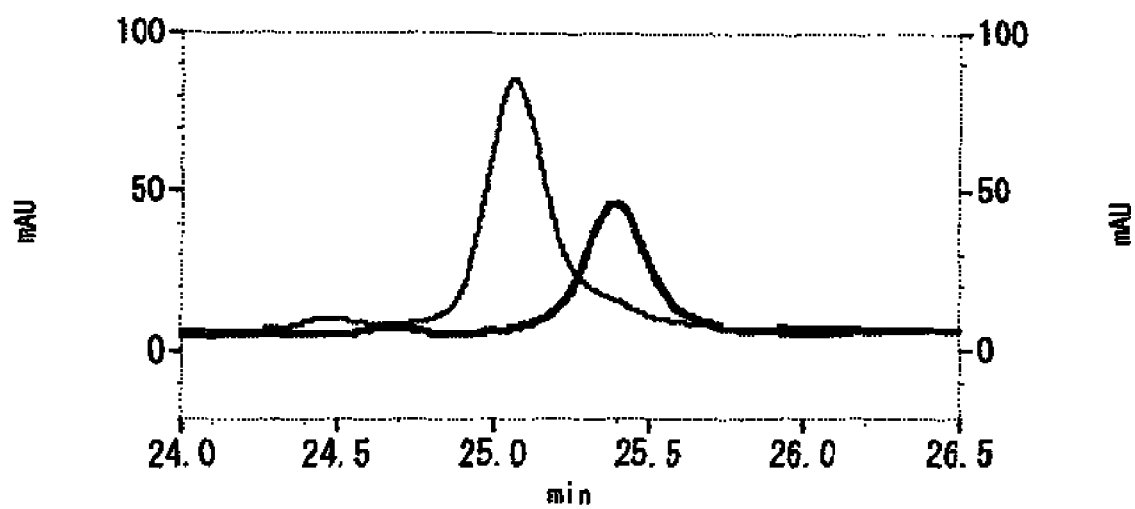
FIG. 1 is one example of a HPLC chart in Example 43 and shows peaks of 18Asn GLP-1-asialo and 18Asn GLP-1-disialo.

"GLP-1" used herein represents glucagon-like peptide-1 and refers to GLP-1 (7-37).

The GLP-1 (7-37) has the amino acid sequence of
His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO: 2).

In the present invention, a "GLP-1 analog" is a peptide structurally similar to GLP-1 and/or a peptide structurally overlapping with GLP-1. Examples of such peptides include: a peptide having the amino acid sequence of GLP-1 with deletion, substitution or addition of one or more amino acids; a peptide having the amino acid sequence of GLP-1 with conservative substitution of one or several amino acids; modified GLP-1; a GLP-1 fragment having GLP-1 activity; elongated GLP-1 having GLP-1 activity; and exendin-4 and its analog (Curr. Opin. Investig. Drugs 8, 842-8 (2007), J. Pharmacol. Exp. Ther. 307, 490-496 (2003), Diabetes 50, 2530-9 (2001), etc.).

The "amino acid" used herein is used in the broadest sense and encompasses not only natural amino acids but also non-natural amino acids such as amino acid variants and derivatives. Taking this broad definition into consideration, those skilled in the art can understand that examples of the amino acid used herein include: natural proteogenic L-amino acids; D-amino acids; chemically modified amino acids such as amino acid variants and derivatives; natural nonproteogenic amino acids such as norleucine, β-alanine and ornithine; and chemically synthesized compounds having properties characteristic of amino acids known in the art. Examples of the nonnatural amino acids include α-methyl amino acids (α-methylalanine etc.), D-amino acids, histidine-like amino acids (2-amino-histidine, β-hydroxy-histidine, homohistidine, α-fluoromethyl-histidine and α-methyl-histidine, etc.), amino acids having extra methylene in the side chain ("homo" amino acids) and amino acids having a carboxylic acid functional group in the side chain substituted with a sulfonic acid group (cysteic acid etc.). Some GLP-1 analogs having GLP-1 activity have been known to contain nonnatural amino acids. In a preferable aspect, the amino acids contained in the compound of the present invention consist only of natural amino acids.

In the phrase "deletion, substitution or addition of one or more amino acids" used herein, the number of amino acids substituted, etc. is not particularly limited as long as GLP-1 activity is maintained. The number of amino acids substituted, etc. is 1 to about 9, preferably 1 to about 5, more preferably 1 to about 3 or corresponds to within 20%, preferably within 10% of the whole length. The amino acids substituted or added may be natural amino acids, nonnatural amino acids or amino acid analogs and are preferably natural amino acids.

The "conservative substitution of one or several amino acids" used herein refers to amino acid substitution that substitutes the original amino acid with an amino acid having hydrophilicity and/or hydrophobicity indexes similar thereto and does not produce evident reduction or loss of GLP-1 activity after the substitution.

The "modified GLP-1" used herein is a compound wherein GLP-1 is naturally or artificially modified. Examples of such modification include alkylation, acylation (e.g., acetylation), amidation, carboxylation, esterification, disulfide bond formation, glycosylation, lipidation, phosphorylation, hydroxylation and labeling of one or several amino acid residues of GLP-1.

The "GLP-1 fragment having GLP-1 activity" used herein is a peptide that has deletion of one or more amino acids from the N terminal and/or C terminal of GLP-1 and maintains GLP-1 activity.

The "elongated GLP-1 having GLP-1 activity" used herein is a peptide that has addition of one or more amino acids to the N terminal and/or C terminal of GLP-1 and maintains GLP-1 activity (see e.g., Endocrinology, 125, 3109-14 (1989)).

In the phrase "peptide having one or several amino acids further added to the C terminal (position 37) of GLP-1" used herein, amino acids added to the C terminal of GLP-1 are sequentially referred to as an amino acid at position 38, an amino acid at position 39, . . . etc. In the "peptide having one or several amino acids further added to the N terminal (position 7) of GLP-1", amino acids added to the N terminal of GLP-1 are sequentially referred to as an amino acid at position 6, an amino acid at position 5, . . . etc. Examples of the "peptide having one amino acid further added to the C terminal (position 37) of GLP-1" include a peptide having Asn or Cys added to 37Gly of GLP-1.

The "oligosaccharide chain added GLP-1 peptide (glycosylated GLP-1 peptide, sugar chain added GLP-1 peptide)" of the present invention is characterized in that at least one amino acid is substituted with an oligosaccharide chain added amino acid.

The "oligosaccharide chain added GLP-1 peptide" used herein encompasses a peptide wherein at least one amino acid of GLP-1 is substituted with an oligosaccharide chain added amino acid and a peptide wherein at least one amino acid of the GLP-1 analog is substituted with an oligosaccharide chain added amino acid. These peptides are incorporated in the oligosaccharide chain added GLP-1 peptide, even when they further have deletion, substitution or addition of one or several amino acids except the oligosaccharide chain added amino acids. A peptide wherein the C terminal of any of these peptides is amidated (e.g., GLP-1 (7-36)NH$_2$ having the amino acid sequence of His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$ (SEQ ID NO: 3), wherein at least one amino acid is substituted with an oligosaccharide chain added amino acid) is also incorporated in the oligosaccharide chain added GLP-1 peptide. Salts of these peptides are also incorporated in the oligosaccharide chain added GLP-1 peptide.

The salts used herein are salts known by those skilled in the art and may be any of acid addition and base addition salts. Acids usually used for forming the acid addition salts are inorganic acids such as hydrochloric acid, hydrobromic acid, hydroiodic acid, sulfuric acid and phosphoric acid and organic acids such as p-toluenesulfonic acid, methanesulfonic acid, oxalic acid, p-bromophenylsulfonic acid, carboxylic acid, succinic acid, citric acid, benzoic acid and acetic acid. Examples of the base addition salts include salts derived from ammonium hydroxide or alkali or alkaline-earth metal hydroxides and salts derived from inorganic bases such as carbonate and bicarbonate. Particularly, pharmaceutically acceptable salts are preferable.

The "oligosaccharide chain added amino acid" used herein is an amino acid linked to an oligosaccharide chain. In this context, the oligosaccharide chain may be linked to the amino acid via a linker. The site of the oligosaccharide chain to which the amino acid is linked is not particularly limited. Preferably, the amino acid is linked to the reducing terminal of the oligosaccharide chain.

The type of the amino acid linked to the oligosaccharide chain is not particularly limited, and both natural and non-natural amino acids can be used. From the viewpoint that the oligosaccharide chain added amino acid is structurally the same as or similar to those existing in a form of glycopeptide (glycoprotein) in vivo, the oligosaccharide chain added amino acid is preferably oligosaccharide chain added Asn such as an N-linked oligosaccharide chain or oligosaccharide chain added Ser and oligosaccharide chain added Thr such as an O-linked oligosaccharide chain, particularly preferably oligosaccharide chain added Asn.

When the oligosaccharide chain is linked to the amino acid via a linker, the amino acid in the oligosaccharide chain added amino acid is preferably: an amino acid having two or more carboxyl groups in the molecule, such as aspartic acid or glutamic acid; an amino acid having two or more amino groups in the molecule, such as lysine, arginine, histidine or tryptophan; an amino acid having a hydroxyl group in the molecule, such as serine, threonine or tyrosine; an amino acid having a thiol group in the molecule, such as cysteine; or an amino acid having an amide group in the molecule, such as asparagine or glutamine, from the viewpoint of easy binding with the linker. Particularly, aspartic acid, glutamic acid, lysine, arginine, serine, threonine, cysteine, asparagine or glutamine is preferable from the viewpoint of reactivity.

In following Test Example 7-4, the oligosaccharide chain added GLP-1 peptides of the present invention exhibited no large difference in the activity of suppressing rise in blood-sugar levels between oligosaccharide chain added Asn (without a linker) and oligosaccharide chain added Cys (via a linker) as an oligosaccharide chain added amino acid, when they had the same oligosaccharide chain structures, the same structures except oligosaccharide chain structures, the same oligosaccharide chain added sites and the same numbers of oligosaccharide chains to be added.

When the oligosaccharide chain is linked to the amino acid via a linker, a wide range of linkers used in the art can be used. Examples thereof may include —NH—(CO)—(CH$_2$)$_a$—CH$_2$—, wherein:

"a" represents an integer, preferably an integer of 0 to 4, but not limited to these numbers unless linker functions of interest are inhibited; and C$_{1-10}$ polymethylene and —CH$_2$—R— wherein R is a group formed by removing one hydrogen atom from a group selected from the group consisting of alkyl, substituted alkyl, alkenyl, substituted alkenyl, alkynyl, substituted alkynyl, aryl, substituted aryl, a carbocyclic group, a substituted carbocyclic group, a heterocyclic group and a substituted heterocyclic group.

The oligosaccharide chain added GLP-1 peptide having the oligosaccharide chain added amino acid wherein the oligosaccharide chain is linked to the amino acid without a linker can have lower antigenicity than that of the oligosaccharide chain added GLP-1 peptide wherein the oligosaccharide chain is linked to the amino acid via a linker. The oligosaccharide chain added GLP-1 peptide having the oligosaccharide chain added amino acid wherein the oligosaccharide chain is linked to the amino acid via a linker can have higher stability in blood than that of the oligosaccharide chain added GLP-1 peptide wherein the oligosaccharide chain is linked to the amino acid without a linker.

A process for producing the oligosaccharide chain added GLP-1 peptide of the present invention is not limited by any means by the description (e.g., the description stating "oligosaccharide chain added GLP-1 peptide wherein an amino acid is substituted with an oligosaccharide chain added amino acid). An oligosaccharide chain added GLP-1 peptide produced by any of following Processes A and B is incorporated in the "oligosaccharide chain added GLP-1 peptide wherein an amino acid is substituted with a oligosaccharide chain added amino acid". Moreover, e.g.: an oligosaccharide chain added GLP-1 peptide wherein an amino acid-unlinked oligosaccharide chain is linked directly or via a linker to an amino acid in the peptide; an oligosaccharide chain added GLP-1 peptide wherein an oligosaccharide chain already added is further elongated by the addition of a sugar or oligosaccharide chain thereto; and an oligosaccharide chain added GLP-1 peptide wherein one or several amino acids bound with amino and/or carboxyl groups of the oligosaccharide chain added amino acid are further linked to one or several GLP-1 fragments are also incorporated in the oligosaccharide chain added GLP-1 peptide of the present invention as long as their final structures are in agreement therewith.

The number of substitutions that substitute an amino acid of GLP-1 with an oligosaccharide chain added amino acid may be adjusted appropriately according to stability in blood, biological activities (e.g., the activity of controlling blood-sugar levels), the number of amino acids existing in the final oligosaccharide chain added GLP-1 peptide, the molecular weights of the oligosaccharide chain added GLP-1 peptide before and after the addition of oligosaccharide chain, etc. For example, 1 to 5 substitutions are preferable, and 1 to 3 substitutions are more preferable. Preferably, one substitution may be selected from the viewpoint of convenience as long as this one substitution produces the desired activity. In general, an oligosaccharide chain added GLP-1 peptide wherein one amino acid of GLP-1 is substituted with an oligosaccharide chain added amino acid exhibits enhanced stability in blood and reduced activity of controlling blood-sugar levels, when one or more amino acids except the oligosaccharide chain added amino acids are further substituted with an oligosaccharide chain added amino acid (however, the reduced activity of controlling blood-sugar levels can be compensated by the enhanced stability in blood).

In the oligosaccharide chain added GLP-1 peptide of the present invention, the substitution site of an amino acid with an oligosaccharide chain added amino acid can be adjusted appropriately according to stability in blood or the activity of controlling blood-sugar levels.

In one aspect of the present invention, the substitution site of an amino acid of GLP-1 with an oligosaccharide chain added amino acid can be selected from any sites of GLP-1 according to the desired activity and is, e.g., at least one site selected from positions 8, 9, 12, 18, 19, 20, 22, 26, 30, 34, 36 and 38 (=addition of an oligosaccharide chain added amino acid to an amino acid at position 37) of GLP1, preferably at least one site selected from positions 18, 20, 22, 26, 30, 34, 36 and 38, e.g., at least one site selected from positions 26, 30, 34 and 36, and particularly at least one site selected from positions 30 and 36.

In one aspect of the present invention, from the viewpoint of the stability of the oligosaccharide chain added GLP-1 peptide in blood, the substitution site of an amino acid with an oligosaccharide chain added amino acid can be selected from any sites of GLP-1 and is, e.g., at least one site selected from positions 9, 10, 11, 12, 14, 16, 18, 19, 20, 22, 24, 25, 26, 27, 28, 30, 32, 34, 36 and 38 (=addition of an oligosaccharide chain added amino acid to an amino acid at position 37) of GLP-1, preferably at least one site selected from positions 9, 10, 11, 12, 14 and 28, and particularly preferably at least one site selected from positions 9, 10, 11 and 12. Particularly, substitution of an amino acid at a site close to the N terminal of GLP-1 is also preferable. Particularly, examples of the substitution sites of two amino acids of GLP-1 with oligosaccharide chain added amino acids may include substitution of positions 18 and 36 and substitution of positions 26 and 34 of GLP-1.

In one aspect of the present invention, from the viewpoint of the effect of controlling blood-sugar levels by the oligosaccharide chain added GLP-1 peptide, the substitution site of an amino acid with an oligosaccharide chain added amino acid is, e.g., at least one site selected from positions 18, 20, 22, 26, 30, 34, 36 and 38 (=addition of an oligosaccharide chain added amino acid to an amino acid at position 37) of GLP-1, preferably at least one site selected from positions 26, 30, 34 and 36, and particularly at least one site selected from positions 30 and 36. Particularly, examples of the substitution sites of two amino acids of GLP-1 with oligosaccharide chain added amino acids may include substitution of positions 18 and 36 and substitution of positions 26 and 34 of GLP-1, from the viewpoint of the effect of controlling blood-sugar levels by the oligosaccharide chain added GLP-1 peptide.

In one aspect of the present invention, from the viewpoint of the ability to synthesize cAMP, of the GLP-1 activities of the oligosaccharide chain added GLP-1 peptide, the substitution site of an amino acid with an oligosaccharide chain added amino acid is preferably at least one site selected from positions 22, 26, 27, 30, 34, 36 and 38 (=addition of an oligosaccharide chain added amino acid to an amino acid at position 37), and more preferably at least one site selected from positions 22, 26, 30, 34, 36 and 38.

In one aspect of the present invention, the substitution site of an amino acid with an oligosaccharide chain added amino acid is at least one site selected from sites except positions 8, 9 and 12 of GLP-1.

In one aspect of the present invention, the substitution site of an amino acid with an oligosaccharide chain added amino acid is at least one site selected from sites except positions 7, 10, 13, 15, 19, 21, 28 and 29 of GLP-1, and particularly at least one site selected from sites except positions 7, 10, 15 and 28.

In one aspect of the present invention, the substitution site of an amino acid with an oligosaccharide chain added amino acid can be determined from the binding sites of GLP-1 to a GLP-1 receptor.

In one aspect of the present invention, when two or more amino acids are substituted with oligosaccharide chain added amino acids, the substitution sites of the amino acids with oligosaccharide chain added amino acids can be selected from, but not limited to, any of combinations of the sites described above. For example, a combination wherein one site is selected from the preferable sites and the other sites are selected from any sites of GLP-1, and a combination wherein one site is selected from the preferable sites and the other sites are selected from any sites of one or several amino acids further added to the C terminal (position 37) of GLP-1 are also incorporated in a preferable aspect of the present invention.

In one aspect of the present invention, preferable examples of the deletion, substitution or addition of one or several amino acids except the oligosaccharide chain added amino acid(s) in GLP-1 may include, but not limited to:

substitution of 8Ala with an amino acid selected from the group consisting of Gly, Ser, Thr, Leu, Ile, Val, Glu, Asp and Lys;

substitution of 9Glu with an amino acid selected from the group consisting of Asp and Lys;

substitution of 11Thr with an amino acid selected from the group consisting of Ala, Gly, Ser, Leu, Ile, Val, Glu, Asp and Lys;

substitution of 12Phe with an amino acid selected from the group consisting of Trp and Tyr;

substitution of 13Thr with Ser;

substitution of 14Ser with an amino acid selected from the group consisting of Ala, Gly, Thr, Leu, Ile, Val, Glu, Asp and Lys;

substitution of 15Asp with Glu;

substitution of 16Val with an amino acid selected from the group consisting of Phe, Ala, Gly, Ser, Thr, Leu, Ile, Tyr, Glu, Asp and Lys;

substitution of 17Ser with an amino acid selected from the group consisting of Ala, Gly, Thr, Leu, Ile, Val, Glu, Asp and Lys;

substitution of 18Ser with an amino acid selected from the group consisting of Ala, Gly, Thr, Leu, Ile, Val, Glu, Asp and Lys;

substitution of 19Tyr with an amino acid selected from the group consisting of Phe, Trp, Glu, Asp and Lys;

substitution of 20Leu with an amino acid selected from the group consisting of Ala, Gly, Ser, Thr, Leu, Ile, Val, Glu, Asp and Lys substitution of 21Glu with an amino acid selected from the group consisting of Asp and Lys;

substitution of 22Gly with an amino acid selected from the group consisting of Ala, Ser, Thr, Leu, Ile, Val, Glu, Asp and Lys;

substitution of 23Gln with an amino acid selected from the group consisting of Asn, Arg, Glu, Asp and Lys;

substitution of 24Ala with an amino acid selected from the group consisting of Gly, Ser, Thr, Leu, Ile, Val, Arg, Glu, Asp and Lys;

substitution of 25Ala with an amino acid selected from the group consisting of Gly, Ser, Thr, Leu, Ile, Val, Glu, Asp and Lys;

substitution of 26Lys with an amino acid selected from the group consisting of Arg, Gln, Glu, Asp and His;

substitution of 27Glu with an amino acid selected from the group consisting of Asp, Ile and Lys;

substitution of 28Phe with Trp;

substitution of 29Ile with an amino acid selected from the group consisting of Leu, Val and Ala;

substitution of 30Ala with an amino acid selected from the group consisting of Gly, Ser, Thr, Leu, Ile, Val, Glu, Asp and Lys;

substitution of 31Trp with an amino acid selected from the group consisting of Phe, Tyr, Glu, Asp and Lys;

substitution of 32Leu with an amino acid selected from the group consisting of Gly, Ala, Ser, Thr, Ile, Val, Glu, Asp and Lys;

substitution of 33Val with an amino acid selected from the group consisting of Gly, Ala, Ser, Thr, Leu, Ile, Glu, Asp and Lys;

substitution of 34Lys with an amino acid selected from the group consisting of Arg, Glu, Asp and His;

substitution of 35Gly with an amino acid selected from the group consisting of Ala, Ser, Thr, Leu, Ile, Val, Glu, Asp and Lys;

substitution of 36Arg with an amino acid selected from the group consisting of Lys, Glu, Asp and His; and/or substitution of 37Gly with an amino acid selected from the group consisting of Ala, Ser, Thr, Leu, Ile, Val, Glu, Asp and Lys.

In one aspect of the present invention, a site of the deletion, substitution or addition of amino acids except the oligosaccharide chain added amino acids is preferably at least one site selected from sites except positions 7, 10, 13, 15, 19, 21, 28 and 29 of GLP-1, e.g., at least one site selected from sites except positions 7, 10, 15 and 28, (Structure-Activity Studies of Glucagon-like Peptide-1, THE JOURNAL OF BIOLOGICAL CHEMISTRY Vol. 269, No. 9, Issue of March 4, pp. 6276-6278. 1994).

Examples of the oligosaccharide chain added GLP-1 peptide of the present invention include an oligosaccharide chain added GLP-1 peptide represented by the general formula (1):

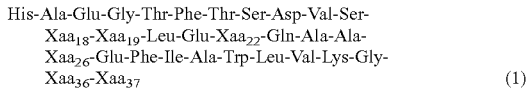

wherein:

$Xaa_{18}$ represents Ser, oligosaccharide chain added Cys or oligosaccharide chain added Asn;

$Xaa_{19}$ represents Tyr, oligosaccharide chain added Cys or oligosaccharide chain added Asn;

$Xaa_{22}$ represents Gly, oligosaccharide chain added Cys or oligosaccharide chain added Asn;

$Xaa_{26}$ represents Lys, oligosaccharide chain added Cys or oligosaccharide chain added Asn;

$Xaa_{36}$ represents Arg, oligosaccharide chain added Cys or oligosaccharide chain added Asn, $Xaa_{37}$ represents Gly, $NH_2$, Gly-oligosaccharide chain added Cys or Gly-oligosaccharide chain added Asn, and when $Xaa_{18}$ is Ser, $Xaa_{19}$ is Tyr, $Xaa_{22}$ is Gly, $Xaa_{26}$ is Lys, and $Xaa_{36}$ is Arg, then $Xaa_{37}$ represents Gly-oligosaccharide chain added Cys or Gly-oligosaccharide chain added Asn. The peptide represented by the general formula (1) is represented by SEQ ID NO: 1 herein.

Specific examples of the oligosaccharide chain added GLP-1 peptide of the present invention may include:

(a1) a peptide represented by the general formula (1) wherein $Xaa_{18}$ represents oligosaccharide chain added Cys, $Xaa_{19}$ represents Tyr, $Xaa_{22}$ represents Gly, $Xaa_{26}$ represents Lys, $Xaa_{36}$ represents Arg and $Xaa_{37}$ represents Gly (SEQ ID NO:4);

(a2) a peptide represented by the general formula (1) wherein $Xaa_{18}$ represents Ser, $Xaa_{19}$ represents Tyr, $Xaa_{22}$ represents oligosaccharide chain added Cys, $Xaa_{26}$ represents Lys, $Xaa_{36}$ represents Arg and $Xaa_{37}$ represents Gly (SEQ ID NO:5);

(a3) a peptide represented by the general formula (1) wherein $Xaa_{18}$ represents Ser, $Xaa_{19}$ represents Tyr, $Xaa_{22}$ represents Gly, $Xaa_{26}$ represents oligosaccharide chain added Cys, $Xaa_{36}$ represents Arg and $Xaa_{37}$ represents Gly (SEQ ID NO:6);

(a4) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{36}$ represents oligosaccharide chain added Cys, and $Xaa_{37}$ represents Gly (SEQ ID NO:7);

(a5) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{36}$ represents Arg and $Xaa_{37}$ represents oligosaccharide chain added Cys (SEQ ID NO:8);

(a6) a peptide represented by the general formula (1) wherein $Xaa_1$ represents Ser, $Xaa_{19}$ represents oligosaccharide chain added Cys, $Xaa_{22}$ represents Gly, $Xaa_{26}$ represents Lys, $Xaa_{36}$ represents Arg and $Xaa_{37}$ represents Gly (SEQ ID NO:9);

(a7) a peptide represented by the general formula (1) wherein $Xaa_{18}$ oligosaccharide chain added Asn, $Xaa_{19}$ represents Tyr, $Xaa_{22}$ represents Gly, $Xaa_{26}$ represents Lys, $Xaa_{36}$ represents Arg and $Xaa_{37}$ represents Gly (SEQ ID NO:10);

(a8) a peptide represented by the general formula (1) wherein $Xaa_{18}$ represents Ser, $Xaa_{19}$ represents Tyr, $Xaa_{22}$ represents oligosaccharide chain added Asn, $Xaa_{26}$ represents Lys, $Xaa_{36}$ represents Arg and $Xaa_{37}$ represents Gly (SEQ ID NO:11);

(a9) a peptide represented by the general formula (1) wherein $Xaa_{18}$ represents Ser, $Xaa_{19}$ represents Tyr, $Xaa_{22}$ represents Gly, $Xaa_{26}$ represents oligosaccharide chain added Asn, $Xaa_{36}$ represents Arg and $Xaa_{37}$ represents Gly (SEQ ID NO:12);

(a10) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{36}$ represents oligosaccharide chain added Asn and $Xaa_{37}$ represents Gly (SEQ ID NO:13);

(a11) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{36}$ represents Arg and $Xaa_{37}$ represents oligosaccharide chain added Asn (SEQ ID NO:14);

(a12) a peptide represented by the general formula (1) wherein $Xaa_{18}$ represents Ser, $Xaa_{19}$ represents oligosaccharide chain added Asn, $Xaa_{22}$ represents Gly, $Xaa_{26}$ represents Lys, $Xaa_{36}$ represents Arg and $Xaa_{37}$ represents Gly (SEQ ID NO:15);

(a13) a peptide represented by the general formula (1) wherein $Xaa_{18}$ represents oligosaccharide chain added Cys, $Xaa_{19}$ represents Tyr, $Xaa_{22}$ represents Gly, $Xaa_{26}$ represents Lys, $Xaa_{36}$ represents Arg and $Xaa_{37}$ represents $NH_2$ (SEQ ID NO:16);

(a14) a peptide represented by the general formula (1) wherein $Xaa_{18}$ represents Ser, $Xaa_{19}$ represents Tyr, $Xaa_{22}$ represents oligosaccharide chain added Cys, $Xaa_{26}$ represents Lys, $Xaa_{36}$ represents Arg and $Xaa_{37}$ represents $NH_2$ (SEQ ID NO:17);

(a15) a peptide represented by the general formula (1) wherein $Xaa_{18}$ represents Ser, $Xaa_{19}$ represents Tyr, $Xaa_{22}$ represents Gly, $Xaa_{26}$ represents oligosaccharide chain added Cys, $Xaa_{36}$ represents Arg and $Xaa_{37}$ represents $NH_2$ (SEQ ID NO:18);

(a16) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{36}$ represents oligosaccharide chain added Cys and $Xaa_{37}$ represents $NH_2$ (SEQ ID NO:19);

(a17) a peptide represented by the general formula (1) wherein $Xaa_{18}$ represents Ser, $Xaa_{19}$ represents oligosaccharide chain added Cys, $Xaa_{22}$ represents Gly, $Xaa_{26}$ represents Lys, $Xaa_{36}$ represents Arg and $Xaa_{37}$ represents $NH_2$ (SEQ ID NO:20);

(a18) a peptide represented by the general formula (1) wherein $Xaa_{18}$ represents oligosaccharide chain added Asn, $Xaa_{19}$ represents Tyr, $Xaa_{22}$ represents Gly, $Xaa_{26}$ represents Lys, $Xaa_{36}$ represents Arg and $Xaa_{37}$ represents $NH_2$ (SEQ ID NO:21);

(a19) a peptide represented by the general formula (1) wherein $Xaa_{18}$ represents Ser, $Xaa_{19}$ represents Tyr, $Xaa_{22}$ represents oligosaccharide chain added Asn, $Xaa_{26}$ represents Lys, $Xaa_{36}$ represents Arg and $Xaa_{37}$ represents $NH_2$ (SEQ ID NO:22);

(a20) a peptide represented by the general formula (1) wherein $Xaa_{18}$ represents Ser, $Xaa_{19}$ represents Tyr, $Xaa_{22}$ represents Gly, $Xaa_{26}$ represents oligosaccharide chain added Asn, $Xaa_{36}$ represents Arg and $Xaa_{37}$ represents $NH_2$ (SEQ ID NO:23);

(a21) a peptide represented by the general formula (1) wherein $Xaa_{18}$ represents Ser, $Xaa_{19}$ represents Tyr, $Xaa_{22}$ represents Gly, $Xaa_{26}$ represents Lys, $Xaa_{36}$ represents oligosaccharide chain added Asn and $Xaa_{37}$ represents $NH_2$ (SEQ ID NO:24);

(a22) a peptide represented by the general formula (1) wherein $Xaa_{18}$ represents Ser, $Xaa_{19}$ represents oligosaccharide chain added Asn, $Xaa_{22}$ represents Gly, $Xaa_{26}$ represents Lys, $Xaa_{36}$ represents Arg and $Xaa_{37}$ represents $NH_2$ (SEQ ID NO:25);

(a23) a peptide represented by the general formula (1) wherein $Xaa_{18}$ represents oligosaccharide chain added Cys, $Xaa_{19}$ represents Tyr, $Xaa_{22}$ represents oligosaccharide chain added Cys, $Xaa_{26}$ represents Lys, $Xaa_{36}$ represents Arg and $Xaa_{37}$ represents Gly-oligosaccharide chain added Cys (SEQ ID NO:26);

(a24) a peptide represented by the general formula (1) wherein $Xaa_{18}$ represents oligosaccharide chain added Cys, $Xaa_{19}$ represents Tyr, $Xaa_{22}$ represents oligosaccharide chain added Cys, $Xaa_{26}$ represents oligosaccharide chain added Cys, $Xaa_{36}$ represents Arg and $Xaa_{37}$ represents Gly (SEQ ID NO:27);

(a25) a peptide represented by the general formula (1) wherein $Xaa_{18}$ represents Ser, $Xaa_{19}$ represents Tyr, represents Gly, $Xaa_{26}$ represents oligosaccharide chain added Asn, $Xaa_{36}$ represents oligosaccharide chain added Asn and $Xaa_{37}$ represents Gly-oligosaccharide chain added Asn (SEQ ID NO:28); and (a26) a peptide represented by the general formula (1) wherein $Xaa_{18}$ represents oligosaccharide chain added Asn, $Xaa_{19}$ represents Tyr, $Xaa_{22}$ represents oligosaccharide chain added Asn, $Xaa_{26}$ represents oligosaccharide chain added Asn, $Xaa_{36}$ represents Arg and $Xaa_{37}$ represents $NH_2$ (SEQ ID NO:29).

The "oligosaccharide chain" used herein refers to a compound composed of at least one sugar unit (monosaccharide and/or its derivative). When two or more sugar units are linked, these sugar units are bound by dehydrating condensation through a glycosidic linkage between them. Examples of such a oligosaccharide chain include, but not limited to, monosaccharides and polysaccharides (glucose, galactose, mannose, fucose, xylose, N-acetylglucosamine, N-acetylgalactosamine, sialic acid and their complexes and derivatives) contained in living bodies as well as a wide range of oligosaccharide chains such as degraded polysaccharides and those degraded or derived from complex biological molecules such as glycoproteins, proteoglycans, glycosaminoglycans and glycolipids. The oligosaccharide chain may be linear or branched.

The "oligosaccharide chain" used herein also encompasses oligosaccharide chain derivatives. Examples of the oligosaccharide chain derivatives include, but not limited to, oligosaccharide chains composed of a sugar having a carboxyl group (e.g., aldonic acid which is carboxylic acid formed by oxidation at C-1 position (e.g., D-gluconic acid formed by the oxidation of D-glucose) and uronic acid wherein the terminal carbon atom has been oxidized to a carboxyl group (D-glucuronic acid formed by the oxidation of D-glucose)); a sugar having an amino group or amino group derivative (e.g., acetylated amino group) (e.g., N-acetyl-D-glucosamine and N-acetyl-D-galactosamine); a sugar having both amino and carboxyl groups (e.g., N-acetylneuraminic acid (sialic acid) and N-acetylmuramic acid); a deoxy sugar (e.g., 2-deoxy-D-ribose); a sulfated sugar containing a sulfuric acid group; and a phosphorylated sugar containing a phosphoric acid group.

In the present invention, preferable oligosaccharide chains enhance stability in blood and, more preferably, do not delete the activity of controlling blood-sugar levels, when added to GLP-1 (i.e., when an amino acid of GLP-1 is substituted with an oligosaccharide chain added amino acid). In one aspect of the present invention, preferable oligosaccharide chains enhance the activity of controlling blood-sugar levels, when added to GLP-1 (i.e., when an amino acid of GLP-1 is substituted with an oligosaccharide chain added amino acid).

From the viewpoint that the oligosaccharide chain added GLP-1 peptide of the present invention is administered to living bodies, the oligosaccharide chain in the oligosaccharide chain added GLP-1 peptide of the present invention exists in vivo in a form of complex carbohydrate (glycopeptide (or glycoprotein), proteoglycan, glycolipid, etc.) and is preferably an N-linked oligosaccharide chain, an O-linked oligosaccharide chain, etc., which is bound in vivo to a peptide (or protein) to form a glycopeptide (or glycoprotein).

Preferably, the oligosaccharide chain used in the present invention is an N-linked oligosaccharide chain. Examples of the N-linked oligosaccharide chain may include a high-mannose type, a complex type and a hybrid type. The complex type is particularly preferable.

In one aspect of the present invention, the oligosaccharide chain in the oligosaccharide chain added GLP-1 peptide of the present invention is preferably an oligosaccharide chain consisting of four or more sugars, e.g., five or more, seven or more, nine or more or eleven or more sugars.

In a preferable aspect of the present invention, the oligosaccharide chain in the oligosaccharide chain added GLP-1 peptide of the present invention consists of five to eleven, nine to eleven or eleven sugars.

In a preferable aspect of the present invention, the oligosaccharide chain in the oligosaccharide chain added GLP-1 peptide of the present invention is an oligosaccharide chain selected from the group consisting of disialo, monosialo, asialo (digalactose), diGlcNAc (diN-acetylglucosamine) and dimannose oligosaccharide chains and is more preferably a disialo oligosaccharide chain.

Examples of preferable oligosaccharide chains usable in the present invention include an oligosaccharide chain represented by the following general formula:

[Formula 3]

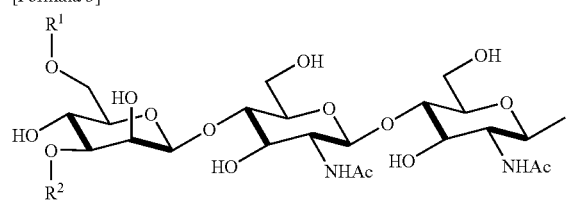

wherein

R¹ and R² are the same or different and each represents

[Formula 4]

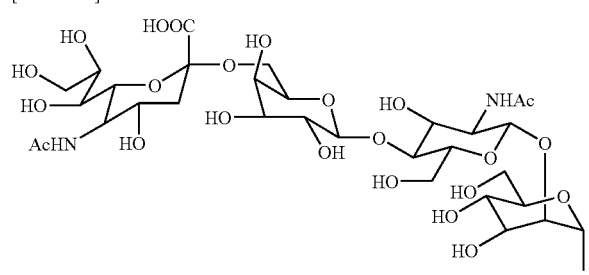

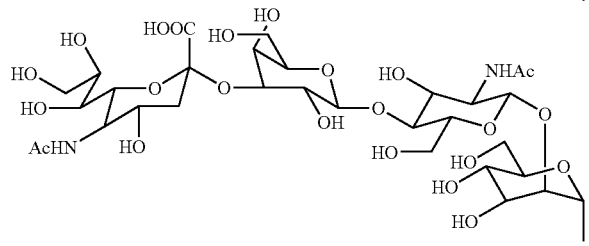

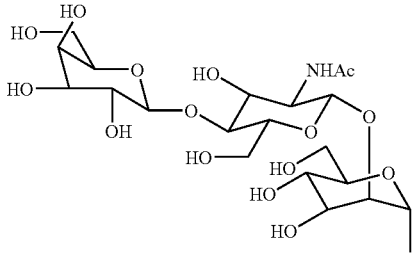

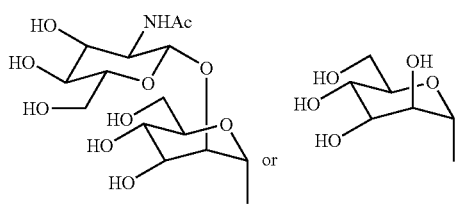

or and

Ac represents an acetyl group.

In the present invention, examples of preferable oligosaccharide chain may include oligosaccharide chain structurally the same as (oligosaccharide chains having the same types of constituent sugars and the same patterns of linkages of the sugars) oligosaccharide chain which is bound to a protein to form a glycoprotein in human bodies (e.g., oligosaccharide chains described in "FEBS LETTERS Vol. 50, No. 3, February 1975"), and oligosaccharide chain lacking one or several sugars from the nonreducing end thereof, which are described in Tables 1 to 4 below.

TABLE 1

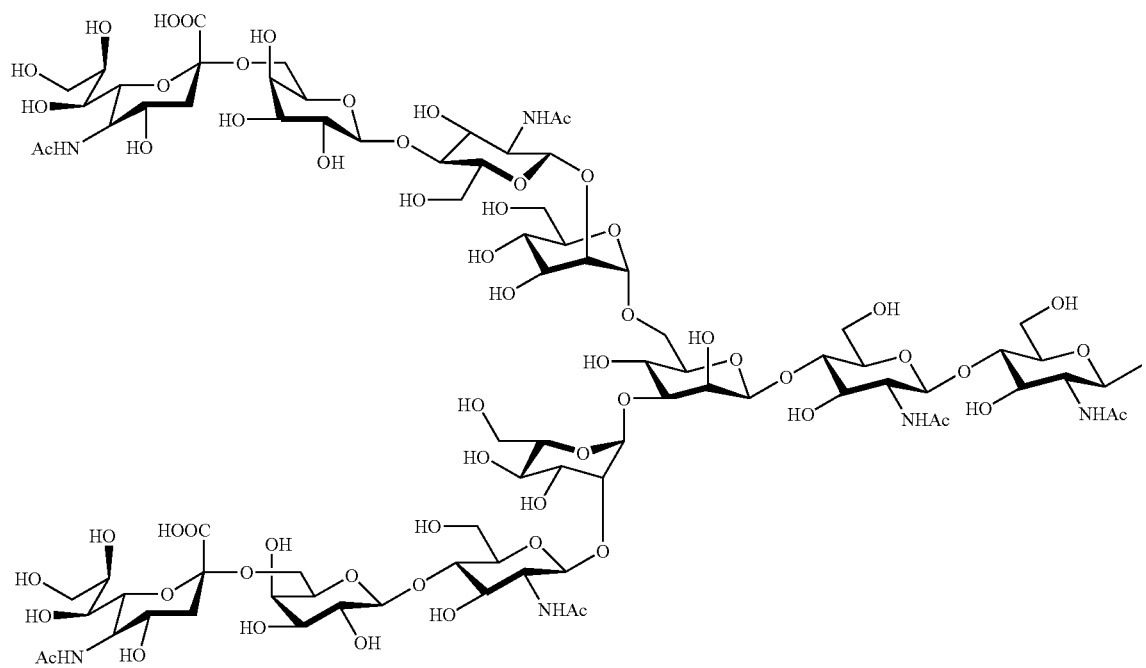

1S2S-11NC,

TABLE 1-continued
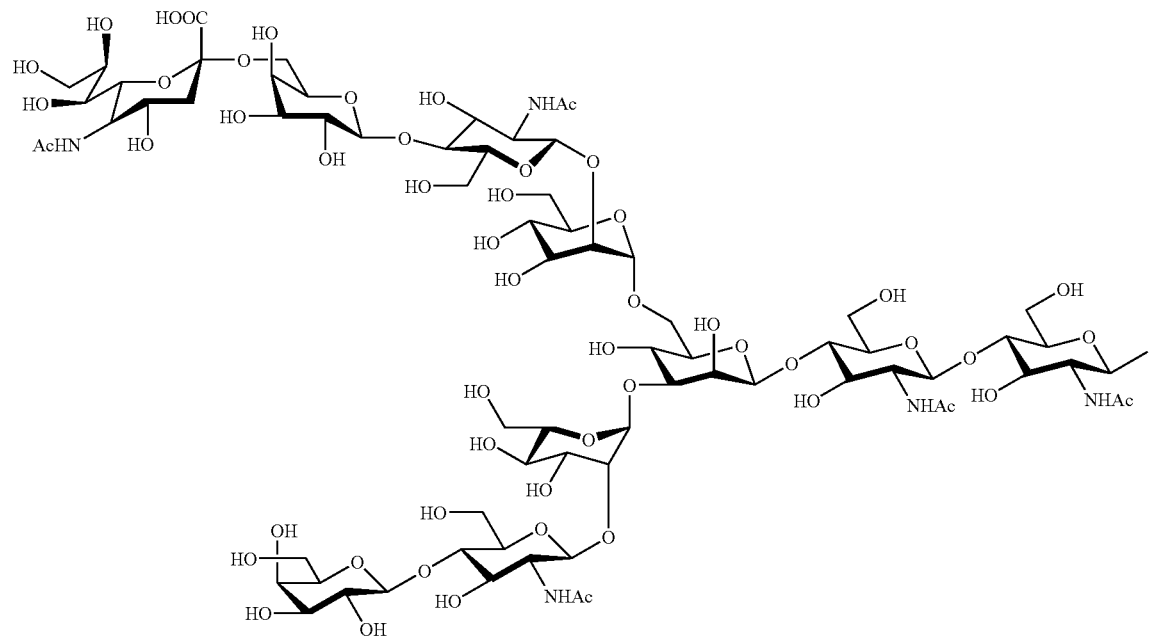
1S2G-10NC,
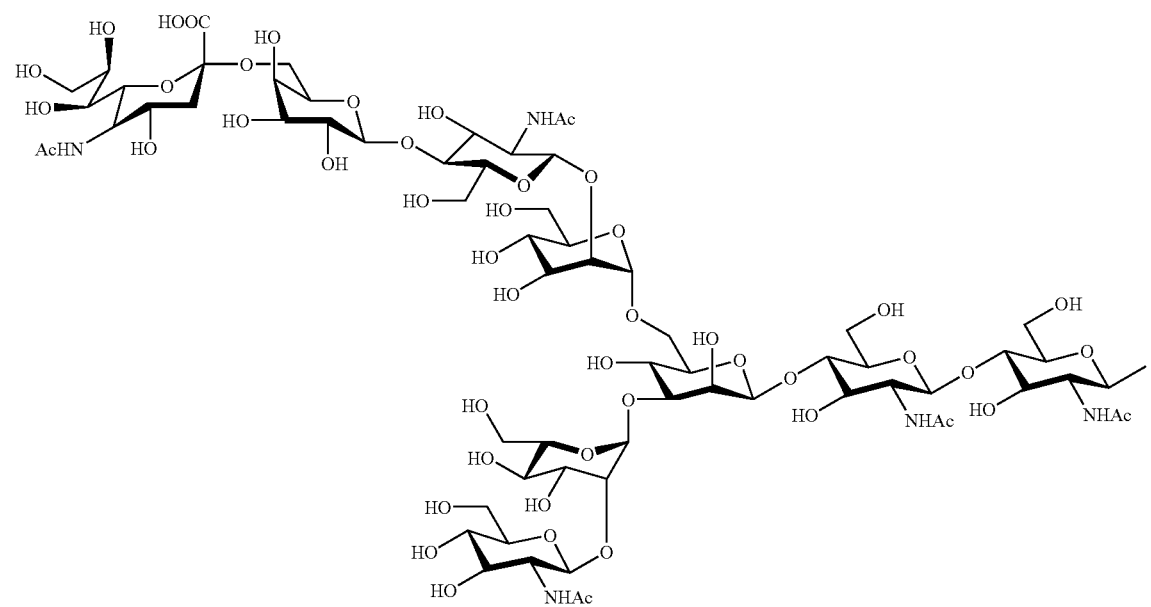
1S2GN-9NC,

TABLE 1-continued
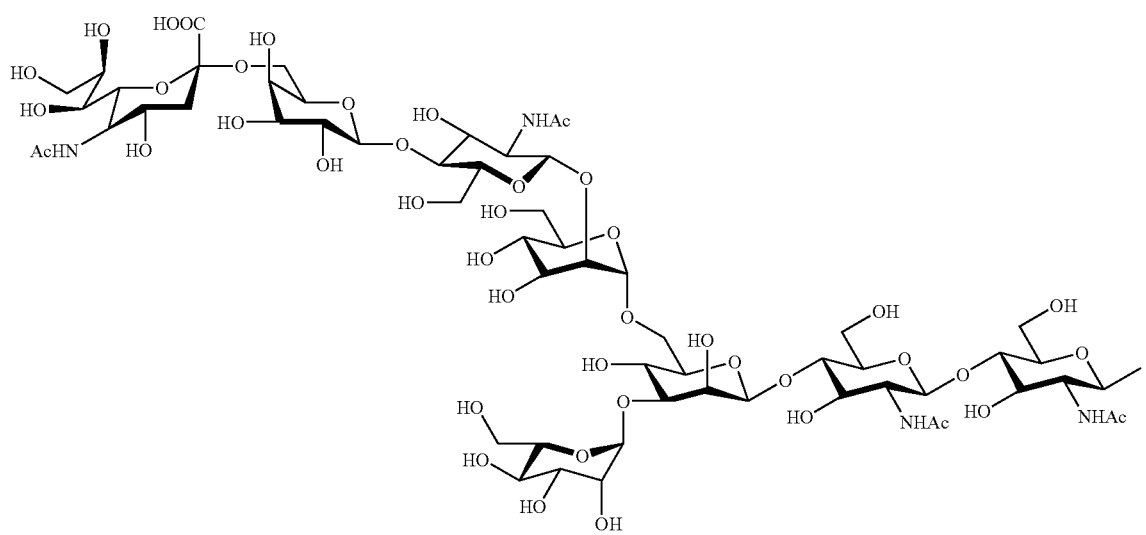
1S2M-8NC,
4
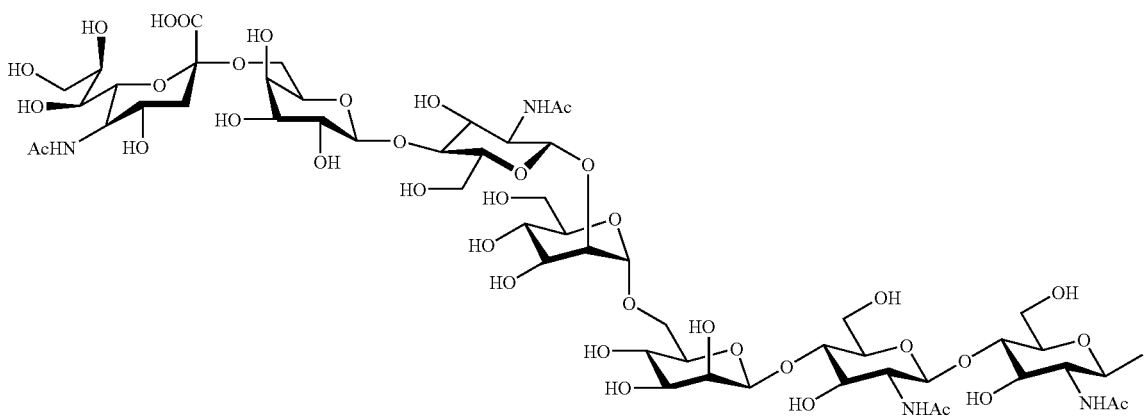
1S-7NC,
5

TABLE 1-continued
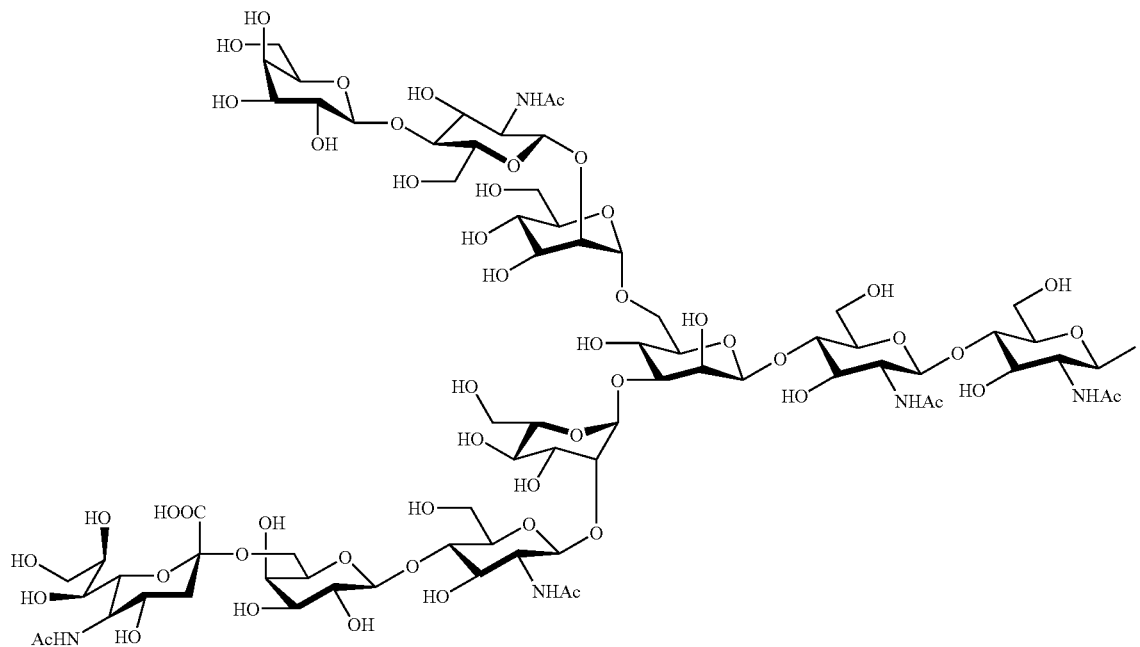
1G2S-10NC,
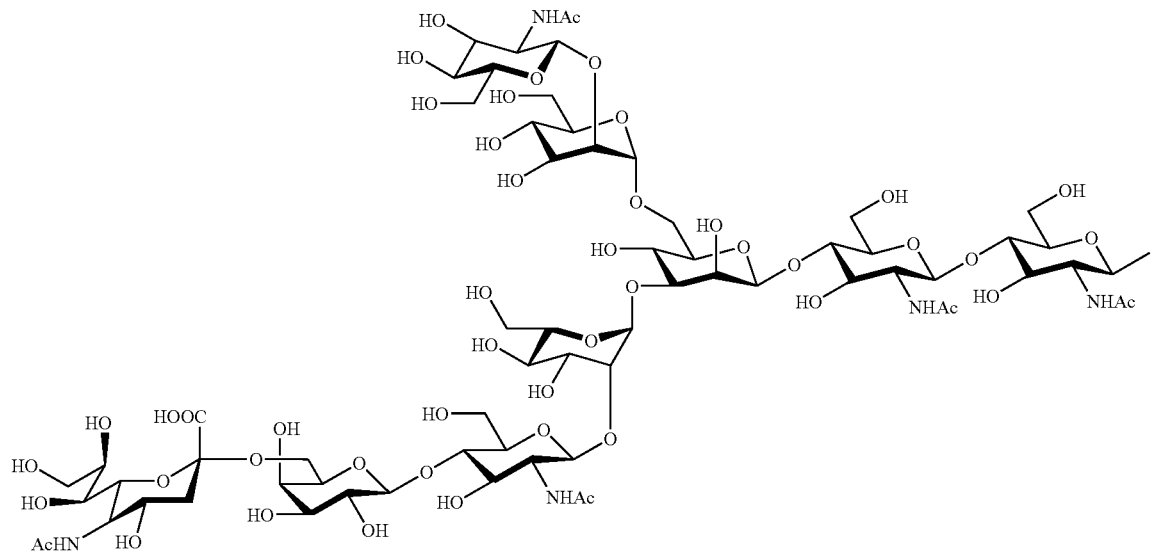
1GN2S-9NC,

TABLE 1-continued
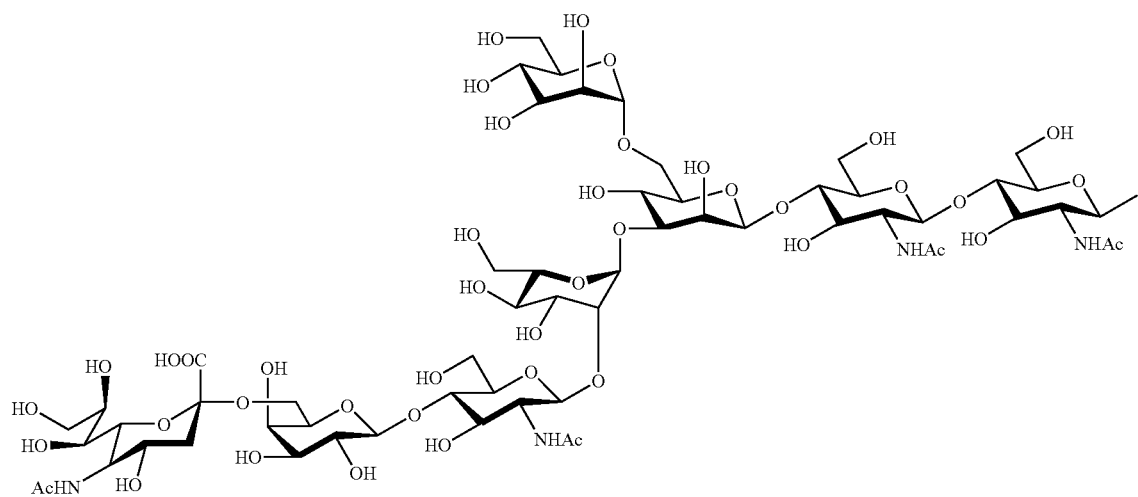
1M2S-8NC,
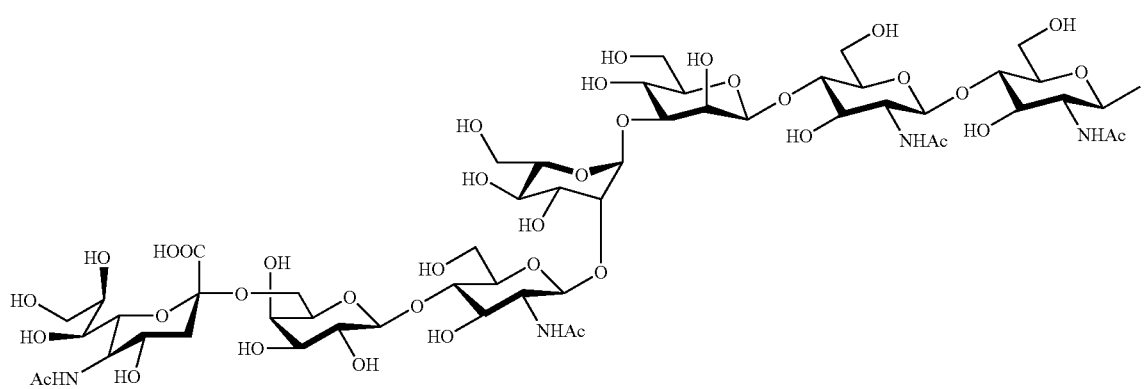
2S-7NC,

TABLE 2
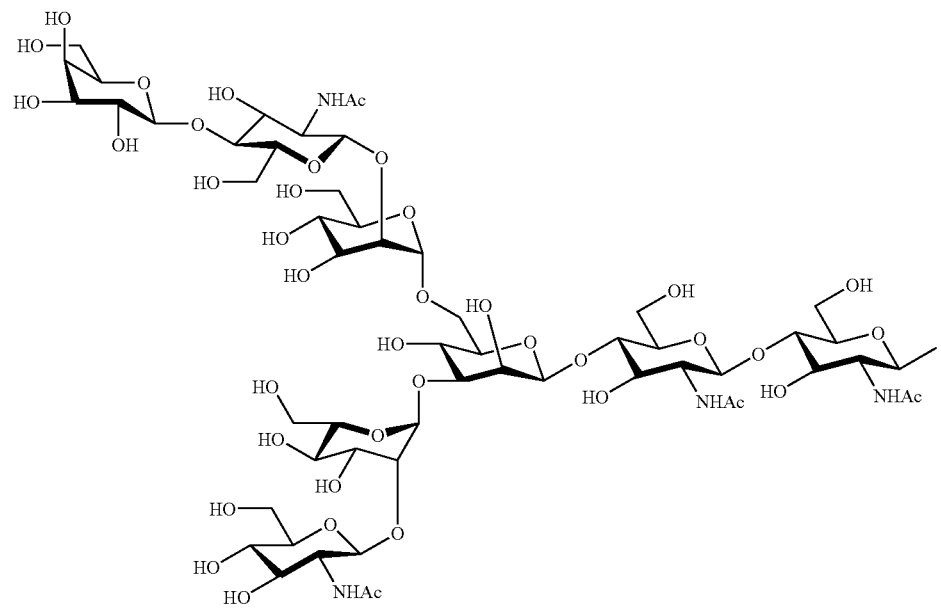
1G2GN-8NC,
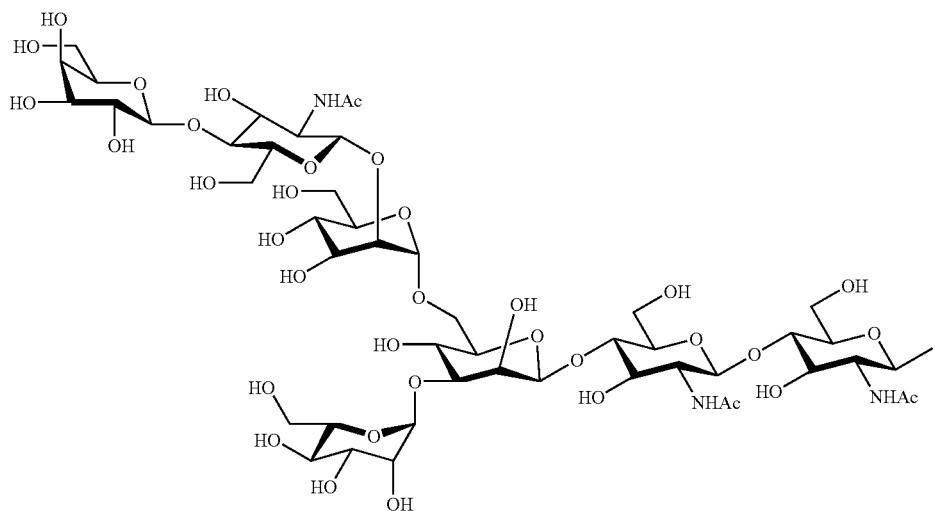
1G2M-7NC,

TABLE 2-continued
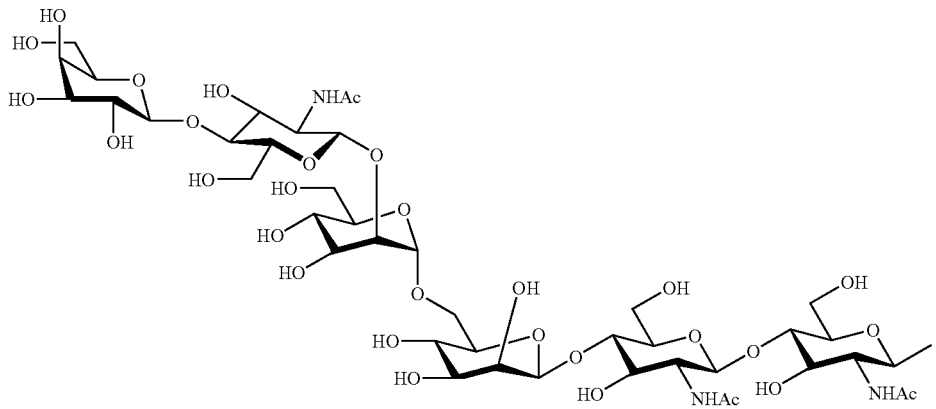
1G-6NC,
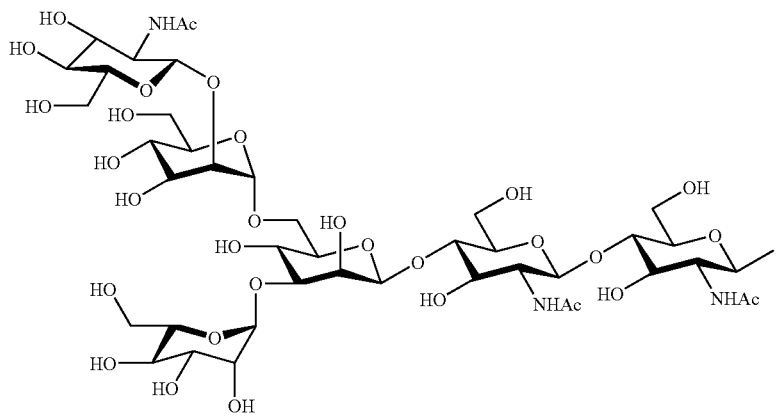
1GN2M-6NC,
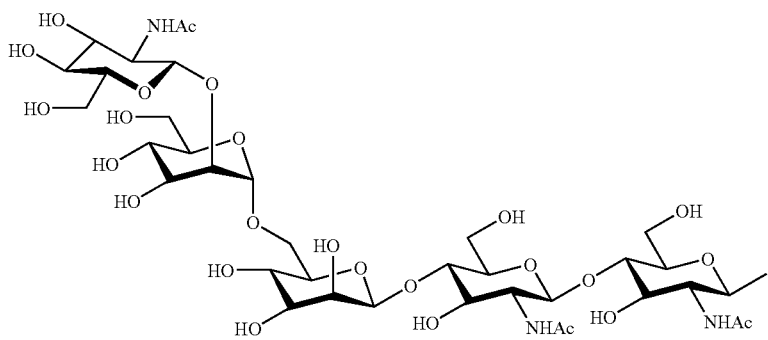
1GN-5NC,

TABLE 2-continued
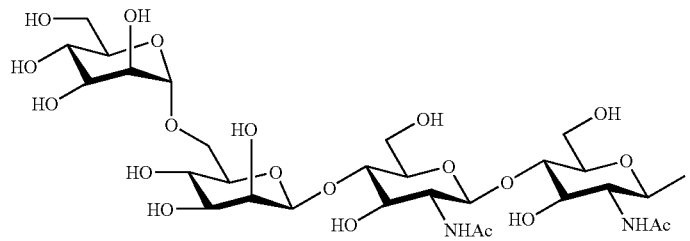
1M-4NC,
15
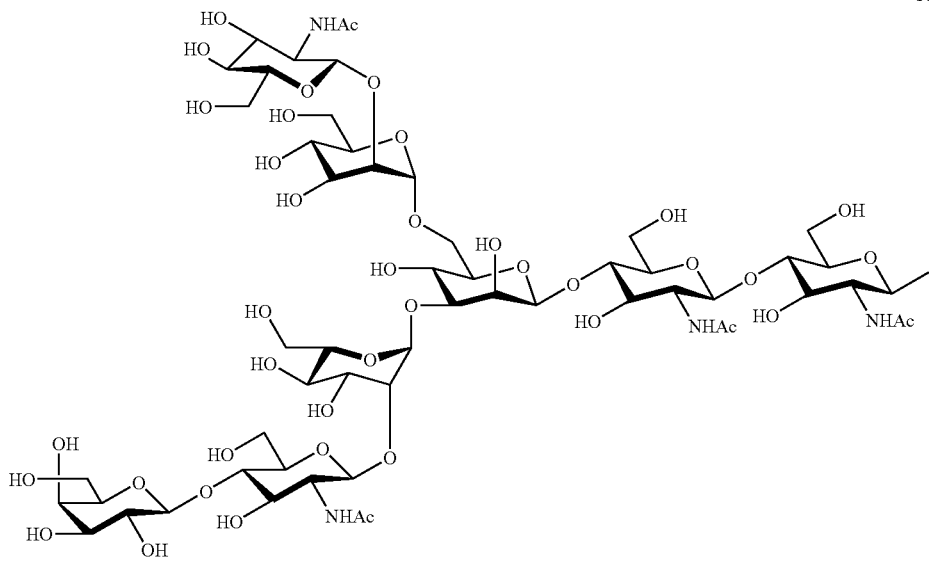
1GN2G-8NC,
16
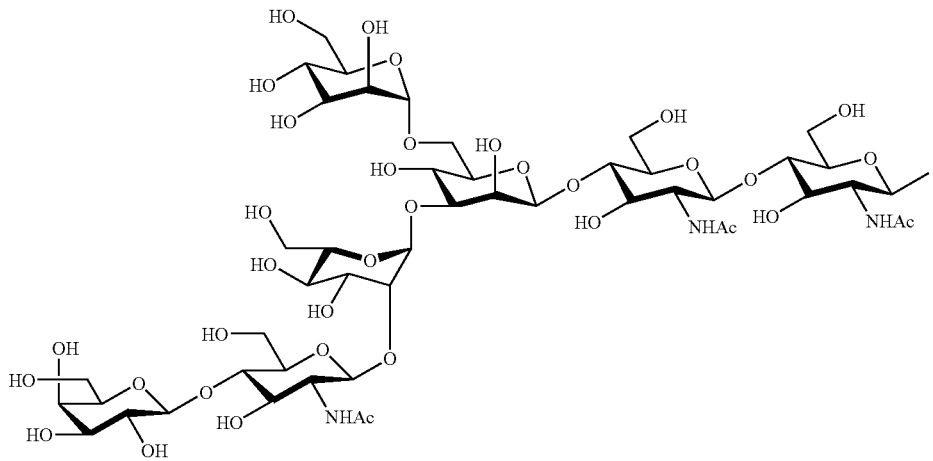
1M2G-7NC,
17

TABLE 2-continued
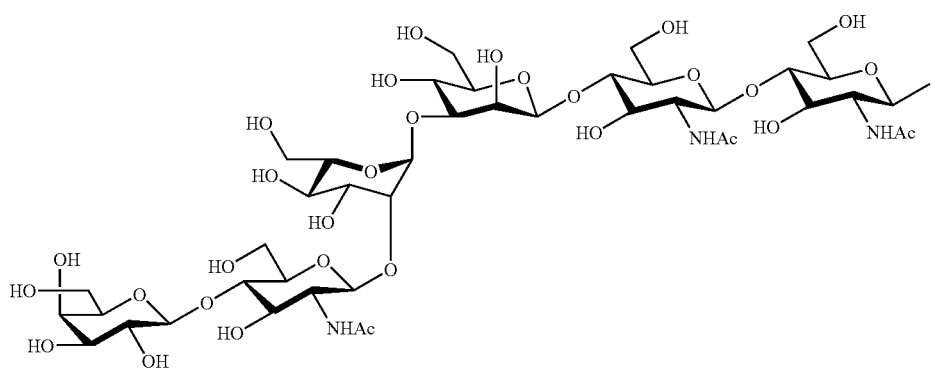
2G-6NC,
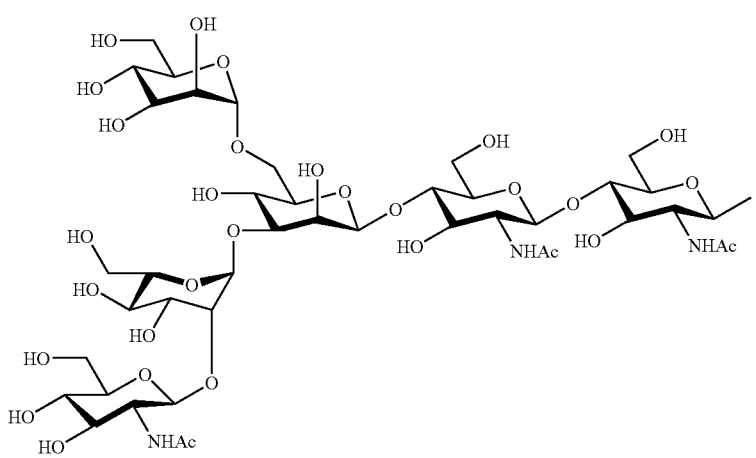
1M2GN-5NC,
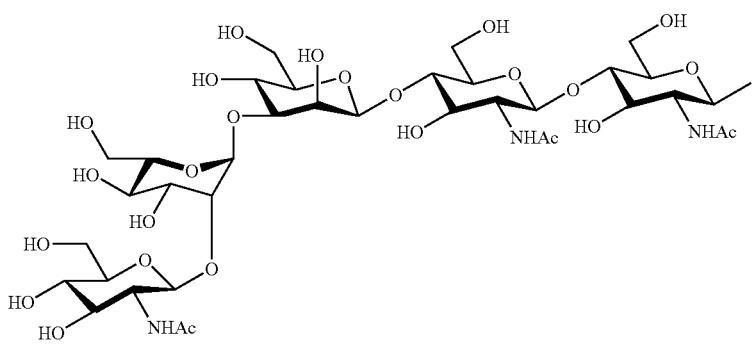
2GN-5NC, TABLE 2-continued
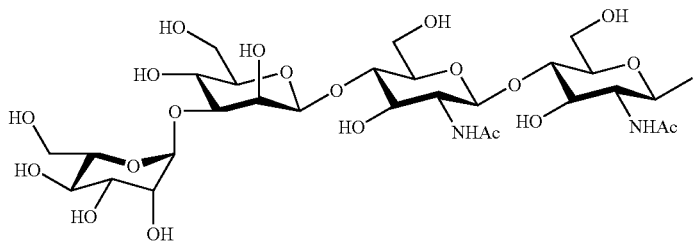
2M-4NC,
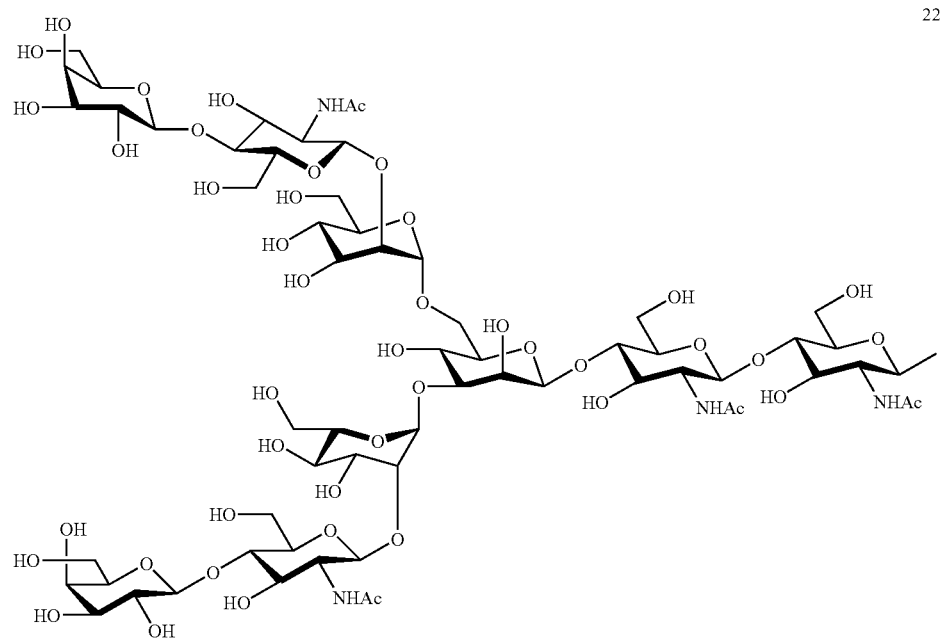
1G2G-9NC,
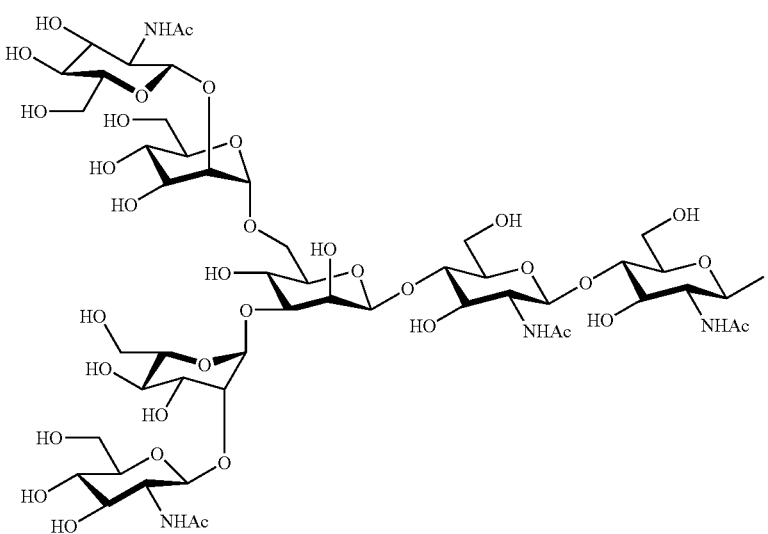
1GN2GN-7NC, TABLE 2-continued
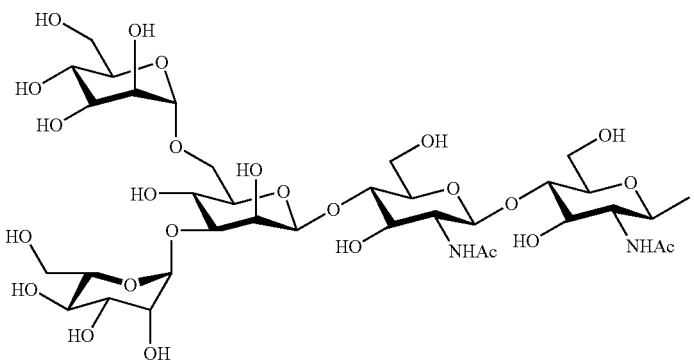
1M2M-5NC,
24
TABLE 3
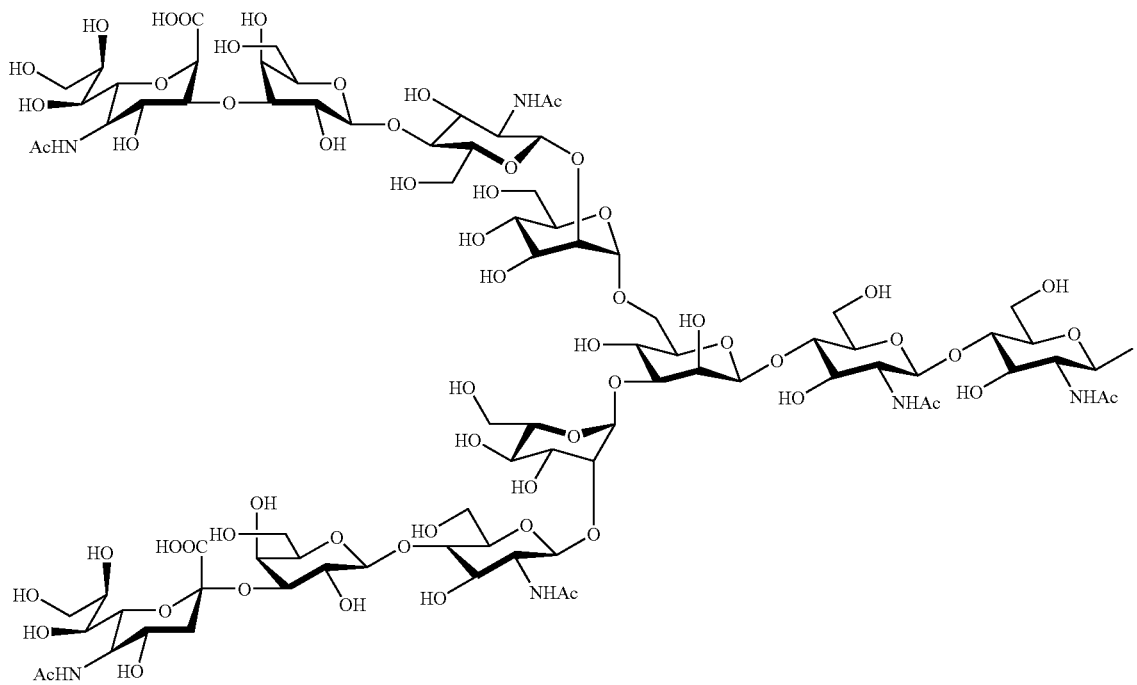
1S(3)2S(3)-11NC,
25

TABLE 3-continued
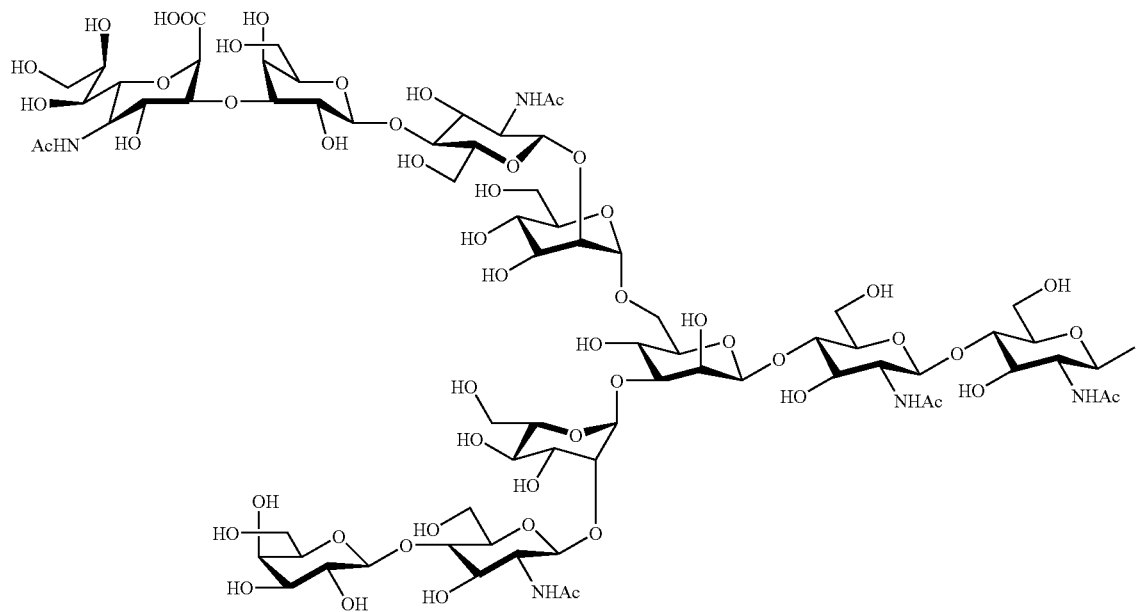
1S(3)2G-10NC,
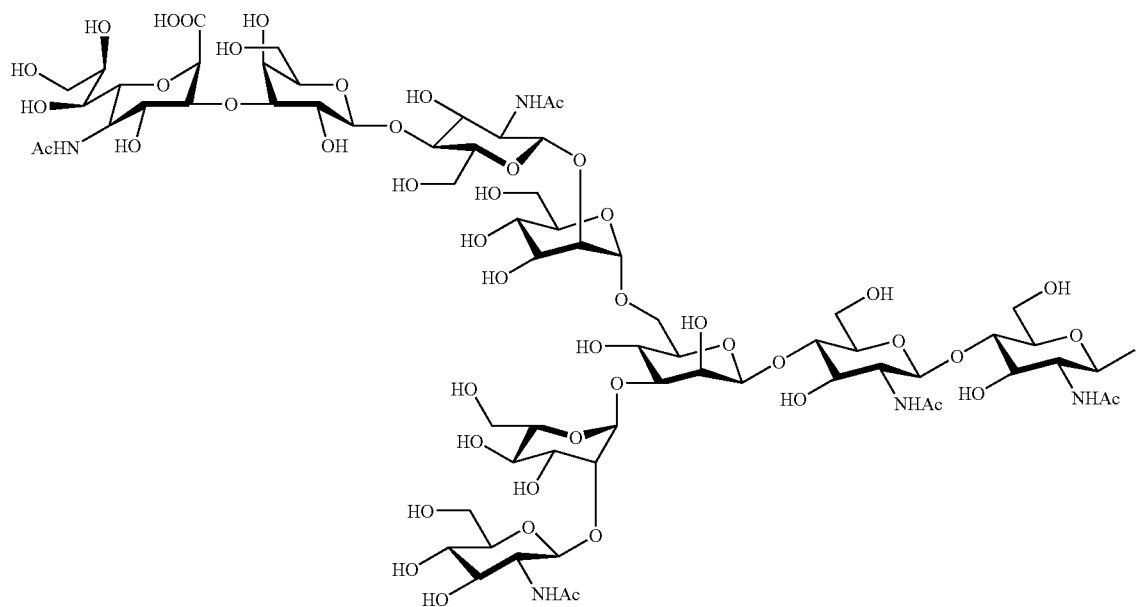
1S(3)2GN-9NC,

TABLE 3-continued
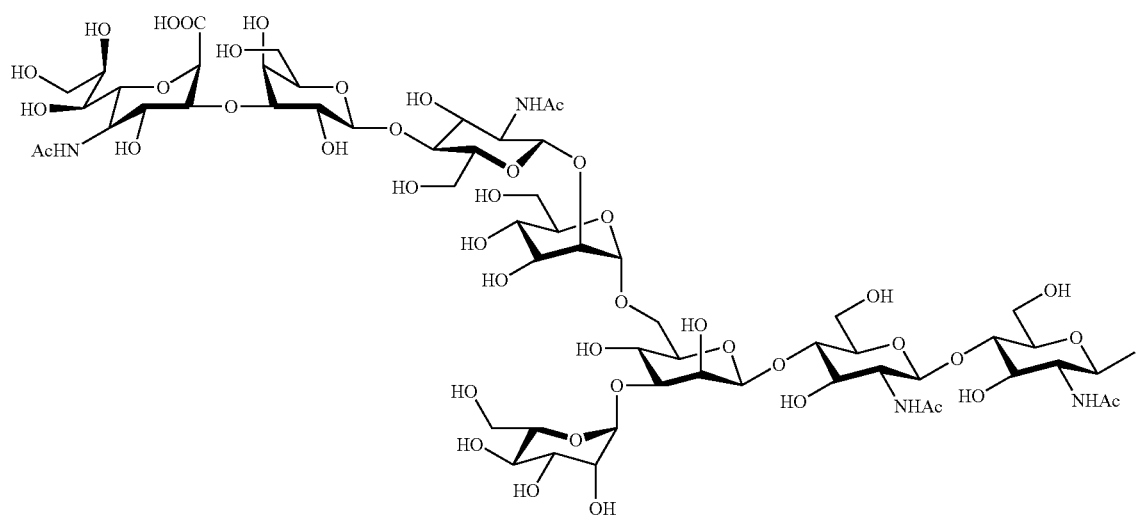
1S(3)2M-8NC,
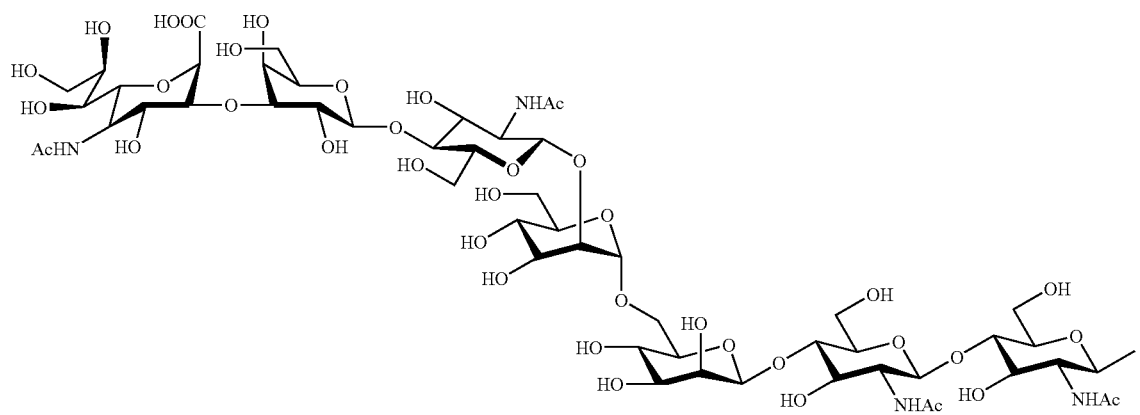
1S(3)-7NC,

TABLE 3-continued
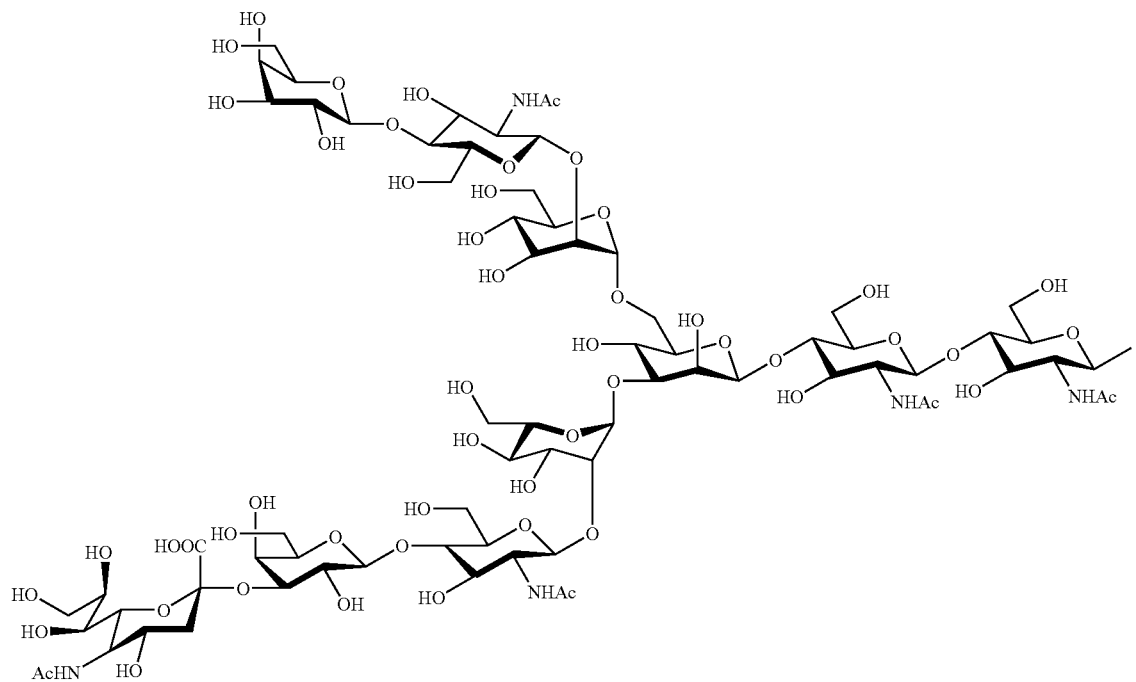
1G2S(3)-10NC,
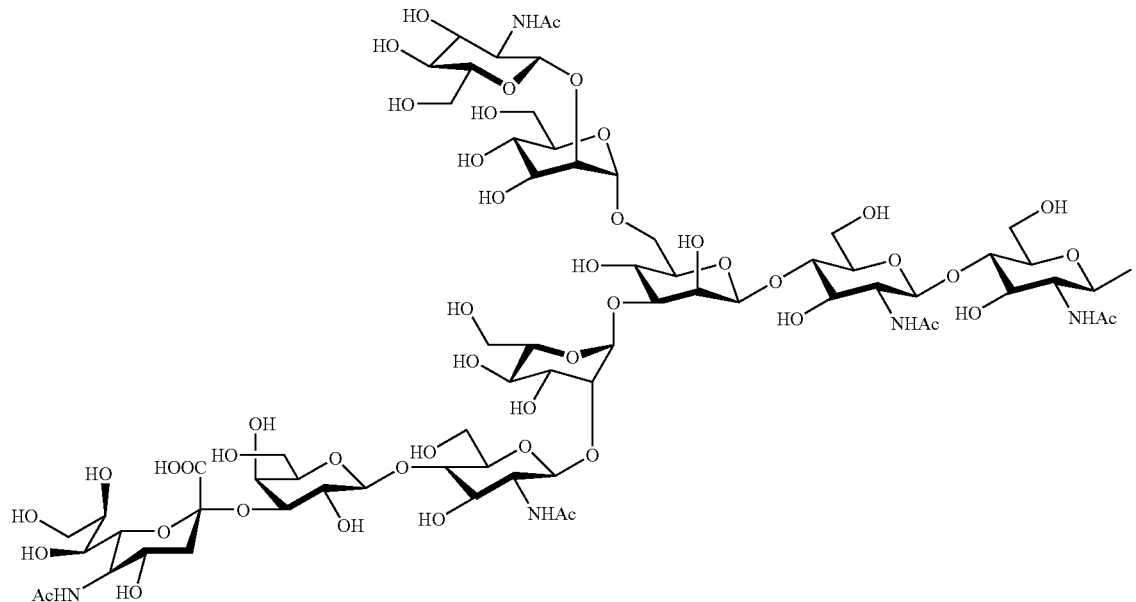
1GN2S(3)-9NC,

TABLE 3-continued
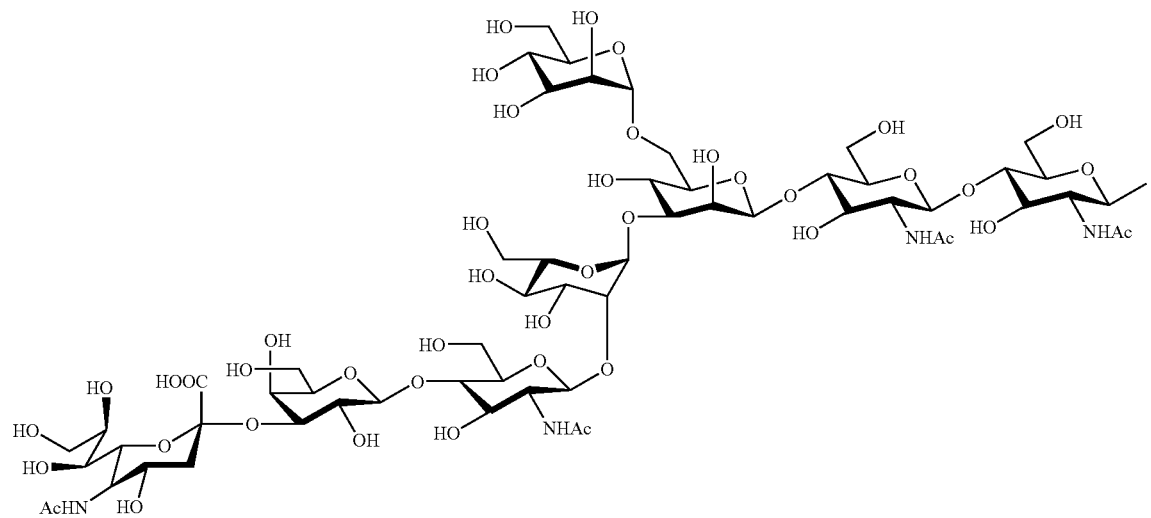
1M2S(3)-8NC,
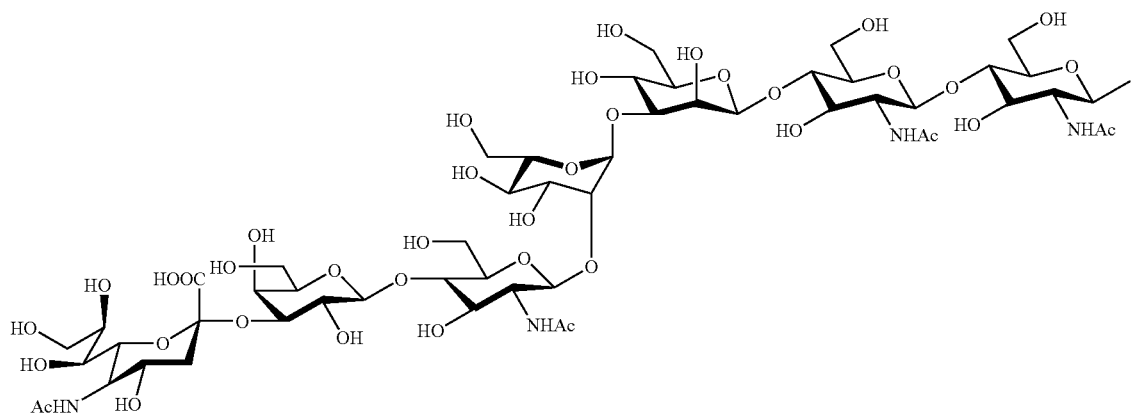
2S(3)-7NC,

TABLE 4

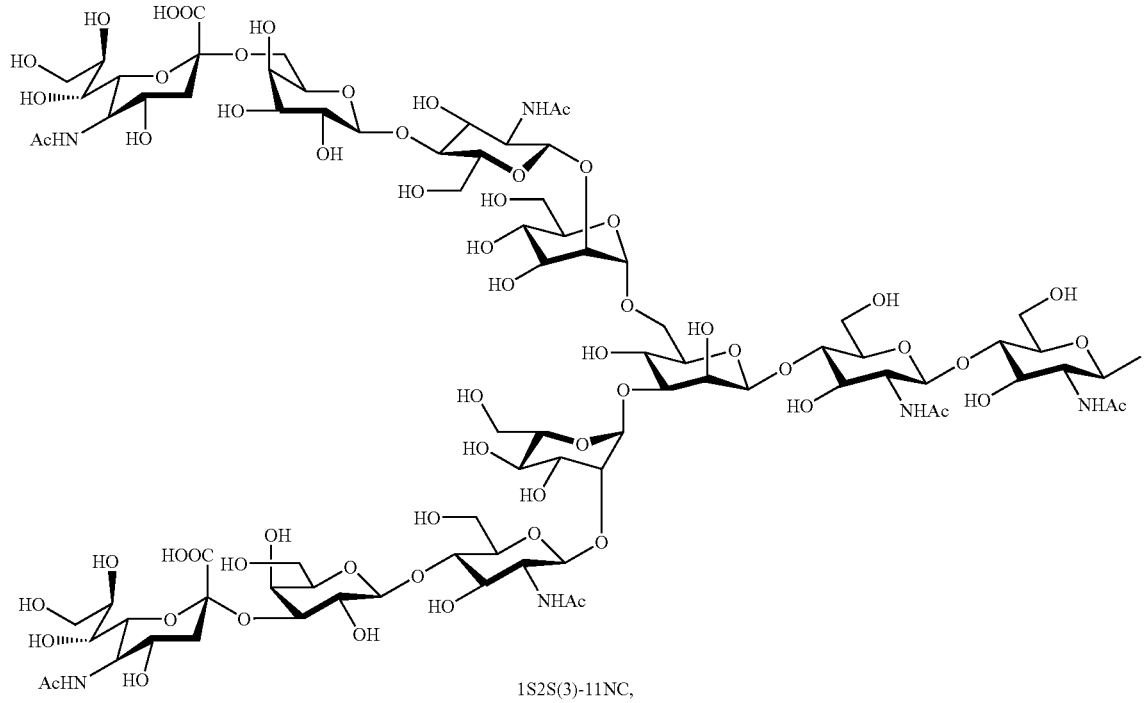

1S2S(3)-11NC,

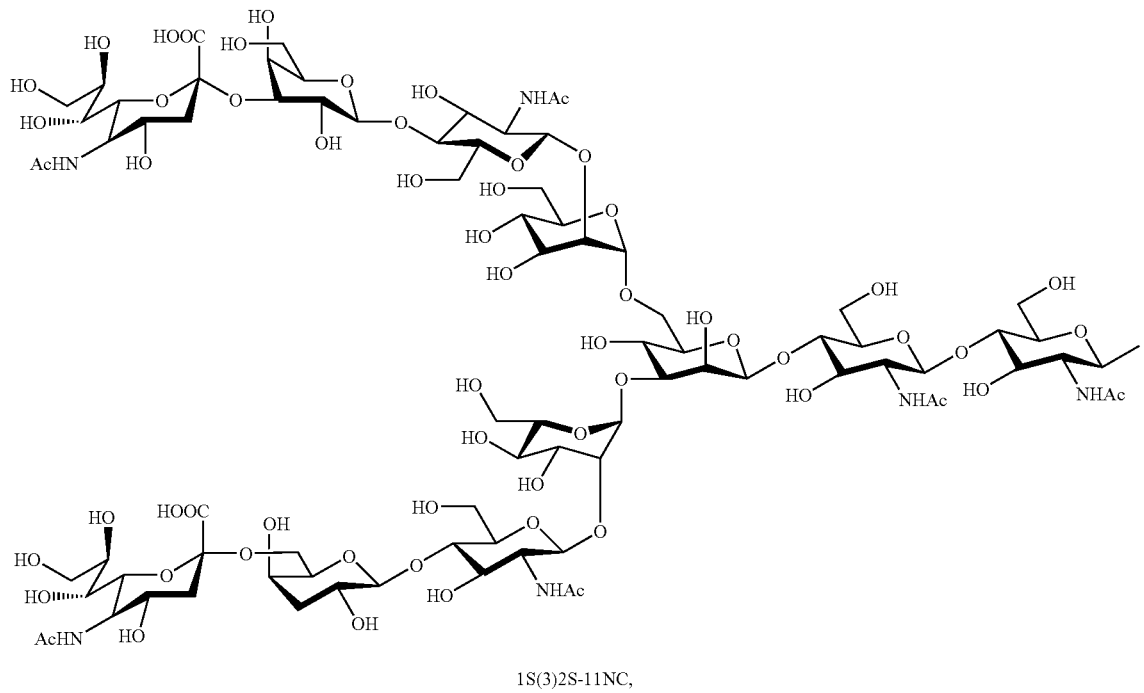

1S(3)2S-11NC,

In a preferable aspect of the present invention, the oligosaccharide chain added GLP-1 peptide of the present invention has a uniform oligosaccharide chain structure. The uniform oligosaccharide chain structure used herein refers to the same type of each constituent sugar in the oligosaccharide chain, the same order wherein the sugars are linked, and the same pattern of linkages between the sugars and means that at least 90%, preferably at least 95%, more preferably at least 99% of oligosaccharide chain added GLP-1 peptides have a uniform oligosaccharide chain structure. The oligosaccharide chain added GLP-1 peptides having a uniform oligosaccharide chain structure have constant quality and are particularly preferable in the field such as pharmaceutical production.

In the present invention, examples of preferable oligosaccharide chain added GLP-1 peptide may include oligosaccharide chain added GLP-1 peptides (SEQ ID NOs:103 to 151)

produced in following Examples 1 to 49. Namely, oligosaccharide chain added GLP-1 peptides having the sequence of His7-Ala8-Glu9-Gly10-Thr11-Phe12-Thr13-Ser14-Asp15-Val16-Ser17-Ser18-Tyr19-Leu20-Glu21-Gly22-Gln23-Ala24-Ala25-Lys26-Glu27-Phe28-Ile29-Ala30-Trp31-Leu32-Val33-Lys34-Gly35-Arg36-Gly37 (SEQ ID NO:2, GLP-1) wherein:

(b1) 18Ser is substituted by disialo oligosaccharide chain added Cys (Example 1) (SEQ ID NO:103);
(b2) 22Gly is substituted by disialo oligosaccharide chain added Cys (Example 2) (SEQ ID NO:104);
(b3) 26Lys is substituted by disialo oligosaccharide chain added Cys (Example 3) (SEQ ID NO:105);
(b4) 36Arg is substituted by disialo oligosaccharide chain added Cys (Example 4) (SEQ ID NO:106);
(b5) 37Gly is substituted by disialo oligosaccharide chain added Cys (Example 5) (SEQ ID NO:107);
(b6) 37Gly is substituted by asialo oligosaccharide chain added Asn (Example 6) (SEQ ID NO:108);
(b7) 19Tyr is substituted by asialo oligosaccharide chain added Asn (Example 7) (SEQ ID NO:109);
(b8) 7His is substituted by disialo oligosaccharide chain added Cys (Example 8) (SEQ ID NO:110);
(b9) 8Ala is substituted by disialo oligosaccharide chain added Cys (Example 9) (SEQ ID NO:111);
(b10) 9Glu is substituted by disialo oligosaccharide chain added Cys (Example 10) (SEQ ID NO:112);
(b11) 10Gly is substituted by disialo oligosaccharide chain added Cys (Example 11) (SEQ ID NO:113);
(b12) 11Thr is substituted by disialo oligosaccharide chain added Cys (Example 12) (SEQ ID NO:114);
(b13) 12Phe is substituted by disialo oligosaccharide chain added Cys (Example 13) (SEQ ID NO:115);
(b14) 14Ser is substituted by disialo oligosaccharide chain added Cys (Example 14) (SEQ ID NO:116);
(b15) 16Val is substituted by disialo oligosaccharide chain added Cys (Example 15) (SEQ ID NO:117);
(b16) 20Leu is substituted by disialo oligosaccharide chain added Cys (Example 16) (SEQ ID NO:118);
(b17) 24Ala is substituted by disialo oligosaccharide chain added Cys (Example 17) (SEQ ID NO:119);
(b18) 25Ala is substituted by disialo oligosaccharide chain added Cys (Example 18) (SEQ ID NO:120);
(b19) 27Glu is substituted by disialo oligosaccharide chain added Cys (Example 19) (SEQ ID NO:121);
(b20) 28Phe is substituted by disialo oligosaccharide chain added Cys (Example 20) (SEQ ID NO:122);
(b21) 30Ala is substituted by disialo oligosaccharide chain added Cys (Example 21) (SEQ ID NO:123);
(b22) 32Leu is substituted by disialo oligosaccharide chain added Cys (Example 22) (SEQ ID NO:124);
(b23) 34Lys is substituted by disialo oligosaccharide chain added Cys (Example 23) (SEQ ID NO:125);
(b24) 22Gly is substituted by asialo oligosaccharide chain added Cys (Example 24) (SEQ ID NO:126);
(b25) 26Lys is substituted by asialo oligosaccharide chain added Cys (Example 25) (SEQ ID NO:127);
(b26) 30Ala is substituted by asialo oligosaccharide chain added Cys (Example 26) (SEQ ID NO:128);
(b27) 34Lys is substituted by asialo oligosaccharide chain added Cys (Example 27) (SEQ ID NO:129);
(b28) 36Arg is substituted by asialo oligosaccharide chain added Cys (Example 28) (SEQ ID NO:130);
(b29) 22Gly is substituted by diGlucNAc oligosaccharide chain added Cys (Example 29) (SEQ ID NO:131);
(b30) 30Ala is substituted by diGlucNAc oligosaccharide chain added Cys (Example 30) (SEQ ID NO:132);
(b31) 34Lys is substituted by diGlucNAc oligosaccharide chain added Cys (Example 31) (SEQ ID NO:133);
(b32) 22Gly is substituted by dimannose oligosaccharide chain added Cys (Example 32) (SEQ ID NO:134);
(b33) 30Ala is substituted by dimannose oligosaccharide chain added Cys (Example 33) (SEQ ID NO:135);
(b34) 34Lys is substituted by dimannose oligosaccharide chain added Cys (Example 34) (SEQ ID NO:136);
(b35) 12Phe is substituted by asialo oligosaccharide chain added Asn (Example 35) (SEQ ID NO:137);
(b36) 18Ser is substituted by asialo oligosaccharide chain added Asn (Example 36) (SEQ ID NO:138);
(b37) 22Gly is substituted by asialo oligosaccharide chain added Asn (Example 37) (SEQ ID NO:139);
(b38) 26Lys is substituted by asialo oligosaccharide chain added Asn (Example 38) (SEQ ID NO:140);
(b39) 27Glu is substituted by asialo oligosaccharide chain added Asn (Example 39) (SEQ ID NO:141);
(b40) 28Phe is substituted by asialo oligosaccharide chain added Asn (Example 40) (SEQ ID NO:142);
(b41) 30Ala is substituted by asialo oligosaccharide chain added Asn (Example 41) (SEQ ID NO:143);
(b42) 36Arg is substituted by asialo oligosaccharide chain added Asn (Example 42) (SEQ ID NO:144);
(b43) 18Ser is substituted by disialo oligosaccharide chain added Asn (Example 43) (SEQ ID NO:145);
(b44) 22Gly is substituted by disialo oligosaccharide chain added Asn (Example 44) (SEQ ID NO:146);
(b45) 30Ala is substituted by disialo oligosaccharide chain added Asn (Example 45) (SEQ ID NO:147);
(b46) 30Ala is substituted by disialo oligosaccharide chain added Asn (Example 46) (SEQ ID NO:148);
(b47) 36Arg is substituted by disialo oligosaccharide chain added Asn (Example 47) (SEQ ID NO:149);
(b48) 26Lys and 34Lys are each substituted by disialo oligosaccharide chain added Cys (Example 48) (SEQ ID NO:150); and
(b49) 18Ser and 36Arg are each substituted by disialo oligosaccharide chain added Cys (Example 49) (SEQ ID NO:151).

The oligosaccharide chain added GLP-1 peptide of the present invention can be produced by incorporating an oligosaccharide chain addition step (glycosylation step) to a peptide synthesis method known by those skilled in the art. For oligosaccharide chain addition, a method using reverse reaction of an enzyme typified by transglutaminase is also usable. However, this method presents problems such as a large amount of necessary oligosaccharide chains to be added, complicated purification after the final step, limited sites to which oligosaccharide chain is added, and limited types of oligosaccharide chains that can be added. Therefore, the method is not practical for large-scale production such as pharmaceutical production, though it may be used in synthesis in small amounts, e.g., for assay use.

A process for conveniently producing the oligosaccharide chain added GLP-1 peptide of the present invention and for stably producing oligosaccharide chain added GLP-1 peptides having a uniform oligosaccharide chain structure is specifically exemplified below by a process for producing an oligosaccharide chain added GLP-1 peptide by using oligosaccharide chain added Asn as an oligosaccharide chain added amino acid and utilizing a peptide synthesis method known in the art such as solid-phase synthesis or liquid-phase synthesis (Process A) and a process for producing an oligosaccharide chain added GLP-1 peptide which comprises producing a peptide wherein any amino acid of GLP-1 is substituted with Cys, according to a peptide synthesis method known in the art and then adding oligosaccharide chain to the Cys through chemical synthesis (Process B). Those skilled in the art can produce various oligosaccharide chain added GLP-1 peptides with reference to these production processes. The oligosaccharide chain added GLP-1 peptides thus obtained and production processes thereof are very useful particularly in the field of pharmaceutical production. These Processes A and B may be performed in combination. For synthesis in small amounts, e.g., for assay use, these processes may also be combined with oligosaccharide chain extension reaction catalyzed by transferase. The Processes A an B can be referred to the descriptions of WO 2004/005330 and WO 2005/010053, respectively. Oligosaccharide chains used in each process can be referred to WO 03/008431, WO 2004/058984, WO 2004/058824, WO 2004/070046, WO 2007/011055, etc. These documents are incorporated herein by reference.

Process for Producing Oligosaccharide Chain Added GLP-1 Peptide (Process A)

First, (1) a hydroxyl group of a resin having the hydroxyl group and a carboxyl group of an amino acid having amino group nitrogen protected with a fat-soluble protective group are subjected to an esterifying reaction. Since the amino group nitrogen of the amino acid is protected with a fat-soluble protective group, the hydroxyl group of the resin is reacted with the carboxyl group of the amino acid, with self-condensation of the amino acid prevented.

Next, (2) the fat-soluble protective group is removed from the resulting ester to form a free amino group, (3) the free amino group is amidated with a carboxyl group of a desired amino acid having amino group nitrogen protected with a fat-soluble protective group, (4) the fat-soluble protective group is removed to form a free amino group, and (5) the steps (3) and (4) are repeated at least once to thereby obtain a peptide having a desired number of desired amino acids as linked and having the resin attached to one end thereof and a free amino group at the other end thereof.

Next, (6) the free amino group is amidated with a carboxyl group of the asparagine portion of an asparagine-linked oligosaccharide (oligosaccharide chain added asparagine) having amino group nitrogen protected with a fat-soluble protective group, (7) the fat-soluble protective group is removed to form a free amino group, (8) the free amino group is amidated with a carboxyl group of a desired amino acid having amino group nitrogen protected with a fat-soluble protective group, (9) the steps (7) and (8) are repeated at least once, and

(10) the fat-soluble protective group is removed to form a free amino group and thereby obtain a glycopeptide having a desired number of desired amino acids as linked and having the resin attached to one end thereof, a free amino group at the other end thereof and an oligosaccharide chain added asparagine at an intermediate position.

(11) The resin is cut off with an acid, whereby a glycopeptide can be prepared which has an oligosaccharide chain added asparagine at a desired position of the peptide chain thereof.

Furthermore, a glycopeptide having at least two oligosaccharide chain added asparagines at a desired position of the peptide chain thereof can be prepared by suitably adding the step (6) of amidating the free amino group and a carboxyl group of the asparagine portion of an oligosaccharide chain added asparagine having amino group nitrogen protected with a fat-soluble protective group. At this time, a glycopeptide having at least two kinds of oligosaccharide chain added asparagines at a desired position of the peptide chain thereof can be prepared by using a different oligosaccharide chain added asparagine.

Alternatively, the oligosaccharide chain added asparagine can be introduced into an end portion of the peptide chain.

The resin having a hydroxyl group may usually be a resin having hydroxyl useful for solid-phase synthesis. Examples of resins usable are Amino-PEGA resin (product of Merck), Wang resin (product of Merck), HMPA-PEGA resin (product of Merck), etc.

All amino acids are usable as such. Examples of amino acids usable are natural amino acids such as serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe) tryptophan (Trp) and proline (Pro).

Examples of fat-soluble protective groups are 9-fluorenyl-methoxycarbonyl (Fmoc) group, tert-butyloxycarbonyl (Boc) group, benzyl group, allyl group, allyloxycarbonyl group, acetyl group and the like, which are carbonate-type or amide-type protective groups. The fat-soluble protective group, e.g., Fmoc group, can be introduced by adding 9-fluorenylmethyl-N-succinimidyl carbonate and sodium hydrogencarbonate to the contemplated compound for reaction. It is preferable to conduct the reaction at 0 to 50 DEG C., preferably at room temperature, for about 1 to about 5 hours.

The above amino acid can be protected with a fat-soluble protective group by the method described above. The above protected amino acid can be those available commercially. Examples are Fmoc-Ser, Fmoc-Asn, Fmoc-Val, Fmoc-Leu, Fmoc-Ile, Fmoc-Ala, Fmoc-Tyr, Fmoc-Gly, Fmoc-Lys, Fmoc-Arg, Fmoc-His, Fmoc-Asp, Fmoc-Glu, Fmoc-Gln, Fmoc-Thr, Fmoc-Cys, Fmoc-Met, Fmoc-Phe, Fmoc-Trp and Fmoc-Pro.

Usable as esterifying catalysts are dehydrating condensation agents such as 1-mesitylenesulfonyl-3-nitro-1,2,4-triazole (MSNT), dicyclohexylcarbodiimide (DCC) and diisopropylcarbodiimide (DIPCI). The dehydrating condensation agent is used in an amount of 1 to 10 wt %, preferably 2 to 5 wt %, based on 1 wt % of an amino acid.

The esterifying reaction is conducted preferably by placing a resin, for example, into a solid-phase column, washing the resin with a solvent and thereafter adding a solution of amino acid in a solvent to the resin. Examples of solvents for washing are dimethylformamide (DMF), 2-propanol, methylene chloride, etc. Examples of solvents for dissolving amino acids are dimethyl sulfoxide (DMSO), DMF, methylene chloride, etc. The reaction is conducted at 0 to 50 DEG C., preferably at room temperature, for about 10 to about 30 hours, preferably about 15 minutes to about 24 hours.

Preferably, the unreacted hydroxyl group remaining on the solid phase at this time is acetylated, for example, with acetic anhydride for capping.

The fat-soluble protective group can be removed, for example, by a treatment with a base. Examples of bases to be used are piperidine, morpholine, etc. This treatment is conducted preferably in the presence of a solvent. Examples of solvents usable are DMSO, DMF, methanol, etc.

The reaction of amidating the free amino group with a carboxyl group of a desired amino acid having amino group nitrogen protected with the fat-soluble group is conducted, preferably in the presence of an activator and a solvent.

Examples of useful activators are dicyclohexylcarbodiimide (DCC), 1-ethyl-3-(3-dimethylaminopropyl)carbodiimide/hydrochloride (WSC/HCl), diphenylphosphorylazide (DPPA), carbonyldiimidazole (CDI), diethylcyanophosphonate (DEPC), diisopropylcarbodiimide (DIPCI), benzotriazole-1-yloxy-trispyrrolidinophosphonium hexafluorophosphate (PyBOP), 1-hydroxybenzotriazole (HOBt), hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 2-(1H-benzotriazole-1-yl)-1,1,3,3-tetramethyluronium hexafluorophosphate (HBTU), O-(7-azabenzotriazole-1-yl)-1,1,3,3-tetramethyluronium hexafluorophosphonate (HATU), O-benzotriazole-1-yl-1,1,3,3-tetramethyluronium tetrafluoroborate (TBTU), 3,4-dihydro-3-hydrodi-4-oxo-1,2,3-benzotriazine (Dhbt).

The activator is used in an amount of 1 to 20 equivalents, preferably 1 to 10 equivalents, more preferably 1 to 5 equivalents, based on an amino acid having amino group nitrogen protected with a fat-soluble protective group.

Examples of useful solvents are DMSO, DMF, methylene chloride, etc. It is desired that the reaction be conducted at 0 to 50 DEG C., preferably at room temperature, for about 10 to about 30 hours, preferably about 15 minutes to about 24 hours. The fat-soluble protective group can be removed in the same manner as described above.

The peptide chain is cut off from the resin, preferably by a treatment with an acid. Examples of acids to be used are trifluoroacetic acid (TFA), hydrogen fluoride (HF), etc.

The glycopeptide having at least two oligosaccharide chain added asparagines at a desired position of the peptide chain thereof can be prepared by suitably additionally performing the steps (6) of amidating the free amino group and a carboxyl group of the asparagine portion of an oligosaccharide chain added asparagine having amino group nitrogen protected with a fat-soluble protective group, and (7) of removing the fat-soluble protective group to form a free amino group.

Further, a glycopeptide having at least one oligosaccharide chain added asparagine at a desired position of the peptide chain thereof can be prepared by performing as final steps the steps (6) of amidating the free amino group and the carboxyl group of the asparagine portion of an oligosaccharide chain added asparagine having amino group nitrogen protected with a fat-soluble protective group, and (7) of removing the fat-soluble protective group to form a free amino group.

Further, a glycopeptide having an oligosaccharide chain added asparagine at an end portion can be prepared by performing the step (1) of esterifying a hydroxyl group of a resin having the hydroxyl group and a carboxyl group of an amino acid having amino group nitrogen protected with a fat-soluble protective group, in place of the step (6) or in addition to the step (6).

In this way, an oligosaccharide chain added GLP-1 peptide substituted with oligosaccharide chain added Asn can be obtained.

Process for Producing Oligosaccharide Chain Added GLP-1 Peptide (Process B)

First, a peptide containing Cys is produced by a method such as solid-phase synthesis, liquid-phase synthesis, cell-based synthesis and separation and extraction of those existing naturally.

Next, a haloacetamide complex-type oligosaccharide chain derivative is allowed to react with the thus-obtained peptide containing Cys for production. The reaction may be conducted usually at 0 to 80° C., preferably 10 to 60° C., more preferably 15 to 35° C. The reaction time is usually preferably about 30 minutes to about 5 hours. After the completion of reaction, the reaction product may be purified appropriately by a method known in the art [e.g., high-performance liquid column chromatography (HPLC)].

The haloacetamide complex-type oligosaccharide chain derivative is, e.g., a compound wherein a hydroxyl group bound to carbon at position 1 of a complex-type asparagine-linked oligosaccharide chain is substituted with —NH—(CO)—$(CH_2)_a$—$CH_2X$, wherein X represents a halogen atom, and a represents an integer, preferably an integer of 0 to 4, but not limited to these numbers unless linker functions of interest are inhibited.

Specifically, the haloacetamide complex-type oligosaccharide chain derivative is allowed to react with the peptide containing Cys in a phosphate buffer at room temperature. After the completion of reaction, an oligosaccharide chain added GLP-1 peptide substituted with oligosaccharide chain added Cys can be obtained by HPLC purification.

The oligosaccharide chain added GLP-1 peptide of the present invention has GLP-1 activity.

The "GLP-1 activity" used herein refers to some or all of biological activities known in the art as to GLP-1. GLP-1 has been known to have, in addition to the effect of controlling blood-sugar levels, e.g., insulin secretion associated with cAMP synthesis induction, pancreatic islet protection (apoptosis suppression) and pancreatic islet growth as effects on a pancreatic islet as well as appetite suppression, gastrointestinal motility suppression, calcitonin secretion promotion and cardioprotective action during ischemia as extra-pancreatic effects. Thus, the GLP-1 activity refers to all or some of biological activities associated with these effects, and these activities can be measured respectively using an approach known by those skilled in the art.

Of the GLP-1 activities, e.g., the activity of controlling blood-sugar levels can be measured using the measurement of the effect of lowering blood-sugar levels in diabetes mice (db/db mice) or the measurement of the effect of suppressing rise in blood-sugar levels in Oral Glucose Tolerance Test (OGTT). The phrase "controlling blood-sugar levels" used herein encompasses both concepts of suppressing rise in blood-sugar levels and lowering blood-sugar levels. Particularly, the effect of controlling blood-sugar levels in db/db mice is also referred to herein as the "effect of lowering blood-sugar levels", and the effect of controlling blood-sugar levels in OGTT is also referred to herein as the "effect of suppressing rise in blood-sugar levels".

The activity of controlling blood-sugar levels in OGTT can be determined by measuring suppression of rise in blood-sugar levels in mice forced to drink sugar. When, e.g., an approach of following Test Example 7 is used, a test compound is first administered to mice fasted overnight. 30 minutes after the administration, a glucose solution is orally administered to the mice. Mouse blood-sugar levels increase due to the glucose administration, reach the maximum about 30 minutes after the administration, and gradually decrease. The blood-sugar levels can be measured 30 minutes after the glucose administration and compared with those obtained by GLP-1 administration to thereby measure the effect of controlling blood-sugar levels by the oligosaccharide chain added GLP-1 peptide. When the blood-sugar levels measured 30 minutes thereafter are compared with those obtained by GLP-1 administration, the oligosaccharide chain added GLP-1 peptide of the present invention exhibits preferably 80% or lower, more preferably 60% or lower, even more preferably 40% or lower, particularly preferably 20% or lower of the control blood sugar levels. The strength of the activity of controlling blood-sugar levels by the oligosaccharide chain added GLP-1 peptide of the present invention can be determined by comparing doses confirmed in OGTT to bring about equivalent effects of suppressing rise in blood-sugar levels. When, e.g., 10 doses of GLP-1 and 1 dose of the oligosaccharide chain added GLP-1 peptide produce the same effects of controlling blood-sugar levels, the activity of controlling blood-sugar levels by the oligosaccharide chain added GLP-1 peptide is 10 times that of the GLP-1. The oligosaccharide chain added GLP-1 peptide of the present invention has the activity of controlling blood-sugar levels preferably at least 5 times, more preferably at least 10 times, even more preferably at least 20 times, particularly preferably at least 50 times that of GLP-1.

The activity of controlling blood-sugar levels in db/db mice can be determined by measuring blood-sugar levels in diabetes mice after administration of a test compound. When, e.g., an approach described in following Test Example 8 is used, blood-sugar levels after test compound administration are measured over time. The effect of lowering blood-sugar levels can be confirmed, if blood-sugar levels measured, e.g., 120 minutes after the administration are lower than those measured at the time of administration. Alternatively, the durability of the effect of lowering blood-sugar levels can be determined by measuring blood-sugar levels, e.g., 300 minutes after the administration. When blood-sugar levels measured 120 minutes after the administration are compared with those obtained by GLP-1 administration using the approach of following Test Example 8, the oligosaccharide chain added GLP-1 peptide of the present invention exhibits preferably 80% or lower, more preferably 70% or lower, particularly preferably 60% or lower of the control blood-sugar levels. Alternatively, when blood-sugar levels measured 120 minutes after the administration are compared with those measured at the time of administration, the oligosaccharide chain added GLP-1 peptide of the present invention exhibits preferably 70% or lower, more preferably 60% or lower, particularly preferably 50% or lower (e.g., 45% or lower) of the control blood-sugar levels. When blood-sugar levels measured 300 minutes after the administration are compared with those obtained by GLP-1 administration, the oligosaccharide chain added GLP-1 peptide of the present invention exhibits preferably 70% or lower, more preferably 50% or lower of the control blood-sugar levels. When blood-sugar levels measured 300 minutes after the administration are compared with those measured at the time of administration, the oligosaccharide chain added GLP-1 peptide of the present invention exhibits preferably 70% or lower, more preferably 50% or lower of the control blood-sugar levels.

Even if the activity of controlling blood-sugar levels by the oligosaccharide chain added GLP-1 peptide of the present invention is lower than that of GLP-1, this low activity can be compensated by enhanced stability in blood.

Of the GLP-1 activities, e.g., insulin secretion activity can be measured using an in-vitro test of the ability to synthesize cAMP. GLP-1 increases intracellular cAMP concentrations through the binding to its receptor and promotes insulin secretion. Thus, e.g., mouse GLP-1 receptor-expressing CHO-K1 cells are stimulated with the oligosaccharide chain added GLP-1 peptide and then, the amount of cAMP synthesized in the cells is measured. Its EC50 value can be compared with that obtained by GLP-1 to thereby measure the insulin secretion activity of the oligosaccharide chain added GLP-1 peptide.

The oligosaccharide chain added GLP-1 peptide of the present invention has higher stability in blood than that of GLP-1. The stability in blood can be measured using an approach known by those skilled in the art and can be determined by measuring, e.g., stability in plasma or resistance to DPP-IV (dipeptidyl peptidase IV) and using a half-life, AUC (area under the blood concentration time curve), etc., as an index. Increased renal clearance also contributes to enhancement in stability in blood.

The stability in plasma can be determined using, e.g., an approach described in following Test Example 1. The oligosaccharide chain added GLP-1 peptide of the present invention has higher stability in plasma than that of GLP-1.

The resistance to DPP-IV can be determined by measuring a half-life in a DPP-IV solution, as shown in, e.g., following Test Example 4. The oligosaccharide chain added GLP-1 peptide of the present invention has higher resistance to DPP-IV than that of GLP-1 and has a half-life at least 1.2 times (e.g., at least 2 times), preferably at least 5 times, more preferably at least 10 times, particularly preferably at least 20 times higher than that of GLP-1, when resistance to DPP-IV is measured using, e.g., the approach of following Test Example 4.

The oligosaccharide chain added GLP-1 peptide of the present invention also has a half-life of preferably at least 1 hour, more preferably at least 3, 5, 7, 10, 15 and 20 hours, even more preferably at least 24 hours, in blood.

Next, a pharmaceutical composition comprising the oligosaccharide chain added GLP-1 peptide of the present invention as an active ingredient will be described.

The pharmaceutical composition comprising the oligosaccharide chain added GLP-1 peptide of the present invention as an active ingredient is effective for the treatment or prevention of diseases associated with GLP-1. GLP-1 has been known to have various effects, as described above, and these effects are associated with various diseases. It has been found that, e.g., GLP-1 stimulates insulin release and thereby causes cellular uptake of glucose and reduction in blood-sugar levels. It has also been found that GLP-1 suppresses gastric and/or intestinal motility, gastric and/or intestinal emptying, and food ingestion. Thus, the diseases associated with GLP-1 encompass, e.g., non-insulin-dependent diabetes mellitus (NIDDM), insulin-dependent diabetes mellitus, stroke (see WO 00/16797 by Efendic), myocardial infarction (see WO 98/08531 by Efendic), obesity (see WO 98/19698 by Efendic), functional dyspepsia, irritable bowel syndrome (see WO 99/64060 by Efendic) and pancreatic islet transplantation. The pharmaceutical composition comprising the oligosaccharide chain added GLP-1 peptide of the present invention as an active ingredient is effective particularly for the treatment or prevention of diabetes, more specifically, for the prevention of type 1 diabetes and the treatment of type 2 diabetes.

The pharmaceutical composition may be formulated in a usual pharmaceutical composition form using diluents or excipients such as fillers, extenders, binders, wetting agents, disintegrants, surfactants and lubricants usually used.

Examples of such a pharmaceutical composition include tablets, pills, powders, liquid formulations, suspensions, emulsions, granules, capsules, suppositories and injections.

The amount of the oligosaccharide chain added GLP-1 peptide of the present invention contained in the pharmaceutical composition is not particularly limited and can be selected appropriately from within a wide range. The oligosaccharide chain added GLP-1 peptide of the present invention is usually contained in an amount of preferably 1 to 70 wt % in the pharmaceutical composition.

The pharmaceutical composition comprising the oligosaccharide chain added GLP-1 peptide of the present invention as an active ingredient may further contain an additional active ingredient or may also be used in combination with a pharmaceutical composition containing an additional active ingredient. Moreover, the pharmaceutical composition comprising the oligosaccharide chain added GLP-1 peptide of the present invention as an active ingredient may further comprise at least one different oligosaccharide chain added GLP-1 peptide of the present invention as an active ingredient or may also be used in combination with a pharmaceutical composition comprising at least one different oligosaccharide chain added GLP-1 peptide of the present invention as an active ingredient.

An administration method of the pharmaceutical composition according to the present invention is not particularly limited. The pharmaceutical composition according to the present invention is administered by a method suitable for various dosage forms, the age and sex of a patient, the severity of a disease and other conditions. Examples of administration methods of tablets, pills, liquid formulations, suspensions, emulsions, granules and capsules include oral administration. Injections can be administered intravenously, intramuscularly, intradermally, subcutaneously or intraperitoneally either alone or as a mixture with a usual glucose or amino acid infusion. Suppositories are administered rectally.

The dose of the pharmaceutical composition may be selected appropriately according to use, the age and sex of a patient, the severity of a disease and other conditions. The pharmaceutical composition is usually administered at a dose of 0.1 to 900 nmol, preferably 1 to 90 nmol, in terms of the oligosaccharide chain added GLP-1 peptide of the present invention per kg of body weight. The oligosaccharide chain added GLP-1 peptide of the present invention has much higher stability in blood than that of GLP-1. In one aspect, the oligosaccharide chain added GLP-1 peptide of the present invention has much higher activity of controlling blood-sugar levels than that of GLP-1. Therefore, its dose can be decreased advantageously.

The number of doses of the pharmaceutical composition may be selected appropriately according to use, the age and sex of a patient, the severity of a disease and other conditions and is, e.g., 3 doses/day, 2 doses/day or 1 dose/day. Alternatively, the pharmaceutical composition may be administered with less frequency (e.g., 1 dose/week, or 1 dose/month) according to its stability in blood. The number of doses of the pharmaceutical composition is preferably 1 dose or less/day. The oligosaccharide chain added GLP-1 peptide of the present invention has much higher stability in blood than that of GLP-1. Therefore, the number of doses can be decreased advantageously.

The oligosaccharide chain added to the oligosaccharide chain added GLP-1 peptide of the present invention is easily degraded in a metabolic system in vivo. In one aspect of the present invention, the oligosaccharide chain has a structure that is bound in a form of glycopeptide (or glycoprotein) in vivo. Thus, the oligosaccharide chain added GLP-1 peptide of the present invention and the pharmaceutical composition comprising this peptide as an active ingredient exhibits neither side effects nor antigenicity, even when administered to living bodies. Therefore, they advantageously produce neither allergic reactions nor a loss of efficacy attributed to antibody production.

Furthermore, the oligosaccharide chain added GLP-1 peptide of the present invention can be supplied stably and conveniently in large amounts and is also very useful from the viewpoint of providing a high-quality drug having stable quality.

The present invention also provides a method for treating or preventing a disease associated with GLP-1, comprising administering an effective amount of the oligosaccharide chain added GLP-1 peptide of the present invention.

EXAMPLE

Hereinafter, the present invention will be described specifically with reference to Examples. However, the present invention is not intended to be limited to them by any means. In FIGS. 7 to 22, e.g., "22Cys GLP-1-disialo" which is an oligosaccharide chain added GLP-1 peptide wherein an amino acid at position 22 of GLP-1 is substituted by disialo oligosaccharide chain added Cys is also referred to as "22Cys-disialoGLP-1", "C22" or "C22-disialo". The same applies to other oligosaccharide chains and amino acid sites.

Example 1

Synthesis of 18Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Cys(Trt)-OH, Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Cys(Trt)-Ser(tBu)-Val-Asp(OtBu)-Ser(tBu)-Thr(tBu)-Phe-Thr(tBu)-Gly-Glu(OtBu)-Ala-His(Trt) (SEQ ID NO:30) on a solid-phase resin. According to the principal of the Fmoc method, the sequence is described to start from the C terminal with the direction of 37→7.

After washing with DCM and DMF, the resin equivalent to 5 μmol of the 31 residue peptide was transferred to an Eppendorf tube.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain a peptide wherein 18Ser of GLP-1 is substituted by Cys.

Bromoacetamidyl disialo oligosaccharide (a) (a product of OTSUKA Chemical Co., Ltd.) (3 mg)

[Formula 5]

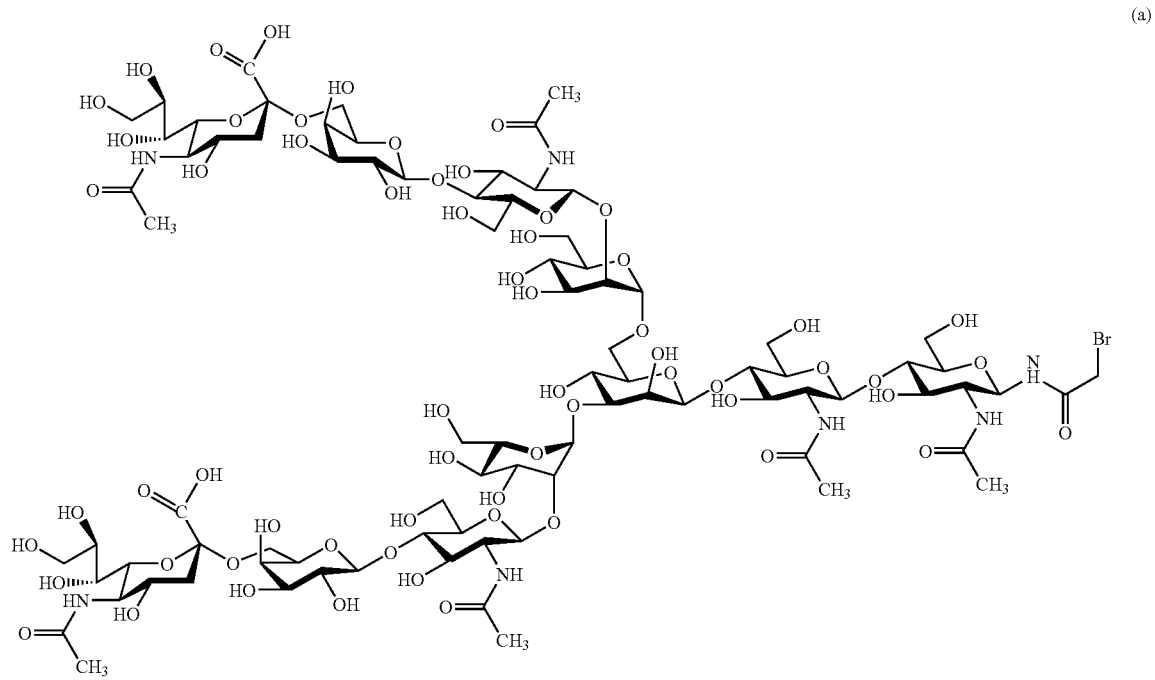

(a)

and the peptide chain synthesized above (1 mg) were dissolved in 100 mM phosphate buffer (pH 7.5, 170 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 1 mg of oligosaccharide chain added GLP-1 peptide (1) wherein 18Ser of GLP-1 is substituted by oligosaccharide chain added Cys (18Cys GLP-1-disialo).

Examples 2 to 5

An oligosaccharide chain added GLP-1 peptide (2) wherein 22Gly of GLP-1 was substituted with oligosaccharide chain added Cys (22Cys GLP-1-disialo), an oligosaccharide chain added GLP-1 peptide (3) wherein 26Lys of GLP-1 was substituted with oligosaccharide chain added Cys (26Cys GLP-1-disialo), an oligosaccharide chain added GLP-1 peptide (4) wherein 36Arg of GLP-1 was substituted with oligosaccharide chain added Cys (36Cys GLP-1-disialo), and an oligosaccharide chain added GLP-1 peptide (5) wherein oligosaccharide chain added Cys was further added to 37Gly of GLP-1 (38Cys GLP-1-disialo) were obtained in the same way as in Example 1 except that the order wherein amino acids were condensed was changed. The results are shown in Table 5.

Comparative Example 1

A solid-phase synthesis column was charged with Amino-PEGA resin (100 μmol), washed thoroughly with DCM and DMF, and thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column, and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in NMP (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After the mixture was stirred at room temperature for 20 minutes, the resin was washed with DCM and DMF, and Fmoc group was removed by using 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg (Pbf), Fmoc-Gly, Fmoc-Lys (Boc), Fmoc-Val, Fmoc-Leu, Fmoc-Trp (Boc), Fmoc-Ala, Fmoc-Ile, Fmoc-Phe, Fmoc-Glu (OtBu), Fmoc-Lys (Boc), Fmoc-Ala, Fmoc-Ala, Fmoc-Gln (Trt), Fmoc-Gly, Fmoc-Glu (OtBu), Fmoc-Leu, Fmoc-Tyr (tBu), Fmoc-Ser (tBu), Fmoc-Ser (tBu), Fmoc-Val, Fmoc-Asp (OtBu), Fmoc-Ser (tBu), Fmoc-Thr (tBu), Fmoc-Phe, Fmoc-Thr (tBu), Fmoc-Gly, Fmoc-Glu (OtBu), Fmoc-Ala and Fmoc-His (Trt) were used as the amino acids protected with Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO: 31) on a solid-phase resin.

After washing with DCM and DMF, the resin equivalent to 5 μmol of the 31-residue peptide was transferred to an Eppendorf tube.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration, and the reaction solution was concentrated under reduced pressure. The resulting residue was purified by HPLC (Cadenza column C18 100×10 mm, developing solvent A: 0.1% aqueous TFA solution, B: 0.1% TFA acetonitrile: water=90:10, gradient A:B=95:5→5:95, 15 min, flow rate: 3.0 ml/min) to obtain GLP-1. The results are shown in Table 5.

TABLE 5

| | | MALDI-TOF mass (Bluker Daltonics, AutoFLEX) |
|---|---|---|
| Example 1 | 18Cys GLP-1-disialo | Calculated for $C_{237}H_{367}N_{47}O_{108}S$ $[M + H]^+$ 5631.47, found. 5632.0 |
| Example 2 | 22Cys GLP-1-disialo | Calculated for $C_{235}H_{369}N_{47}O_{109}S$ $[M + H]^+$ 5661.44, found. 5662.1 |
| Example 3 | 26Cys GLP-1-disialo | Calculated for $C_{234}H_{360}N_{46}O_{109}S$ $[M + H]^+$ 5590.38, found. 5591.7 |
| Example 4 | 36Cys GLP-1-disialo | Calculated for $C_{234}H_{360}N_{44}O_{109}S$ $[M + H]^+$ 5562.37, found. 5562.9 |
| Example 5 | 38Cys GLP-1-disialo | Calculated for $C_{240}H_{372}N_{45}O_{110}S$ $[M + H]^+$ 5718.47, found. 5719.1 |
| Comparative Example 1 | GLP-1 | |

Example 6

Synthesis of 38Asn-asialo Oligosaccharide Chain Added GLP-1 Peptide

A solid-phase synthesis column was charged with Amino-PEGA resin (100 μmol), washed thoroughly with DCM and DMF, and thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column, and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in NMP (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After the mixture was stirred at room temperature for 20 minutes, the resin was washed with DCM and DMF, and Fmoc group was removed by using 20% piperidine/DMF solution (2 ml) for 15 minutes. This operation was repeatedly performed using an amino acid protected with Fmoc group (0.5 mmol) to sequentially condense amino acids.

(Boc-His(Trt)-OH was used for the final amino acid and used for condensation in the same way as in Fmoc-His(Trt)-OH.)

Fmoc-Gly, Fmoc-Arg (Pbf), Fmoc-Gly, Fmoc-Lys (Boc), Fmoc-Val, Fmoc-Leu, Fmoc-Trp (Boc), Fmoc-Ala, Fmoc-Ile, Fmoc-Phe, Fmoc-Glu (OtBu), Fmoc-Lys (Boc), Fmoc-Ala, Fmoc-Ala, Fmoc-Gln (Trt), Fmoc-Gly, Fmoc-Glu (OtBu), Fmoc-Leu, Fmoc-Tyr (tBu), Fmoc-Ser (tBu), Fmoc-Ser (tBu), Fmoc-Val, Fmoc-Asp (OtBu), Fmoc-Ser (tBu), Fmoc-Thr (tBu), Fmoc-Phe, Fmoc-Thr (tBu), Fmoc-Gly, Fmoc-Glu (OtBu), Fmoc-Ala and Fmoc-His (Trt) were used as the amino acids protected with Fmoc group and Boc-His (Trt)-OH was used as the amino acid protected with Boc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO: 32) on a solid-phase resin.

After washing with DCM and DMF, a solution mixture of trifluoroethanol and acetic acid (1:1) was added such that the resin was thoroughly soaked and stirred at room temperature for 18 hours. The resin was removed by filtration, and the reaction solution was concentrated under reduced pressure. The obtained residue was concentrated to obtain a protected peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt)-Boc (Sequence No. 33). The 31-residue protected peptide (equivalent to 2 μmol) was transferred to an eggplant flask and dissolved in DMF (0.03 ml). In an Eppendorf tube separately prepared, asialo oligosaccharide chain added asparagine (amine-free) (4.9 mg, 1 μmol), PyBOP (1 mg, 1.9 μmol) and HOBt (0.3 mg, 2 μmol) dissolved in DMF (0.04 ml) were placed, and DIPEA (0.00052 ml, 3 μmol) was finally added thereto. The solution mixture in this Eppendorf tube was placed in the eggplant flask prepared in advance and stirred at room temperature for 2.5 hours. After completion of the reaction, the solution was concentrated. To the residue, trifluoroacetic acid:water:TIPS (=95:2.5:2.5) was added and stirred at room temperature. After 2 hours, the solution was added to diethyl ether (150 ml) separately prepared to obtain a crystal. The solution portion was removed by a membrane filter to obtain a residue containing the oligosaccharide chain added GLP-1 peptide of interest. The obtained residue was purified by HPLC [column: SHISEIDO UG-120 (C18 5 μm), φ20×250 mm, gradient: A solution: 0.1% TFA water, B solution: 0.09% TFA/10% water/90% AN 8.0 ml/min; 35→60% B solution, 20 min linear gradient] to obtain a oligosaccharide chain added GLP-1 peptide wherein position 38 of GLP-1 was substituted with oligosaccharide chain added Asn (38Asn-GLP-1-asialo).

ESI-MS: Calcd for $C_{217}H_{336}N_{46}O_{94}$: $[M+3H]^{3+}$ 1697.8, found. 1697.9.

Example 7

Synthesis of 19Asn-asialo Oligosaccharide Chain Added GLP-1 Peptide

A solid-phase synthesis column was charged with Amino-PEGA resin (100 μmol), washed thoroughly with DCM and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in NMP (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), and Fmoc-Leu were used as the amino acids protected by Fmoc group to obtain a 18-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu (SEQ ID NO:34) on a solid-phase resin.

After washing with DCM and DMF, the resin equivalent to 5 μmol of the 18 residue peptide was transferred to an Eppendorf tube.

Oligosaccharide chain added asparagine (b) (a product of OTSUKA Chemical Co., Ltd.) (18 mg, 10 μmol)

[Formula 6]

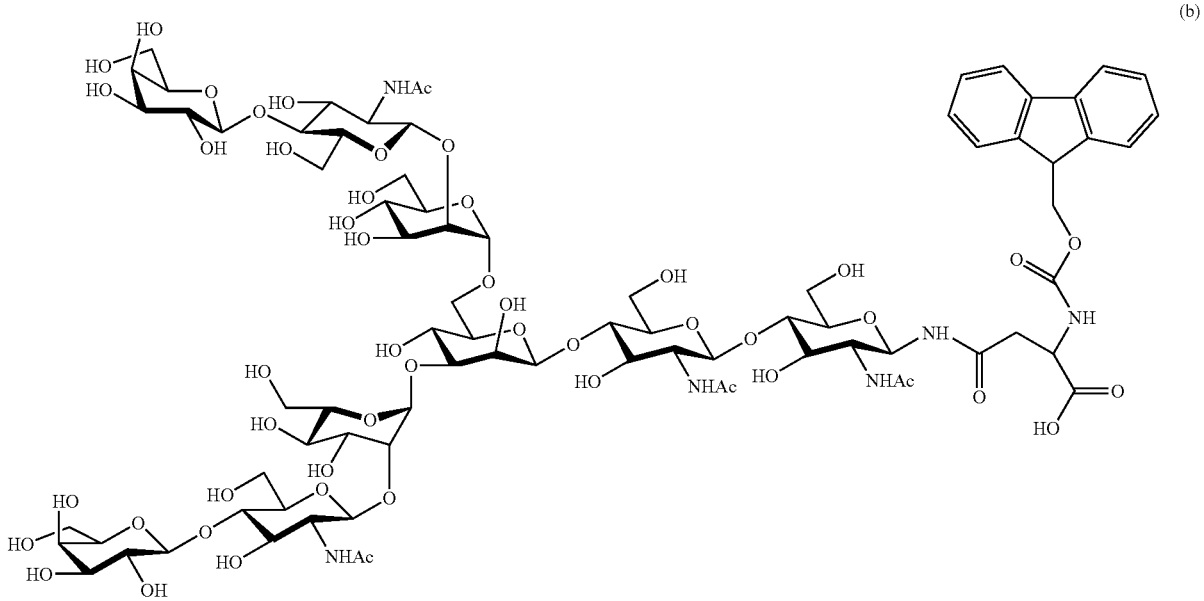

(b)

and DEPBT(4.5 mg, 15 μmol) were dissolved in DMF(0.34 ml), and placed in Eppendorf tube. DIPEA (2.6 μl, 15 μmol) was added and the mixture was stirred at room temperature for 24 hours. After washing with DMF and DCM, oligosaccharide chain added 19-residue peptide of Gly-Arg(Pbf)-Gly-Lys(Boc)-Val-Leu-Trp(Boc)-Ala-Ile-Phe-Glu(OtBu)-Lys (Boc)-Ala-Ala-Gln(Trt)-Gly-Glu(OtBu)-Leu-Asn (Oligosaccharide chain) (SEQ ID NO:35) was obtained on a solid phase. The amino acid having an amino group protected with Fmoc group was then condensed using HOBt (3.4 mg, 0.025 mmol), DIPCI (3.8 μl, 0.025 mmol) and DMF (0.1) to obtain oligosaccharide chain added 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Asn(Oligosaccharide chain)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:36) on a solid phase.

The obtained resin having an oligosaccharide chain added peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 7.0 ml/min; 35→60% B, 20 min linear gradient] to obtain oligosaccharide chain added peptide wherein position 19 of GLP-1 is substituted by oligosaccharide chain added Asn (19Asn GLP-1-asialo). ESI-MS: Calcd for $C_{214}H_{331}N_{45}O_{92}$: $[M+3H]^{3+}$ 1668.8, found. 1668.1.

TABLE 6

| | | EMI-MS |
|---|---|---|
| Example 6 | 38Asn GLP-1-asialo | Calculated for $C_{217}H_{336}N_{45}O_{94}$ $[M + 3H]^{3+}$ 1697.8, found. 1697.9 |
| Example 7 | 19Asn GLP-1-asialo | Calculated for $C_{214}H_{331}N_{45}O_{92}$ $[M + 3H]^{3+}$ 1668.8, found. 1668.1 |

Example 8

Synthesis of 6Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala, Fmoc-His(Trt) and Fmoc-Cys(Trt) were used as the amino acids protected by Fmoc group to obtain a 32-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt)-Cys(Trt) (SEQ ID NO:37) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% 20 min linear gradient] to obtain peptide having Cys on 6 position of GLP-1.

Bromoacetamidyl disialo oligosaccharide (a) (a product of OTSUKA Chemical Co., Ltd.) (34 mg) and the peptide chain synthesized above (9.6 mg) were dissolved in 100 mM phosphate buffer (pH 7.5, 1 ml) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 20×250 mm, gradient: A solution: 0.1% TFA water, B solution: 0.09% TFA/10% water/90% AN 8.0 ml/min; 35→60% B, 20 min linear gradient] to obtain 9.9 mg of oligosaccharide chain added GLP-1 peptide wherein an oligosaccharide chain added Cys was added on position 6 of GLP-1 (6Cys GLP-1-disialo).

Example 9

Synthesis of 8Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Cys(Trt) and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Cys(Trt)-His(Trt) (SEQ ID NO:38) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 µm), φ 20×250 mm, gradient: A solution: 0.1% TFA water, B solution: 0.09% TFA/10% water/90% AN 8.0 ml/min; 35→60% 20 min linear gradient] to obtain peptide wherein 8Ala of GLP-1 is substituted by Cys.

Bromoacetamidyl disialo oligosaccharide (a) (a product of OTSUKA Chemical Co., Ltd.) (25 mg) and the peptide chain synthesized above (7.3 mg) were dissolved in 100 mM phosphate buffer (pH 7.5, 730 µl) and allowed to react at 37° C. for 4 hours. After complete consumption of raw materials were confirmed by HPLC, the reaction solution was directly subjected to purification by HPLC [column: SHISEIDO UG-120 (C18, 5 µm), φ 20×250 mm, gradient: A solution: 0.1% TFA water, B solution: 0.09% TFA/10% water/90% AN 8 ml/min; 35→60% B, 20 min linear gradient] to obtain 9.3 mg of oligosaccharide chain added GLP-1 peptide wherein 8Ala of GLP-1 is substituted by oligosaccharide chain added Cys (8Cys GLP-1-disialo).

Example 10

Synthesis of 9Cys-disialo Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Cys(Trt), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Cys(Trt)-Ala-His(Trt) (SEQ ID NO:39) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 µm), φ 20×250 mm, gradient: A solution: 0.1% TFA water, B solution: 0.09% TFA/10% water/90% AN 8.0 ml/min; 35→60% B, 20 min linear gradient] to obtain peptide wherein 9Glu of GLP-1 is substituted by Cys.

Bromoacetamidyl disialo oligosaccharide (a) (a product of OTSUKA Chemical Co., Ltd.) (50 mg) and the peptide chain synthesized above (16.4 mg) were dissolved in 100 mM phosphate buffer (pH 7.5, 1.7 ml) and allowed to react at 37° C. for 4 hours. After complete consumption of raw materials were confirmed by HPLC, the reaction solution was directly subjected to purification by HPLC [column: SHISEIDO UG-120 (C18, 5 µm), φ 20×250 mm, gradient: A solution: 0.1% TFA water, B solution: 0.09% TFA/10% water/90% AN 8 ml/min; 35→60% B, 20 min linear gradient] to obtain 7.3 mg of oligosaccharide chain added GLP-1 peptide wherein 9Glu of GLP-1 is substituted by oligosaccharide chain added Cys (9Cys GLP-1-disialo).

Example 11

Synthesis of 10Cys-disialo Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Cys(Trt), Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Cys(Trt)-Glu(OtBu)-Ala-His(Trt) (SEQ ID NO:40) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 10Gly of GLP-1 is substituted by Cys.

Bromoacetamidyl disialo oligosaccharide (a) (a product of OTSUKA Chemical Co., Ltd.) (16.8 mg) and the peptide chain synthesized above (5.6 mg) were dissolved in 100 mM phosphate buffer (pH 7.5, 560 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 3.0 mg of oligosaccharide chain added GLP-1 peptide wherein 10Gly of GLP-1 is substituted by oligosaccharide chain added Cys (10Cys GLP-1-disialo).

Example 12

Synthesis of 11Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Cys(Trt), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Cyc(Trt)-Gly-Glu(OtBu)-Ala-His(Trt) (SEQ ID NO:41) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 11Thr of GLP-1 is substituted by Cys.

Bromoacetamidyl disialo oligosaccharide (a) (a product of OTSUKA Chemical Co., Ltd.) (41 mg) and the peptide chain synthesized above (12.8 mg) were dissolved in 100 mM phosphate buffer (pH 7.5, 1.3 ml) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 20×250 mm, gradient: A solution: 0.1% TFA water, B solution: 0.09% TFA/10% water/90% AN 8.0 ml/min; 35→60% B, 20 min linear gradient] to obtain 11.9 mg of oligosaccharide chain added GLP-1 peptide wherein 11Thr of GLP-1 is substituted by oligosaccharide chain added Cys (11Cys GLP-1-disialo).

Example 13

Synthesis of 12Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Cys(Trt), Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Cyc(Trt)-Thr(tBu)-Gly-Glu(OtBu)-Ala-His(Trt) (SEQ ID NO:42) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 12Phe of GLP-1 is substituted by Cys.

Bromoacetamidyl disialo oligosaccharide (a) (a product of OTSUKA Chemical Co., Ltd.) (33 mg) and the peptide chain synthesized above (9.5 mg) were dissolved in 100 mM phosphate buffer (pH 7.5, 1 ml) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 20×250 mm, gradient: A solution: 0.1% TFA water, B solution: 0.09% TFA/10% water/90% AN 8.0 ml/min; 35→60% B, 20 min linear gradient] to obtain 10.0 mg of oligosaccharide chain added GLP-1 peptide wherein 12Phe of GLP-1 is substituted by oligosaccharide chain added Cys (12Cys GLP-1-disialo).

Example 14

Synthesis of 14Cys disialo Oligosaccharide Chain Added GLP-1 Peptide

A solid-phase synthesis column was charged with Amino-PEGA resin (100 μmol) (product of Merck); washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Cys(Trt), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Cys(Trt)-Thr(tBu)-Phe-Thr(tBu)-Gly-Glu(OtBu)-Ala-His(Trt) (SEQ ID NO:43) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 14Ser of GLP-1 is substituted by Cys.

Bromoacetamidyl disialo oligosaccharide (a) (a product of OTSUKA Chemical Co., Ltd.) (32 mg) and the peptide chain synthesized above (8.8 mg) were dissolved in 100 mM phosphate buffer (pH 7.5, 1 ml) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 20×250 mm, gradient: A solution: 0.1% TFA water, B solution: 0.09% TFA/10% water/90% AN 8.0 ml/min; 35→60% B, 20 min linear gradient] to obtain 8.4 mg of oligosaccharide chain added GLP-1 peptide wherein 14Ser of GLP-1 is substituted by oligosaccharide chain added Cys (14Cys GLP-1-disialo).

Example 15

Synthesis of 16Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Cys(Trt), Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Cys(Trt)-Asp(OtBu)-Ser(tBu)-Thr(tBu)-Phe-Thr(tBu)-Gly-Glu(OtBu)-Ala-His(Trt) (SEQ ID NO:44) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 16Val of GLP-1 is substituted by Cys.

Bromoacetamidyl disialo oligosaccharide (a) (a product of OTSUKA Chemical Co., Ltd.) (36 mg) and the peptide chain synthesized above (12 mg) were dissolved in 100 mM phosphate buffer (pH 7.5, 1.2 ml) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 20×250 mm, gradient: A solution: 0.1% TFA water, B solution: 0.09% TFA/10% water/90% AN 8.0 ml/min; 35→60% B, 20 min linear gradient] to obtain 8.4 mg of oligosaccharide chain added GLP-1 peptide wherein 16Val of GLP-1 is substituted by oligosaccharide chain added Cys (16Cys GLP-1-disialo).

Example 16

Synthesis of 20Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Cys(Trt), Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Cys(Trt)-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:45) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 20Leu of GLP-1 is substituted by Cys.

Bromoacetamidyl disialo oligosaccharide (a) (a product of OTSUKA Chemical Co., Ltd.) (36.9 mg) and the peptide chain synthesized above (12.3 mg) were dissolved in 100 mM phosphate buffer (pH 7.5, 1.5 ml) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 20×250 mm, gradient: A solution: 0.1% TFA water, B solution: 0.09% TFA/10% water/90% AN 8.0 ml/min; 35→60% B, 20 min linear gradient] to obtain 13.4 mg of oligosaccharide chain added GLP-1 peptide wherein 20Leu of GLP-1 is substituted by oligosaccharide chain added Cys (20Cys GLP-1-disialo).

Example 17

Synthesis of 24Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Cys(Trt), Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Cys(Trt)-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:46) on a solid-phase resin.

The obtained resin having a peptide-formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 24Ala of GLP-1 is substituted by Cys.

Bromoacetamidyl disialo oligosaccharide (a) (a product of OTSUKA Chemical Co., Ltd.) (6.6 mg) and the peptide chain synthesized above (2.2 mg) were dissolved in 100 mM phosphate buffer (pH 7.5, 250 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 1.8 mg of oligosaccharide chain added GLP-1 peptide wherein 24Ala of GLP-1 is substituted by oligosaccharide chain added Cys (24Cys GLP-1-disialo).

Example 18

Synthesis of 25Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Cys (Trt), Fmoc-Ala, Fmoc-Gln(Trt), Fmoc-Gly, Fmoc-Glu (OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Cys(Trt)-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu (OtBu)-Ala-His(Trt) (SEQ ID NO:47) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 25Ala of GLP-1 is substituted by Cys.

Bromoacetamidyl disialo oligosaccharide (a) (a product of OTSUKA Chemical Co., Ltd.) (28 mg) and the peptide chain synthesized above (8.3 mg) were dissolved in 100 mM phosphate buffer (pH 7.5, 830 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 8.0 ml/min; 35→60% B, 20 min linear gradient] to obtain 5.6 mg of oligosaccharide chain added GLP-1 peptide wherein 25Ala of GLP-1 is substituted by oligosaccharide chain added Cys (25Cys GLP-1-disialo).

Example 19

Synthesis of 27Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Cys(Trt), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr (tBu), Fmoc-Phe, Fmoc-Thr(tBu), Fmoc-Gly, Fmoc-Glu (OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Cys(Trt)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:48) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 27Glu of GLP-1 is substituted by Cys.

Bromoacetamidyl disialo oligosaccharide (a) (a product of OTSUKA Chemical Co., Ltd.) (34 mg) and the peptide chain synthesized above (10.8 mg) were dissolved in 100 mM phosphate buffer (pH 7.5, 1.1 ml) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 20×250 mm, gradient: A solution: 0.1% TFA water, B solution: 0.09% TFA/10% water/90% AN 8 ml/min; 35→60% B, 20 min linear gradient] to obtain 8.7 mg of oligosaccharide chain added GLP-1 peptide wherein 27Glu of GLP-1 is substituted by oligosaccharide chain added Cys (27Cys GLP-1-disialo).

Example 20

Synthesis of 28Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Cys(Trt), Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Cys(Trt)-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:49) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 28Phe of GLP-1 is substituted by Cys.

Bromoacetamidyl disialo oligosaccharide (a) (a product of OTSUKA Chemical Co., Ltd.) (30.6 mg) and the peptide chain synthesized above (10.2 mg) were dissolved in 100 mM phosphate buffer (pH 7.5, 1.2 ml) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 20×250 mm, gradient: A solution: 0.1% TFA water, B solution: 0.09% TFA/10% water/90% AN 8 ml/min; 35→60% B, 20 min linear gradient] to obtain 10.3 mg of oligosaccharide chain added GLP-1 peptide wherein 28Phe of GLP-1 is substituted by oligosaccharide chain added Cys (28Cys GLP-1-disialo).

Example 21

Synthesis of 30Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Cys(Trt), Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Cys(Trt)-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:50) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 30Ala of GLP-1 is substituted by Cys.

Bromoacetamidyl disialo oligosaccharide (a) (a product of OTSUKA Chemical Co., Ltd.) (21.3 mg) and the peptide chain synthesized above (7.1 mg) were dissolved in 100 mM phosphate buffer (pH 7.5, 0.7 ml) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 20×250 mm, gradient: A solution:

0.1% TFA water, B solution: 0.09% TFA/10% water/90% AN 8.0 ml/min; 35→60% B, 20 min linear gradient] to obtain 6.6 mg of oligosaccharide chain added GLP-1 peptide wherein 30Ala of GLP-1 is substituted by oligosaccharide chain added Cys (30Cys GLP-1-disialo).

Example 22

Synthesis of 32Cys-disialo Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Cys(Trt), Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu (OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Cys (Trt)-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu (OtBu)-Ala-His(Trt) (SEQ ID NO:51) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 µm), φ 20×250 mm, gradient: A solution: 0.1% TFA water, B solution: 0.09% TFA/10% water/90% AN 8.0 ml/min; 35→60% B, 20 min linear gradient] to obtain peptide wherein 32Leu of GLP-1 is substituted by Cys.

Bromoacetamidyl disialo oligosaccharide (a) (a product of OTSUKA Chemical Co., Ltd.) (20 mg) and the peptide chain synthesized above (5.6 mg) were dissolved in 100 mM phosphate buffer (pH 7.5, 600 µl) and allowed to react at 37° C. for 4 hours. After complete consumption of raw materials were confirmed by HPLC, the reaction solution was directly subjected to purification by HPLC [column: SHISEIDO UG-120 (C18, 5 µm), φ 4.6×250 mm, gradient: A solution: 0.1% TFA water, B solution: 0.09% TFA/10% water/90% AN 0.7 ml/min; 35→60% B, 20 min linear gradient] to obtain 3.5 mg of oligosaccharide chain added GLP-1 peptide wherein 32Leu of GLP-1 is substituted by oligosaccharide chain added Cys (32Cys GLP-1-disialo).

Example 23

Synthesis of 34Cys-disialo Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Cys(Trt), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr (tBu), Fmoc-Phe, Fmoc-Thr(tBu), Fmoc-Gly, Fmoc-Glu (OtBu), Fmoc-Ala and Fmoc-His(Trt) were used as the amino acids protected by Fmoc group to obtain a 31-residue peptide of Gly-Arg(Pbf)-Gly-Cys(Trt)-Val-Leu-Trp(Boc)-Ala-Ile-Phe-Glu(OtBu)-Lys(Boc)-Ala-Ala-Gln(Trt)-Gly-Glu (OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His (Trt) (SEQ ID NO:52) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 µm), φ 20×250 mm, gradient: A solution: 0.1% TFA water, B solution: 0.09% TFA/10% water/90% AN 8.0 ml/min; 35→60% B, 20 min linear gradient] to obtain peptide wherein 34Lys of GLP-1 is substituted by Cys.

Bromoacetamidyl disialo oligosaccharide (a) (a product of OTSUKA Chemical Co., Ltd.) (33 mg) and the peptide chain synthesized above (10.0 mg) were dissolved in 100 mM phosphate buffer (pH 7.5, 1 ml) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 20×250 mm, gradient: A solution: 0.1% TFA water, B solution: 0.09% TFA/10% water/90% AN 8.0 ml/min; 35→60% B, 20 min linear gradient] to obtain 7.9 mg of oligosaccharide chain added GLP-1 peptide wherein 34Lys of GLP-1 is substituted by oligosaccharide chain added Cys (34Cys GLP-1-disialo).

Example 24

Synthesis of 22Cys-asialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Cys(Trt), Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Cys(Trt)-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:53) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 22Gly of GLP-1 is substituted by Cys.

Bromoacetamidyl digalactose oligosaccharide (c) (a product of OTSUKA Chemical Co., Ltd.) (15 mg)

[Formula 7]

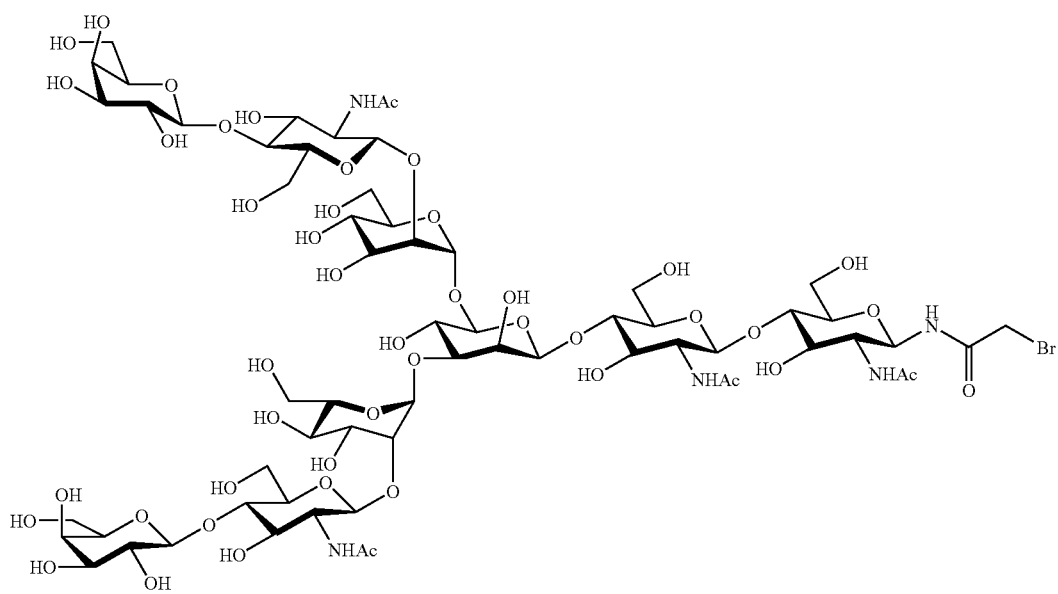

(c)

and the peptide chain synthesized above (3.4 mg) were dissolved in 100 mM phosphate buffer (pH 7.5, 340 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 0.7 mg of oligosaccharide chain added GLP-1 peptide wherein 22Gly of GLP-1 is substituted by oligosaccharide chain added Cys (22Cys GLP-1-asialo).

Example 25

Synthesis of 26Cys-asialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Cys(Trt), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Cys(Trt)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:54) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 26Lys of GLP-1 is substituted by Cys.

Bromoacetamidyl digalactose oligosaccharide (c) (a product of OTSUKA Chemical Co., Ltd.) (13 mg) and the peptide chain synthesized above (3.9 mg) were dissolved in 100 mM phosphate buffer (pH 7.5, 400 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 1.0 mg of oligosaccharide chain added GLP-1 peptide wherein 26Lys of GLP-1 is substituted by oligosaccharide chain added Cys (26Cys GLP-1-asialo).

Example 26

Synthesis of 30Cys-asialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Cys(Trt), Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Cys(Trt)-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:55) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 µm), φ 20×250 mm, gradient: A solution: 0.1% TFA water, B solution: 0.09% TFA/10% water/90% AN 8.0 ml/min; 35→60% B, 20 min linear gradient] to obtain peptide wherein 30Ala of GLP-1 is substituted by Cys.

Bromoacetamidyl digalactose oligosaccharide (c) (a product of OTSUKA Chemical Co., Ltd.) (9.0 mg) and the peptide chain synthesized above (4.1 mg) were dissolved in 100 mM phosphate buffer (pH 7.5, 410 µl) and allowed to react at 37° C. for 4 hours. After complete consumption of raw materials were confirmed by HPLC, the reaction solution was directly subjected to purification by HPLC [column: SHISEIDO UG-120 (C18, 5 µm), φ 4.6×250 mm, gradient: A solution: 0.1% TFA water, B solution: 0.09% TFA/10% water/90% AN 0.7 ml/min; 35→60% B, 20 min linear gradient] to obtain 2.4 mg of oligosaccharide chain added GLP-1 peptide wherein 30Ala of GLP-1 is substituted by oligosaccharide chain added Cys (30Cys GLP-1-asialo).

Example 27

Synthesis of 34Cys-asialo Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Cys(Trt), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr (tBu), Fmoc-Phe, Fmoc-Thr(tBu), Fmoc-Gly, Fmoc-Glu (OtBu), Fmoc-Ala and Fmoc-His(Trt) were used as the amino acids protected by Fmoc group to obtain a 31-residue peptide of Gly-Arg(Pbf)-Gly-Cys(Trt)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His (Trt) (SEQ ID NO:56) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 µm), φ 20×250 mm, gradient: A solution: 0.1% TFA water, B solution: 0.09% TFA/10% water/90% AN 8.0 ml/min; 35→60% B, 20 min linear gradient] to obtain peptide wherein 34Lys of GLP-1 is substituted by Cys.

Bromoacetamidyl digalactose oligosaccharide (c) (a product of OTSUKA Chemical Co., Ltd.) (10 mg) and the peptide chain synthesized above (3.5 mg) were dissolved in 100 mM phosphate buffer (pH 7.5, 350 µl) and allowed to react at 37° C. for 4 hours. After complete consumption of raw materials were confirmed by HPLC, the reaction solution was directly subjected to purification by HPLC [column: SHISEIDO UG-120 (C18, 5 µm), φ 4.6×250 mm, gradient: A solution: 0.1% TFA water, B solution: 0.09% TFA/10% water/90% AN 0.7 ml/min; 35→60% B, 20 min linear gradient] to obtain 2.2 mg of oligosaccharide chain added GLP-1 peptide wherein 34Lys of GLP-1 is substituted by oligosaccharide chain added Cys (34Cys GLP-1-asialo).

Example 28

Synthesis of 36Cys-asialo Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Cys(Trt), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr (tBu), Fmoc-Phe, Fmoc-Thr(tBu), Fmoc-Gly, Fmoc-Glu (OtBu), Fmoc-Ala and Fmoc-His(Trt) were used as the amino acids protected by Fmoc group to obtain a 31-residue peptide of Gly-Cys(Trt)-Gly-Lys(Boc)-Val-Leu-Trp(Boc)-Ala-Ile- Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:57) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 36Arg of GLP-1 is substituted by Cys.

Bromoacetamidyl digalactose oligosaccharide (c) (a product of OTSUKA Chemical Co., Ltd.) (3.0 mg) and the peptide chain synthesized above (0.5 mg) were dissolved in 100 mM phosphate buffer (pH 7.5, 100 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 0.2 mg of oligosaccharide chain added GLP-1 peptide wherein 36Arg of GLP-1 is substituted by oligosaccharide chain added Cys (36Cys GLP-1-asialo).

Example 29

Synthesis of 22Cys-diGlcNAc Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Cys(Trt), Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Cys(Trt)-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:58) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 22Gly of GLP-1 is substituted by Cys.

Bromoacetamidyl diN-acetylglucosamine oligosaccharide (d) (a product of OTSUKA Chemical Co., Ltd.) (8.4 mg)

[Formula 8]

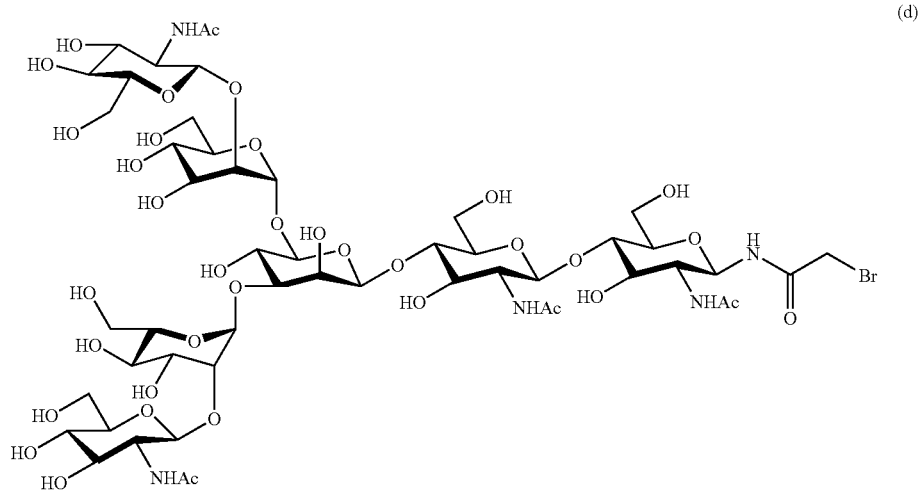

(d)

and the peptide chain synthesized above (3.4 mg) were dissolved in 100 mM phosphate buffer (pH 7.5, 340 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 2.2 mg of oligosaccharide chain added GLP-1 peptide wherein 22Gly of GLP-1 is substituted by oligosaccharide chain added Cys (22Cys GLP-1-diGlcNAc).

Example 30

Synthesis of 30Cys-diGlcNAc Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Cys(Trt), Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu (OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Cys(Trt)-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu (OtBu)-Ala-His(Trt) (SEQ ID NO:59) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 30Ala of GLP-1 is substituted by Cys.

Bromoacetamidyl diN-acetylglucosamine oligosaccharide (d) (a product of OTSUKA Chemical Co., Ltd.) (9.3 mg) and the peptide chain synthesized above (4.1 mg) were dissolved in 100 mM phosphate buffer (pH 7.5, 410 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 2.2 mg of oligosaccharide chain added GLP-1 peptide wherein 30Ala of GLP-1 is substituted by oligosaccharide chain added Cys (30Cys GLP-1-diGlcNAc).

Example 31

Synthesis of 34Cys-diGlcNAc Oligosaccharide Chain Added GLP-1 Peptide

A solid-phase synthesis column was charged with Amino-PEGA resin (100 mmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Cys(Trt), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu (OtBu), Fmoc-Ala and Fmoc-His(Trt) were used as the amino acids protected by Fmoc group to obtain a 31-residue peptide of Gly-Arg(Pbf)-Gly-Cys(Trt)-Val-Leu-Trp(Boc)-Ala-Ile-Phe-Glu(OtBu)-Lys(Boc)-Ala-Ala-Gln(Trt)-Gly-Glu (OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His (Trt) (SEQ ID NO:60) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 34Lys of GLP-1 is substituted by Cys.

Bromoacetamidyl diN-acetylglucosamine oligosaccharide (d) (a product of OTSUKA Chemical Co., Ltd.) (12 mg) and the peptide chain synthesized above (3.9 mg) were dissolved in 100 mM phosphate buffer (pH 7.5, 390 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 1.5 mg of oligosaccharide chain added GLP-1 peptide wherein 34Lys of GLP-1 is substituted by oligosaccharide chain added Cys (34Cys GLP-1-diGlcNAc).

Example 32

Synthesis of 22Cys-dimannose Oligosaccharide Chain Added GLP-1 Peptide Having

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Cys(Trt), Fmoc-Glu (OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln (Trt)-Cys(Trt)-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu (OtBu)-Ala-His(Trt) (SEQ ID NO:61) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain peptide wherein 22Gly of GLP-1 is substituted by Cys.

Bromoacetamidyl dimannose oligosaccharide (e) (a product of OTSUKA Chemical Co., Ltd.) (7.2 mg)

[Formula 9]

(e)

and the peptide chain synthesized above (3.4 mg) were dissolved in 100 mM phosphate buffer (pH 7.5, 340 µl) and allowed to react at 37° C. for 4 hours. After complete consumption of raw materials were confirmed by HPLC, the reaction solution was directly subjected to purification by HPLC [column: SHISEIDO UG-120 (C18, 5 µm), φ 4.6×250 mm, gradient: A solution: 0.1% TFA water, B solution: 0.09% TFA/10% water/90% AN 0.7 ml/min; 35→60% B, 20 min linear gradient] to obtain 1.6 mg of oligosaccharide chain added GLP-1 peptide wherein 22Gly of GLP-1 is substituted by oligosaccharide chain added Cys (22Cys GLP-1-dimannose).

Example 33

Synthesis of 30Cys-dimannose Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Cys(Trt), Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu (OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as the amino acids protected by Fmoc group to obtain a 31-residue peptide of Gly-Arg(Pbf)-Gly-Lys(Boc)-Val-Leu-Trp(Boc)-Cys(Trt)-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu (OtBu)-Ala-His(Trt) (SEQ ID NO:62) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 µm), φ 20×250 mm, gradient: A solution: 0.1% TFA water, B solution: 0.09% TFA/10% water/90% AN 8.0 ml/min; 35→60% B, 20 min linear gradient] to obtain peptide wherein 30Ala of GLP-1 is substituted by Cys.

Bromoacetamidyl dimannose oligosaccharide (e) (a product of OTSUKA Chemical Co., Ltd.) (10.2 mg) and the peptide chain synthesized above (4.1 mg) were dissolved in 100 mM phosphate buffer (pH 7.5, 410 µl) and allowed to react at 37° C. for 4 hours. After complete consumption of raw materials were confirmed by HPLC, the reaction solution was directly subjected to purification by HPLC [column: SHISEIDO UG-120 (C18, 5 µm), φ 4.6×250 mm, gradient: A solution: 0.1% TFA water, B solution: 0.09% TFA/10% water/90% AN 0.7 ml/min; 35→60% B, 20 min linear gradient] to obtain 2.4 mg of oligosaccharide chain added GLP-1 peptide wherein 30Ala of GLP-1 is substituted by oligosaccharide chain added Cys (30Cys GLP-1-dimannose).

Example 34

Synthesis of 34Cys-dimannose Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Cys(Trt), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr (tBu), Fmoc-Phe, Fmoc-Thr(tBu), Fmoc-Gly, Fmoc-Glu (OtBu), Fmoc-Ala and Fmoc-His(Trt) were used as the amino acids protected by Fmoc group to obtain a 31-residue peptide of Gly-Arg(Pbf)-Gly-Cys(Trt)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:63) on a solid-phase resin.

The obtained resin having a peptide formed thereon was partly taken in a solid-phase synthesis column. Trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 µm), φ 20×250 mm, gradient: A solution: 0.1% TFA water, B solution: 0.09% TFA/10% water/90% AN 8.0 ml/min; 35→60% B, 20 min linear gradient] to obtain peptide wherein 34Lys of GLP-1 is substituted by Cys.

Bromoacetamidyl dimannose oligosaccharide (e) (a product of OTSUKA Chemical Co., Ltd.) (10 mg) and the peptide chain synthesized above (3.9 mg) were dissolved in 100 mM phosphate buffer (pH 7.5, 390 µl) and allowed to react at 37° C. for 4 hours. After complete consumption of raw materials were confirmed by HPLC, the reaction solution was directly subjected to purification by HPLC [column: SHISEIDO UG-120 (C18, 5 µm), φ 4.6×250 mm, gradient: A solution: 0.1% TFA water, B solution: 0.09% TFA/10% water/90% AN 0.7 ml/min; 35→60% B, 20 min linear gradient] to obtain 1.3 mg of oligosaccharide chain added GLP-1 peptide wherein 34Lys of GLP-1 is substituted by oligosaccharide chain added Cys (34Cys GLP-1-dimannose).

Example 35

Synthesis of 12Asn-asialo Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Ala (0.50 mmol), MSNT (0.50 mmol) and N-methylimidazole (0.375 mmol) were dissolved in DCM (2 ml), loaded to a solid-phase synthesis column and stirred at 25° C. for 4 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu and Fmoc-Thr(tBu) were used as the amino acids protected by Fmoc group to obtain a 12-residue peptide of Ala-Gln(Trt)-Gly-Glu(OtBu)-Leu-Tyr(tBu)-Ser(tBu)-Ser(tBu)-Val-Asp(OtBu)-Ser(tBu)-Thr(tBu) (SEQ ID NO:64) on a solid-phase resin. The 12-residue peptide (equivalent to 7.0 µmol) was transferred to a separate solid phase synthesis column, Fmoc group was removed by using 20% piperidine/DMF solution (1 ml) for 15 minutes, and washed with DMF. To a separate centrifuge tube, asialo oligosaccharide chain added asparagine (b) (a product of OTSUKA Chemical Co., Ltd.) 27.7 mg (14.0 µmol) and DEPBT 6.3 mg (21.1 µmol) were dissolved in DMF/DMSO (1:4 mixture solution, 0.35 ml) and loaded to the solid-phase synthesis column. After addition of DIPEA 2.4 µl (14.1 µmol), the mixture was stirred at room temperature for 18 hours. After washing with DMF and DCM, oligosaccharide chain added 13-residue peptide of Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Asn(Oligosaccharide chain) (SEQ ID NO:65) was obtained on a solid phase.

The amino acid having an amino group protected with Fmoc group and HOBt (4.7 mg, 0.03 mmol), and DIPCI (5.4 µl, 0.03 mmol) were dissolved in DMF (0.875 ml). After activation for 15 minutes, the mixture was loaded to a solid-phase synthesis column. After stirring at room temperature for one hour, Fmoc group was removed by using a 20% piperidine/DMF solution (1 ml) for 20 minutes. This operation was repeatedly performed to sequentially condense amino acids. Fmoc-Thr(tBu), Fmoc-Gly, Fmoc-Glu(OtBu) and Fmoc-Ala were used as amino acids protected with Fmoc group, and Boc-His(Trt) was used as amino acids protected with Boc group to obtain a oligosaccharide chain added 18-residue peptide of Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Asn(Oligosaccharide chain)-Thr(tBu)-Gly-Glu(OtBu)-Ala-His(Trt) (SEQ ID NO:66) on a solid phase resin.

After washing with DCM and DMF, mixture solution of trifluoroethanol and acetic acid (1:1) was added such that the resin was thoroughly soaked and stirred at room temperature for 18 hours. The resin was removed by filtration and the reaction solution was concentrated under reduced pressure. The resulting residue was concentrated to obtain oligosaccharide chain added protected peptide of Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Asn(Oligosaccharide chain)-Thr(tBu)-Gly-Glu(OtBu)-Ala-His(Trt)-NH-Boc (SEQ ID NO:67).

The oligosaccharide chain added 18-residue protected peptide (equivalent to 2.45 µmol) was transferred to an eggplant flask, dissolved in DMF (0.1 ml) and cooled to −15 to −20° C. under an argon atmosphere. To this, benzylthiol (8.7 µl, 73.6 µmol) was added and separately prepared DMF solution (0.231 ml) of PyBOP (6.4 mg, 12.3 µmol) was added, and subsequently, DIPEA 2.1 µl (12.3 µmol) was added. The mixture was stirred at −15 to −20° C. for 2 hours and added to cool diethyl ether (150 ml). After precipitation of peptide component, the solution portion was removed by a membrane filter. To the residue, trifluoroacetic acid:water:TIPS (=95:2.5:2.5) was added and stirred at room temperature. After 2 hours, the solution was once again added to separately prepared diethyl ether (150 ml) to obtain a precipitate. Thereafter, the solution portion was removed by a membrane filter to obtain a residue containing a desired peptide thioester compound. This residue was purified by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain 2.1 mg of peptide having benzyl thioester at C terminal: PhS-Ala-Gln-Gly-Glu-Leu-Tyr-Ser-Ser-Val-Asp-Ser-Thr-Asn(Oligosaccharide chain)-Thr-Gly-Glu-Ala-His (SEQ ID NO:68).

On the other hand, a solid-phase synthesis column was charged with Amino-PEGA resin (product of Merck) (100 μmol), washed thoroughly with dichloromethane (DCM) and DMF and thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to the solid-phase synthesis column and stirred at 25° C. for 4 hours. After stirring, the resin was washed with DCM and DMF. Fmoc group was removed by using a 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc) were used as the amino acids protected by Fmoc group and Boc-Cys(Trt) was used as an amino acid protected by Boc group to obtain 13-residue peptide of Gly-Arg(Pbf)-Gly-Lys(Boc)-Val-Leu-Trp(Boc)-Ala-Ile-Phe-Glu(OtBu)-Lys(Boc)-Cys(Trt) (SEQ ID NO:69) on a solid-phase resin. To this, trifluoroacetic acid:water:TIPS (=95:2.5:2.5) was added and stirred at room temperature for 3.5 hours. The mixture was then added to separately prepared diethyl ether (150 ml) to obtain a precipitate. Thereafter, the solution portion was removed by a membrane filter to obtain a residue containing a desired peptide thioester compound. This residue was purified by HPLC [column: SHISEIDO UG-120 (C18 5 μm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain desired peptide: Gly-Arg-Gly-Lys-Val-Leu-Trp-Ala-Ile-Phe-Glu-Lys-Cys (SEQ ID NO:70).

The two types of peptides thus prepared: the 18-residue peptide having benzylthio ester at C terminal (2.1 mg) and the 13-residue peptide (2.6 mg) were placed in a same centrifuge tube and dissolved in a buffer solution (pH 6.8, 0.58 ml) (prepared with 6 M guanidine hydrochloride solution and 0.2 mM phosphoric acid solution). Thiophenol (2.9 μl) was then added at room temperature and a reaction was performed at room temperature. After 24 hours, the reaction solution was purified by HPLC [column: SHISEIDO UG-120 (C18 5 μm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain 1.5 mg of oligosaccharide chain added 31-residue peptide.

The obtained oligosaccharide chain added peptide was placed in a centrifuge tube and dissolved in a buffer solution (pH 7.0, prepared from 35 mM TCEP solution, 6 M guanidine hydrochloride solution and 0.2 mM phosphoric acid solution). To the reaction solution, activated Raney Nickel was added at room temperature. After 26 hours, completion of the reaction was confirmed by HPLC. Thereafter, the reaction solution was filtrated by a membrane filter and the filtrate portion containing desired oligosaccharide chain added GLP-1 peptide was subjected to purification by HPLC [column: SHISEIDO UG-120 (C18 5 μm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain 0.8 mg of desired oligosaccharide chain added GLP-1 peptide wherein 12Phe of GLP-1 is substituted by asialo oligosaccharide chain added Asn (12Asn GLP-1-asialo).

Example 36

Synthesis of 18Asn-asialo Oligosaccharide Chain Added GLP-1 Peptide

A solid-phase synthesis column was charged with Amino-PEGA resin (50 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.125 mmol), TBTU (0.125 mmol) and N-ethylmorpholine (0.125 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.25 mmol), MSNT (0.25 mmol) and N-methylimidazole (0.175 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.25 mmol), the resulting mixture was loaded to a solid-phase synthesis column. Subsequently, 0.9 M DIPEA/NMP (0.25 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.25 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu and Fmoc-Tyr(tBu) were used as the amino acids protected by Fmoc group to obtain a 19-residue peptide of Gly-Arg(Pbf)-Gly-Lys(Boc)-Val-Leu-Trp(Boc)-Ala-Ile- Phe-Glu(OtBu)-Lys(Boc)-Ala-Ala-Gln(Trt)-Gly-Glu(OtBu)-Leu-Tyr(tBu) (SEQ ID NO:71) on a solid-phase resin.

Asialo oligosaccharide chain added asparagine (b) (a product of OTSUKA Chemical Co., Ltd.) 198 mg (100 mmol) and DEPBT 30.0 mg (100 μmol) were dissolved in NMP/DMSO (2.4/0.6 ml) and loaded to the solid-phase synthesis column. After addition of DIPEA 26 μl (150 μmol), the mixture was stirred at room temperature for 24 hours. After washing with DMF and DCM, oligosaccharide chain added 20-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Asn(Oligosaccharide chain) (SEQ ID NO:72) was obtained on a solid phase. Subsequently, the amino acid having an amino group protected with Fmoc group was condensed by HOBt 34 mg (0.25 mmol), DIPCI 38 μl (0.25 mmol) and DMF (1 ml) to form oligosaccharide chain added 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Asn(Oligosaccharide chain)-Ser(tBu)-Val-Asp(OtBu)-Ser(tBu)-Thr(tBu)-Phe-Thr(tBu)-Gly-Glu(OtBu)-Ala-His(Trt) (SEQ ID NO:73).

To the obtained resin having an oligosaccharide chain added peptide formed thereon, trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain 8.2 mg of oligosaccharide chain added GLP-1 peptide wherein 18Ser of GLP-1 is substituted with asialo oligosaccharide chain added Asn (18Asn GLP-1-asialo).

Example 37

Synthesis of 22Asn-asialo Oligosaccharide Chain Added GLP-1 Peptide

A solid-phase synthesis column was charged with Amino-PEGA resin (50 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.125 mmol), TBTU (0.125 mmol) and N-ethylmorpholine (0.125 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.25 mmol), MSNT (0.25 mmol) and N-methylimidazole (0.175 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.25 mmol), the resulting mixture was loaded to a solid-phase synthesis column. Subsequently, 0.9 M DIPEA/NMP (0.25 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.25 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala and Fmoc-Gln(Trt) were used as the amino acids protected by Fmoc group to obtain a 15-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt) (SEQ ID NO:74) on a solid-phase resin.

Asialo oligosaccharide chain added asparagine (b) (a product of OTSUKA Chemical Co., Ltd.) 198 mg (100 μmol) and DEPBT 30 mg (100 μmol) were dissolved in NMP/DMSO (2.4/0.6 ml) and loaded to the solid-phase synthesis column. After addition of DIPEA (26 μl, 150 μmol), the mixture was stirred at room temperature for 24 hours. After washing with DMF and DCM, oligosaccharide chain added 16-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Asn (Oligosaccharide chain) (SEQ ID NO:75) was obtained on a solid phase. Subsequently, the amino acid having an amino group protected with Fmoc group was condensed by HOBt 34 mg (0.25 mmol), DIPCI 38 μl (0.25 mmol) and DMF (1 ml) to form oligosaccharide chain added 31-residue peptide of Gly-Arg(Pbf)-Gly-Lys(Boc)-Val-Leu-Trp(Boc)-Ala-Ile-Phe-Glu(OtBu)-Lys(Boc)-Ala-Ala-Gln(Trt)-Asn(Oligosaccharide chain)-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:76).

To the obtained resin having an oligosaccharide chain added peptide formed thereon, trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 7.0 ml/min; 35→60% B, 20 min linear gradient] to obtain 12.2 mg of oligosaccharide chain added GLP-1 peptide wherein 22Gly of GLP-1 is substituted with asialo oligosaccharide chain added Asn (22Asn GLP-1-asialo).

Example 38

Synthesis of 26Asn-asialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to a solid-phase synthesis column and stirred at 25° C. for 4 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr (tBu), Fmoc-Phe, Fmoc-Thr(tBu), Fmoc-Gly, Fmoc-Glu (OtBu) and Fmoc-Ala were used as the amino acids protected by Fmoc group and Boc-His(Trt) was used as the amino acid protected by Boc group to obtain a 18-residue peptide of Ala-Gln(Trt)-Gly-Glu(OtBu)-Leu-Tyr(tBu)-Ser(tBu)-Ser (tBu)-Val-Asp(OtBu)-Ser(tBu)-Thr(tBu)-Phe-Thr(tBu)- Gly-Glu(OtBu)-Ala-His(Trt) (SEQ ID NO:77) on a solid-phase resin.

After washing with DCM and DMF, a mixture solution of trifluoroethanol and acetic acid (1:1) was added such that the resin was thoroughly soaked and stirred at room temperature for 18 hours. The resin was removed by filtration and the reaction solution was concentrated under reduced pressure. The resulting residue was concentrated to obtain protected peptide of Ala-Gln(Trt)-Gly-Glu(OtBu)-Leu-Tyr(tBu)-Ser (tBu)-Ser(tBu)-Val-Asp(OtBu)-Ser(tBu)-Thr(tBu)-Phe-Thr (tBu)-Gly-Glu(OtBu)-Ala-His(Trt)-NHBoc (SEQ ID NO:78).

The 18-residue protected peptide (equivalent to 35 μmol) was transferred to an eggplant flask, dissolved in DMF (3.7 ml) and cooled to −15 to −20° C. under an argon atmosphere. To this, benzylthiol (125 μl, 1.06 mmol) was added and separately prepared DMF solution (1.0 ml) of PyBOP (94.7 mg, 182 μmol) was added, and subsequently, DIPEA (29.8 μl, 175 μmol) was added. The mixture was stirred at −15 to −20° C. for 2 hours and added to cool diethyl ether (150 ml). After precipitation of peptide component, the solution portion was removed by a membrane filter. To the residue, trifluoroacetic acid:water:TIPS (=95:2.5:2.5) was added and stirred at room temperature. After 2 hours, the solution was once again added to separately prepared diethyl ether (150 ml) to obtain a precipitate. Thereafter, the solution portion was removed by a membrane filter to obtain a residue containing a desired peptide thioester compound. This residue was purified by HPLC [column: SHISEIDO UG-120 (C18 5 μm), φ 20×250 mm, gradient: A solution: 0.1% TFA water, B solution: 0.09% TFA/10% water/90% AN 7.0 ml/min; 25→45% B (15 min)→ 60% B (10 min)→95% B (10 min), linear gradient] to obtain 18-residue peptide having benzyl thioester at C terminal: PhS-Ala-Gln-Gly-Glu-Leu-Tyr-Ser-Ser-Val-Asp-Ser-Thr-Phe-Thr-Gly-Glu-Ala-His (SEQ ID NO:79).

On the other hand, a solid-phase synthesis column was charged with Amino-PEGA resin (product of Merck) (100 μmol), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to the solid-phase synthesis column and stirred at 25° C. for 4 hours. After stirring, the resin was washed with DCM and DMF. Fmoc group was removed by using a 20% piperidine/DMF solution (2 ml) for 15 minutes. After washing with DMF, amino acids were sequentially condensed in accordance with the method shown below to extend a peptide chain.

The amino acid having an amino group protected with Fmoc group and HOBt (67.6 mg, 0.50 mmol) and DIPCI (77.0 μl, 63.1 mg, 0.50 mmol) were dissolved in DMF (2 ml). After activation for 15 minutes, the resulting mixture was loaded to a solid-phase synthesis column. After stirring at room temperature for one hour, Fmoc group was removed by using a 20% piperidine/DMF solution (2 ml) for 20 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, Fmoc-Phe and Fmoc-Glu(OtBu) were used as the amino acids protected by Fmoc group to obtain 11-residue peptide of Fmoc-Gly-Arg(Pbf)-Gly-Lys(Boc)-Val-Leu-Trp(Boc)- Ala-Ile-Phe-Glu(OtBu) (SEQ ID NO:80) on a solid-phase resin. The 11-residue peptide (equivalent to 10 μmol) was transferred to a separately prepared solid-phase synthesis column, Fmoc group was removed using 20% piperidine/ DMF solution (2 ml) for 15 minutes, and washed with DMF. To a separate centrifuge tube, asialo oligosaccharide chain added asparagine (b) (a product of OTSUKA Chemical Co., Ltd.) 40.0 mg (20.0 μmol) and DEPBT 9.0 mg (30.0 μmol) were dissolved in DMF/DMSO (4:1 mixture solution, 0.5 ml) and loaded to the solid-phase synthesis column. After addition of DIPEA 3.4 μl (20 μmol), the mixture was stirred at room temperature for 16 hours.

After stirring, the resin was washed with DCM and DMF. Fmoc group was removed by using a 20% piperidine/DMF solution (1 ml) for 15 minutes and then, washed with DMF. Boc-Cys(Trt), HOBt 6.8 mg (0.05 mmol), and DIPCI 7.7 μl (0.05 mmol) were dissolved in DMF (1 ml). After activation for 15 minutes, the mixture was loaded to a solid-phase synthesis column. After stirring at room temperature for one hour, the resin was washed with DCM and DMF to obtain oligosaccharide chain added 13-residue peptide of Gly-Arg (Pbf)-Gly-Lys(Boc)-Val-Leu-Trp(Boc)-Ala-Ile-Phe-Glu (OtBu)-Asn(Oligosaccharide chain)-Cys(trt) (SEQ ID NO:81) on a solid phase resin. To this, trifluoroacetic acid: water:TIPS (=95:2.5:2.5) was added and stirred at room temperature for 3.5 hours. Thereafter, the solution was added to a separately prepared diethyl ether (150 ml) to obtain precipitation, and subjected to centrifugation to separate a precipitate containing a desired oligosaccharide chain added peptide and a solution portion. After the solution portion was removed, it was subjected to purification by HPLC [column: SHISEIDO UG-120 (C18 5 μm), φ 20×250 mm, gradient: A solution: 0.1% TFA water, B solution: 0.09% TFA/10% water/90% AN 7.0 ml/min; 25→45% B (15 min)→60% B (10 min)→95% B (10 min) linear gradient] to obtain 7.1 mg of desired oligosaccharide chain added peptide.

The two types of peptides thus prepared: the 18-residue peptide having benzylthio ester at C terminal (1.6 mg) and the oligosaccharide chain added 13-residue peptide (2.5 mg) were placed in a same centrifuge tube and dissolved in a buffer solution (pH 6.8, 0.8 ml) (prepared with 6 M guanidine hydrochloride solution and 0.2 mM phosphoric acid solution). Thiophenol (8.0 µl) was then added at room temperature and a reaction was performed at room temperature. After 24 hours, the completion of the reaction was confirmed by HPLC. Thereafter, the reaction solution was directly purified by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain 2.0 mg of desired oligosaccharide chain added 31-residue peptide.

The obtained oligosaccharide chain added peptide (1.0 mg) was placed in a centrifuge tube and dissolved in a buffer solution (pH 7.0, prepared from 35 mM TCEP solution, 6 M guanidine hydrochloride solution and 0.2 mM phosphoric acid solution). To the reaction solution, activated Raney Nickel was added at room temperature. After 18 hours, completion of the reaction was confirmed by HPLC. Thereafter, the reaction solution was filtrated by a membrane filter and the filtrate portion containing desired oligosaccharide chain added peptide was subjected to purification by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain 0.2 mg of desired oligosaccharide chain added GLP-1 peptide wherein 26Lys of GLP-1 is substituted by asialo oligosaccharide chain added Asn (26Asn GLP-1-asialo).

Example 39

Synthesis of 27Asn-asialo Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Ala (0.50 mmol), MSNT (0.50 mmol) and N-methylimidazole (0.375 mmol) were dissolved in DCM (2 ml), loaded to a solid-phase synthesis column and stirred at 25° C. for 4 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu) and Fmoc-Ala were used as the amino acids protected by Fmoc group and Boc-His(Trt) was used as the amino acid protected by Boc group to obtain a 18-residue peptide of Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:82) on a solid-phase resin.

After washing with DCM and DMF, a mixture solution of trifluoroethanol and acetic acid (1:1) was added such that the resin was thoroughly soaked and stirred at room temperature for 18 hours. The resin was removed by filtration and the reaction solution was concentrated under reduced pressure. The resulting residue was concentrated to obtain 18-residue protected peptide of Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt)-NHBoc (SEQ ID NO:83).

The 18-residue protected peptide (equivalent to 35 µmol) was transferred to an eggplant flask, dissolved in DMF (3.7 ml) and cooled to −15 to −20° C. under an argon atmosphere. To this, benzylthiol (125 µl, 1.06 mmol) was added and separately prepared DMF solution (1.0 ml) of PyBOP (94.7 mg, 182 µmol) was added, and subsequently, DIPEA (29.8 µl, 175 µmol) was added. The mixture was stirred at −15 to −20° C. for 2 hours and added to cool diethyl ether (150 ml). After precipitation of peptide component, the solution portion was removed by a membrane filter. To the residue, trifluoroacetic acid:water:TIPS (=95:2.5:2.5) was added and stirred at room temperature. After 2 hours, the solution was once again added to separately prepared diethyl ether (150 ml) to obtain a precipitate. Thereafter, the solution portion was removed by a membrane filter to obtain a residue containing a desired peptide thioester compound. This residue was purified by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain 18-residue peptide having benzyl thioester at C terminal: PhS-Ala-Gln-Gly-Glu-Leu-Tyr-Ser-Ser-Val-Asp-Ser-Thr-Phe-Thr-Gly-Glu-Ala-His (SEQ ID NO:84).

On the other hand, a solid-phase synthesis column was charged with Amino-PEGA resin (product of Merck) (100 µmol), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to the solid-phase synthesis column and stirred at 25° C. for 4 hours.

After stirring, the resin was washed with DCM and DMF. Fmoc group was removed by using a 20% piperidine/DMF solution (2 ml) for 15 minutes. After washing with DMF, amino acids were sequentially condensed in accordance with the method shown below to extend a peptide chain.

The amino acid having an amino group protected with Fmoc group and HOBt (67.6 mg, 0.50 mmol) and DIPCI (77.0 µl, 63.1 mg, 0.50 mmol) were dissolved in DMF (2 ml). After activation for 15 minutes, the resulting mixture was loaded to a solid-phase synthesis column. After stirring at room temperature for one hour, Fmoc group was removed by using a 20% piperidine/DMF solution (2 ml) for 20 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala, Fmoc-Ile, and Fmoc-Phe were used as the amino acids protected by Fmoc group to obtain 10-residue peptide of Gly-Arg(Pbf)-Gly-Lys(Boc)-Val-Leu-Trp(Boc)-Ala-Ile-Phe (SEQ ID NO:85) on a solid-phase resin. The 10-residue peptide (equivalent to 10 µmol) was transferred to a separately prepared solid-phase synthesis column. Fmoc group was removed using 20% piperidine/DMF solution (1 ml) for 15 minutes, and washed with DMF. To a separate centrifuge tube, asialo oligosaccharide chain added asparagine (b) (a product of OTSUKA Chemical Co., Ltd.) 37.2 mg (18.8 µmol) and DEPBT 8.5 mg (28.4 µmol) were dissolved in DMF/DMSO (4:1 mixture solution, 1.0 ml) and loaded to the solid-phase synthesis column. After addition of DIPEA 3.2 µl (18.8 µmol), the mixture was stirred at room temperature for 16 hours.

After stirring, the resin was washed with DCM and DMF. Fmoc group was removed by using a 20% piperidine/DMF solution (1 ml) for 15 minutes. After washing with DMF, amino acids were sequentially condensed in accordance with the method shown below to extend a peptide chain.

The amino acid having an amino group protected with Fmoc group and HOBt (6.8 mg, 0.05 mmol) and DIPCI (7.7 µl, 0.05 mmol) were dissolved in DMF (1 ml). After activation for 15 minutes, the resulting mixture was loaded to a solid-phase synthesis column. After stirring at room temperature for one hour, Fmoc group was removed by using a 20% piperidine/DMF solution (1 ml) for 20 minutes. This operation was repeatedly performed to sequentially condense amino acids. Fmoc-Lys(Boc) was used as the amino acid protected by Fmoc group and Boc-Cys(Trt) was used as the amino acid protected by Boc group to obtain oligosaccharide chain added 13-residue peptide of Gly-Arg(Pbf)-Gly-Lys(Boc)-Val-Leu-Trp(Boc)-Ala-Ile-Phe-Asn(Oligosaccharide chain)-Lys(Boc)-Cys(Trt) (SEQ ID NO:86) on a solid-phase resin. To this, trifluoroacetic acid:water:TIPS (=95:2.5:2.5) was added and stirred at room temperature for 3.5 hours. Thereafter, the solution was added to a separately prepared diethyl ether (150 ml) to obtain precipitation, and subjected to centrifugation to separate a precipitate containing a desired oligosaccharide chain added peptide and a solution portion. The solution portion was removed and desired product was confirmed by HPLC. After purification by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min) linear gradient] to obtain 6.1 mg of oligosaccharide chain added 13-residue peptide.

The two types of peptides thus prepared: the 18-residue peptide having benzylthio ester at C terminal (1.3 mg) and the oligosaccharide chain added 13-residue peptide (2.0 mg) were placed in a same centrifuge tube and dissolved in a buffer solution (pH 6.8, 0.64 ml) (prepared with 6 M guanidine hydrochloride solution and 0.2 mM phosphoric acid solution). Thiophenol (6.4 µl) was then added at room temperature and a reaction was performed at room temperature.

After 24 hours, the completion of the reaction was confirmed by HPLC. Thereafter, the reaction solution was directly purified by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain 1.0 mg of oligosaccharide chain added 31-residue peptide.

The obtained oligosaccharide chain added peptide (1.0 mg) was placed in a centrifuge tube and dissolved in a buffer solution (pH 7.0, prepared from 35 mM TCEP solution, 6 M guanidine hydrochloride solution and 0.2 mM phosphoric acid solution). To the reaction solution, activated Raney Nickel was added at room temperature. After 18 hours, completion of the reaction was confirmed by HPLC. Thereafter, the reaction solution was filtrated by a membrane filter and the filtrate portion containing oligosaccharide chain added peptide was subjected to purification by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain 0.5 mg of desired oligosaccharide chain added GLP-1 peptide wherein 27Glu of GLP-1 is substituted by asialo oligosaccharide chain added Asn (27Asn GLP-1-asialo).

Example 40

Synthesis of 28Asn-asialo Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Ala (0.50 mmol), MSNT (0.50 mmol) and N-methylimidazole (0.375 mmol) were dissolved in DCM (2 ml), loaded to a solid-phase synthesis column and stirred at 25° C. for 4 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the resulting mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. This operation was repeatedly performed using an amino acid protected with Fmoc group (0.5 mmol) to sequentially condense amino acids.

Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr (tBu), Fmoc-Phe, Fmoc-Thr(tBu), Fmoc-Gly, Fmoc-Glu (OtBu) and Fmoc-Ala were used as the amino acids protected by Fmoc group and Boc-His(Trt) was used as the amino acid protected by Boc group to obtain a 18-residue peptide of Ala-Gln(Trt)-Gly-Glu(OtBu)-Leu-Tyr(tBu)-Ser(tBu)-Ser (tBu)-Val-Asp(OtBu)-Ser(tBu)-Thr(tBu)-Phe-Thr(tBu)-Gly-Glu(OtBu)-Ala-His(Trt) (SEQ ID NO:87) on a solid-phase resin.

After washing with DCM and DMF, a mixture solution of trifluoroethanol and acetic acid (1:1) was added such that the resin was thoroughly soaked and stirred at room temperature for 18 hours. The resin was removed by filtration and the reaction solution was concentrated under reduced pressure. The resulting residue was concentrated to obtain 18-residue protected peptide of Ala-Gln(Trt)-Gly-Glu(OtBu)-Leu-Tyr (tBu)-Ser(tBu)-Ser(tBu)-Val-Asp(OtBu)-Ser(tBu)-Thr (tBu)-Phe-Thr(tBu)-Gly-Glu(OtBu)-Ala-His(Trt)-NHBoc (SEQ ID NO:88).

The 18-residue protected peptide (equivalent to 35 µmol) was transferred to an eggplant flask, dissolved in DMF (3.7 ml) and cooled to −15 to −20° C. under an argon atmosphere. To this, benzylthiol (125 µl, 1.06 µmol) was added and separately prepared DMF solution (1.0 ml) of PyBOP (94.7 mg, 182 µmol) was added, and subsequently, DIPEA (29.8 µl, 175 µmol) was added. The mixture was stirred at −15 to −20° C. for 2 hours and added to cool diethyl ether (150 ml). After precipitation of peptide component, the solution portion was removed by a membrane filter. To the residue, trifluoroacetic acid:water:TIPS (=95:2.5:2.5) was added and stirred at room temperature. After 2 hours, the solution was once again added to separately prepared diethyl ether (150 ml) to obtain a precipitate. Thereafter, the solution portion was removed by a membrane filter to obtain a residue containing a desired peptide thioester compound. This residue was purified by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain 18-residue peptide having benzyl thioester at C terminal: PhS-Ala-Gln-Gly-Glu-Leu-Tyr-Ser-Ser-Val-Asp-Ser-Thr-Phe-Thr-Gly-Glu-Ala-His (SEQ ID NO:89).

On the other hand, a solid-phase synthesis column was charged with Amino-PEGA resin (product of Merck) (100 µmol), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to the solid-phase synthesis column and stirred at 25° C. for 4 hours. After stirring, the resin was washed with DCM and DMF. Fmoc group was removed by using a 20% piperidine/DMF solution (2 ml) for 15 minutes. After washing with DMF, amino acids were sequentially condensed in accordance with the method shown below to extend a peptide chain.

The amino acid having an amino group protected with Fmoc group and HOBt (67.6 mg, 0.50 mmol) and DIPCI (77.0 µl, 63.1 mg, 0.50 mmol) were dissolved in DMF (2 ml). After activation for 15 minutes, the resulting mixture was loaded to a solid-phase synthesis column. After stirring at room temperature for one hour, Fmoc group was removed by using a 20% piperidine/DMF solution (2 ml) for 20 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu, Fmoc-Trp(Boc), Fmoc-Ala and Fmoc-Ile were used as the amino acids protected by Fmoc group to obtain 9-residue peptide of Gly-Arg(Pbf)-Gly-Lys (Boc)-Val-Leu-Trp(Boc)-Ala-Ile (SEQ ID NO:90) on a solid-phase resin. The 9-residue peptide (equivalent to 11 µmol) was transferred to a separately prepared solid-phase synthesis column, Fmoc group was removed using 20% piperidine/ DMF solution (1 ml) for 15 minutes, and washed with DMF. To a separate centrifuge tube, asialo oligosaccharide chain added asparagine (b) (a product of OTSUKA Chemical Co., Ltd.) 82.6 mg (41.8 µmol) and DEPBT 18.7 mg (62.5 µmol) were dissolved in DMF/DMSO (4:1 mixture solution, 1.4 ml) and loaded to the solid-phase synthesis column. After addition of DIPEA 7.0 µl (41.2 µmol), the mixture was stirred at room temperature for 16 hours.

After stirring, the resin was washed with DCM and DMF. Fmoc group was removed by using a 20% piperidine/DMF solution (1 ml) for 15 minutes. After washing with DMF, amino acids were sequentially condensed in accordance with the method shown below to extend a peptide chain.

The amino acid having an amino group protected with Fmoc group and HOBt 6.8 mg (0.05 mmol), and DIPCI 7.7 µl (0.05 mmol) were dissolved in DMF (1 ml). After activation for 15 minutes, the mixture was loaded to a solid-phase synthesis column. After stirring at room temperature for one hour, Fmoc group was removed by using a 20% piperidine/ DMF solution (1 ml) for 20 minutes. This operation was repeatedly performed to sequentially condense amino acids. Fmoc-Glu(OtBu) and Fmoc-Lys(Boc) were used as the amino acids protected by Fmoc group and Boc-Cys(Trt) was used as the amino acid protected by Boc group to obtain oligosaccharide chain added 13-residue peptide of Gly-Arg (Pbf)-Gly-Lys(Boc)-Val-Leu-Trp(Boc)-Ala-Ile-Asn(Oligosaccharide chain)-Glu(OtBu)-Lys(Boc)-Cys(Trt) (SEQ ID NO:91) on a solid-phase resin. To this, trifluoroacetic acid: water:TIPS (=95:2.5:2.5) was added and stirred at room temperature for 3.5 hours. Thereafter, the solution was added to a separately prepared diethyl ether (150 ml) to obtain precipitation, and subjected to centrifugation to separate a precipitate containing a desired oligosaccharide chain added peptide and a solution portion. After the solution portion was removed, it was subjected to purification by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min) linear gradient] to obtain 10.1 mg of oligosaccharide chain added 13-residue peptide.

The two types of peptides thus prepared: the 18-residue peptide having benzylthio ester at C terminal (3.6 mg) and the oligosaccharide chain added 13-residue peptide (5.6 mg) were placed in a same centrifuge tube and dissolved in a buffer solution (pH 6.8, 1.8 ml) (prepared with 6 M guanidine hydrochloride solution and 0.2 mM phosphoric acid solution). Thiophenol (18 µl) was then added at room temperature and a reaction was performed at room temperature. After 24 hours, the completion of the reaction was confirmed by HPLC. Thereafter, the reaction solution was directly purified by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain 3.8 mg of oligosaccharide chain added 31-residue peptide.

The obtained oligosaccharide chain added peptide (1.3 mg) was placed in a centrifuge tube and dissolved in a buffer solution (pH 7.0, prepared from 35 mM TCEP solution, 6 M guanidine hydrochloride solution and 0.2 mM phosphoric acid solution). To the reaction solution, activated Raney Nickel was added at room temperature. After 40 hours, completion of the reaction was confirmed by HPLC. Thereafter, the reaction solution was filtrated by a membrane filter and the filtrate portion containing oligosaccharide chain added peptide was subjected to purification by HPLC [column: SHISEIDO UG-120 (C18 5 μm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain 0.8 mg of desired oligosaccharide chain added GLP-1 peptide wherein 28Phe of GLP-1 is substituted by asialo oligosaccharide chain added Asn (28Asn GLP-1-asialo).

Example 41

Synthesis of 30 Asn-asialo Oligosaccharide Chain Added GLP-1 Peptide

A solid-phase synthesis column was charged with Amino-PEGA resin (50 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.125 mmol), TBTU (0.125 mmol) and N-ethylmorpholine (0.125 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.25 mmol), MSNT (0.25 mmol) and N-methylimidazole (0.175 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.25 mmol), the resulting mixture was loaded to a solid-phase synthesis column. Subsequently, 0.9 M DIPEA/NMP (0.25 mmol) was added to the solid-phase synthesis column. After stirring at room temperature for 20 minutes, the resin was washed with DCM and DMF, and Fmoc group was removed by using a 20% piperidine/DMF solution (2 ml) for minutes. This operation was repeatedly performed using an amino acid protected with Fmoc group (0.25 mmol) to sequentially condense amino acids.

Fmoc-Gly, Fmoc-Arg(Pbf), Fmoc-Gly, Fmoc-Lys(Boc), Fmoc-Val, Fmoc-Leu and Fmoc-Trp(Boc) were used as the amino acids protected by Fmoc group to obtain a 7-residue peptide of Gly-Arg(Pbf)-Gly-Lys(Boc)-Val-Leu-Trp(Boc) (SEQ ID NO:92) on a solid-phase resin.

Asialo oligosaccharide chain added asparagine (b) (a product of OTSUKA Chemical Co., Ltd.) 198 mg (100 μmol) and DEPBT 30.0 mg (100 μmol) were dissolved in NMP/DMSO (2.4/0.6 ml) and loaded to the solid-phase synthesis column. After addition of DIPEA 26 μl (150 μmol), the mixture was stirred at room temperature for 24 hours. After washing with DCM and DMF, oligosaccharide chain added 8-residue peptide of Gly-Arg(Pbf)-Gly-Lys(Boc)-Val-Leu-Trp(Boc)-Asn (Oligosaccharide chain) (SEQ ID NO:93) was obtained on the solid phase. Subsequently, the amino acid having an amino group protected with Fmoc group was condensed by HOBt 34 mg (0.25 mmol), DIPCI 38 μl (0.25 mmol) and DMF (1 ml) to form oligosaccharide chain added 31-residue peptide of Gly-Arg(Pbf)-Gly-Lys(Boc)-Val-Leu-Trp(Boc)-Asn(Oligosaccharide chain)-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:94).

To the obtained resin having an oligosaccharide chain added peptide formed thereon, trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 7.0 ml/min; 35→60% B, 20 min linear gradient] to obtain 6.4 mg of oligosaccharide chain added GLP-1 peptide wherein 30Ala of GLP-1 is substituted with asialo oligosaccharide chain added Asn (30Asn GLP-1-asialo).

Example 42

Synthesis of 36Asn asialo Oligosaccharide Chain Added GLP-1 Peptide

A solid-phase synthesis column was charged with Amino-PEGA resin (50 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.125 mmol), TBTU (0.125 mmol) and N-ethylmorpholine (0.125 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.25 mmol), MSNT (0.25 mmol) and N-methylimidazole (0.175 mmol) were dissolved in DCM (2 ml), loaded to a solid-phase synthesis column and stirred at 25° C. for 3 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.25 mmol), the resulting mixture was loaded to a solid-phase synthesis column. Subsequently, 0.9 M DIPEA/NMP (0.25 mmol) was added to the solid-phase synthesis column. After stirring at room temperature for 20 minutes, the resin was washed with DCM and DMF, and Fmoc group was removed by using a 20% piperidine/DMF solution (2 ml) for 15 minutes. Asialo oligosaccharide chain added asparagine (b) (a product of OTSUKA Chemical Co., Ltd.) 198 mg (100 μmol) and DEPBT 30.0 mg (100 μmol) were dissolved in NMP/DMSO (2.4/0.6 ml) and loaded to the solid-phase synthesis column. After addition of DIPEA 26 μl (150 μmol), the mixture was stirred at room temperature for 24 hours. After washing with DCM and DMF, oligosaccharide chain added 2-residue peptide of Gly-Asn(Oligosaccharide chain) was obtained on the solid phase.

Subsequently, the amino acid having an amino group protected with Fmoc group was condensed by HOBt 34 mg (0.25 mmol), DIPCI 38 μl (0.25 mmol) and DMF (1 ml) to form oligosaccharide chain added 31-residue peptide of Gly-Asn (Oligosaccharide chain)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:95).

To the obtained resin having an oligosaccharide chain added peptide formed thereon, trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 7.0 ml/min; 35→60% B, 20 min linear gradient] to obtain 8.0 mg of oligosaccharide chain added GLP-1 peptide wherein 36Aeg of GLP-1 is substituted with asialo oligosaccharide chain added Asn (36Asn GLP-1-asialo).

Example 43

Synthesis of 18Asn-disialo Oligosaccharide Chain Added GLP-1 Peptide

18 Asn GLP-1-asialo synthesized in Example 36 (0.6 mg) was dissolved in 50 mM cacodylate buffer (pH=5.0, 200 μl) and bovine serum albumine (BSA, 1 mg) was added. CMP-sialic acid (5 mg) and alkaline phosphatase (1 μl) were further added and the mixture was homogenized. Finally, α2,6-Sialyltransferase (product of Japan Tobacco Inc., 10 mU) was added and reaction was performed at 30° C. for 24 hours. (Reaction monitoring condition by HPLC: column: SHISEIDO CAPCELPAK C18 UG120, φ 4.6×250 mm, developing solvent A: 0.1% TFA aqueous solution, developing solvent B: 0.09% TFA acetonitrile/water=90/10, gradient A/B=60/40→30/60 40 minutes, flow rate: 0.7 ml/min). FIG. 1 shows an exemplary chart of the HPLC. In FIG. 1, the front peak shows 18 Asn GLP-1-asialo (material), and the back peak shows 18 Asn GLP-1-disialo. After purification by HPLC under the same condition, 0.3 mg of gly oligosaccharide chain added cosylated GLP-1 peptide wherein 18Ser of GLP-1 is substituted with disialo oligosaccharide chain added Asn (18Asn GLP-1-disialo) was obtained.

Example 44

Synthesis of 22Asn-disialo Oligosaccharide Chain Added GLP-1 Peptide

Figure 2:
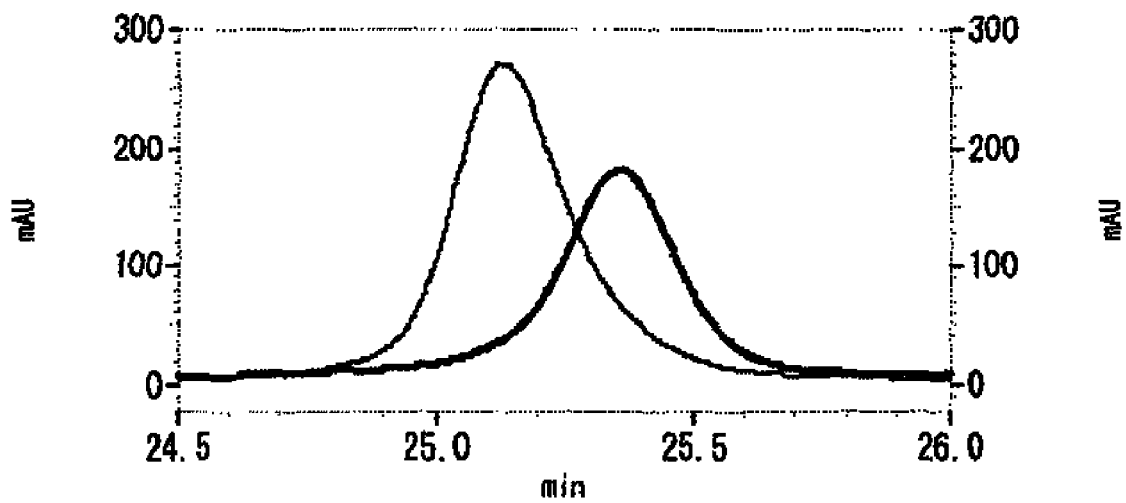
FIG. 2 is one example of a HPLC chart in Example 44 and shows peaks of 22Asn GLP-1-asialo and 22Asn GLP-1-disialo.

22 Asn GLP-1-asialo synthesized in Example 37 (1.3 mg) was dissolved in 50 mM cacodylate buffer (pH=5.0, 200 μl) and bovine serum albumine (BSA, 1 mg) was added. CMP-sialic acid (5 mg) and alkaline phosphatase (1 μl) were further added and the mixture was homogenized. Finally, α2,6-Sialyltransferase (product of Japan Tobacco Inc., 10 mU) was added and reaction was performed at 30° C. for 24 hours. (Reaction monitoring condition by HPLC: column: SHISEIDO CAPCELPAK C18 UG120, φ 4.6×250 mm, developing solvent A: 0.1% TFA aqueous solution, developing solvent B: 0.09% TFA acetonitrile/water=90/10, gradient A/B=60/40→30/60 40 minutes, flow rate: 0.7 ml/min). FIG. 2 shows an exemplary chart of the HPLC. In FIG. 2, the front peak shows 22 Asn GLP-1-asialo (material), and the back peak shows 22 Asn GLP-1-disialo. After purification by HPLC under the same condition, 1.3 mg of oligosaccharide chain added GLP-1 peptide wherein 22Gly of GLP-1 is substituted with disialo oligosaccharide chain added Asn (22Asn GLP-1-disialo) was obtained.

Example 45

Synthesis of 30Asn-disialo Oligosaccharide Chain Added GLP-1 Peptide

Figure 3:
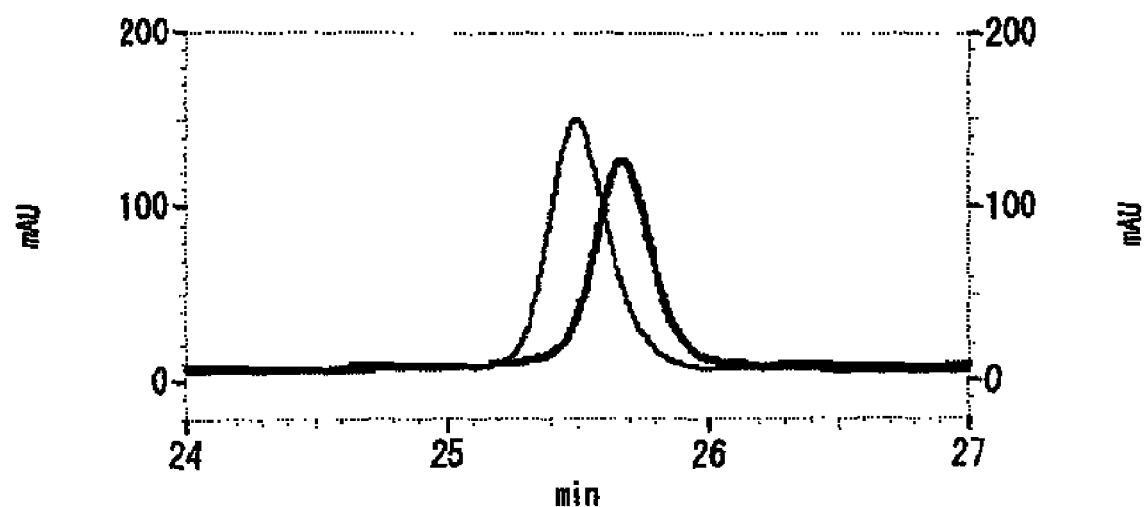
FIG. 3 is one example of a HPLC chart in Example 45 and shows peaks of 30Asn GLP-1-asialo and 30Asn GLP-1-disialo.

30 Asn GLP-1-asialo synthesized in Example 41 (0.9 mg) was dissolved in 50 mM cacodylate buffer (pH=5.0, 200 μl) and bovine serum albumine (BSA, 1 mg) was added. CMP-sialic acid (5 mg) and alkaline phosphatase (1 μl) were further added and the mixture was homogenized. Finally, α2,6-Sialyltransferase (product of Japan Tobacco Inc., 10 mU) was added and reaction was performed at 30° C. for 24 hours. (Reaction monitoring condition by HPLC: column: SHISEIDO CAPCELPAK C18 UG120, φ 4.6×250 mm, developing solvent A: 0.1% TFA aqueous solution, developing solvent B: 0.09% TFA acetonitrile/water=90/10, gradient A/B=60/40→30/60 40 minutes, flow rate: 0.7 ml/min). FIG. 3 shows an exemplary chart of the HPLC. In FIG. 3, the front peak shows 30 Asn GLP-1-asialo (material), and the back peak shows 30 Asn GLP-1-disialo. After purification by HPLC under the same condition, 0.6 mg of oligosaccharide chain added GLP-1 peptide wherein 30Ala of GLP-1 is substituted with disialo oligosaccharide chain added Asn (30Asn GLP-1-disialo) was obtained.

Example 46

Synthesis of 30Asn-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Ala (0.50 mmol), MSNT (0.50 mmol) and N-methylimidazole (0.375 mmol) were dissolved in DCM (2 ml), loaded to the solid-phase synthesis column and stirred at 25° C. for 4 hours.

After stirring, the resin was washed with DCM and DMF. Fmoc group was removed by using a 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using 20% piperidine/DMF solution (2 ml) for 15 minutes. This operation was repeatedly performed using an amino acid protected with Fmoc group (0.5 mmol) to sequentially condense amino acids.

Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu) and Fmoc-Ala were used as amino acids protected by Fmoc group, and Boc-His (Trt) was used as the amino acid protected by Boc group, to obtain 18-residue peptide of Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:96) on a solid phase resin.

After washing with DCM and DMF, a mixture solution of trifluoroethanol and acetic acid (1:1) was added such that the resin was soaked thoroughly and stirred at room temperature for 18 hours. The resin was removed by filtration and the reaction solution was concentrated under reduced pressure. The obtained residue was concentrated to obtain a protected peptide: Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt)-NHBoc (SEQ ID NO:97).

The 18-residue protected peptide (equivalent to 35 µmol) was transferred to an eggplant flask, dissolved in DMF (3.7 ml) and cooled to −15 to −20° C. under an argon atmosphere. To this, benzylthiol 125 µl (1.06 mmol) was added and separately prepared DMF solution (1.0 ml) of PyBOP 94.7 mg (182 µmol) was added, and subsequently, DIPEA 29.8 µl (175 µmol) was added. The mixture was stirred at −15 to −20° C. for 2 hours and added to cool diethyl ether (150 ml). After precipitation of peptide component, the solution portion was removed by a membrane filter. To the residue, trifluoroacetic acid:water:TIPS (=95:2.5:2.5) was added and stirred at room temperature. After 2 hours, the solution was once again added to separately prepared diethyl ether (150 ml) to obtain a precipitate. Thereafter, the solution portion was removed by a membrane filter to obtain a residue containing a desired peptide thioester compound. This residue was purified by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min) linear gradient] to obtain a 18-residue peptide having benzyl thioester at C terminal: PhS-Ala-Gln-Gly-Glu-Leu-Tyr-Ser-Ser-Val-Asp-Ser-Thr-Phe-Thr-Gly-Glu-Ala-His (SEQ ID NO:98).

ESI-MS: Calcd for $C_{88}H_{125}N_{21}O_{31}S$: $[M+2H]^{2+}$ 1002.9, found. 1003.3

On the other hand, a solid-phase synthesis column was charged with Amino-PEGA resin (product of Merck) (100 µmol), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to the solid-phase synthesis column and stirred at 25° C. for 4 hours.

After stirring, the resin was washed with DCM and DMF. Fmoc group was removed by using 20% piperidine/DMF solution (2 ml) for 15 minutes. After washing with DMF, amino acids were sequentially condensed in accordance with the method shown below to extend a peptide chain.

The amino acid having an amino group protected with Fmoc group and HOBt 67.6 mg (0.50 mmol)) and DIPCI 77.0 µl (63.1 mg, 0.50 mmol) were dissolved in DMF (2 ml). After activation for 15 minutes, the resulting mixture was loaded to a solid-phase synthesis column. After stirring at room temperature for one hour, Fmoc group was removed by using a 20% piperidine/DMF solution (2 ml) for 20 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Lys(Boc), Fmoc-Val, Fmoc-Leu and Fmoc-Trp(Boc) were used as amino acids protected by Fmoc group to obtain 7-residue peptide of Gly-Arg(Pbf)-Gly-Lys(Boc)-Val-Leu-Trp(Boc) (SEQ ID NO:99) on a solid phase resin. The 7-residue peptide (34.6 µmol) was transferred to a separately prepared solid-phase synthesis column to remove Fmoc group by using a 20% piperidine/DMF solution (2 ml) for 15 minutes and washed with DMF. To a separate centrifuge tube, oligosaccharide chain added asparagine (f) (a product of OTSUKA Chemical Co., Ltd.) 132.7 mg (48.4 µmol) and DEPBT 31.2 mg (104.3 µmol) were dissolved in DMF/DMSO (1:4 mixture solution, 0.6 ml) and loaded to the solid-phase synthesis column. After addition of DIPEA 18.1 µl (103.8 µmol), the mixture was stirred at room temperature for 18 hours.

[Formula 10]

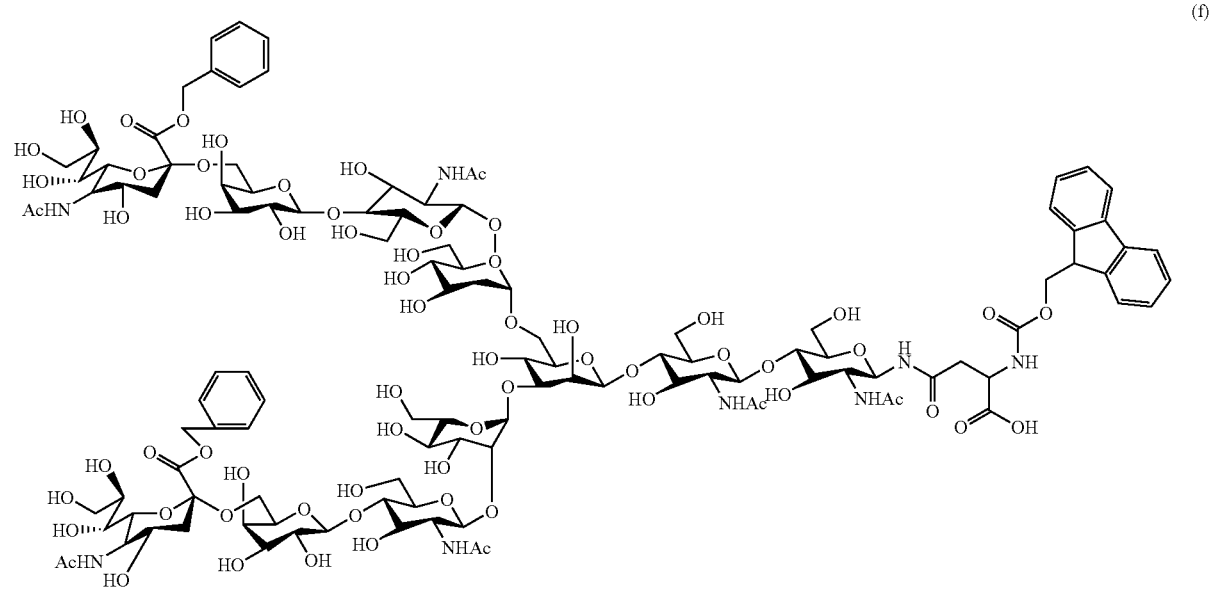

(f)

After stirring, the resin was washed with DCM and DMF. Fmoc group was removed by using a 20% piperidine/DMF solution (1 ml) for 15 minutes. After washing with DMF, amino acids were sequentially condensed in accordance with the method shown below to extend a peptide chain.

The amino acid having an amino group protected with Fmoc group and HOBt 33.8 mg (0.25 mmol), and DIPCI 38.5 µl (31.5 mg, 0.25 mmol) were dissolved in DMF (1 ml). After activation for 15 minutes, the mixture was loaded to a solid-phase synthesis column. After stirring at room temperature for one hour, Fmoc group was removed by using a 20% piperidine/DMF solution (1 ml) for 20 minutes. This operation was repeatedly performed to sequentially condense amino acids. Fmoc-Ile, Fmoc-Phe, Fmoc-Glu(OtBu) and Fmoc-Lys(Boc) were used as amino acids protected by Fmoc group, and Boc-Cys (Trt) was used as amino acids protected by Boc group to obtain oligosaccharide chain added 13-residue peptide of Gly-Arg(Pbf)-Gly-Lys(Boc)-Val-Leu-Trp(Boc)-Asn(Oligosaccharide chain)-Ile-Phe-Glu(OtBu)-Lys(Boc)-Cys(trt) (SEQ ID NO:100) on a solid phase resin. To this, trifluoroacetic acid:water:TIPS (=95:2.5:2.5) was added and stirred at room temperature for 3.5 hours. Thereafter, the solution was added to a separately prepared diethyl ether (150 ml) to obtain precipitation, and subjected to centrifugation to separate a precipitate containing an oligosaccharide chain added peptide and a solution portion. After removing the solution portion, the obtained precipitate was dissolved in a 50 mM dithiothreitol solution buffer pH 6.8 (prepared from 50 mM dithiothreitol solution, 6 M guanidine hydrochloride solution and 0.2 mM phosphoric acid solution) and allowed to react overnight. After desired product was confirmed by HPLC, the reaction solution was directly subjected to purification by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min) linear gradient] to obtain an oligosaccharide chain added 13-residue peptide (18.2 mg).

ESI-MS: Calcd for $C_{169}H_{260}N_{26}O_{78}S$: $[M+3H]^{3+}$ 1312.2, found. 1313.0

The two types of peptides thus prepared: the 18-residue peptide having benzylthio ester at C terminal (9.3 mg) and the oligosaccharide chain added 13-residue peptide (18.2 mg) were placed in a same centrifuge tube and dissolved in a buffer solution (pH 6.8, 0.15 ml) (prepared from 6 M guanidine hydrochloride solution and 0.2 mM phosphoric acid solution). Thiophenol (15.4 µl) was then added at room temperature and a reaction was performed at 37° C. After 24 hours, the reaction solution was directly subjected to purification by HPLC, [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain an oligosaccharide chain added 31-residue peptide (9.2 mg).

ESI-MS: Calcd for $C_{250}H_{377}N_{47}O_{109}S$: $[M+4H]^{4+}$ 1454.4, found. 1455.0

The obtained oligosaccharide chain added peptide (9.2 mg) was placed in a centrifuge tube and dissolved in a buffer solution (pH 7.0, prepared from 35 mM TCEP solution, 6 M guanidine hydrochloride solution and 0.2 mM phosphoric acid solution). To the reaction solution, activated Raney Nickel was added at room temperature. After 72 hours, completion of the reaction was confirmed by HPLC. Thereafter, the reaction solution was filtrated by a membrane filter and the filtrate portion containing desired oligosaccharide chain added peptide was subjected to purification by HPLC [column: SHISEIDO UG-120 (C18 5 µm), φ 20×250 mm, gradient: A solution: 0.1% TFA water, B solution: 0.09% TFA/10% water/90% AN 7.0 ml/min; 25→45% B (15 min)→60% B (10 min)→95% B (10 min), linear gradient] to obtain a oligosaccharide chain added 31-residue peptide (1.3 mg).

ESI-MS: Calcd for $C_{250}H_{377}N_{47}O_{109}$: $[M+4H]^{4+}$ 1446.4, found. 1447.2

The oligosaccharide chain added 31-residue peptide (1.3 mg) thus obtained was placed in an Eppendorf tube and dissolved with distilled water (25 µl). To this solution, a 100 mM aqueous sodium hydroxide solution (25 µl) was added at room temperature. After 30 minutes, production of desired product was confirmed by HPLC and the solution was cooled to 0° C. and neutralized by adding 50 mM aqueous acetic acid solution (50 µl). The solution was purified by HPLC [column: Vydac column (C18 5 µm), φ 4.6×250 mm, gradient: A solution: 0.1% TFA water, B solution: 0.09% TFA/10% water/ 90% AN 7.0 ml/min; 25→45% B (15 min)→60% B (10 min)→95% B (10 min), linear gradient] to obtain 0.3 mg of desired oligosaccharide chain added GLP-1 peptide wherein 30Ala of GLP-1 is substituted by disialo oligosaccharide chain added Asn (30Asn GLP-1-disialo).

ESI-MS: Calcd for $C_{236}H_{365}N_{47}O_{109}$: $[M+4H]^{4+}$ 1401.4, found. 1402.1

Example 47

Synthesis of 36Asn-disialo Oligosaccharide Chain Added GLP-1 Peptide

Figure 4:
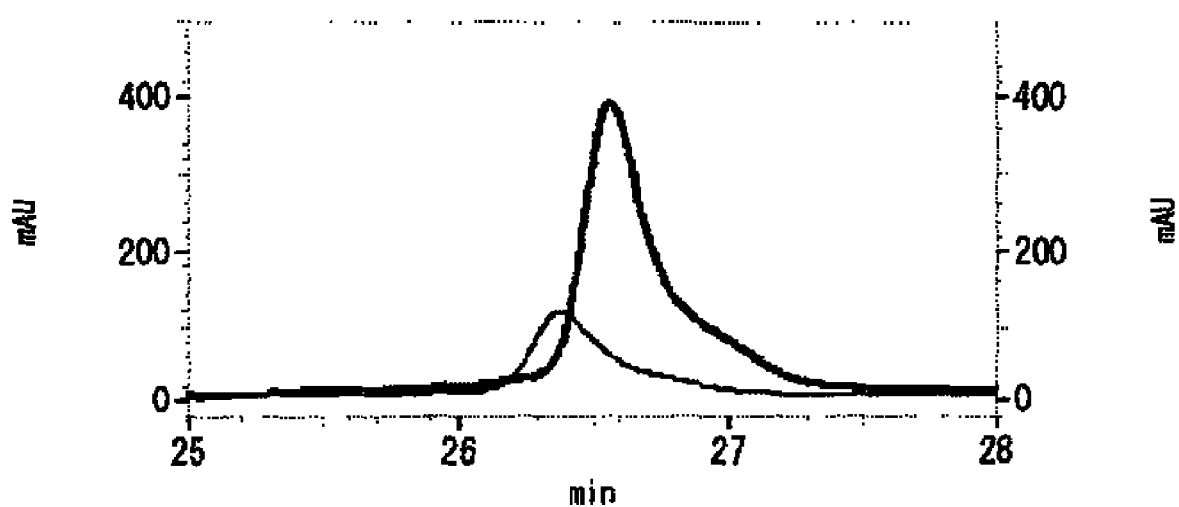
FIG. 4 is one example of a HPLC chart in Example 47 and shows peaks of 36Asn GLP-1-asialo and 36Asn GLP-1-disialo.

36 Asn GLP-1-asialo synthesized in Example 42 (0.8 mg) was dissolved in 50 mM cacodylate buffer (pH=5.0, 200 µl) and bovine serum albumine (BSA, 1 mg) was added. CMP-sialic acid (5 mg) and alkaline phosphatase (1 µl) were further added and the mixture was homogenized. Finally, α2,6-Sialyltransferase (product of Japan Tobacco Inc., 10 mU) was added and reaction was performed at 30° C. for 24 hours. (Reaction monitoring condition by HPLC: column: SHISEIDO CAPCELPAK C18 UG120, φ 4.6×250 mm, developing solvent A: 0.1% TFA aqueous solution, developing solvent B: 0.09% TFA acetonitrile/water=90/10, gradient A/B=60/40→30/60 40 minutes, flow rate: 0.7 ml/min). FIG. 4 shows an exemplary chart of the HPLC. In FIG. 4, the front peak shows 36 Asn GLP-1-asialo (material), and the back peak shows 36 Asn GLP-1-disialo. After purification by HPLC under the same condition, 0.6 mg of oligosaccharide chain added GLP-1 peptide wherein 36Arg of GLP-1 is substituted by disialo oligosaccharide chain added Asn (36Asn GLP-1-disialo) was obtained.

Example 48

Synthesis of 26 and 34Cys-disialo Oligosaccharide Chain Added GLP-1 Peptide

A solid-phase synthesis column was charged with Amino-PEGA resin (100 µmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to the solid-phase synthesis column and stirred at 25° C. for 3 hours.

After stirring, the resin was washed with DCM and DMF. Fmoc group was removed by using a 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Arg(Pbf), Fmoc-Gly, Fmoc-Cys(Trt), Fmoc-Val, Fmoc-Leu, Fmoc-Trp(Boc), Fmoc-Ala, Fmoc-Ile, Fmoc-Phe, Fmoc-Glu(OtBu), Fmoc-Cys(Trt), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Ser(tBu), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as amino acids protected by Fmoc group to obtain 31-residue peptide of Gly-Arg(Pbf)-Gly-Cys(Trt)-Val-Leu-Trp(Boc)-Ala-Ile-Phe-Glu(OtBu)-Cys(Trt)-Ala-Ala-Gln(Trt)-Gly-Glu(OtBu)-Leu-Tyr(tBu)-Ser(tBu)-Ser(tBu)-Val-Asp(OtBu)-Ser(tBu)-Thr(tBu)-Phe-Thr(tBu)-Gly-Glu(OtBu)-Ala-His(Trt) (SEQ ID NO:101) on a solid phase resin.

A part of the obtained resin having a peptide formed thereon was transferred in a solid phase synthesis column, trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain a peptide wherein 26 and 34Lys of GLP-1 are each substituted with Cys.

Bromoacetamidyl disialo oligosaccharide (a) (a product of OTSUKA Chemical Co., Ltd.) (10.5 mg) and the peptide chain synthesized above (2.1 mg) were dissolved in 100 mM phosphate buffer (pH 7.5, 210 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 0.1 mg of oligosaccharide chain added GLP-1 peptide wherein 26 and 34Lys of GLP-1 are each substituted by oligosaccharide chain added Cys (26-34Cys GLP-1-disialo).

Example 49

Synthesis of 18 and 36Cys-disialo Oligosaccharide Chain Added GLP-1 Peptide

A solid-phase synthesis column was charged with Amino-PEGA resin (100 μmol) (product of Merck), washed thoroughly with dichloromethane (DCM) and DMF and the resin was thoroughly swollen with DMF. 4-hydroxymethyl-3-methoxyphenoxybutyric acid (HMPB) (0.25 mmol), TBTU (0.25 mmol) and N-ethylmorpholine (0.25 mmol) were dissolved in DMF (2 ml), loaded to the column, and stirred at room temperature for 4 hours. The resin was washed thoroughly with DMF and DCM to obtain HMPB-PEGA resin, which was used as a solid phase for solid-phase synthesis.

Fmoc-Gly (0.50 mmol), MSNT (0.50 mmol) and N-methylimidazole (0.375 mmol) were dissolved in DCM (2 ml), loaded to the solid-phase synthesis column and stirred at 25° C. for 3 hours.

After stirring, the resin was washed with DCM and DMF. Fmoc group was removed by using a 20% piperidine/DMF solution (2 ml) for 15 minutes. After washing with DMF, amino acids were sequentially condensed in accordance with the method shown below to extend a peptide chain.

The amino acid having an amino group protected with Fmoc group was dissolved in N-methylpyrrolidone (NMP) (1 ml). After addition of 0.45 M HCTU·HOBT/NMP (0.4 mmol), the mixture was loaded to a solid-phase synthesis column. Subsequently, 0.9 M DIPEA/NMP (0.8 mmol) was added to the solid-phase synthesis column. After stirring at room temperature for 20 minutes, the resin was washed with DCM and DMF, and Fmoc group was removed by using 20% piperidine/DMF solution (2 ml) for 15 minutes. This operation was repeatedly performed using an amino acid protected with Fmoc group (0.5 mmol) to sequentially condense amino acids.

Fmoc-Gly, Fmoc-Cys(Trt), Fmoc-Gly, Fmoc-Lys(Boc), Fmoc-Val, Fmoc-Leu, Fmoc-Trp(Boc), Fmoc-Ala, Fmoc-Ile, Fmoc-Phe, Fmoc-Glu(OtBu), Fmoc-Lys(Boc), Fmoc-Ala, Fmoc-Ala, Fmoc-Gln(Trt), Fmoc-Gly, Fmoc-Glu(OtBu), Fmoc-Leu, Fmoc-Tyr(tBu), Fmoc-Cys(Trt), Fmoc-Ser(tBu), Fmoc-Val, Fmoc-Asp(OtBu), Fmoc-Ser(tBu), Fmoc-Thr(tBu), Fmoc-Phe, Fmoc-Thr(tBu), Fmoc-Gly, Fmoc-Glu(OtBu), Fmoc-Ala and Fmoc-His(Trt) were used as amino acids protected by Fmoc group to obtain 31-residue peptide of Gly-Cys(Trt)-Gly-Lys(Boc)-Val-Leu-Trp(Boc)-Ala-Ile-Phe-Glu(OtBu)-Lys(Boc)-Ala-Ala-Gln(Trt)-Gly-Glu(OtBu)-Leu-Tyr(tBu)-Cys(Trt)-Ser(tBu)-Val-Asp(OtBu)-Ser(tBu)-Thr(tBu)-Phe-Thr(tBu)-Gly-Glu(OtBu)-Ala-His (Trt) (SEQ ID NO:102) on a solid phase resin.

A part of the obtained resin having a peptide formed thereon was transferred in a solid phase synthesis column, trifluoroacetic acid:water:TIPS (=95:2.5:2.5) was added such that the resin was thoroughly soaked and stirred at room temperature for 3 hours. The resin was removed by filtration and the reaction solution was concentrated under reduced pressure. The resulting residue was purified by HPLC [column: SHISEIDO UG-120 (C18 5 μm), φ 20×250 mm, gradient: A solution: 0.1% TFA water, B solution: 0.09% TFA/10% water/90% AN 8.0 ml/min; 35→60% B, 20 min linear gradient] to obtain a peptide wherein 18Ser and 36Arg of GLP-1 are each substituted with Cys.

Bromoacetamidyl disialo oligosaccharide (a) (a product of OTSUKA Chemical Co., Ltd.) (10.5 mg) and the peptide chain synthesized above (2.1 mg) were dissolved in 100 mM phosphate buffer (pH 7.5, 210 μl) and allowed to react at 37° C. for 4 hours. After complete consumption of raw materials were confirmed by HPLC, the reaction solution was directly subjected to purification by HPLC [column: SHISEIDO UG-120 (C18, 5 μm), φ 4.6×250 mm, gradient: A solution: 0.1% TFA water, B solution: 0.09% TFA/10% water/90% AN 0.7 ml/min; 35→60% B, 20 min linear gradient] to obtain 0.8 mg of oligosaccharide chain added GLP-1 peptide wherein 18Ser and 36Arg of GLP-1 are each substituted by oligosaccharide chain added Cys (18-36Cys GLP-1-disialo).

Table 7 below shows MS spectrum data of oligosaccharide chain added GLP-1 peptides obtained in Examples 8 to 49. In the table, [M+H]$^+$ represents measurement results by MALDI-TOF mass, and [M+3H]$^{3+}$ and [M+4H]$^{4+}$ represent measurement results by EMI-MS.

ous TFA solution, B: 0.1% TFA acetonitrile: water=90:10, gradient A:B=95:5→5:95, 15 min, flow rate: 0.7 ml/min). The results are shown in FIGS. 5 (Example 7) and 6 (Comparative Example 1).

Figure 5:
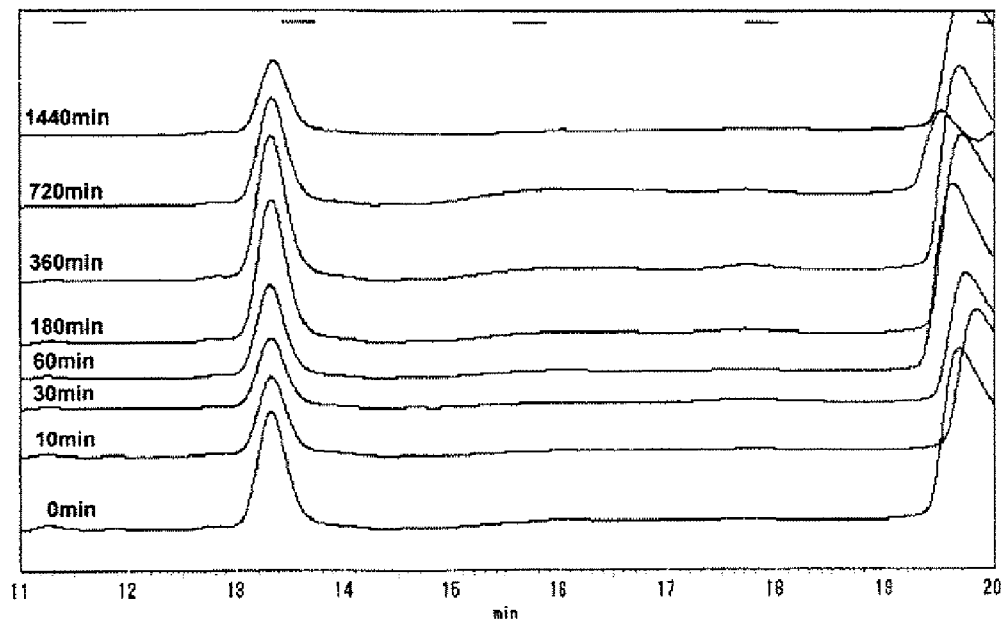
FIG. 5 is a graph showing HPLC analysis results of an oligosaccharide chain added GLP-1 peptide of Example 7 in Test Example 1 (Test of stability in plasma)

In FIG. 5, peaks of the oligosaccharide chain added GLP-1 peptide are observed around 13.3 minutes. As shown in FIG. 5, the oligosaccharide chain added GLP-1 peptide of

TABLE 7

| | | | | | | | |
|---|---|---|---|---|---|---|---|
| Example 8 | 6Cys GLP-1-disialo | Calcurated for | $C_{240}H_{372}N_{48}O_{110}S$ | [M + H]$^+$ | 5719.5 | found. | 5721.9 |
| Example 9 | 8Cys GLP-1-disialo | Calcurated for | $C_{237}H_{387}N_{47}O_{109}S$ | [M + H]$^+$ | 5648.4 | found. | 5649.3 |
| Example 10 | 9Cys GLP-1-disialo | Calcurated for | $C_{235}H_{365}N_{47}O_{107}S$ | [M + H]$^+$ | 5590.4 | found. | 5590.7 |
| Example 11 | 10Cys GLP-1-disialo | Calcurated for | $C_{238}H_{369}N_{47}O_{109}S$ | [M + H]$^+$ | 5662.5 | found. | 5665.4 |
| Example 12 | 11Cys GLP-1-disialo | Calcurated for | $C_{236}H_{365}N_{47}O_{108}S$ | [M + H]$^+$ | 5618.4 | found. | 5618.5 |
| Example 13 | 12Cys GLP-1-disialo | Calcurated for | $C_{231}H_{363}N_{47}O_{109}S$ | [M + H]$^+$ | 5572.4 | found. | 5571.2 |
| Example 14 | 14Cys GLP-1-disialo | Calcurated for | $C_{237}H_{387}N_{47}O_{108}S$ | [M + H]$^+$ | 5632.5 | found. | 5632.6 |
| Example 15 | 16Cys GLP-1-disialo | Calcurated for | $C_{235}H_{363}N_{47}O_{109}S$ | [M + H]$^+$ | 5620.4 | found. | 5623.5 |
| Example 16 | 20Cys GLP-1-disialo | Calcurated for | $C_{234}H_{361}N_{47}O_{109}S$ | [M + H]$^+$ | 5606.4 | found. | 5606.0 |
| Example 17 | 24Cys GLP-1-disialo | Calcurated for | $C_{237}H_{367}N_{47}O_{109}S$ | [M + H]$^+$ | 5648.4 | found. | 5648.2 |
| Example 18 | 25Cys GLP-1-disialo | Calcurated for | $C_{237}H_{367}N_{47}O_{109}S$ | [M + H]$^+$ | 5648.4 | found. | 5650.5 |
| Example 19 | 27Cys GLP-1-disialo | Calcurated for | $C_{235}H_{365}N_{47}O_{107}S$ | [M + H]$^+$ | 5590.4 | found. | 5592.4 |
| Example 20 | 28Cys GLP-1-disialo | Calcurated for | $C_{231}H_{363}N_{47}O_{109}S$ | [M + H]$^+$ | 5572.4 | found. | 5575.2 |
| Example 21 | 30Cys GLP-1-disialo | Calcurated for | $C_{237}H_{387}N_{47}O_{109}S$ | [M + H]$^+$ | 5648.4 | found. | 5651.7 |
| Example 22 | 32Cys GLP-1-disialo | Calcurated for | $C_{234}H_{381}N_{47}O_{109}S$ | [M + H]$^+$ | 5606.4 | found. | 5606.2 |
| Example 23 | 34Cys GLP-1-disialo | Calcurated for | $C_{234}H_{380}N_{48}O_{109}S$ | [M + H]$^+$ | 5591.4 | found. | 5591.1 |
| Example 24 | 22Cys GLP-1-asialo | Calcurated for | $C_{216}H_{335}N_{45}O_{93}S$ | [M + H]$^+$ | 5080.3 | found. | 5081.9 |
| Example 25 | 26Cys GLP-1-asialo | Calcurated for | $C_{212}H_{325}N_{44}O_{93}S$ | [M + H]$^+$ | 5009.2 | found. | 5010.1 |
| Example 26 | 30Cys GLP-1-asialo | Calcurated for | $C_{215}H_{333}N_{45}O_{93}S$ | [M + H]$^+$ | 5066.3 | found. | 5068.0 |
| Example 27 | 34Cys GLP-1-asialo | Calcurated for | $C_{212}H_{325}N_{44}O_{93}S$ | [M + H]$^+$ | 5009.2 | found. | 5010.1 |
| Example 28 | 36Cys GLP-1-asialo | Calcurated for | $C_{212}H_{325}N_{42}O_{93}S$ | [M + H]$^+$ | 4981.2 | found. | 4983.1 |
| Example 29 | 22Cys GLP-1-diGlcNAc | Calcurated for | $C_{204}H_{315}N_{45}O_{83}S$ | [M + H]$^+$ | 4756.2 | found. | 4758.2 |
| Example 30 | 30Cys GLP-1-diGlcNAc | Calcurated for | $C_{203}H_{313}N_{45}O_{83}S$ | [M + H]$^+$ | 4742.1 | found. | 4742.0 |
| Example 31 | 34Cys GLP-1-diGlcNAc | Calcurated for | $C_{200}H_{306}N_{44}O_{83}S$ | [M + H]$^+$ | 4685.1 | found. | 4686.8 |
| Example 32 | 22Cys GLP-1-dimannose | Calcurated for | $C_{188}H_{283}N_{43}O_{73}S$ | [M + H]$^+$ | 4350.0 | found. | 4351.0 |
| Example 33 | 30Cys GLP-1-dimannose | Calcurated for | $C_{187}H_{287}N_{43}O_{73}S$ | [M + H]$^+$ | 4336.0 | found. | 4338.0 |
| Example 34 | 34Cys GLP-1-dimannose | Calcurated for | $C_{184}H_{290}N_{42}O_{73}S$ | [M + H]$^+$ | 4278.9 | found. | 4280.3 |
| Example 35 | 12Asn GLP-1-Asialo | Calcurated for | $C_{208}H_{327}N_{45}O_{93}$ | [M + 3H]$^{3+}$ | 1648.7 | found. | 1649.5 |
| Example 36 | 18Asn GLP-1-Asialo | Calcurated for | $C_{214}H_{331}N_{45}O_{92}$ | [M + H]$^+$ | 5004.3 | found. | 5003.4 |
| Example 37 | 22Asn GLP-1-asialo | Calcurated for | $C_{215}H_{333}N_{45}O_{93}$ | [M + H]$^+$ | 5034.3 | found. | 5035.9 |
| Example 38 | 26Asn GLP-1-asialo | Calcurated for | $C_{211}H_{324}N_{44}O_{93}$ | [M + 3H]$^{3+}$ | 1656.0 | found. | 1655.8 |
| Example 39 | 27Asn GLP-1-asialo | Calcurated for | $C_{212}H_{329}N_{45}O_{91}$ | [M + 3H]$^{3+}$ | 1655.7 | found. | 1655.5 |
| Example 40 | 28Asn GLP-1-asialo | Calcurated for | $C_{208}H_{327}N_{45}O_{93}$ | [M + 3H]$^{3+}$ | 1648.7 | found. | 1649.6 |
| Example 41 | 30Asn GLP-1-asialo | Calcurated for | $C_{214}H_{331}N_{45}O_{93}$ | [M + H]$^+$ | 5020.3 | found. | 5020.8 |
| Example 42 | 36Asn GLP-1-asialo | Calcurated for | $C_{211}H_{324}N_{42}O_{93}$ | [M + H]$^+$ | 4935.2 | found. | 4936.7 |
| Example 43 | 18Asn GLP-1-disialo | Calcurated for | $C_{235}H_{365}N_{47}O_{108}$ | [M + H]$^+$ | 5586.5 | found. | 5588.6 |
| Example 44 | 22Asn GLP-1-disialo | Calcurated for | $C_{237}H_{367}N_{47}O_{109}$ | [M + H]$^+$ | 5616.5 | found. | 5618.4 |
| Example 45 | 30Asn GLP-1-disialo | Calcurated for | $C_{236}H_{365}N_{47}O_{109}$ | [M + H]$^+$ | 5602.5 | found. | 5606.2 |
| Example 46 | 30Asn GLP-1-disialo | Calcurated for | $C_{236}H_{365}N_{47}O_{109}$ | [M + 4H]$^{4+}$ | 1401.4 | found. | 1402.1 |
| Example 47 | 36Asn GLP-1-disialo | Calcurated for | $C_{233}H_{358}N_{44}O_{109}$ | [M + H]$^+$ | 5517.4 | found. | 5521.7 |
| Example 48 | 26,34Cys GLP-1-disialo | Calcurated for | $C_{317}H_{492}N_{52}O_{171}S_2$ | [M + H]$^+$ | 7828.1 | found. | 7828.8 |
| Example 49 | 18,36Cys GLP-1-disialo | Calcurated for | $C_{320}H_{449}N_{51}O_{170}S_2$ | [M + H]$^+$ | 7841.1 | found. | 7845.3 |

Test Example 1

Stability in Plasma 0.1 mg of the peptide prepared in Example 7 or Comparative Example 1 was placed in an Eppendorf tube, and PBS (0.08 ml, 70% of the whole amount) and plasma (0.034 ml, 30% of the whole amount) were sequentially placed therein to bring about the solution amount to 0.114 ml in total. The mixture was allowed to react at 37° C.

The time when plasma was added to the reaction vessel was defined as 0 min. 0.01 ml aliquots were taken from the reaction solution on 10, 30, 60, 180, 360, 720 and 1440 minutes for sampling.

Each sampled reaction solution was mixed with 0.02 ml of 10% trifluoroacetic acid solution prepared in advance in an Eppendorf tube and then centrifuged. A 0.025 ml aliquot of the supernatant of the solution mixture was injected into HPLC to analyze the composition of the reaction solution (reaction monitoring conditions: Shiseido CAPCELL PAK C18, UG120, 250×4.6 mm, developing solvent A: 0.1% aqueous TFA solution, B: 0.1% TFA acetonitrile: water=90:10, gradient A:B=95:5→5:95, 15 min, flow rate: 0.7 ml/min).

Example 7 mostly remained even after 24 hours (1440 minutes) after the plasma addition.

Figure 6:
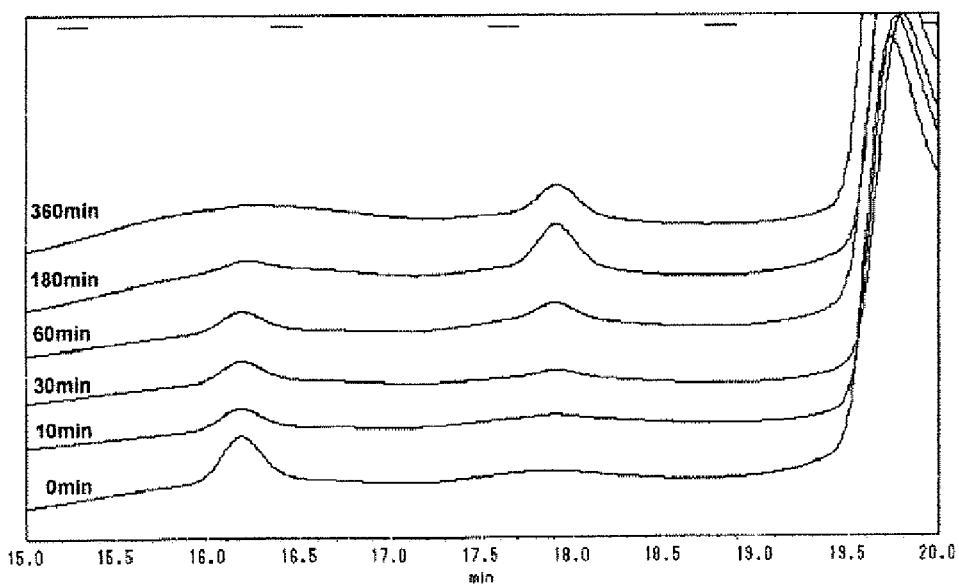
FIG. 6 is a graph showing HPLC analysis results of GLP-1 of Comparative Example 1 in Test Example 1 (Test of stability in plasma)

On the other hand, in FIG. 6, a peak observed between 16 and 16.5 minutes indicates undegraded GLP-1, and peaks observed between 17.5 and 18 minutes indicate a GLP-1 fragment (9-36) from which 7His-8Ala was removed. As shown in FIG. 6, the GLP-1 without oligosaccharide chain addition of Comparative Example 1 was mostly degraded by 180 minutes after the plasma addition.

Test Example 2

Effect of Lowering Blood-Sugar Levels in db/db Mice-1

The peptide prepared in each of Examples 1 to 5 or Comparative Example 1 was intraperitoneally administered as the same sample at a dose of 8 ml in total per kg of body weight (sample concentration: 9 nmol/kg of body weight) to each of three 8-week-old male type-2 diabetes model mice (BK-S.Cg-+Lepr$^{db}$/Lepr$^{db}$/Jcl*). Specifically, the peptide in a PBS solution (9 nmol/10 ml) was intraperitoneally administered at a dose of 10 ml/kg to the BKS.Cg-+Lepr$^{db}$/+Lepr$^{db}$/Jcl mice (8 week old, male). 0, 30, 60, 90, 120 and 180 minutes after the administration, 0.03 ml of peripheral blood from the retro-orbital venous plexus was collected. The obtained blood was diluted with PBS to 0.3 ml in total, and the solution was centrifuged to separate plasma and hemocyte components. Then, only the plasma component was transferred to an Eppendorf tube separately prepared and refrigerated. A glucose concentration in plasma was measured in accordance with Glucose CII-Test Wako using an absorptiometer. The results were obtained by statistical processing. The results are shown in FIG. 7.

Figure 7:
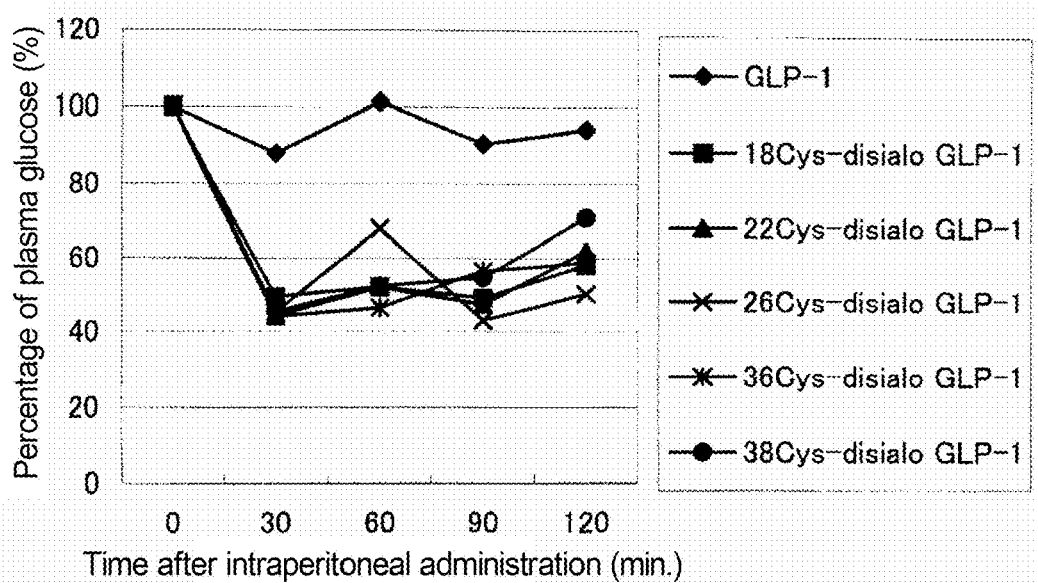
FIG. 7 is a graph showing changes of blood-sugar levels after administration of oligosaccharide chain added GLP-1 peptides of Examples 1 to 5 and a GLP-1 compound of Comparative Example 1 in Test Example 2 (Test of effect of lowering blood-sugar levels in db/db mice)

As shown in FIG. 7, the GLP-1 without oligosaccharide chain addition of Comparative Example 1 hardly lowered blood-sugar levels. By contrast, all the oligosaccharide chain added GLP-1 peptides of Examples 1 to 5 significantly lowered blood-sugar levels, and their effects were sustained even after 120 minutes.

Test Example 3

Effect of Lowering Blood-Sugar Levels in db/db Mice-2

The peptide prepared in Example 5 or Comparative Example 1 was intraperitoneally administered as the same sample at a dose of 8 ml in total per kg of body weight (sample concentration per kg of body weight: 0.9 nmol/kg, 9 nmol/kg, 90 nmol/kg or 900 nmol/kg) to each of three 8-week-old male type-2 diabetes model mice (BKS.Cg-+Lepr$^{db}$/Lepr$^{db}$/Jcl*). Specifically, the peptide in a PBS solution (0.9 nmol/10 ml, 9 nmol/10 ml, 90 nmol/10 ml or 900 nmol/10 ml) was intraperitoneally administered at a dose of 10 ml/kg to the BKS.Cg-+Lepr$^{db}$/+Lepr$^{db}$/Jcl mice (8 week old, male). 0, 30, 60, 90 and 120 minutes after the sample administration, 0.03 ml of peripheral blood from the retro-orbital venous plexus was collected. The obtained blood was diluted with PBS to 0.3 ml in total, and the solution was centrifuged to separate plasma and hemocyte components. Then, only the plasma component was transferred to an Eppendorf tube separately prepared and refrigerated. A glucose concentration in plasma was measured in accordance with Glucose CII-Test Wako using an absorptiometer. The results were obtained by statistical processing. The results are shown in FIG. 8.

Figure 8:
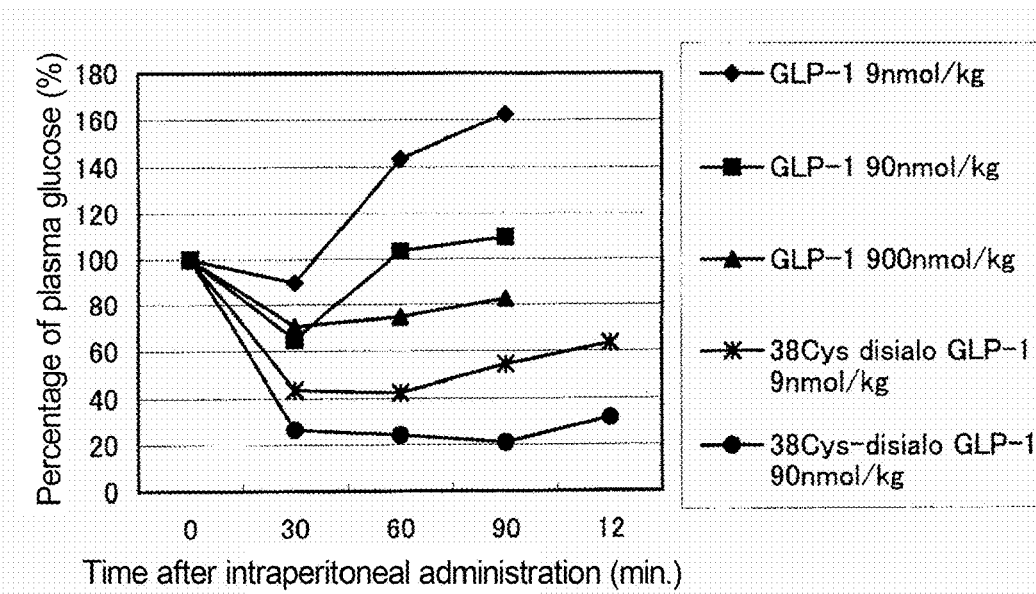
FIG. 8 is a graph showing changes of blood-sugar levels after administration of oligosaccharide chain added GLP-1 peptides of Example 5 and a GLP-1 of Comparative Example 1 in Test Example 3 (Test of effect of lowering blood-sugar levels in db/db mice)

The results of FIG. 8 shows that the oligosaccharide chain added GLP-1 peptide exhibits excellent effect of lowering blood-sugar levels even at a dose that is ¹/₁₀₀ of the GLP-1 dose of 900 nmol/kg.

Test Example 4

Test of Resistance to Dipeptidyl Peptidase IV (DPP-IV)-1

17.7 nmol of the oligosaccharide chain added GLP-1 peptide prepared in each of Examples 1 to 5, 13 to 23, 25, 27, 31, 34, 36, 48 or 49 or the GLP-1 prepared in Comparative Example 1 was added together with 2.2 mU of DPP-IV (dipeptidyl peptidase IV from porcine kidney, product of SIGMA) to a 0.5-ml Eppendorf tube. Each solution mixture was adjusted with 100 mM sodium phosphate buffer to 100 μl in total and allowed to react at 37° C. A 10 μl aliquot of the reaction solution was mixed with 15 μl of 10% trifluoroacetic acid prepared in advance in another Eppendorf tube. 20 μl thereof was injected into HPLC to monitor complete consumption of raw materials (HPLC conditions: column: SHISEIDO CAPCELPAK C18 UG120, φ4.6×250 mm, developing solvent A: 0.1% aqueous TFA solution, developing solvent B: 0.09% TFA acetonitrile/water=90/10, gradient A/B=65/30→30/60, 20 min, flow rate: 0.7 ml/min).

The half-life (t½), which serves as an index for resistance to DPP-IV, of the GLP-1 without oligosaccharide chain addition of Comparative Example 1 was defined as a standard (=1). A value evaluated on the oligosaccharide chain added GLP-1 peptide of each Example is shown in Table 8.

TABLE 8

| Example | Compound | Relative Resistance |
| --- | --- | --- |
| Example 13 | 12Cys GLP-1-disialo | 34.4 |
| Example 14 | 14Cys GLP-1-disialo | 6.3 |
| Example 15 | 16Cys GLP-1-disialo | 1.2 |
| Example1 | 18Cys GLP-1-disialo | 1.6 |
| Example 16 | 20Cys GLP-1-disialo | 2.6 |
| Example 2 | 22Cys GLP-1-disialo | 3.1 |
| Example 17 | 24Cys GLP-1-disialo | 3.0 |
| Example 18 | 25Cys GLP-1-disialo | 3.1 |
| Example 3 | 26Cys GLP-1-disialo | 4.6 |
| Example 19 | 27Cys GLP-1-disialo | 2.3 |
| Example 20 | 28Cys GLP-1-disialo | 9.0 |
| Example 21 | 30Cys GLP-1-disialo | 2.4 |
| Example 22 | 32Cys GLP-1-disialo | 3.7 |
| Example 23 | 34Cys GLP-1-disialo | 3.0 |
| Example 4 | 36Cys GLP-1-disialo | 1.6 |
| Example 5 | 38Cys GLP-1-disialo | 1.7 |
| Example 25 | 26Cys GLP-1-asialo | 4.6 |
| Example 27 | 34Cys GLP-1-asialo | 2.0 |
| Example 31 | 34Cys GLP-1-diGlcNAc | 2.0 |
| Example 34 | 34Cys GLP-1-dimannose | 1.6 |
| Example 36 | 18Asn GLP-1-asialo | 1.3 |
| Example 48 | 26, 34Cys GLP-1-disialo | 23.6 |
| Example 49 | 18, 36Cys GLP-1-disialo | 128.6 |

The oligosaccharide chain added GLP-1 peptide of each Example exhibited DPP-IV resistance 1.2 to 128 times that of the GLP-1 of Comparative Example 1. The maximum resistance was exhibited by the 18,36Cys-disialo oligosaccharide chain added GLP-1 peptide, followed by 12Cys-disialo, 26,34Cys-disialo, 28Cys-disialo, 14Cys-disialo, 26Cys-disialo, 26Cys-asialo, 32Cys-disialo, 25Cys-disialo, 22Cys-disialo, 24Cys-disialo, 34Cys-disialo, 20Cys-disialo, 30Cys-disialo, 27Cys-disialo, 34Cys-asialo, 34Cys-diGlcNAc, 38Cys-disialo, 36Cys-disialo, 34Cys-dimannose, 18Cys-disialo, 18Asn-asialo and 16Cys-disialo in this order.

The oligosaccharide chain added GLP-1 peptides of Examples 3, 23 and 48 or Examples 1, 4 and 49 were compared in DPP-IV resistance. The results demonstrated that the oligosaccharide chain added GLP-1 peptide having 2 oligosaccharide chains has higher DPP-IV resistance than that of the oligosaccharide chain added GLP-1 peptide having 1 oligosaccharide chain, and that the addition of 2 or more oligosaccharide chains thus produces a synergistic effect.

In terms of oligosaccharide chain structures to be added to the oligosaccharide chain added GLP-1 peptides, higher DPP-IV resistance was exhibited in the order of disialo oligosaccharide chain>asialo oligosaccharide chain>diGlcNAc oligosaccharide chain>dimannose oligosaccharide chain.

Test Example 5

Test of Resistance to Dipeptidyl Peptidase IV (DPP-IV)-2

17.7 nmol of the oligosaccharide chain added GLP-1 peptide prepared in each of Examples 10 to 13 was added together with 22 mU of DPP-IV (dipeptidyl peptidase IV from porcine kidney, product of SIGMA) to a 0.5-ml Eppendorf tube. Each solution mixture was adjusted with 100 mM sodium phosphate buffer to 100 µl in total and allowed to react at 37° C. A 10 µl aliquot of the reaction solution was mixed with 15 µl of 10% trifluoroacetic acid prepared in advance in another Eppendorf tube. 20 µl thereof was injected into HPLC to monitor complete consumption of raw materials (HPLC conditions: column: SHISEIDO CAPCELPAK C18 UG120, φ4.6×250 mm, developing solvent A: 0.1% aqueous TFA solution, developing solvent B: 0.09% TFA acetonitrile/water=90/10, gradient A/B=65/30→30/60, 20 min, flow rate: 0.7 ml/min).

The half-life (t½), which serves as an index for resistance to DPP-IV, of the oligosaccharide chain added GLP-1 peptide of Example 13 was defined as a standard (=1). A value evaluated on the oligosaccharide chain added GLP-1 peptides of Examples 10 to 12 is shown in Table 9.

TABLE 9

| Example | Compound | Relative Resistance |
|---|---|---|
| Example 10 | 9Cys GLP-1-disialo | 17.2 |
| Example 11 | 10Cys GLP-1-disialo | 9.0 |
| Example 12 | 11Cys GLP-1-disialo | 1.1 |
| Example 13 | 12Cys GLP-1-disialo | 1.0 |

In Test Example 4, the oligosaccharide chain added GLP-1 peptide of Example 13 exhibited DPP-IV resistance about 34 times that of the GLP-1 without oligosaccharide chain addition of Comparative Example 1. The oligosaccharide chain added GLP-1 peptides of Examples 10 to 12 exhibited DPP-IV resistance 1.1 to 17.2 times that of the oligosaccharide chain added GLP-1 peptide of Example 13 (12Cys-disialo). The maximum resistance was exhibited by 9Cys-disialo, followed by 10Cys-disialo, 11Cys-disialo and 12Cys-disialo in this order, and higher DPP-IV resistance was produced by adding oligosaccharide chain at a site closer to the N terminal of GLP-1. A reactive site for DPP-IV has been known to exist at the N terminal of GLP-1, and the oligosaccharide chain added GLP-1 peptide exhibited higher DPP-IV resistance by adding oligosaccharide chain at this site.

Test Example 6

Test of Ability to Synthesize cAMP

1. Construction of Mouse GLP-1 Receptor-Expressing Vector

A mouse GLP1 receptor sense primer (5'-GTTGCTAGCGCCACCATGGCCAGCACCCCAAGCCT-3') (SEQ ID NO: 152) and a mouse GLP-1 receptor antisense primer (5'-CCTGAATTCTCAGCTGTAGGAACTCTGGCAG-3') (SEQ ID NO: 153) capable of binding to the 5' and 3' ends of mouse GLP-1 receptor cDNA were separately synthesized. PCR was performed using Ex Taq polymerase (TaKaRa) with cDNA (Clone ID: 40046534, Open Biosystems) as a template. Specifically, 50 µL in total of reaction solution consisting of 1 µL of template cDNA (10 ng/µL), 4 µL of 2.5 mM dNTPs, 1 µL of primer solution mixtures (each 50 µM), 5 µL of ×10 Ex Taq polymerase Buffer, 0.25 µL of Ex Taq polymerase and 38.75 µL of sterilized water was used and allowed to react by 94° C. for 1 minute; 94° C. for 45 seconds, 55° C. for 1 minute and 72° C. for 2 minutes (35 cycles); and 72° C. for 10 minutes. The PCR reaction product was electrophoresed on 1% agarose gel, and the cDNA fragment was purified using Wizard SV Gel and PCR Clean-up System (Promega) and treated with restriction enzymes (EcoRI and NheI) to obtain mouse GLP-1 receptor cDNA.

To efficiently obtain cells highly expressing a mouse GLP-1 receptor, a pIRES-gfp vector was used as an expression vector. This vector was prepared by inserting, to a vector pEGFP-N1 (Clontech), an IRES gene-containing DNA fragment obtained by the restriction enzyme treatment (Sal I and BamHI) of pIRESpuro2 (Clontech).

The mouse GLP-1 receptor cDNA fragment was inserted into pIRES-gfp to thereby obtain a mouse GLP-1 receptor-expressing vector mGLP-1R/pIRES-gfp. The DNA sequence of the obtained vector was confirmed using ABI3100-Avant (Applied Biosystems).

2. Preparation of Mouse GLP-1 Receptor-Expressing CHO-K1 Cells

CHO-K1 cells (ATCC catalog No. CCL-61) were transfected with the obtained mGLP-1R/pIRES-gfp using FuGENE (registered trademark) (Roche) according to the instruction manual. The transfected CHO-K1 cells were cultured in RPMI1640 medium (Wako Pure Chemical Industries) containing 10% FCS (Hyclone) and penicillin-streptomycin (SIGMA). Drug selection was conducted by the addition of 1.0 mg/ml G418 (Wako Pure Chemical Industries). The drug resistance cells were sorted with a cell sorter (EPICS ALTRA, Beckman Coulter) using a GFP expression level as an index. After the sorting, the limiting dilution method was conducted to obtain cells highly expressing GFP, namely, cells highly expressing a mouse GLP-1 receptor. The obtained cells were used as mouse GLP-1 receptor-expressing CHO-K1 cells in the experiment shown below.

3. Analysis of Agonist Effect of Oligosaccharide Chain Added GLP-1 Peptide (Ability to Synthesize cAMP)

The mouse GLP-1 receptor-expressing CHO-K1 cells prepared in the preceding paragraph 2 were used to evaluate the agonist effect of the oligosaccharide chain added GLP-1 peptide using the ability to synthesize cAMP as an index.

The mouse GLP-1 receptor-expressing CHO-K1 cells were suspended at a concentration of $5 \times 10^5$ cells/ml in RPMI1640 medium containing 10% FCS. The cell suspension was seeded at a concentration of 100 µL per well to a flat-bottomed 96-well plate (Falcon) and cultured at 5% $CO_2$ at 37° C. for 16 hours. The culture supernatant was discarded. The oligosaccharide chain added GLP-1 peptide dissolved in Krebs Ringer bicarbonate Buffer containing 2.5 mM glucose was added at a concentration of 100 µL/well and cultured at 37° C. for 30 minutes. The culture supernatant was immediately discarded. The amount of cAMP synthesized in the mouse GLP-1 receptor-expressing CHO-K1 cells was measured using cAMP ELISA Kit (GE Healthcare or Cayman) and used as an index for the agonist effect of the oligosaccharide chain added GLP-1 peptide on mouse GLP-1 receptors.

GLP-1 increases intracellular cAMP concentrations through the binding to its receptor and promotes insulin secretion. Thus, the activity of the oligosaccharide chain added GLP-1 peptide was evaluated using the ability to synthesize cAMP as an index. The mouse GLP-1 receptor-expressing CHO-K1 cells were stimulated with the oligosaccharide chain added GLP-1 peptide. The amount of cAMP synthesized in the cells was measured. The EC50 value of the GLP-1 without oligosaccharide chain addition of Comparative Example 1 was defined as 1. The relative activities of the oligosaccharide chain added GLP-1 peptides of Examples 1 to 5, 8 to 23, 25 and 27 are shown in Table 10.

TABLE 10

| Example | Compound | Relative Activity |
| --- | --- | --- |
| Example 8 | 6Cys GLP-1-disialo | <0.1 |
| Example 9 | 8Cys GLP-1-disialo | <0.1 |
| Example 10 | 9Cys GLP-1-disialo | <0.1 |
| Example 11 | 10Cys GLP-1-disialo | <0.1 |
| Example 12 | 11Cys GLP-1-disialo | <0.1 |
| Example 13 | 12Cys GLP-1-disialo | <0.1 |
| Example 14 | 14Cys GLP-1-disialo | <0.1 |
| Example 15 | 16Cys GLP-1-disialo | <0.1 |
| Example 1 | 18Cys GLP-1-disialo | <0.1 |
| Example 16 | 20Cys GLP-1-disialo | <0.1 |
| Example 2 | 22Cys GLP-1-disialo | 1.0 |
| Example 17 | 24Cys GLP-1-disialo | <0.1 |
| Example 18 | 25Cys GLP-1-disialo | <0.1 |
| Example 3 | 26Cys GLP-1-disialo | 0.2 |
| Example 19 | 27Cys GLP-1-disialo | 0.2 |
| Example 20 | 28Cys GLP-1-disialo | <0.1 |
| Example 21 | 30Cys GLP-1-disialo | 0.6 |
| Example 22 | 32Cys GLP-1-disialo | <0.1 |
| Example 23 | 34Cys GLP-1-disialo | 0.7 |
| Example 4 | 36Cys GLP-1-disialo | 1.9 |
| Example 5 | 38Cys GLP-1-disialo | 1.9 |
| Example 25 | 26Cys GLP-1-asialo | 0.8 |
| Example 27 | 34Cys GLP-1-asialo | 2.2 |

The oligosaccharide chain added GLP-1 peptides 22Cys GLP-1-disialo, 26Cys GLP-1-asialo, 30Cys GLP-1-disialo, 34Cys GLP-1-disialo, 34Cys GLP-1-asialo, 36Cys GLP-1-disialo and 38Cys GLP-1-disialo of Examples were found to exhibit activity equal to or more than that of the GLP-1 without oligosaccharide chain addition of Comparative Example 1, suggesting that an amino acid at position 22, 26, 30, 34, 36 or 38 (=addition of an oligosaccharide chain added amino acid to an amino acid at position 37) is a site suitable for addition of oligosaccharide chain.

Test Example 7

Oral Glucose Tolerance Test (OGTT)

A PBS solution of the oligosaccharide chain added GLP-1 peptide prepared in each of Examples 1 to 5, 9, 10, 13, 16, 21, 23 to 27, 29 to 34, 38, 45, 48 or 49 or the GLP-1 prepared in Comparative Example 1 was intraperitoneally administered at a dose of 10 ml/kg to C57BL/6JJcl mice (10 week old, male) fasted overnight. After 30 minutes, a glucose solution was orally administered at a dose of 1 mg/g. Blood was collected from the orbits before the glucose administration and 30 minutes, 60 minutes and 120 minutes after the glucose administration. Blood-sugar levels were measured using ACCU-CHEK Aviva (Roche Diagnostics).

Test Example 7-1

OGTT of Various Oligosaccharide Chain Added GLP-1 Peptides

Figure 9:
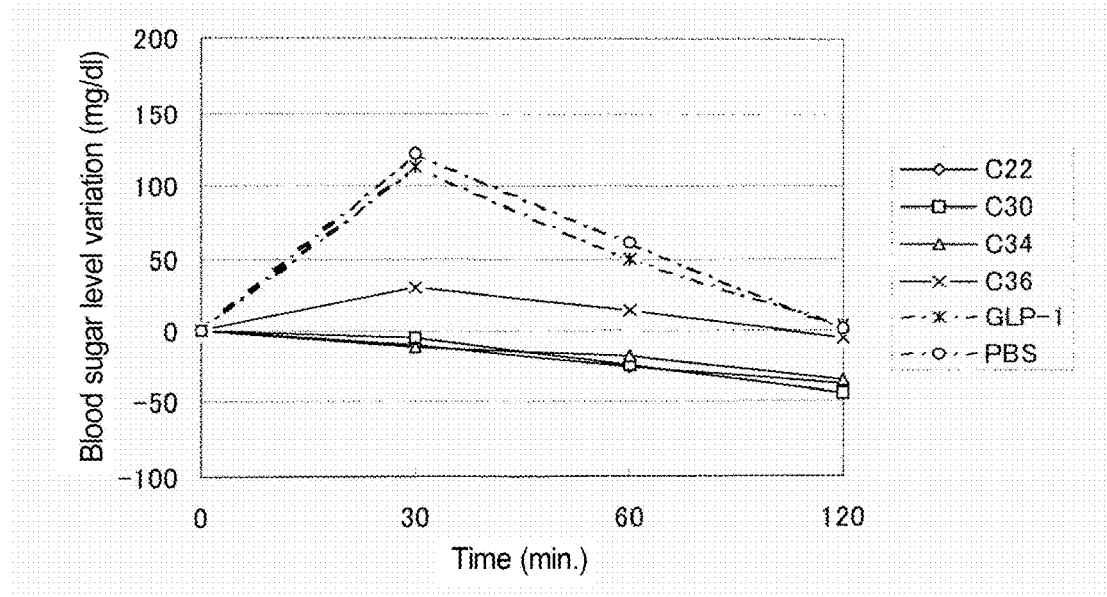
FIG. 9 is a graph showing changes of blood-sugar levels after addition of oligosaccharide chain added GLP-1 peptides of Examples and GLP-1 of Comparative Example 1 in Test Example 7-1 which is Oral Glucose Tolerance Test (OGTT) conducted for examining the effect of suppressing rise in blood-sugar levels by the oligosaccharide chain added GLP-1 peptides.
Figure 10:
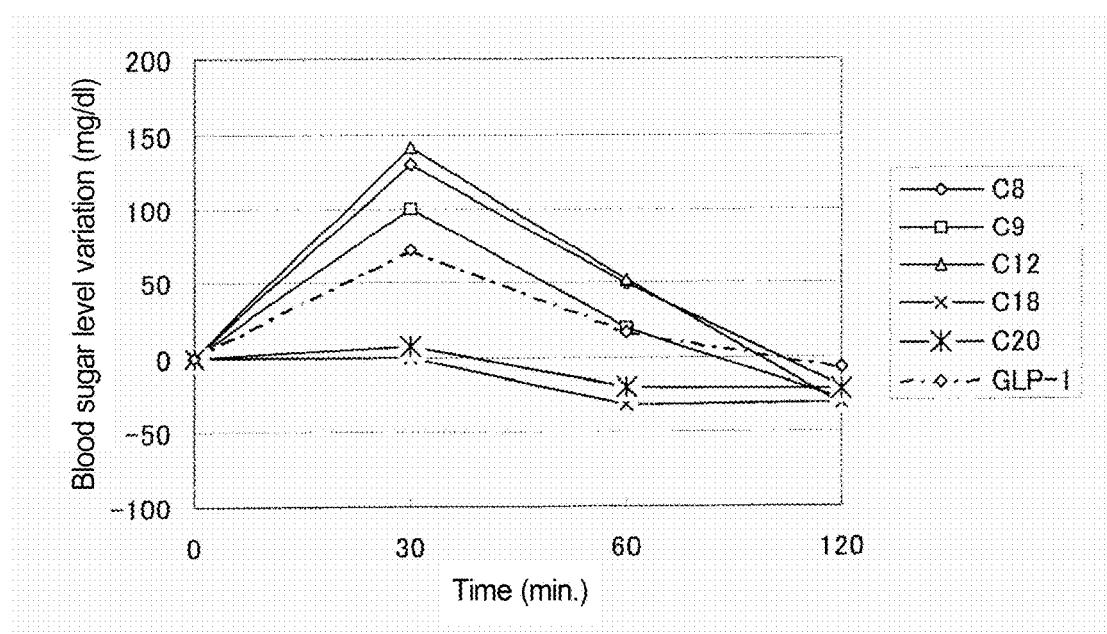
FIG. 10 is a graph showing changes of blood-sugar levels after addition of oligosaccharide chain added GLP-1 peptides of Examples and GLP-1 of Comparative Example 1 in Test Example 7-1 which is Oral Glucose Tolerance Test (OGTT) conducted for examining the effect of suppressing rise in blood-sugar levels by the oligosaccharide chain added GLP-1 peptides.
Figure 11:
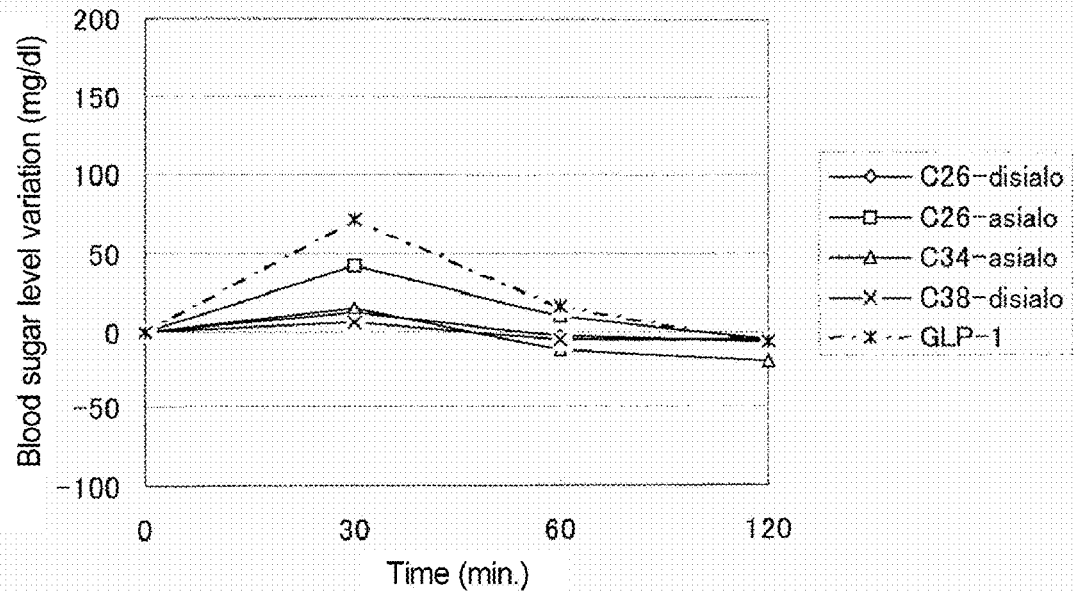
FIG. 11 is a graph showing changes of blood-sugar levels after addition of oligosaccharide chain added GLP-1 peptides of Examples and GLP-1 of Comparative Example 1 in Test Example 7-1 which is Oral Glucose Tolerance Test (OGTT) conducted for examining the effect of suppressing rise in blood-sugar levels by the oligosaccharide chain added GLP-1 peptides.

After the oral administration of the glucose solution to the mice fasted overnight, blood was collected over time, and blood-sugar levels were measured. The mouse blood-sugar levels increase due to the glucose administration, reach the maximum 30 minutes after the administration, and then gradually decrease. 30 minutes before the glucose administration, the oligosaccharide chain added GLP-1 peptide (8Cys GLP-1-disialo, 9Cys GLP-1-disialo, 12Cys GLP-1-disialo, 18Cys GLP-1-disialo, 20Cys GLP-1-disialo, 22Cys GLP-1-disialo, 26Cys GLP-1-disialo, 26Cys GLP-1-asialo, 30Cys GLP-1-disialo, 34Cys GLP-1-disialo, 34Cys GLP-1-asialo, 36Cys GLP-1-disialo or 38Cys GLP-1-disialo) prepared in each Example or the GLP-1 prepared in Comparative Example 1 was intraperitoneally administered at a dose of 9 nmol/kg to each mouse, and their effects of suppressing rise in blood-sugar levels were compared. The results are shown in FIGS. 9 to 11.

The GLP-1 without oligosaccharide chain addition of Comparative Example 1 has low stability in blood and has small effect of suppressing rise in blood-sugar levels because it is quickly degraded after administration.

By contrast, the oligosaccharide chain added GLP-1 peptides 18Cys GLP-1-disialo, 20Cys GLP-1-disialo, 22Cys GLP-1-disialo, 26Cys GLP-1-disialo, 26Cys GLP-1-asialo, 30Cys GLP-1-disialo, 34Cys GLP-1-disialo, 34Cys GLP-1-asialo, 36Cys GLP-1-disialo and 38Cys GLP-1-disialo exhibited strong effect of suppressing rise in blood-sugar levels.

Test Example 7-2

Figure 12:
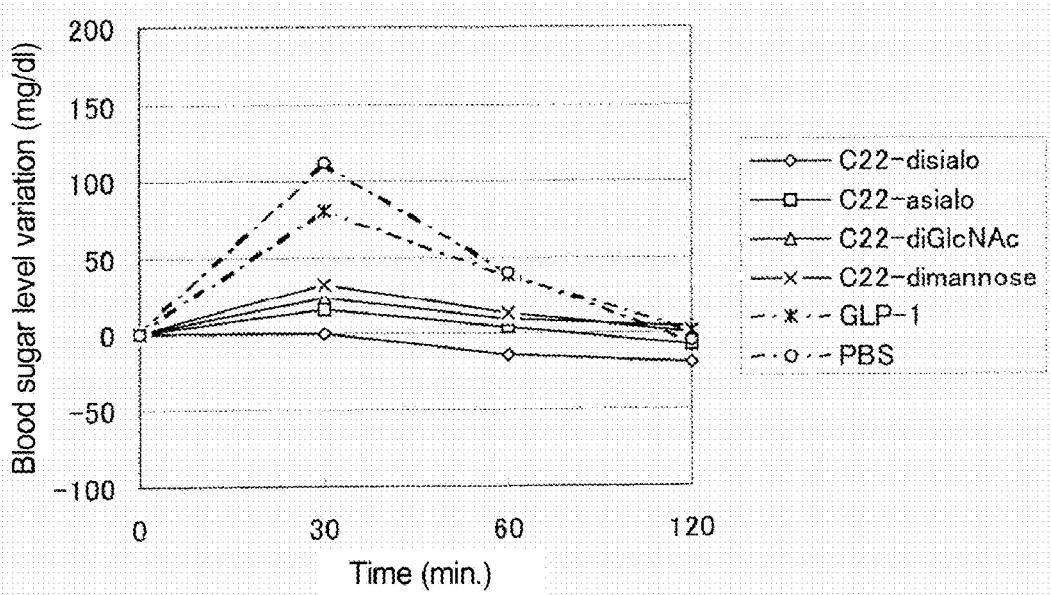
FIG. 12 is a graph showing changes of blood-sugar levels after addition of oligosaccharide chain added GLP-1 peptides of Examples and GLP-1 of Comparative Example 1 in Test Example 7-2 which is Oral Glucose Tolerance Test (OGTT) conducted for examining the influence of oligosaccharide chain structures of the peptides on the effect of suppressing rise in blood-sugar levels by the oligosaccharide chain added GLP-1 peptides.
Figure 13:
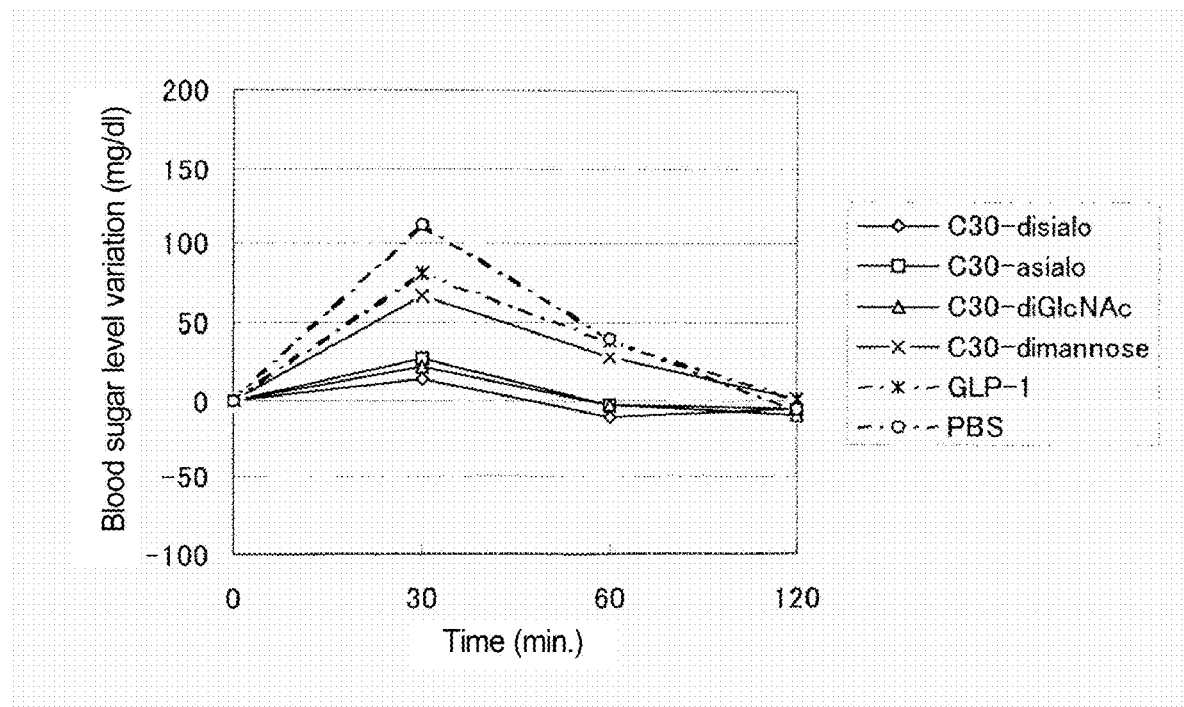
FIG. 13 is a graph showing changes of blood-sugar levels after addition of oligosaccharide chain added GLP-1 peptides of Examples and GLP-1 of Comparative Example 1 in Test Example 7-2 which is Oral Glucose Tolerance Test (OGTT) conducted for examining the influence of oligosaccharide chain structures of the peptides on the effect of suppressing rise in blood-sugar levels by the oligosaccharide chain added GLP-1 peptides.
Figure 14:
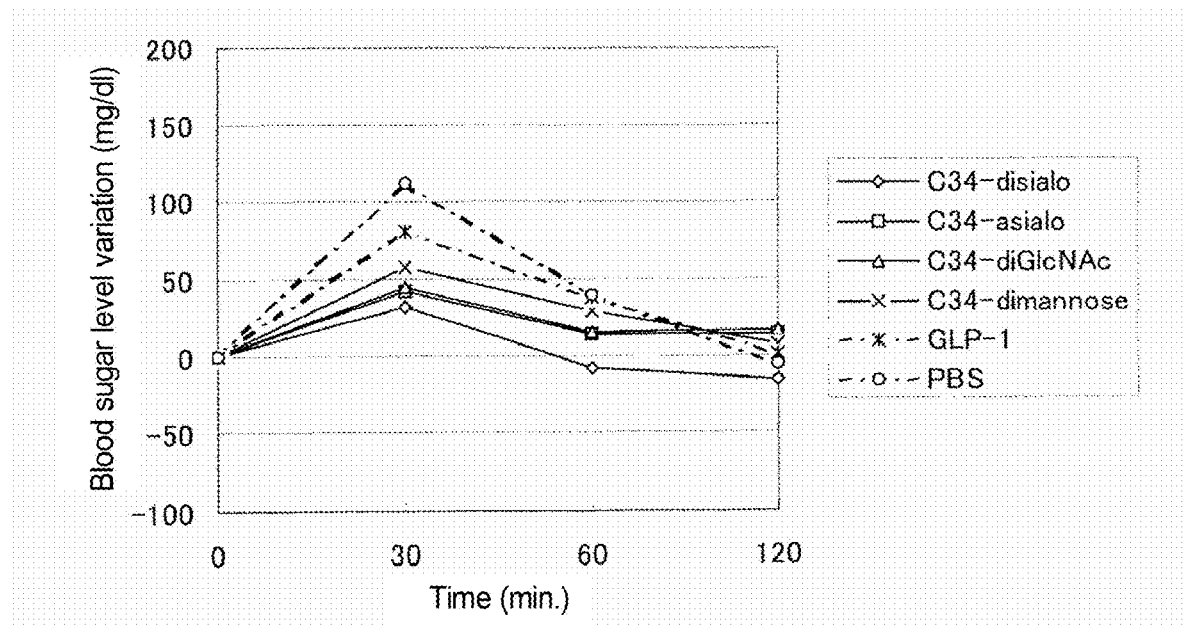
FIG. 14 is a graph showing changes of blood-sugar levels after addition of oligosaccharide chain added GLP-1 peptides of Examples and GLP-1 of Comparative Example 1 in Test Example 7-2 which is Oral Glucose Tolerance Test (OGTT) conducted for examining the influence of oligosaccharide chain structures of the peptides on the effect of suppressing rise in blood-sugar levels by the oligosaccharide chain added GLP-1 peptides.
Figure 15:
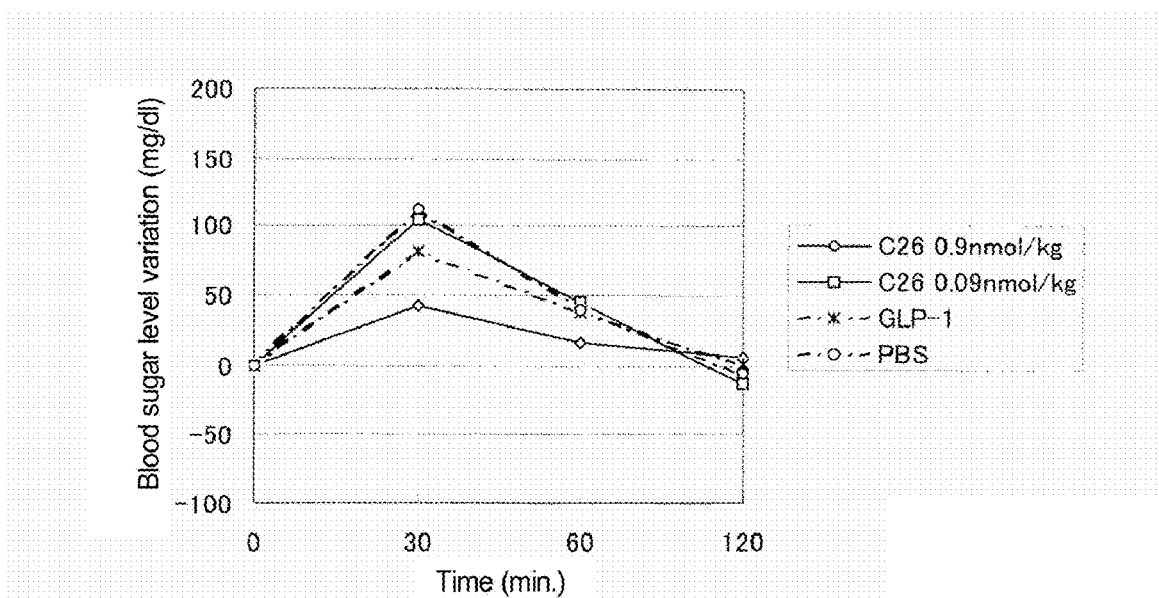
FIG. 15 is a graph showing changes of blood-sugar levels after addition of oligosaccharide chain added GLP-1 peptides of Examples and GLP-1 of Comparative Example 1 in Test Example 7-3 which is Oral Glucose Tolerance Test (OGTT) conducted for examining the influence of oligosaccharide chain structures of the peptides on the effect of suppressing rise in blood-sugar levels by the oligosaccharide chain added GLP-1 peptides.
Figure 16:
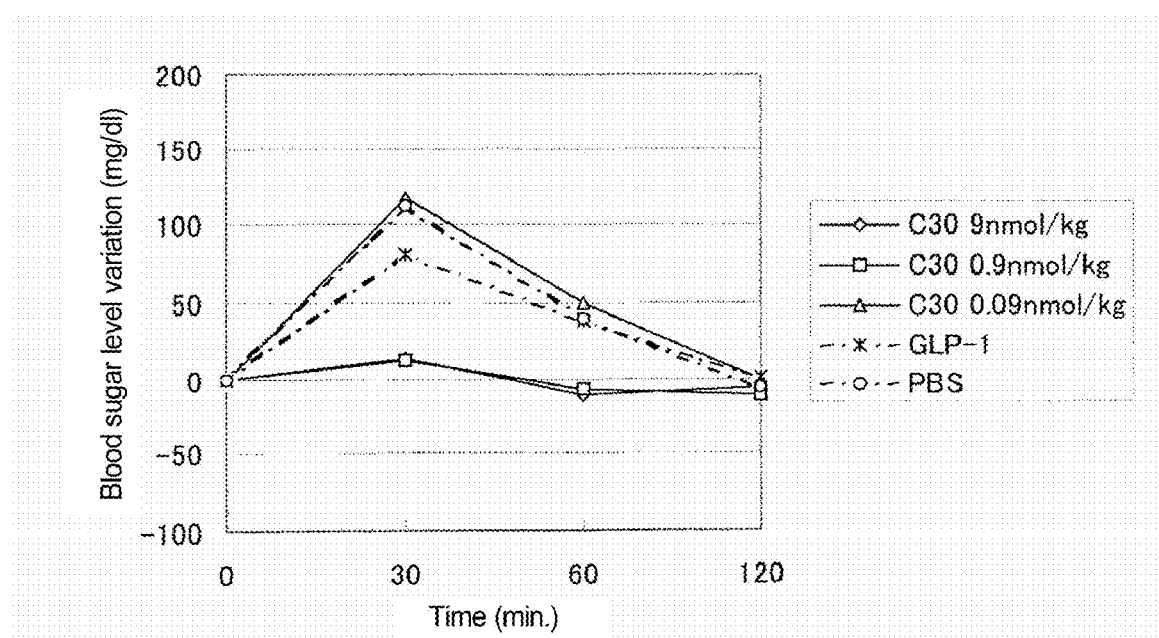
FIG. 16 is a graph showing changes of blood-sugar levels after addition of oligosaccharide chain added GLP-1 peptides of Examples and GLP-1 of Comparative Example 1 in Test Example 7-3 which is Oral Glucose Tolerance Test (OGTT) conducted for examining the influence of oligosaccharide chain structures of the peptides on the effect of suppressing rise in blood-sugar levels by the oligosaccharide chain added GLP-1 peptides.
Figure 17:
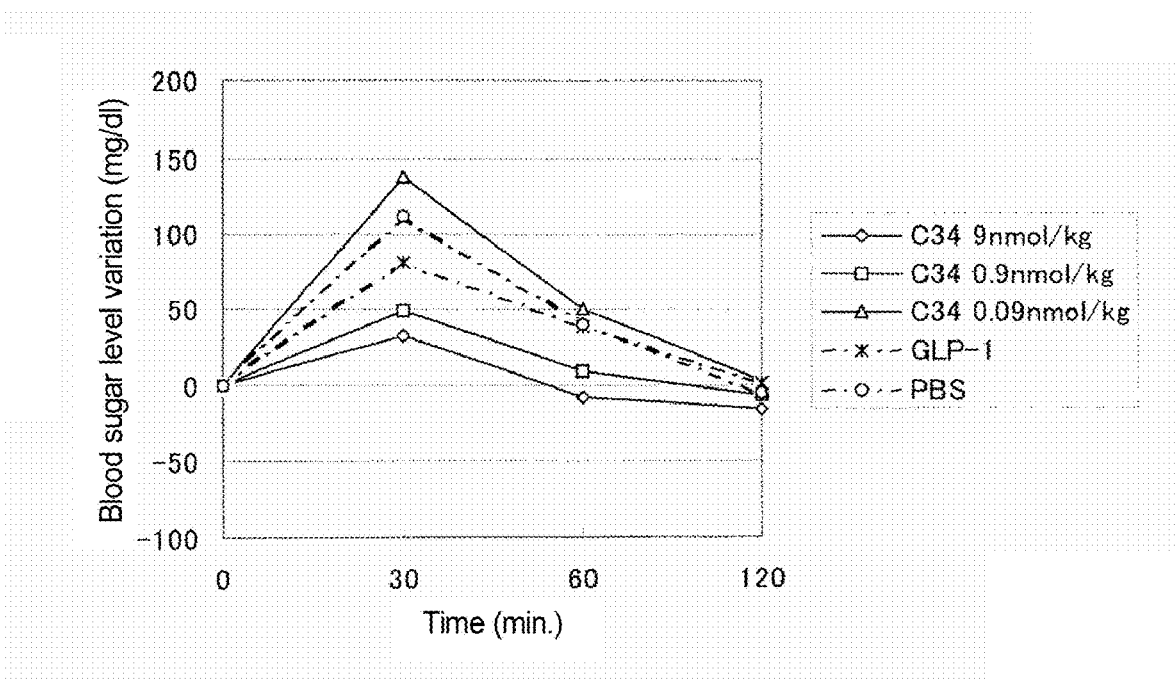
FIG. 17 is a graph showing changes of blood-sugar levels after addition of oligosaccharide chain added GLP-1 peptides of Examples and GLP-1 of Comparative Example 1 in Test Example 7-3 which is Oral Glucose Tolerance Test (OGTT) conducted for examining the influence of doses of the peptides on the effect of suppressing rise in blood-sugar levels by the oligosaccharide chain added GLP-1 peptides.
Figure 18:
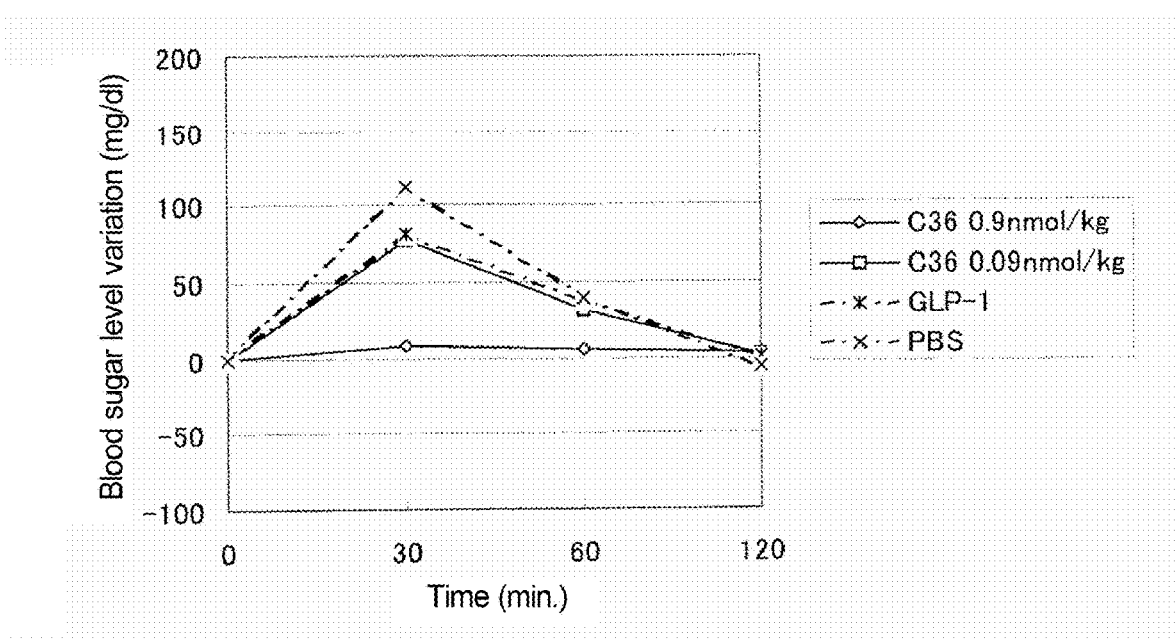
FIG. 18 is a graph showing changes of blood-sugar levels after addition of oligosaccharide chain added GLP-1 peptides of Examples and GLP-1 of Comparative Example 1 in Test Example 7-3 which is Oral Glucose Tolerance Test (OGTT) conducted for examining the influence of doses of the peptides on the effect of suppressing rise in blood-sugar levels by the oligosaccharide chain added GLP-1 peptides.

Influence of Oligosaccharide Chain Structure in OGTT of Oligosaccharide Chain Added GLP-1 Peptide The oligosaccharide chain added GLP-1 peptide having oligosaccharide chain of eleven sugars (disialo oligosaccharide chain), nine sugars (asialo oligosaccharide chain), seven sugars (diGlcNAc oligosaccharide chain) or five sugars (dimannose oligosaccharide chain) (22Cys GLP-1-disialo, 22Cys GLP-1-asialo, 22Cys GLP-1-diGlcNAc, 22Cys GLP-1-dimannose, 30Cys GLP-1-disialo, 30Cys GLP-1-asialo, 30Cys GLP-1-diGlcNAc, 30Cys GLP-1-dimannose, 34Cys GLP-1-disialo, 34Cys GLP-1-asialo, 34Cys GLP-1-diGlcNAc or 34Cys GLP-1-dimannose) or the GLP-1 prepared in Comparative Example 1 was intraperitoneally administered at a dose of 9 nmol/kg to each mouse. The correlation between the oligosaccharide chain structure and the activity was studied in mouse OGTT. The results are shown in FIGS. 12 to 14.

The strongest effect of suppressing rise in blood-sugar levels was exhibited by the oligosaccharide chain added GLP-1 peptides having oligosaccharide chain of eleven sugars (disialo oligosaccharide chain), which was largest, at any of the addition sites (positions 22, 30 and 34). Higher activity of suppressing rise in blood-sugar levels was produced in the order of eleven sugars≧nine sugars≧seven sugars≧five sugars.

Test Example 7-3

Influence of Dose in OGTT of Oligosaccharide Chain Added GLP-1 Peptide

To rank highly active oligosaccharide chain added GLP-1 peptides, 26Cys GLP-1-disialo, 30Cys GLP-1-disialo, 34Cys GLP-1-disialo and 36Cys GLP-1-disialo were separately evaluated by mouse OGTT using a dose of 1/10 (0.9 nmol/kg) or 1/100 (0.09 nmol/kg). The results are shown in FIGS. 15 to 18. In FIGS. 15 to 18, the OGTT results of GLP-1 were obtained at a dose of 9 nmol/kg according to Test Example 7-2.

All the oligosaccharide chain added GLP-1 peptides 26Cys GLP-1-disialo, 30Cys GLP-1-disialo, 34Cys GLP-1-disialo and 36Cys GLP-1-disialo exhibited dose-dependent activity of suppressing rise in blood-sugar levels. At a dose of 0.9 nmol/kg, rise in blood-sugar levels was suppressed most strongly by the 30Cys GLP-1-disialo and the 36Cys GLP-1-disialo, which suppressed rise in blood-sugar levels almost completely.

The 36Cys GLP-1-disialo at a dose of 0.09 nmol/kg exhibited the activity of suppressing rise in blood-sugar levels equivalent to that of the GLP-1 at a dose of 9 nmol/kg, suggesting that the activity of the 36Cys GLP-1-disialo was about 100 times higher than that of the GLP-1. Likewise, the 30Cys GLP-1-disialo at a dose of 0.09 nmol/kg had weaker activity of suppressing rise in blood-sugar levels than that of the 36Cys GLP-1-disialo at the same dose, suggesting that the activity of the 30Cys GLP-1-disialo is up to 10 to 100 times that of the GLP-1. The 26Cys GLP-1-disialo and the 34Cys GLP-1-disialo at a dose of 0.9 nmol/kg had efficacy about ½ of the activities of suppressing rise in blood-sugar levels by the 30Cys GLP-1-disialo and the 36Cys GLP-1-disialo at the same dose, suggesting that the activities of the 26Cys GLP-1-disialo and the 34Cys GLP-1-disialo are about 5 to 50 times that of the GLP-1. The oligosaccharide chain addition sites that exhibited high activity in the OGTT were positions 30 and 36.

Test Example 7-4

Figure 19:
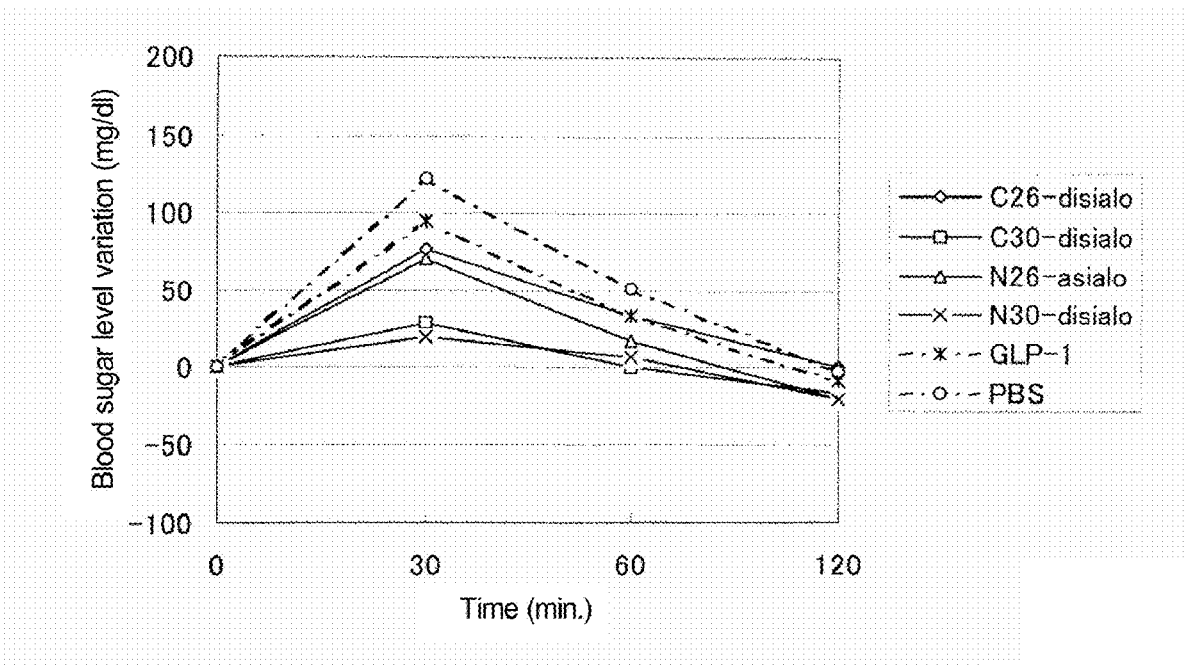
FIG. 19 is a graph showing changes of blood-sugar levels after addition of oligosaccharide chain added GLP-1 peptides of Examples and GLP-1 of Comparative Example 1 in Test Example 7-4 which is Oral Glucose Tolerance Test (OGTT) conducted for examining the effect of suppressing rise in blood-sugar levels by the Asn oligosaccharide chain added GLP-1 peptides.

OGTT of Oligosaccharide Chain Added GLP-1 Peptide Having Oligosaccharide Chain Added Asn The oligosaccharide chain added GLP-1 peptide wherein an amino acid at position 22 or 30 of GLP-1 was substituted with oligosaccharide chain added Asn (naturally occurring type of linked oligosaccharide chain) or oligosaccharide chain added Cys were compared in activity at a dose of 0.9 nmol/kg in mouse OGTT. The results are shown in FIG. 19. In FIG. 19, the OGTT results of GLP-1 were obtained at a dose of 9 nmol/kg according to Test Example 7-2.

In the cases of adding oligosaccharide chain of nine sugars (asialo oligosaccharide chain) at position 22 and adding oligosaccharide chain of eleven sugars (disialo oligosaccharide chain) at position 30, both cases showed no difference in the effect of suppressing rise in blood-sugar levels by the oligosaccharide chain added GLP-1 peptide between oligosaccharide chain added Asn and oligosaccharide chain added Cys. The oligosaccharide chain added GLP-1 peptides having any of the oligosaccharide chain added amino acids exhibited activity.

Test Example 7-5

Figure 20:
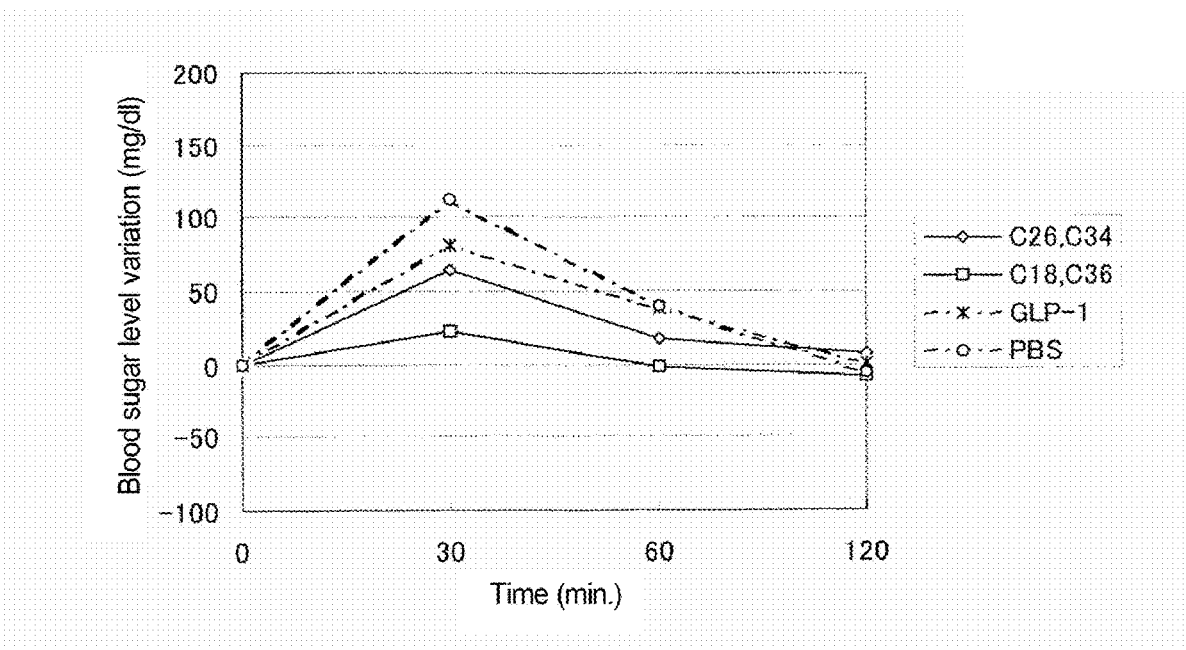
FIG. 20 is a graph showing changes of blood-sugar levels after addition of oligosaccharide chain added GLP-1 peptides of Examples and GLP-1 of Comparative Example 1 in Test Example 7-5 which is Oral Glucose Tolerance Test (OGTT) conducted for examining the influence of the number of oligosaccharide chains to be added of the peptides on the effect of suppressing rise in blood-sugar levels by the oligosaccharide chain added GLP-1 peptides.

Influence of the Number of Oligosaccharide Chains to be Added in OGTT of Oligosaccharide Chain Added GLP-1 Peptide The oligosaccharide chain added GLP-1 peptides of Examples 48 and 49 having 2 oligosaccharide chains were evaluated for their effects of suppressing rise in blood-sugar levels using mouse OGTT. The OGTT results of 26,34Cys GLP-1-disialo and 18,36Cys GLP-1-disialo at a dose of 9 nmol/kg are shown in FIG. 20. In FIG. 20, the OGTT results of GLP-1 were obtained at a dose of 9 nmol/kg according to Test Example 7-2.

The 18,36Cys GLP-1-disialo at a dose of 9 nmol/kg had effect almost equivalent to that of the 36Cys GLP-1-disialo shown in FIG. 5 or 14. The 26,34Cys GLP-1-disialo at a dose of 9 nmol/kg had slightly better activity of suppressing rise in blood-sugar levels than that of the GLP-1 at the same dose.

Figure 21:
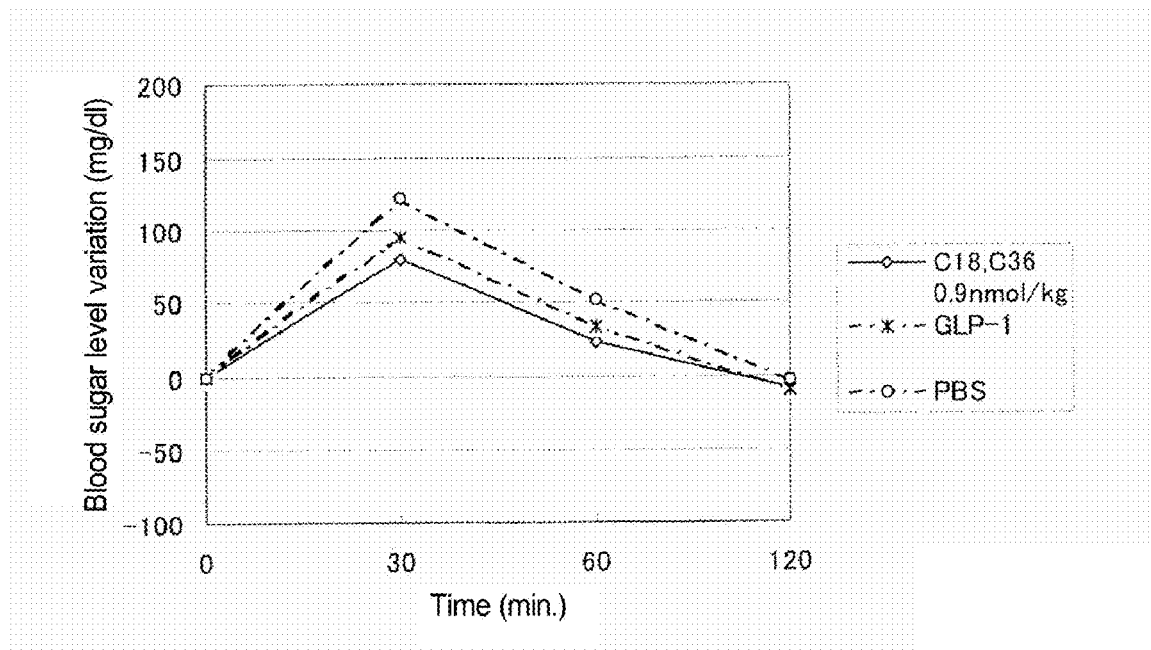
FIG. 21 is a graph showing changes of blood-sugar levels after addition of oligosaccharide chain added GLP-1 peptide of Example and GLP-1 of Comparative Example 1 in Test Example 7-5 which is Oral Glucose Tolerance Test (OGTT) conducted for examining the influence of the number of oligosaccharide chains to be added of the peptides on the effect of suppressing rise in blood-sugar levels by the oligosaccharide chain added GLP-1 peptides.

Next, the 18,36Cys GLP-1-disialo was evaluated by OGTT using a dose of 1/10 (0.9 nmol/kg). Likewise, GLP-1 at a dose of 9 nmol/kg was evaluated by OGTT and compared with the 18,36Cys GLP-1-disialo. The results are shown in FIG. 21.

The 18,36Cys GLP-1-disialo at a dose of 0.9 nmol/kg had the effect of lowering blood-sugar levels almost equivalent to that of the GLP-1 at a dose of 9 nmol/kg, suggesting that the activity of suppressing rise in blood-sugar levels by the 18,36Cys GLP-1-disialo is about 10 times higher than that of the GLP-1.

Test Example 8

Effect of Lowering Blood-Sugar Levels in Diabetes Model Mice by Oligosaccharide Chain Added GLP-1 Peptide The oligosaccharide chain added GLP-1 peptide prepared in Example 2, 3, 4, 21 or 23 or the GLP-1 prepared in Comparative Example 1 in a PBS solution (9 nmol/10 ml) was intraperitoneally administered at a dose of 10 ml/kg to BKS.Cg-+$Lepr^{db}$/+$Lepr^{db}$/Jcl mice (10 week old, male). Blood was collected from the orbits before the compound administration and 30 minutes, 60 minutes, 120 minutes, 180 minutes and 300 minutes after the compound administration. Blood-sugar levels were measured using ACCU-CHEK Aviva (Roche Diagnostics).

The db/db (BKS.Cg-+$Lepr^{db}$/+$Lepr^{db}$/Jcl) mice serving as diabetes model mice have a mutation in a receptor of leptin which is anorexigenic/energy metabolism-accelerating hormone and develops conditions such as obesity or hyperglycemia.

Figure 22:
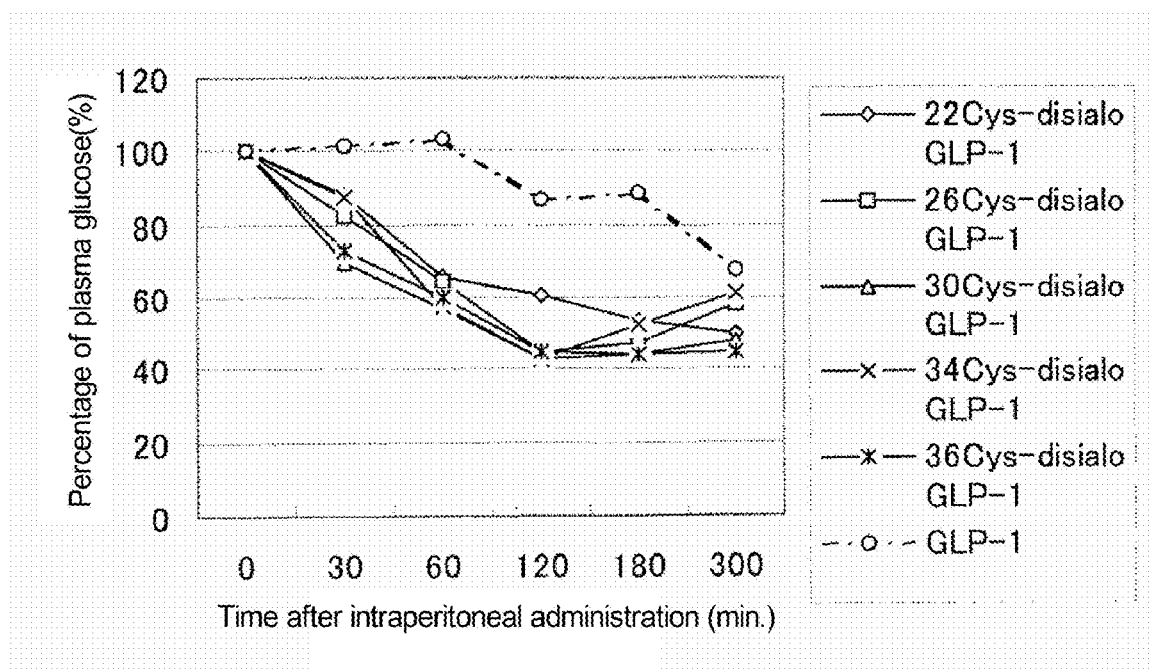
FIG. 22 is a graph showing changes of blood-sugar levels after addition of oligosaccharide chain added GLP-1 peptides of Examples and GLP-1 of Comparative Example 1 in Test Example 8 conducted for examining the effect of suppressing rise in blood-sugar levels in diabetes model mice by the oligosaccharide chain added GLP-1 peptides.

Of the oligosaccharide chain added GLP-1 peptides that exhibited the activity of suppressing rise in blood-sugar levels in mouse OGTT (Test Example 7), 22Cys GLP-1-disialo, 26Cys GLP-1-disialo, 30Cys GLP-1-disialo, 34Cys GLP-1-disialo or 36Cys GLP-1-disialo was intraperitoneally administered at a dose of 9 nmol/kg to the db/db mice. Blood-sugar levels were measured over time, and their effects of lowering blood-sugar levels were compared with that of the GLP-1 without oligosaccharide chain addition of Comparative Example 1. The results are shown in FIG. 22.

GLP-1 has low stability in blood and has low effect of lowering blood-sugar levels because it is quickly degraded after administration. Therefore, blood-sugar levels in GLP-1-administered mice were almost equal to those in PBS-administered mice.

By contrast, the oligosaccharide chain added GLP-1 peptides (26Cys GLP-1-disialo, 30Cys GLP-1-disialo, 34Cys GLP-1-disialo and 36Cys GLP-1-disialo) exhibited strong effect of lowering blood-sugar levels. Those exhibiting the activity of suppressing rise in blood-sugar levels in mouse OGTT also exhibited the effect of lowering blood-sugar levels in the db/db mice (effect of lowering blood-sugar levels on 120 minutes: 26Cys GLP-1-disialo, 30Cys GLP-1-disialo, 34Cys GLP-1-disialo and 36Cys GLP-1-disialo≧22Cys GLP-1-disialo).

When 26Cys GLP-1-disialo or 34Cys GLP-1-disialo were administered, blood-sugar levels gradually increased after the administration, and their effects of lowering blood-sugar levels were slightly weakened over time. When 30Cys GLP-1-disialo or 36Cys GLP-1-disialo were administered, blood-sugar levels were kept at low levels after 300 minutes (effect of lowering blood-sugar levels on 300 minutes: 30Cys GLP-1-disialo and 36Cys GLP-1-disialo≧22Cys GLP-1-disialo, 26Cys GLP-1-disialo and 34Cys GLP-1-disialo).

Sequence Listing Free Text

SEQ ID NO:1 is oligosaccharide chain added GLP-1 peptide represented by the general formula (1).

SEQ ID NO:2 is GLP-1 (7-37).
SEQ ID NO:3 is GLP-1 (7-36NH$_2$.
SEQ ID NO:4 is oligosaccharide chain added GLP-1 peptide represented by (a1).
SEQ ID NO:5 is oligosaccharide chain added GLP-1 peptide represented by (a2).
SEQ ID NO:6 is oligosaccharide chain added GLP-1 peptide represented by (a3).
SEQ ID NO:7 is oligosaccharide chain added GLP-1 peptide represented by (a4).
SEQ ID NO:8 is oligosaccharide chain added GLP-1 peptide represented by (a5).
SEQ ID NO:9 is oligosaccharide chain added GLP-1 peptide represented by (a6).
SEQ ID NO:10 is oligosaccharide chain added GLP-1 peptide represented by (a7).
SEQ ID NO:11 is oligosaccharide chain added GLP-1 peptide represented by (a8).
SEQ ID NO:12 is oligosaccharide chain added GLP-1 peptide represented by (a9).
SEQ ID NO:13 is oligosaccharide chain added GLP-1 peptide represented by (a10).
SEQ ID NO:14 is oligosaccharide chain added GLP-1 peptide represented by (a11).
SEQ ID NO:15 is oligosaccharide chain added GLP-1 peptide represented by (a12).
SEQ ID NO:16 is oligosaccharide chain added GLP-1 peptide represented by (a13).
SEQ ID NO:17 is oligosaccharide chain added GLP-1 peptide represented by (a14).
SEQ ID NO:18 is oligosaccharide chain added GLP-1 peptide represented by (a15).
SEQ ID NO:19 is oligosaccharide chain added GLP-1 peptide represented by (a16).
SEQ ID NO:20 is oligosaccharide chain added GLP-1 peptide represented by (a17).
SEQ ID NO:21 is oligosaccharide chain added GLP-1 peptide represented by (a18).
SEQ ID NO:22 is oligosaccharide chain added GLP-1 peptide represented by (a19).
SEQ ID NO:23 is oligosaccharide chain added GLP-1 peptide represented by (a20).
SEQ ID NO:24 is oligosaccharide chain added GLP-1 peptide represented by (a21).
SEQ ID NO:25 is oligosaccharide chain added GLP-1 peptide represented by (a22).
SEQ ID NO:26 is oligosaccharide chain added GLP-1 peptide represented by (a23).
SEQ ID NO:27 is oligosaccharide chain added GLP-1 peptide represented by (a24).
SEQ ID NO:28 is oligosaccharide chain added GLP-1 peptide represented by (a25).
SEQ ID NO:29 is oligosaccharide chain added GLP-1 peptide represented by (a26).
SEQ ID NO:30 is 31-residue peptide with protective groups synthesized in Example 1.
SEQ ID NO:31 is 31-residue peptide with protective groups synthesized in Comparative Example 1.
SEQ ID NO:32 is 31-residue peptide with protective groups synthesized in Example 6.
SEQ ID NO:33 is 31-residue peptide with protective groups synthesized in Example 6.
SEQ ID NO:34 is 18-residue peptide with protective groups synthesized in Example 7.
SEQ ID NO:35 is oligosaccharide chain added 19-residue peptide with protective groups synthesized in Example 7.
SEQ ID NO:36 is oligosaccharide chain added 31-residue peptide with protective groups synthesized in Example 7.
SEQ ID NO:37 is 31-residue peptide with protective groups synthesized in Example 8.
SEQ ID NO:38 is 31-residue peptide with protective groups synthesized in Example 9.
SEQ ID NO:39 is 31-residue peptide with protective groups synthesized in Example 10.
SEQ ID NO:40 is 31-residue peptide with protective groups synthesized in Example 11.
SEQ ID NO:41 is 31-residue peptide with protective groups synthesized in Example 12.
SEQ ID NO:42 is 31-residue peptide with protective groups synthesized in Example 13.
SEQ ID NO:43 is 31-residue peptide with protective groups synthesized in Example 14.
SEQ ID NO:44 is 31-residue peptide with protective groups synthesized in Example 15.
SEQ ID NO:45 is 31-residue peptide with protective groups synthesized in Example 16.
SEQ ID NO:46 is 31-residue peptide with protective groups synthesized in Example 17.
SEQ ID NO:47 is 31-residue peptide with protective groups synthesized in Example 18.
SEQ ID NO:48 is 31-residue peptide with protective groups synthesized in Example 19.
SEQ ID NO:49 is 31-residue peptide with protective groups synthesized in Example 20.
SEQ ID NO:50 is 31-residue peptide with protective groups synthesized in Example 21.
SEQ ID NO:51 is 31-residue peptide with protective groups synthesized in Example 22.
SEQ ID NO:52 is 31-residue peptide with protective groups synthesized in Example 23.
SEQ ID NO:53 is 31-residue peptide with protective groups synthesized in Example 24.
SEQ ID NO:54 is 31-residue peptide with protective groups synthesized in Example 25.
SEQ ID NO:55 is 31-residue peptide with protective groups synthesized in Example 26.
SEQ ID NO:56 is 31-residue peptide with protective groups synthesized in Example 27.
SEQ ID NO:57 is 31-residue peptide with protective groups synthesized in Example 28.
SEQ ID NO:58 is 31-residue peptide with protective groups synthesized in Example 29.
SEQ ID NO:59 is 31-residue peptide with protective groups synthesized in Example 30.
SEQ ID NO:60 is 31-residue peptide with protective groups synthesized in Example 31.
SEQ ID NO:61 is 31-residue peptide with protective groups synthesized in Example 32.
SEQ ID NO:62 is 31-residue peptide with protective groups synthesized in Example 33.
SEQ ID NO:63 is 31-residue peptide with protective groups synthesized in Example 34.
SEQ ID NO:64 is 12-residue peptide with protective groups synthesized in Example 35.
SEQ ID NO:65 is 13-residue peptide with protective groups synthesized in Example 35.
SEQ ID NO:66 is oligosaccharide chain added 18-residue peptide with protective groups synthesized in Example 35.
SEQ ID NO:67 is oligosaccharide chain added 18-residue peptide with protective groups synthesized in Example 35.
SEQ ID NO:68 is oligosaccharide chain added 18-residue peptide with leaving group synthesized in Example 35.

SEQ ID NO:69 is 13-residue peptide with protective groups synthesized in Example 35.
SEQ ID NO:70 is 13-residue peptide synthesized in Example 35.
SEQ ID NO:71 is 19-residue peptide with protective groups synthesized in Example 36.
SEQ ID NO:72 is oligosaccharide chain added 20-residue peptide with protective groups synthesized in Example 36.
SEQ ID NO:73 is oligosaccharide chain added 31-residue peptide with protective groups synthesized in Example 36.
SEQ ID NO:74 is 15-residue peptide with protective groups synthesized in Example 37.
SEQ ID NO:75 is oligosaccharide chain added 16-residue peptide with protective groups synthesized in Example 37.
SEQ ID NO:76 is oligosaccharide chain added 31-residue peptide with protective groups synthesized in Example 37.
SEQ ID NO:77 is 18-residue peptide with protective groups synthesized in Example 38.
SEQ ID NO:78 is 18-residue peptide with protective groups synthesized in Example 38.
SEQ ID NO:79 is 18-residue peptide with leaving group synthesized in Example 38.
SEQ ID NO:80 is 11-residue peptide with protective groups synthesized in Example 38.
SEQ ID NO:81 is oligosaccharide chain added 13-residue peptide with protective groups synthesized in Example 38.
SEQ ID NO:82 is 18-residue peptide with protective groups synthesized in Example 39.
SEQ ID NO:83 is 18-residue peptide with protective groups synthesized in Example 39.
SEQ ID NO:84 is 18-residue peptide with leaving group synthesized in Example 39.
SEQ ID NO:85 is 10-residue peptide with protective groups synthesized in Example 39.
SEQ ID NO:86 is oligosaccharide chain added 13-residue peptide with protective groups synthesized in Example 39.
SEQ ID NO:87 is 18-residue peptide with protective groups synthesized in Example 40.
SEQ ID NO:88 is 18-residue peptide with protective groups synthesized in Example 40.
SEQ ID NO:89 is 18-residue peptide with leaving group synthesized in Example 40.
SEQ ID NO:90 is 9-residue peptide with protective groups synthesized in Example 40.
SEQ ID NO:91 is oligosaccharide chain added 13-residue peptide with protective groups synthesized in Example 40.
SEQ ID NO:92 is 7-residue peptide with protective groups synthesized in Example 41.
SEQ ID NO:93 is oligosaccharide chain added 8-residue peptide with protective groups synthesized in Example 41.
SEQ ID NO:94 is oligosaccharide chain added 31-residue peptide with protective groups synthesized in Example 41.
SEQ ID NO:95 is oligosaccharide chain added 31-residue peptide with protective groups synthesized in Example 42.
SEQ ID NO:96 is 18-residue peptide with protective groups synthesized in Example 46.
SEQ ID NO:97 is 18-residue peptide with protective groups synthesized in Example 46.
SEQ ID NO:98 is 18-residue peptide with leaving group synthesized in Example 46.
SEQ ID NO:99 is 7-residue peptide with protective groups synthesized in Example 46.
SEQ ID NO:100 is oligosaccharide chain added 13-residue peptide with protective groups synthesized in Example 46.
SEQ ID NO:101 is 31-residue peptide with protective groups synthesized in Example 48.
SEQ ID NO:102 is 31-residue peptide with protective groups synthesized in Example 49.
SEQ ID NO:103 is oligosaccharide chain added GLP-1 peptide represented by (b1).
SEQ ID NO:104 is oligosaccharide chain added GLP-1 peptide represented by (b2).
SEQ ID NO:105 is oligosaccharide chain added GLP-1 peptide represented by (b3).
SEQ ID NO:106 is oligosaccharide chain added GLP-1 peptide represented by (b4).
SEQ ID NO:107 is oligosaccharide chain added GLP-1 peptide represented by (b5).
SEQ ID NO:108 is oligosaccharide chain added GLP-1 peptide represented by (b6).
SEQ ID NO:109 is oligosaccharide chain added GLP-1 peptide represented by (b7).
SEQ ID NO:110 is oligosaccharide chain added GLP-1 peptide represented by (b8).
SEQ ID NO:111 is oligosaccharide chain added GLP-1 peptide represented by (b9).
SEQ ID NO:112 is oligosaccharide chain added GLP-1 peptide represented by (b10).
SEQ ID NO:113 is oligosaccharide chain added GLP-1 peptide represented by (b11).
SEQ ID NO:114 is oligosaccharide chain added GLP-1 peptide represented by (b12).
SEQ ID NO:115 is oligosaccharide chain added GLP-1 peptide represented by (b13).
SEQ ID NO:116 is oligosaccharide chain added GLP-1 peptide represented by (b14).
SEQ ID NO:117 is oligosaccharide chain added GLP-1 peptide represented by (b15).
SEQ ID NO:118 is oligosaccharide chain added GLP-1 peptide represented by (b16).
SEQ ID NO:119 is oligosaccharide chain added GLP-1 peptide represented by (b17).
SEQ ID NO:120 is oligosaccharide chain added GLP-1 peptide represented by (b18).
SEQ ID NO:121 is oligosaccharide chain added GLP-1 peptide represented by (b19).
SEQ ID NO:122 is oligosaccharide chain added GLP-1 peptide represented by (b20).
SEQ ID NO:123 is oligosaccharide chain added GLP-1 peptide represented by (b21).
SEQ ID NO:124 is oligosaccharide chain added GLP-1 peptide represented by (b22).
SEQ ID NO:125 is oligosaccharide chain added GLP-1 peptide represented by (b23).
SEQ ID NO:126 is oligosaccharide chain added GLP-1 peptide represented by (b24).
SEQ ID NO:127 is oligosaccharide chain added GLP-1 peptide represented by (b25).
SEQ ID NO:128 is oligosaccharide chain added GLP-1 peptide represented by (b26).
SEQ ID NO:129 is oligosaccharide chain added GLP-1 peptide represented by (b27).
SEQ ID NO:130 is oligosaccharide chain added GLP-1 peptide represented by (b28).
SEQ ID NO:131 is oligosaccharide chain added GLP-1 peptide represented by (b29).
SEQ ID NO:132 is oligosaccharide chain added GLP-1 peptide represented by (b30).
SEQ ID NO:133 is oligosaccharide chain added GLP-1 peptide represented by (b31).
SEQ ID NO:134 is oligosaccharide chain added GLP-1 peptide represented by (b32).

SEQ ID NO:135 is oligosaccharide chain added GLP-1 peptide represented by (b33).
SEQ ID NO:136 is oligosaccharide chain added GLP-1 peptide represented by (b34).
SEQ ID NO:137 is oligosaccharide chain added GLP-1 peptide represented by (b35).
SEQ ID NO:138 is oligosaccharide chain added GLP-1 peptide represented by (b36).
SEQ ID NO:139 is oligosaccharide chain added GLP-1 peptide represented by (b37).
SEQ ID NO:140 is oligosaccharide chain added GLP-1 peptide represented by (b38).
SEQ ID NO:141 is oligosaccharide chain added GLP-1 peptide represented by (b39).
SEQ ID NO:142 is oligosaccharide chain added GLP-1 peptide represented by (b40).
SEQ ID NO:143 is oligosaccharide chain added GLP-1 peptide represented by (b41).
SEQ ID NO:144 is oligosaccharide chain added GLP-1 peptide represented by (b42).
SEQ ID NO:145 is oligosaccharide chain added GLP-1 peptide represented by (b43).
SEQ ID NO:146 is oligosaccharide chain added GLP-1 peptide represented by (b44).
SEQ ID NO:147 is oligosaccharide chain added GLP-1 peptide represented by (b45).
SEQ ID NO:148 is oligosaccharide chain added GLP-1 peptide represented by (b46).
SEQ ID NO:149 is oligosaccharide chain added GLP-1 peptide represented by (b47).
SEQ ID NO:150 is oligosaccharide chain added GLP-1 peptide represented by (b48).
SEQ ID NO:151 is oligosaccharide chain added GLP-1 peptide represented by (b49).
SEQ ID NO:152 is 45-residue mouse GLP-1 receptor sense primer synthesized in Test Example 6.
SEQ ID NO:153 is 41-residue mouse GLP-1 receptor anti-sense primer synthesized in Test Example 6.

INDUSTRIAL APPLICABILITY

The present invention provides an oligosaccharide chain added GLP-1 peptide that has higher stability in blood than that of GLP-1 and, preferably, exhibits higher activity of controlling blood-sugar levels than that of GLP-1. The present invention is useful particularly in pharmaceutical field.

The invention claimed is:

1. An oligosaccharide chain added glucagon-like peptide-1 (GLP-1) peptide having GLP-1 activity, wherein one amino acid is substituted with an oligosaccharide chain added amino acid, wherein said oligosaccharide chain is not an O-linked oligosaccharide chain in GLP-1; wherein said oligosaccharide chain added GLP-1 peptide is:
   (a) an oligosaccharide chain added GLP-1 peptide having one amino acid further added to the C terminal (position 37) of GLP-1, wherein said added amino acid is substituted with an oligosaccharide chain added amino acid;
   (b) an oligosaccharide chain added GLP-1 peptide having one amino acid further added to the N terminal (position 7) of GLP-1, wherein said added amino acid is substituted with an oligosaccharide chain added amino acid; or
   (c) an oligosaccharide chain added GLP-1 peptide wherein one or more amino acid site(s) selected from positions 18, 20, 22, 26, 30, 34 and 36 of GLP-1 is substituted with an oligosaccharide chain added amino acid; wherein: said oligosaccharide chain added amino acid is oligosaccharide chain added Asn; in said oligosaccharide chain added amino acid, the oligosaccharide chain is linked to the amino acid without a linker; said oligosaccharide chain consists of four or more sugars; and said oligosaccharide chain is selected from the group consisting of disialo, monosialo, asialo, diGlcNAc and dimannose oligosaccharide chains.

2. The oligosaccharide chain added GLP-1 peptide according to claim 1, having at least one of the following properties:
   higher stability in blood than that of GLP-1;
   activity of controlling blood-sugar levels at least 10 times that of GLP-1 in OGTT (Oral Glucose Tolerance Test); and
   DPP-IV resistance at least 30 times that of GLP-1.

3. A pharmaceutical composition comprising the oligosaccharide chain added GLP-1 peptide according to claim 1 for treating disease associated with GLP-1.

4. The pharmaceutical composition according to claim 3, wherein said disease associated with GLP-1 is diabetes.

5. The pharmaceutical composition according to claim 4 wherein said oligosaccharide chain has at least 90% uniformity.

6. An oligosaccharide chain added glucagon-like peptide-1 (GLP-1) peptide having GLP-1 activity, wherein one amino acid is substituted with an oligosaccharide chain added amino acid, wherein said oligosaccharide chain added amino acid is oligosaccharide chain added Asn or oligosaccharide chain added Cys, wherein said oligosaccharide chain is not an O-linked oligosaccharide chain in GLP-1.

7. The oligosaccharide chain added GLP-1 peptide according to claim 6, wherein in said oligosaccharide chain added amino acid, the oligosaccharide chain is linked to the amino acid without a linker.

8. The oligosaccharide chain added GLP-1 peptide according to claim 6, wherein said oligosaccharide chain consists of four or more sugars.

9. The oligosaccharide chain added GLP-1 peptide according to claim 6, wherein said oligosaccharide chain is selected from the group consisting of disialo, monosialo, asialo, diGlcNAc and dimannose oligosaccharide chains.

10. The oligosaccharide chain added GLP-1 peptide according to claim 6, wherein said oligosaccharide chain is represented by the following formula:

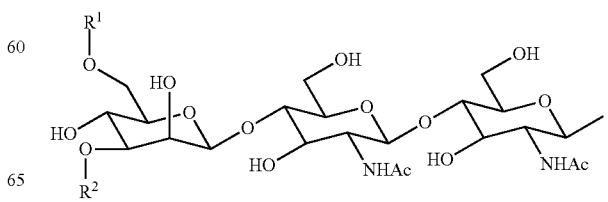

wherein

R¹ and R² are the same or different and each represents

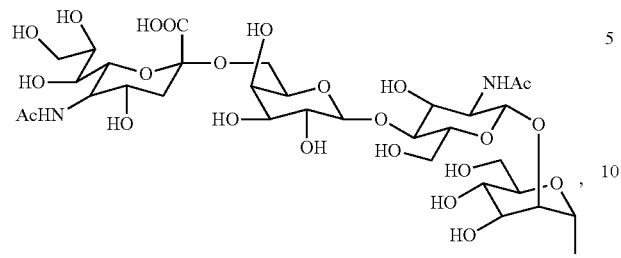

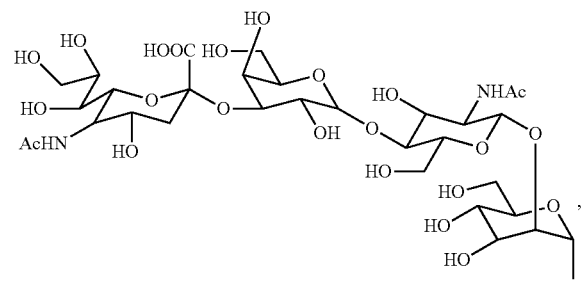

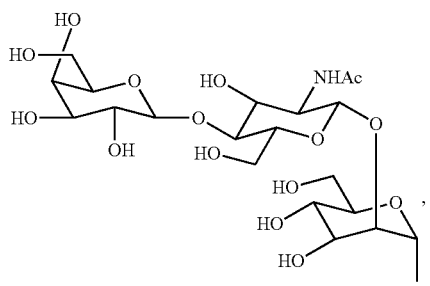

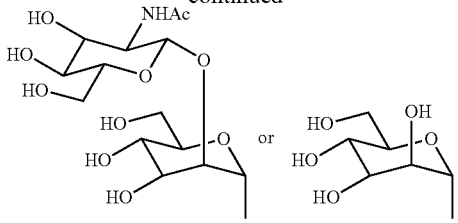

and

Ac represents an acetyl group.

11. The oligosaccharide chain added GLP-1 peptide according to claim 6, having at least one of the following properties:
   higher stability in blood than that of GLP-1;
   activity of controlling blood-sugar levels at least 10 times that of GLP-1 in OGTT (Oral Glucose Tolerance Test); and
   DPP-IV resistance at least 30 times that of GLP-1.

12. A pharmaceutical composition comprising the oligosaccharide chain added GLP-1 peptide according to claim 6 for treating disease associated with GLP-1.

13. The pharmaceutical composition according to claim 12, wherein said disease associated with GLP-1 is diabetes.

14. The pharmaceutical composition according to claim 13 wherein said oligosaccharide chain has at least 90% uniformity.

* * * * *

UNITED STATES PATENT AND TRADEMARK OFFICE
CERTIFICATE OF CORRECTION

| | | |
|---|---|---|
| PATENT NO. | : 7,985,731 B2 | |
| APPLICATION NO. | : 12/140866 | |
| DATED | : July 26, 2011 | |
| INVENTOR(S) | : Yasuhiro Kajihara et al. | |

It is certified that error appears in the above-identified patent and that said Letters Patent is hereby corrected as shown below:

<u>On the Title Page</u>

The title page should reflect that the Assignee of the patent is "Otsuka Chemical Co., Ltd., Osaka, Japan."

Signed and Sealed this
Twentieth Day of September, 2011

David J. Kappos
*Director of the United States Patent and Trademark Office*

UNITED STATES PATENT AND TRADEMARK OFFICE
CERTIFICATE OF CORRECTION

PATENT NO. : 7,985,731 B2
APPLICATION NO. : 12/140866
DATED : July 26, 2011
INVENTOR(S) : Yasuhiro Kajihara et al.

It is certified that error appears in the above-identified patent and that said Letters Patent is hereby corrected as shown below:

In column 61, Table 5, third column, second entry under "(Bluker Daltonics, AutoFLEX)", after "Calculated for" replace "$C_{235}$" with --$C_{238}$--.

In column 61, Table 5, third column, fifth entry under "(Bluker Daltonics, AutoFLEX)", after "Calculated for $C_{240}H_{372}$" replace "$N_{45}$" with --$N_{48}$--.

In column 65, Table 6, third column, first entry under "EMI-MS" after "Calculated for $C_{217}H_{336}$" replace "$N_{45}$" with --$N_{46}$--.

In column 101, line 5, after "198 mg" replace "(100 mmol" with --(100 μmol--.

In columns 121-122, table 7, second entry under "TABLE 7", after "Calculated for $C_{237}$" replace "$H_{387}$" with --$H_{367}$--.

In columns 121-122, table 7, fourteenth entry under "TABLE 7", after "Calculated for $C_{237}$" replace "$H_{387}$" with --$H_{367}$--.

In columns 121-122, table 7, fifteenth entry under "TABLE 7", after "Calculated for $C_{234}$" replace "$H_{381}$" with --$H_{361}$--.

In columns 121-122, table 7, sixteenth entry under "TABLE 7", after "Calculated for $C_{234}$" replace "$H_{380}N_{48}$" with --$H_{360}N_{46}$--.

In columns 121-122, table 7, eighteenth entry under "TABLE 7", after "Calculated for $C_{212}$" replace "$H_{325}$" with --$H_{326}$--.

In columns 121-122, table 7, twentieth entry under "TABLE 7", after "Calculated for $C_{212}$" replace "$H_{325}$" with --$H_{326}$--.

Signed and Sealed this
Third Day of July, 2012

David J. Kappos
*Director of the United States Patent and Trademark Office*

CERTIFICATE OF CORRECTION (continued)

U.S. Pat. No. 7,985,731 B2

In columns 121-122, table 7, twenty first entry under "TABLE 7", after "Calculated for $C_{212}$" replace "$H_{325}$" with --$H_{326}$--.

In columns 121-122, table 7, twenty fifth entry under "TABLE 7", after "Calculated for $C_{188}$" replace "$H_{283}$" with --$H_{289}$--.

In columns 121-122, table 7, twenty seventh entry under "TABLE 7", after "Calculated for $C_{184}$" replace "$H_{290}$" with --$H_{280}$--.

In columns 121-122, table 7, thirty sixth entry under "TABLE 7", after "Calculated for" replace "$C_{235}$" with --$C_{236}$--.

UNITED STATES PATENT AND TRADEMARK OFFICE
CERTIFICATE OF CORRECTION

PATENT NO. : 7,985,731 B2  
APPLICATION NO. : 12/140866  
DATED : July 26, 2011  
INVENTOR(S) : Yasuhiro Kajihara et al.

Page 1 of 1

It is certified that error appears in the above-identified patent and that said Letters Patent is hereby corrected as shown below:

In the Specifications:

In column 14, line 52, after "and" replace "$Xaa_{37}$ represents oligosaccharide chain added Asn" with --$Xaa_{37}$ represents Gly-oligosaccharide chain added Asn--.

In column 132, line 3, after "ID NO:37 is" replace "31-residue" with --32-residue--.

In column 136, line 11, after "ID NO:152 is" replace "45-residue" with --35-residue--.

In column 136, line 13, after "ID NO:153 is" replace "41-residue" with --31-residue--.

Signed and Sealed this  
Fourth Day of June, 2013

Teresa Stanek Rea  
*Acting Director of the United States Patent and Trademark Office*